US011332723B2

(12) United States Patent
Dueber et al.

(10) Patent No.: US 11,332,723 B2
(45) Date of Patent: May 17, 2022

(54) ENGINEERED MICROORGANISMS FOR PRODUCTION OF COMMODITY CHEMICALS AND CELLULAR BIOMASS

(71) Applicant: The Regents of the University of California, Oakland, CA (US)

(72) Inventors: John E. Dueber, San Francisco, CA (US); Ryan Joseph Protzko, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 55 days.

(21) Appl. No.: 16/336,403

(22) PCT Filed: Oct. 2, 2017

(86) PCT No.: PCT/US2017/054759
§ 371 (c)(1),
(2) Date: Mar. 25, 2019

(87) PCT Pub. No.: WO2018/067458
PCT Pub. Date: Apr. 12, 2018

(65) Prior Publication Data
US 2019/0218527 A1    Jul. 18, 2019

Related U.S. Application Data

(60) Provisional application No. 62/403,523, filed on Oct. 3, 2016.

(51) Int. Cl.
C12N 9/04        (2006.01)
C12N 15/00       (2006.01)
C12P 7/44        (2006.01)
C12P 7/18        (2006.01)
C12N 9/00        (2006.01)
C12P 19/04       (2006.01)
C12P 7/58        (2006.01)
C12N 9/02        (2006.01)
C12N 9/88        (2006.01)
C12P 7/20        (2006.01)
A61K 38/00       (2006.01)

(52) U.S. Cl.
CPC ............ *C12N 9/0006* (2013.01); *C12N 9/00* (2013.01); *C12N 9/0008* (2013.01); *C12N 9/88* (2013.01); *C12P 7/18* (2013.01); *C12P 7/20* (2013.01); *C12P 7/44* (2013.01); *C12P 7/58* (2013.01); *C12P 19/04* (2013.01); *C12Y 101/01001* (2013.01); *C12Y 101/01088* (2013.01); *C12Y 101/01203* (2013.01); *C12Y 102/01004* (2013.01)

(58) Field of Classification Search
CPC .............. C12N 9/0004; C12Y 101/01203
See application file for complete search history.

(56) References Cited

U.S. PATENT DOCUMENTS

| 8,835,147 | B2 | 9/2014 | Moon et al. | |
| 8,895,273 | B2 | 11/2014 | Boer et al. | |
| 2006/0177916 | A1 | 8/2006 | Stewart et al. | |
| 2011/0124065 | A1* | 5/2011 | Moon | C12P 19/00 435/137 |
| 2011/0275119 | A1* | 11/2011 | Suga | C12P 21/02 435/68.1 |
| 2012/0045804 | A1* | 2/2012 | Boer | C12P 7/44 435/142 |

(Continued)

FOREIGN PATENT DOCUMENTS

WO    WO 2009/145838       12/2009
WO    WO-2009145838 A2 *   12/2009   .............. C12P 19/00

(Continued)

OTHER PUBLICATIONS

Benz et al. (2014) Identification and characterization of a galacturonic acid transporter from Neurospora crassa and its application for *Saccharomyces cerevisiae* fermentation processes Biotechcol, Biofuels, vol. 7, issue 20, pp. 1-13.*
Reference "Gal-A transporter NCU00988" (2020) pp. 1-7.*
Pick et al. (2015) Characterization of uronate dehydrogenases catalysing the initial step in an oxidative pathway, Microb. Biotechnol., vol. 8, No. 4, pp. 633-643.*
Nakamura et al. (2003) Metabolic engineering for the microbial production of 1,3-propanediol, Curr. Opin. Biotechnol., vol. 14, pp. 454-459.*

(Continued)

*Primary Examiner* — Manjunath N Rao
*Assistant Examiner* — Samuel W Liu
(74) *Attorney, Agent, or Firm* — Paula A. Borden; Bozicevic Field & Francis, LLP

(57) ABSTRACT

The present disclosure provides methods of producing commodity products, the methods involving culturing a host cell that is genetically modified to produce a uronate dehydrogenase (UDH) that converts a sugar acid to its corresponding 1,5-aldonolactone, that uses $NADP^+$ or $NAD^+$ as a cofactor, and that produces NADPH or NADH, respectively, where the host cell coexpresses an endogenous or a heterologous reductase that utilizes the produced NADPH or NADH to generate the commodity product or a precursor thereof. The present disclosure provides a method of producing downstream products of glycerol and pyruvate in a genetically modified microbial host cell, the method involving culturing a genetically modified microbial host cell of the present disclosure in a culture medium comprising D-galacturonic acid. The present disclosure provides variant UDH polypeptides that utilize $NADP^+$, nucleic acids encoding the variant UDH polypeptides; and host cells genetically modified with the nucleic acids.

19 Claims, 37 Drawing Sheets

Specification includes a Sequence Listing.

(56) References Cited

U.S. PATENT DOCUMENTS

| | | | |
|---|---|---|---|
| 2013/0055471 A1* | 2/2013 | Holman | C12N 15/8243 800/290 |
| 2013/0130347 A1* | 5/2013 | Delisa | C12P 7/42 435/188 |
| 2014/0186915 A1* | 7/2014 | Mori | C12N 9/0077 435/167 |
| 2014/0308715 A1 | 10/2014 | Hilditch et al. | |
| 2015/0093794 A1* | 4/2015 | Moon | C12N 15/8243 435/137 |
| 2016/0053287 A1 | 2/2016 | Burk et al. | |
| 2016/0230195 A1 | 8/2016 | Osterhout et al. | |

FOREIGN PATENT DOCUMENTS

| | | | |
|---|---|---|---|
| WO | WO 2012/125027 | 9/2012 | |
| WO | WO-2013115959 A1 * | 8/2013 | C07K 14/28 |
| WO | WO 2015/084265 | 6/2015 | |

OTHER PUBLICATIONS

Sloothaak et al. (2014) Overexpression of the Aspergillus niger GatA transporter leads to preferential use of D-galacturonic acid over D-xylose, AMB Express, vol. 4, No. 66, pp. 1-9.*

NCBI_XP-680936 (2018) https://www.ncbi.nlm.nih.gov/protein/XP_680936, pp. 1-3.*

Galagan et al. (2005) Sequencing of Aspergillus nidulans and comparative analysis with A. fumigatus and A. oryzae, Nature, vol. 438, 22/29, pp. 1105-1115.*

Biz, et al.; "The introduction of the fungal d-galacturonate pathway enables the consumption of d-galacturonic acid by Saccharomyces cerevisiae"; Microbial Cell Factories; vol. 15, No. 144, 11 pages (2016).

Drozdzynska, et al.; "Biotechnological production of 1,3-propanediol from crude glycerol"; Journal of Biotechnology, Computational Biology and Bionanotechnology; vol. 92, No. 1, pp. 92-100 (2011).

Ehrensberger, et al.; "Structure-guided engineering of xylitol dehydrogenase cosubstrate specificity"; Structure; vol. 14, No. 3, pp. 567-575 (Mar. 2006).

Hong, et al.; "Improved 1,3-propanediol production by Escherichia coli from glycerol due to Co-expression of glycerol dehydratase reactivation factors and succinate addition"; Biotechnology and Bioprocess Engineering; vol. 20, No. 5, pp. 849-855 (Sep. 2015).

Jiang, et al.; "Key enzymes catalyzing glycerol to 1,3-propanediol"; Biotechnology for Biofuels; vol. 9, No. 57, 19 pages (2016).

NCBI Reference Sequence Accession WP_004150927.1. MULTISPECIES: 1,3-propanediol dehydrogenase [Enterobacteriaceae]. [online] Mar. 22, 2015 [retrieved Jan. 30, 2018]. Available on the internet : <URL: https://www.ncbi.nlm.nih.gov/protein/490252907?sat=5&satkey=93673294>.

Polen, et al.; "Toward biotechnological production of adipic acid and precursors from biorenewables"; J. Biotechnol.; vol. 167, No. 2, pp. 75-84 (Aug. 20, 2013).

Tai, et al.; "Engineering nonphosphorylative metabolism to generate lignocellulose-derived products"; Nature Chemical Biology; vol. 12, pp. 247-253 (Apr. 2016).

UniProt Accession Q888H1. (URODH_PSESM). [online] Sep. 7, 2016 [retrieved Jan. 30, 2018]. Available on the internet:<http://www.uniprot.org/uniprot/Q888H 1 .txt?version=87>. Especially p. 1.

* cited by examiner

FIG. 2

*Aspergillus nidulans* D-galacturonic acid transporter     (SEQ ID NO:1)

MSFFKNSRVYMLSAVAYMGSFLFGYDTGVMGSVLALDSFKHDFHMATGSTGFASSKEAEISSNVVALLTAGC
FFGAIAGAIANDRYGRKNSLLVLSVIFMIGAAVQTGGRGTIAYIYGGRVIAGFGIGGMSAITPIYVSENCPPNVR
GRIAGLFQEFLVIGVTVSYWLCYGVEKNIAPSTKQWRIPIGFQLVPSGLMFIGLWFLKESPRWLMKQGRREEA
TASLAFTRRADPNSDEVQQELAEIRASIEEELRSTEGVTWREVLLPGNRLRFLNAFLIMFWQQFSGTNSIGYYA
PQLFQTIGVASTDTSLFTTGIYGVVKVVSTGLFLLIGIDRFGRKWSLVGGGWAMAVFMFILGAVLVSYPPVNT
DTISNASIAMIVMIYLYVISYSASWGPIPWVYISEIFPTRLRAYGVGMGSATQWLFNFVVTKFTPSAISNIGWRT
FIMFGVFCFAMGLWVCIFIKETKGKRLEDMDDIFGGKTVEQMQKDIEQADVEEQTEVEKTQTRHEEQVVR*

FIG. 3

*Aspergillus niger* D-galacturonic acid transporter     (SEQ ID NO:2)

MSLLKNYRVYLLTAVAYSGSLLFGYDTGVMGSVLSLTSFKEDFGIPTGSSGFASSKSSEISSNVVSLLTAGCFFGA
IFAAPLNERIGRRYALMIFTVIFLIGAAVQVASKHHIGQIYGGRVIAGLGIGGMSSITPVFVSENCPPSIRGRVAG
MFQEFLVIGSTFAYWLDYGVSLHIPSSTKQWRVPVAVQLIPGGLMLLGLFFLKESPRWLAGKGRHEEALQSLA
YIRNESPDSEEIQKEFAEIRAAIDEEVAATEGLTYKEFIQPSNLKRFGFAFTLMLSQQFTGTNSIGYYAPEIFQTIG
LSATNSSLFATGVYGTVKVVATAIFLFVGIDRWGRKLSLVGGSIWMASMMFIIGAVLATHPPDTSASGVSQAS
IAMVVMIYLYVIGYSASWGPTPWVYVSEIFPTRLRSYGVGLAATSQWLWSFVVTEITPKAVHNIGWRTFLMF
GIFCVAMCVFVIVFAKETKGRSLEDMDILFGAVNEADRRAAVEHTMHKRGSSHIEDVDEETERVRHEQDKV*

FIG. 4

*Neurospora crassa* D-galacturonic acid transporter     (SEQ ID NO:3)

MGLSIGNRILRKIVKNEAMAEDPPEIYGWRVYLLACSACFGAMSFGWDSSVIGGVIELEPFKHDFGFIGNDKA
KANLGANIVSTLQAGCFLGALIASPITDRFGRKWCLIAVSLVVIIGIIMQAAASGNLAPMYIGRFVAGVGVGAA
SCINPVFVSENAPRSIRGLLTGLYQLFIVTGGMIAFWINYSVSLHFKGKSMYIFPLAIQGLPAGLLCVCMLLCHES
PRWLARRDRWEECKSVLARIRNLPPDHPYIVDEFREIQDQLEQERRLQGDATYWDLTRDMWTVAGNRKRA
LISIFLMICQQMTGTNAINTYAPTIFKNLGITGTSTSLFSTGIYGIVKVVSCVIFLLFLADSLGRRRSLLWTSIAQGL
AMFYIGLYVRISPPIDGQPVPPAGYVALVCIFLFAAFFQFGWGPACWIYASEIPAARLRSLNVSYAAATQWLFN
FVVARAVPTMLVTVGPHGYGTYLIFGSFCLSMFVFVWFFVPETKGISLEHMDELFGVTDGPAAEKSSVHGGD
DVGSEMGKGDQKSKHVEVYV

FIG. 5

*Trichoderma reesei* D-galacturonic acid transporter  (SEQ ID NO:4)

MGVTSKFLRAIVRNEAMRTDPDEIYGWRVFTLVFSACFGGMLFGWDTGSIGGILTMPAFQEKFHYAHSSPK
AKSNMNQNIVSTLQAGCFAACFFTSWVTDRYGRRFALIAAGLLTIVGIIFQAASAADGTLAVMYVGRFIAGLGI
GAASALTPLYVSECAPRAIRGGLTAFYQLFNVFGIMLAFWVNYGCLLHVSAPAIYIIPLTLQALPAVFLMVGMFI
SPESPRWCARRDDWDRATKVLVKLRGLPADSEYVQNEIQEMADQLEHERRLTGDATFKTLLREMWTIPGNR
NRAVISILLMIFQQMTGVNAINYYAPQIFTNLGMTGNDSSLFATGVYGVVKTAACAVFLVFVADSLGRRWSLL
WTAAAQGIFLYIVGIYGRVQPPIAGQPVTAFGYVAITCIYLWAASFQFGWGPVCWILVSEIPTARLRAMNVAI
GAATQWLFNFVCARSVLTMQTTMGKAGYGMFFMFGTFCFIMGIFVWFFVPETKGLSLEHMDDLFGVTELV
KKVEAEPELGHPDSIREERADIKS*

FIG. 6

*Trichoderma reesei* D-galacturonic acid reductase  (SEQ ID NO:5)

MVATSFKLNNGLEIPAVGLGTWQSKAGEVKAAVSYALQIGYKLIDGAYCYGNEDEVGEGLKEAFAAGVKREDI
FVVTKIWATYNTRVVLGLDKSLRSLGLDYVDLLLVHWPVLLNPEGNHDKFPTLPDGKRDVIWDYNHVDGWK
QMEAVLATGKTKSIGVSNYSKKYLEQLLPHATVIPAVNQIENHPSLPQQEIVDFCKEKGIHIMAYSPLGSTGSPL
MSADPVVKIAEKKGISPTTVLLSYHVNRGSTVLAKSVTPARIKANLEIVDLDDEDMKLLNDYSNDLASKGELKRY
VYPPFGIDFGFPDKS*

FIG. 7

*Aspergillus niger* D-galacturonic acid reductase  (SEQ ID NO:6)

MAPPAVLMVGTGEYTTGYVGGTASTSDKKVGVVGLTLFDLRRRGKVGDLSMVGVSGSKFPGIRAHLQKNISE
VYNGLDVSFTSFPADNTSDPEAYKAAIDALPAGSAITIFTPDPTHYPIALYAIQRKIHVLITKPATKLLSDHLDLLAE
SRKHNVVVYIEHHKRFDPAYSDARAKAAKLGDFNYFYSYMSQPKSQLETFKAWAGKDSDISYYLNSHHVDVN
ESMVPDYVPVKVTASAATGTAVELGCAHETEDTITLLVEWKKKDGSRMATGVYTSSWTAPQRAGVHSNQYF
HYMGSKGEIRVNQAKRGYDVAEDEAGLSWINPFYMKYAPDEEGNFGGQTGYGYISFEKFIDAVTAVNEGRLT
LDQLDARPIPTLKNTIATTAILHAGRISLDEKRSVEIVTEDGKWELK*

FIG. 8

*Rhodosporidium toruloides* (RHTO_03963) D-galacturonic acid reductase  (SEQ ID NO:7)

MSSKSVPTVQLHNGKSFPLIGFGTWQSAPGEVGNAVSVALKAGYRHLDLAKVYQNQKEIAPAIANSGVPREE
MFITSKLWNSQHRPDLVEPALDDTLKELGLSYLDLYLIHWPVAFPAEGDPHQNLFPKANDNEVKIDDSVSLVD
TWKAMIKLLDTGKVKSIGVSNFSPEMVDAITEATGVKPVVNQIERHPHLLQRELIEHHKKANIVITAYSGFGNN
SEGVPLLVQHPIVKKIAEKHGADGGQVLIAWGMHGGHAIIPKSVTDSRIQSNFKIIQISDEDVKEIDSIGEKEPR
RFNTPIRYTPLWPVNCFNEESERSAKYQVKIKGS*

FIG. 9

*T. reesei* (Venus-LGD1) L-galactonate dehydratase  (SEQ ID NO:8)

MSKGEELFTGVVPILVELDGDVNGHKFSVSGEGEGDATYGKLTLKLICTTGKLPVPWPTLVTTLGYGLQCFARY
PDHMKQHDFFKSAMPEGYVQERTIFFKDDGNYKTRAEVKFEGDTLVNRIELKGIDFKEGGNILGHKLEYNYNS
HNVYITADKQKNGIKANFKIRHNIEDGGVQLADHYQQNTPIGDGPVLLPDNHYLSYQSALSKDPNEKRDHMV
LLEFVTAAGITHGMDELYKGSSEVTITGFRSRDVRFPTSLDKTGSDAMNAAGDYSAAYCILETDSAHSGHGMT
FTIGRGNDIVCAAINHVADRLKGKKLSSLVADWGKTWRYLVNDSQLRWIGPEKGVIHLALGAVVNAVWDLW
AKTLNKPVWRIVADMTPEEYVRCIDFRYITDAITPEEAVAMLREQEAGKAKRIEEALQNRAVPAYTTSAGWLG
YGEDKMKQLLRETLAAGYRHFKVKVGGSVEEDRRRLGIAREILGFDKGNVLMVDANQVWSVPEAIDYMKQL
SEYKPWFIEEPTSPDDIMGHKAIRDALKPYGIGVATGEMCQNRVMFKQLIMTGAIDICQIDACRLGGVNEVLA
VLLMAKKYGVPIVPHSGGVGLPEYTQHLSTIDYVVVSGKLSVLEFVDHLHEHFLHPSVIKDGYYQTPTEAGYSV
EMKPESMDKYEYPGKKGVSWWTTDEALPILNGEKIGS*

FIG. 10

*A. niger* (GAAB) L-galactonate dehydratase  (SEQ ID NO:9)

MAPIKSIEYFRVKPRWLFVKVTDSEDKFGWGEATLEGHTQAVEGALDEIIGRIVGYEADDIEHVWQTIWRLGF
YRGGPVFMSALSGIDIALWDLKGRRLNVPVYQLLGGKVRNKVQVYAWIGGDRPSDVEVAAKARIAQGLKCV
KMNATEDMNWLDSPSVLDSCIERIKQVKALGLDAGLDFHGRLHRPMAKQLAKALEPYRPLFIEEPLLVEHPEA
IKQLSQHTTIPIAFGERLYTRWDVKRFLEDASVDVLQPDIAHAGGISETKRIATMAETYDVAIAPHCPLGPIALA
ASMQVALSTPNFVIQEMSLGMHYNVEAGDIDLTSYLTNPTVFNIEEGYVPAPTGAGLGVEIDEELVRRISRETE
PWLPKEFYGVDGGIREW*

FIG. 11

*T. reesei* (LGD1) L-galactonate dehydratase  (SEQ ID NO:10)

MSEVTITGFRSRDVRFPTSLDKTGSDAMNAAGDYSAAYCILETDSAHSGHGMTFTIGRGNDIVCAAINHVAD
RLKGKKLSSLVADWGKTWRYLVNDSQLRWIGPEKGVIHLALGAVVNAVWDLWAKTLNKPVWRIVADMTPE
EYVRCIDFRYITDAITPEEAVAMLREQEAGKAKRIEEALQNRAVPAYTTSAGWLGYGEDKMKQLLRETLAAGY
RHFKVKVGGSVEEDRRRLGIAREILGFDKGNVLMVDANQVWSVPEAIDYMKQLSEYKPWFIEEPTSPDDIMG
HKAIRDALKPYGIGVATGEMCQNRVMFKQLIMTGAIDICQIDACRLGGVNEVLAVLLMAKKYGVPIVPHSGG
VGLPEYTQHLSTIDYVVVSGKLSVLEFVDHLHEHFLHPSVIKDGYYQTPTEAGYSVEMKPESMDKYEYPGKKG
VSWWTTDEALPILNGEKI*

FIG. 12

*R. toruloides* (RHTO_05818) L-galactonate dehydratase (SEQ ID NO:11)

MTQDSFIASFTVEDLRFPTSLTGDGTDANNRECDYSAAYCTLRTNLGEVGYGLTFTIGRGNDIVCAAVEQVAG
KLMNMKTAELFSAPGLGRMWNYLLSDPQLRWIGPEKGVIHIATAAVVNAVWDMYARHLKKPLWQVVAEF
TPEEFVAATTFRYITDMITPEEALALLKEKEAGKAERLAKLKAEGYPAYTTSVGWFGYPDEKVARLTREAIAQGF
NHFKMKVGADVAMDQRRLALIRSIIDDPKECEGRPVPSAESLVGKNAGPTGSVLMIDSNQVWDVREAIDYV
KALKDANPWFIEEPTAPDDILGHAEIRKQLKPYKIGVATGEHAHNRMVFKQLLAAEAIDVCQIDSCRLAGVNEI
LGVLLMAAKKGVPVCPHAGGVGLTNYVVHLSIIDYLCVSGTKERNVLEYVDHLHEHFTNPPTINSHGYYNIPSD
PTEGYSIGMHEASKAAYVYPNGSYWTNDHAAARLVAIKNGYIKAGS*

FIG. 13

*A. niger* (GAAC) 2-keto-3-deoxy-l-galactonate aldolase (SEQ ID NO:12)

MPFTPLRPGVYAPTMTFFDPSTEDLDVPTIRKHAVRLAKAGLVGLVCMGSNGEAVHLTRAERKTVINETRSAL
VEAGFSNVPVIAGASEQSIRGTIELCKESYEAGAEYALIVPPSYYRYATGNDQTLYEFFTSVADGSPIPLILYNYPG
AVAGIDMDSDLIIRISQHPNIVGTKFTCANTGKLTRVASALHAITPPSPLAPAQRKFPSTKTEANHPYVAFGGIA
DFSLQTLASGGSAILAGGANVIPKLCVQIFNLWSAGRFTEAMEAQELLSRADWVLTKAAIPGTKSAIQSYYGYG
GFPRRPLARLSAEQAEAVAEKIKDAMEVEKSLPDIA*

FIG. 14

*T. reesei* (LGA1) 2-keto-3-deoxy-l-galactonate aldolase (SEQ ID NO:13)

MAPPSLPCGIYAPTMTFFHPESEDIDIPTIKHHAQRLAKAGLAGLVVMGSNGEAVHCTRDEKIAVLSATREAL
DAAGFQSVPVLFGATEGSVRGTIELCKLAAAAGAAAALVLPPSYYRAQTDEASIEAYFVAVADASPIPLVLYNYP
GAVSGIDMDSDLLIRLAQHKNIVGTKFTCGNTGKLTRVALATDAKTPFRDGSGYMAFGGMCDFTLQTLVSGG
SGIIAGGANVMPKLCVKVWDSYSQGNRDEAEKLQKVLSRGDWPLTKAAIAGTKSAIQTYYGYGGYPRRPLKR
LEQARVSAIEEGIREAMEIEKTL*

FIG. 15

*R. toruloides* (RHTO_05820) 2-keto-3-deoxy-l-galactonate aldolase (SEQ ID NO:14)

MPSTKFGKNLPHGVYAPVLTFYKGNDEELDLETYKKHVQFVARGGVNIVALGSMGESVQLTHQERNQVVKA
ARSALDADSSLSQVPLIAGTGASSTKETIELTKEAAEAGADFAMVISPGYFAGAMSRKAIKQFFVDVAEASPIPV
LVYNYPGASAGIDIDSDLMAEIAAAAPNIVGCKLTCGSVGKLTRLTTLRDDFAVLGGFIDFLGPSLLAKAAGGIT
GVGNVAPKTCAKLYKDTLAALSGQASVSSAQDLQFIVSRADWALAKTGIAGAKWVLDQLEGYGGKPRRPLLP
FDESDGKGKQLLDDLKEILEVEKSLGS*

FIG. 16

*A. niger* (GADD) L-glyceraldehyde reductase   (SEQ ID NO:15)

MSLGKKVTLNSGAQIPQLGFGTWQSAPGQVGDAVYEALKAGYRHLDLATIYQNQREVAEGIKRAYKDVPGL
KREDIFITSKLWNSQHDPAVVEKALDECLAELELDYLDLYLVHWPVSFTTGSELFPLVKDSSVEGGDVVINDDIS
IVDTWKAMTQLPKSKARTVGVSNHMIPHLEAIINATGVVPAVNQIERHPVLQSNELIEYCQKKGIHVTAYSAF
GNNGFGVPLLVTRPEVKEVAESASKRLGTTVTPAQVILAWSQVGGHSVIPKSVTPSRIHENFKEVELTPEEIAK
VSELGKDRRRYNTPYVANTPRWDIDIFGEEEEKPAGHKIWSPVLFAAGYSSSAWVGRGKVSWDTVHLVGNH
TPLLRQQTTPRFARLSFGS*

FIG. 17

*T. reesei* (GCY1) L-glyceraldehyde reductase   (SEQ ID NO:16)

MPATLHDSTKILSLNTGAQIPQIGLGTWQSKENDAYKAVLTALKDGYRHIDTAAIYRNEDQVGQAIKDSGVPR
EEIFVTTKLWCTQHHEPEVALDQSLKRLGLDYVDLYLMHWPARLDPAYIKNEDILSVPTKKDGSRAVDITNWN
FIKTWELMQELPKTGKTKAVGVSNFSINNLKDLLASQGNKLTPAANQVEIHPLLPQDELINFCKSKGIVVEAYS
PLGSTDAPLLKEPVILEIAKKNNVQPGHVVISWHVQRGYVVLPKSVNPDRIKTNRKIFTLSTEDFEAINNISKEKG
EKRVVHPNWSPFEVFKGS*

FIG. 18

*R. toruloides* (RHTO_00641) L-glyceraldehyde reductase   (SEQ ID NO:17)

MPSYIDVPSFPLSHGGKAIPAVGLGTWQSNPGEVSNAVKIALQNGYRHIDGAWIYGNEKEVGEGIKASGVPR
EEIFVTSKLWCTKHRNVEAAVKESLELLGLDYLDLYLIHWPVPLNGQGNDPKFPKLPDGSRDRDTEWSINQT
WEQMEAILEKGLVKAIGVSNFSEAYLDQLLTTAKVVPAVNQIELHPYLPQHELLQYLAKKNILAEAYSPLGSTDS
PLLKDEVIKKIADKHGVSVGTVLISYQVNRNVVVLPKSVTEKRIIDNYKIVKLDEEDMRTLNELYKTKGKRFIKPD
WGVDLKFSHWGS*

FIG. 19

*Pseudomonas syringae* uronate dehydrogenase   (SEQ ID NO:18)

MASAHTTQTPFNRLLLTGAAGGLGKVLRETLRPYSHILRLSDIAEMAPAVGDHEEVQVCDLADKDAVHRLVE
GVDAILHFGGVSVERPFEEILGANICGVFHIYEAARRHGVKRVIFASSNHVIGFYKQNETIDAHSPRRPDSYYGL
SKSYGEDMASFYFDRYGIETVSIRIGSSFPEPQNRRMMSTWLSFDDLTRLLERALYTPDVGHTVVYGVSDNKT
VWWDNRFASKLDYAPKDSSEVFRAKVDAQPMPADDDPAMVYQGGAFVASGPFGDKGS*

FIG. 20

*Limnohabitans sp. Rim47* uronate dehydrogenase  (SEQ ID NO:19)

MPNTSTPTSNSGIRFPRLLLTGAGGNLGQELRPRLKAYCDVLRVSHRRDLGPAAAGEEVQTASLEDAEHMLSL
LDGVSAVVHMGGVSTEQPWAPILAGNIVGMVNLYEAARLKGVKRIVFASSNHVTGFYRQDEVVNTRMPPK
PDGFYGLSKAFGEDLAQLYWDRWGVETVSIRIGSSFTEPRDRRMLATYLSYDDLERLVVAALTAPIVGHSIIYG
MSDNQTTWWDNTHAKHIGYRPQDSSDVFRHAVEARQQTIDKQDPAAIYQGGAFVKATPHGGS*

FIG. 21

Variant uronate dehydrogenase   (SEQ ID NO:20)

MASAHTTQTPFNRLLLTGAAGGLGKVLRETLRPYSHILRLSDXAEMAPAVGDHEEVQVCDLADKDAVHRLVE
GVDAILHFGGVSVERPFEEILGANICGVFHIYEAARRHGVKRVIFASSNHVIGFYKQNETIDAHSPRRPDSYYGL
SKSYGEDMASFYFDRYGIETVSIRIGSSFPEPQNRRMMSTWLSFDDLTRLLERALYTPDVGHTVVYGVSDNKT
VWWDNRFASKLDYAPKDSSEVFRAKVDAQPMPADDDPAMVYQGGAFVASGPFGDKGS*

FIG. 22

MIOX – *Mus musculus*    (SEQ ID NO:21)

```
  1 MKVDVGPDPS LVYRPDVDPE MAKSKDSFRN YTSGPLLDRV FTTYKLMHTH QTVDFVSRKR
 61 IQYGGFSYKK MTIMEAVGML DDLVDESDPD VDFPNSFHAF QTAEGIRKAH PDKDWFHLVG
121 LLHDLGKIMA LWGEPQWAVV GDTFPVGCRP QASVVFCDST FQDNPDLQDP RYSTELGMYQ
181 PHCGLENVLM SWGHDEYLYQ MMKFNKFSLP SEAFYMIRFH SFYPWHTGGD YRQLCSQQDL
241 DMLPWVQEFN KFDLYTKCPD LPDVESLRPY YQGLIDKYCP GTLSW
```

FIG. 23

MIPS – *Saccharomyces cerevisiae*  (SEQ ID NO:22)

```
  1 MTEDNIAPIT SVKVVTDKCT YKDNELLTKY SYENAVVTKT ASGRFDVTPT VQDYVFKLDL
 61 KKPEKLGIXL IGLGGNNGST LVASVLANKH NVEFQTKEGV KQPNYFGSXT QCSTLKLGID
121 AEGNDVYAPF NSLLPXVSPN DFVVSGWDIN NADLYEAXQR SQVLEYDLQQ RLKAKXSLVK
181 PLPSIYYPDF IAANQDERAN NCINLDEKGN VTTRGKWTHL QRIRRDIQNF KEENALDKVI
241 VLWTANTERY VEVSPGVNDT XENLLQSIKN DHEEIAPSTI FAAASILEGV PYINGSPQNT
301 FVPGLVQLAE HEGTFIAGDD LKSGQTKLKS VLAQFLVDAG IKPVSIASYN HLGNNDGYNL
361 SAPKQFRSKE ISKSSVIDDI IASNDILYND KLGKKVDHCI VIKYXKPVGD SKVAXDEYYS
421 ELXLGGHNRI SIHNVCEDSL LATPLIIDLL VXTEFCTRVS YKKVDPVKED AGKFENFYPV
481 LTFLSYWLKA PLTRPGFHPV NGLNKQRTAL ENFLRLLIGL PSQNELRFEE RLL
```

FIG. 24A 1,3-propanediol oxidoreductase – *Klebsiella pneumoniae*    (SEQ ID NO:23)

```
  1 MSYRMFDYLV PNVNFFGPNA ISVVGERCQL LGGKKALLVT DKGLRAIKDG AVDKTLHYLR
 61 EAGIEVAIFD GVEPNPKDTN VRDGLAVFRR EQCDIIVTVG GGSPHDCGKG IGIAATHEGD
121 LYQYAGIETL TNPLPPIVAV NTTAGTASEV TRHCVLTNTE TKVKFVIVSW RNLPSVSIND
181 PLLMIGKPAA LTAATGMDAL THAVEAYISK DANPVTDAAA MQAIRLIARN LRQAVALGSN
241 LQARENMAYA SLLAGMAFNN ANLGYVHAMA HQLGGLYDMP HGVANAVLLP HVARYNLIAN
301 PEKFADIAEL MGENITGLST LDAAEKAIAA ITRLSMDIGI PQHLRDLGVK EADFPYMAEM
361 ALKDGNAFSN PRKGNEQEIA AIFRQAF
```

FIG. 24B yqhD homologues from E coli:    (SEQ ID NO:24)
>sp|Q46856|YQHD_ECOLI Alcohol dehydrogenase YqhD OS=Escherichia coli (strain K12) GN=yqhD PE=1 SV=1

```
MNNFNLHTPTRILFGKGAIAGLREQIPHDARVLITYGGGSVKKTGVLDQVLDALKGMDVL
EFGGIEPNPAYETLMNAVKLVREQKVTFLLAVGGGSVLDGTKFIAAAANYPENIDPWHIL
QTGGKEIKSAIPMGCVLTLPATGSESNAGAVISRKTTGDKQAFHSAHVQPVFAVLDPVYT
YTLPPRQVANGVVDAFVHTVEQYVTKPVDAKIQDRFAEGILLTLIEDGPKALKEPENYDV
RANVMWAATQALNGLIGAGVPQDWATHMLGHELTAMHGLDHAQTLAIVLPALWNEKRDTK
RAKLLQYAERVWNITEGSDDERIDAAIAATRNFFEQLGVPTHLSDYGLDGSSIPALLKKL
EEHGMTQLGENHDITLDVSRRIYEAAR
```

FIG. 28
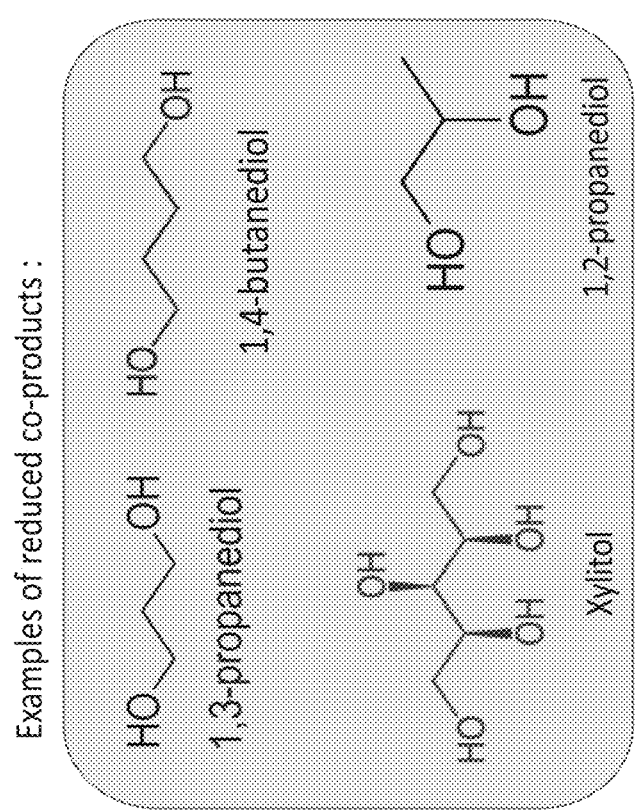
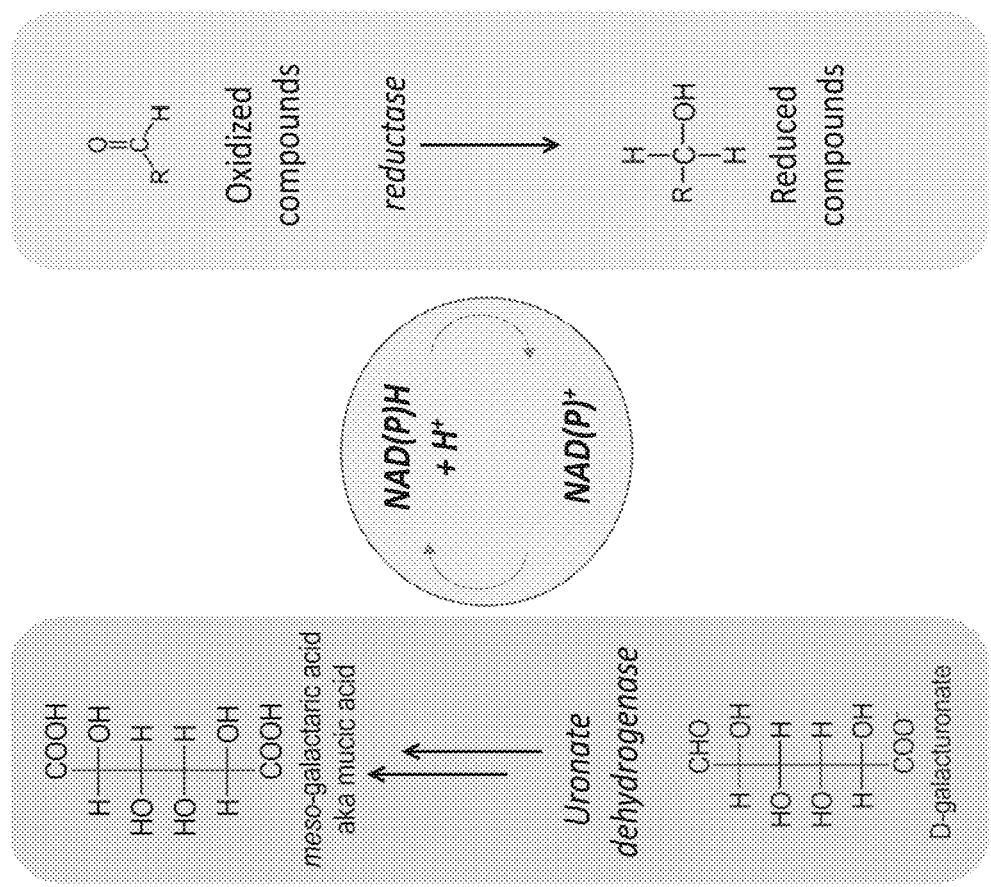

| Sample | Well | Amino acid position | | | Cofactor Preference | SPECIFIC ACTIVITY [μmol/min/mg] | |
|---|---|---|---|---|---|---|---|
| | | 42 | 43 | 44 | | NAD+ | NADP+ |
| 5 | B7 | Asp | Arg | Ser | NAD+<NADP+ | 9.78 | 12.85 |
| 10 (WT) | F12 | Asp | Ile | Ala | NAD+ | 10.21 | 0.01 |
| 11 | G1 | Asp | Arg | Ala | NAD+=NADP+ | 9.53 | 9.32 |
| 18 | H6 | Ala | Arg | Ser | NAD+>NADP+ | 10.01 | 6.18 |
| 21 | H11 | Ala | Arg | Ala | NAD+<NADP+ | 6.27 | 10.23 |

FIG. 39
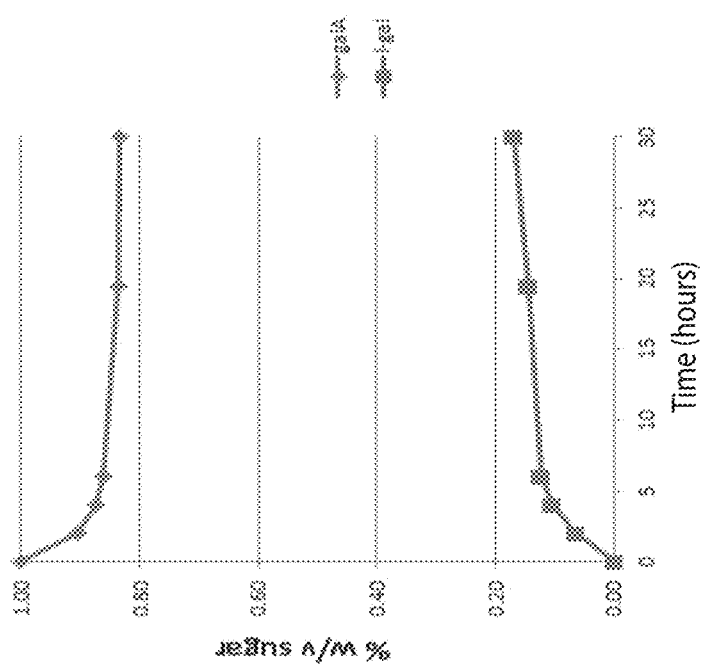
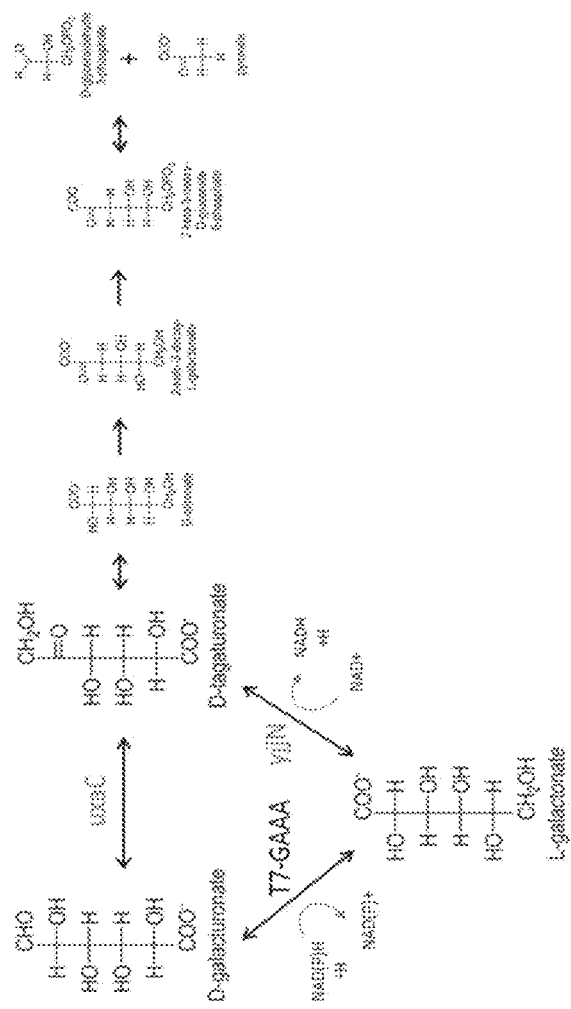

FIG. 42
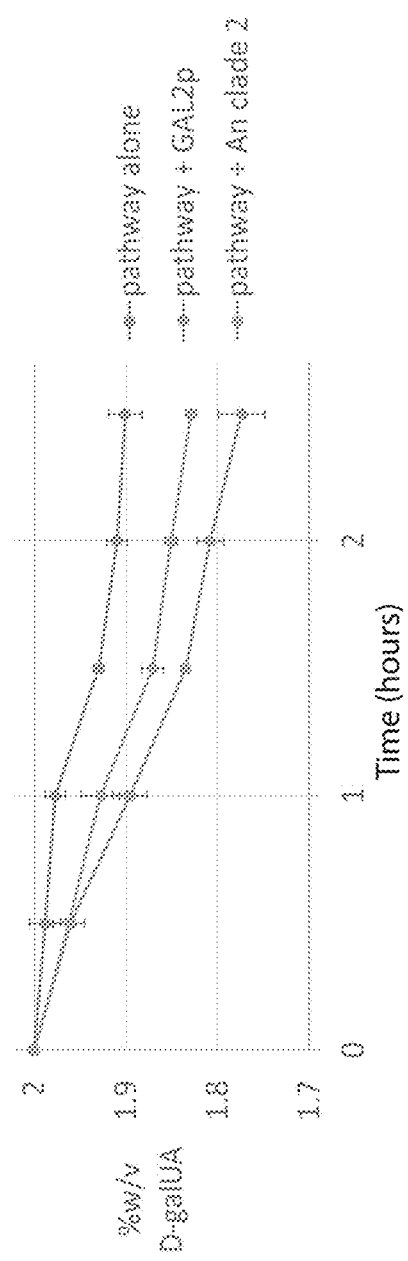
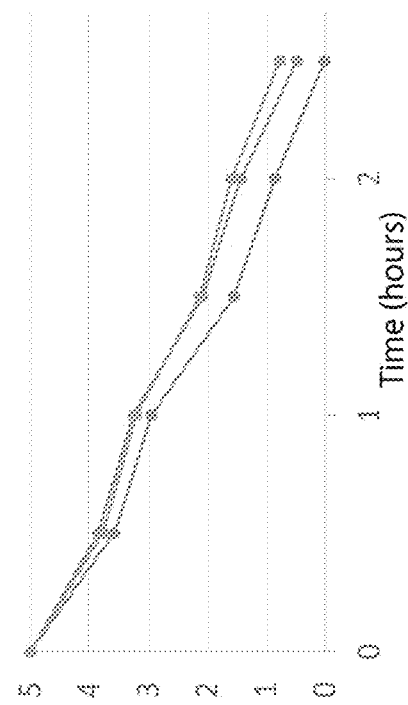
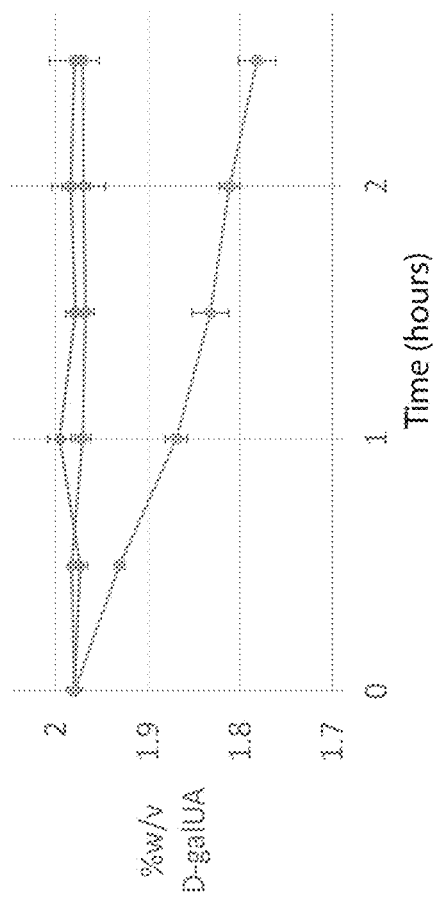

FIG. 47
*Streptomyces venezuelae* UDH  (SEQ ID NO:25)

```
  1 mspprtvllt gaaggvgtlm relippygye lrlildvapvp gapdaivadl adraalreav
 61 rgvdaivhla gislestfdk imaaniagty nlyeaareeg vrrvvfassn havgfirqpr
121 pgdplvpvdt phrpdtfygl skcifgediaq lywdlhgiet vsvrigscfp eptsvrmlsm
181 wlspadcarl lhatltaedv ahtvvygssa ntrawwdlst araigfepvd dsevhaekli
241 aekglppeds adarylgghf cvdpprwph
```

FIG. 48
*Agrobacterium fabrum* UDH  (SEQ ID NO:26)

```
  1 mkrllvtgaa gqlgrvmrer lapmaeiirl adispldpag pneecvqcdl adanavnamv
 61 agcdgivhlg gisvekpfeq ilqgniigly nlyeaarahg qpriviassn htigyypqte
121 rlgpdvparp dglygvskcf genlarmyfd kfggetalvr igsctpepnn yrmlstwfsh
181 ddfvslieav frapvlgcpv vwgasandag wwdnshlgfl gwkpkdnaea frrhitettp
241 ppdpndalvr fqggtfvdnp ifkqs
```

FIG. 49
*Pseudomonas putida* (KT2440) UDH  (SEQ ID NO:27)

```
  1 mtttpfnrll ltgaagglgk vlrerlkgya evlrlrisdisp mapaagphee vitcdladka
 61 avhtlvegvd aiihiggvst ehafeeilgp nicgvfhvye aarkhgvkri ifassnhtig
121 fyrqderida haprrpdsyy glskcygedv asfyfdrygi etvsirigss fpqpqnirml
181 ctwlsyddlv qlierglftp gvghtivyga sdnrtvwwdn rhaahlgyvp kdssetfraa
241 veaqpapaaad dpsmvyqgga favagpfin
```

FIG. 50
*Ralstonia solanacearum* UDH (SEQ ID NO:28)

```
  1 mttihtqala dplagiatrc hrllltgagg nlgkvlrerl tryaevlrvs ditdlgaara
 61 geevvpcdla daqavdalvk gvdaivhlgg isverpfdei lpaniqgtyh lyeaarrhgv
121 kriafassnh aigfyrqgev idarvptrpd gyyglskvfg eqlgsfyfdr ygietvairi
181 gssfpeakdr rmlvtwlgyd dleqlirral fvpnvgftiv ygmsgnreaw wnnrhaahlg
241 yvpaqsseaf raqveaqppl aaddpaarfq ggafvkagpf gd
```

FIG. 51

*Burkholderia* (RPE64) UDH (SEQ ID NO:29)

```
  1 mkrvlitgaa gvigrvlrag fagqyalrla diapqapage heeivtadit rperlreime
 61 gvdtvvhlag ipdedtwqki rdmnidgcyn vfeaarqagv krmvfassnh avgfhrrdrm
121 iddtvmvrpd srygvskafg ealgrlyadk ygmsvaclri gsfraddqpt aprhlyswis
181 hrdmvqltrr cidapdyhfv ivygvsdnar nrwsnanara lgyrpeddaq thapeilasa
241 eaedatealf hggfgclref dgdphrid
```

FIG. 52

*Bradyrhizobium sp. WSM471* UDH (SEQ ID NO:30)

```
  1 mprilmtgas ggigtrlrkl lppiypdlll sdirppadlg aneqfkaadl sdlaqceaic
 61 egvdgiihfg gysvegpwnd ilqaniiggy nlfeaayrkg vkrvvfassn havgfyprhh
121 kigtdvtprp dgrygvskvf geavgalyad khglkvtclr ignfgdvpld hrrisiwlkp
181 edlvqlcqig lehpdihfei fygvslnera wwdnhrayef gyrptgrsed hvahamaeqa
241 klkpdpigdh yqggafcsne fdgdtsriid wnkr
```

FIG. 53

1,2 propanediol pathways

FIG. 55

MYRISNIYVLAGFGTIGGALFGFDVSSMSAWIGTDQYLEYFNHPDSDLQGGITAS
MSAGSFAGALAAGFISDRIGRRYSLMLACCIWVIGAAIQCSAQNVAHLVAGRVIS
GLSVGITSSQVCVYLAELAPARIRGRIVGIQQWAIEWGMLIMYLISYGCGQGLAG
AASFRVSWGVQGIPALILLAALPFFPESPRWLASKERWEEALDTLALLHAKGDR
NDPVVQVEYEEVQEAARIAQEAKDISFFSLFGPKIWKRTLCGVSAQVWQQLLGG
NVAMYYVVYIFNMAGMSGNTTLYSSAIQYVIFLVTTGTILPFVDRIGRRLLLLTG
SVLCMACHFAIAGLMASRGHHVDSVDGNANLKWSITGPPGKGVIACSYIFVAVY
GFTWAPVAWIYASEVFPLKYRAKGVGLSAAGNWIFNFALAYFVAPAFTNIQWK
TYIIFGVFCTVMTFHVFFFYPETARRSLEDIDLMFETDMKPWKTHQIHDRFGEEV
ERHKHKDMADQEKGVVSTHDEMAGSVSKGEELIKENMRMKVVMEGSVNGHQ
FKCTGEGEGNPYMGTQTMRIKVIEGGPLPFAFDILATSFMYGSRTFIKYPKGIPDF
FKQSFPEGFTWERVTRYEDGGVVTVMQDTSLEDGCLVYHVQVRGVNFPSNGPV
MQKKTKGWEPNTEMMYPADGGLRGYTHMALKVDGGGHLSCSFVTTYRSKKT
VGNIKMPGIHAVDHRLERLEESDNEMFVVQREHAVAKFAGLGGGMDELYK
(SEQ ID NO:38)

FIG. 57

*Rhodotorula toruloides NP11*
Sugar transporter

MAPPPKRSLVTRFTNNYVAGMLPTLAGFMFGCDLISMSGQVSNPAYLEQFNHPNSNLQGAITAAMPAGSFGGALINSYLSD
KIGRKWCIIISGWVWVLGCIIQAASFNVRTLVAGRVVAGLAVGLGSAIVTIYQAEITRPAIRGRIVATQQLAITFSELLQYFVSF
GCSYIANDASFRMPWALQAIPGLILGILMFAFPESPRWLMDHGREEQALQILADVHAEGETENELVQLEYLEIKRQVEFDRTL
AARSYLDLLKPEYFRRTFLACITQMWSQLSGNNVMMYVVVYFQSAGIVGRRGGLIASGVQYALHFVATIPAVIWVDKWG
RRPTMMIGMFAMGCCLFAVGAIQATLGQPLHSGSSATTWTIVGHTSARNAVIVLSYIFVMLFSMTYGPCSWIFPSEIHHMR
VRGKAVSAATATNWMFNFALAWSTPPAFRNIQYKTYFVYGTFCICAAINVFFMFPEIKGRTLEEMDDLFAAGHAFSAWRLS
SVPKKTLAEVEAEVADSDMRSEGDNKHTMNHIEKSSSDHLEQAGRHV (SEQ ID NO:39)

SEQUENCE LISTING

```
<160> NUMBER OF SEQ ID NOS: 39

<210> SEQ ID NO 1
<211> LENGTH: 512
<212> TYPE: PRT
<213> ORGANISM: Aspergillus nidulans

<400> SEQUENCE: 1

Met Ser Phe Phe Lys Asn Ser Arg Val Tyr Met Leu Ser Ala Val Ala
1               5                   10                  15

Tyr Met Gly Ser Phe Leu Phe Gly Tyr Asp Thr Gly Val Met Gly Ser
            20                  25                  30

Val Leu Ala Leu Asp Ser Phe Lys His Asp Phe His Met Ala Thr Gly
        35                  40                  45

Ser Thr Gly Phe Ala Ser Ser Lys Glu Ala Glu Ile Ser Ser Asn Val
    50                  55                  60

Val Ala Leu Leu Thr Ala Gly Cys Phe Phe Gly Ala Ile Ala Gly Ala
65                  70                  75                  80

Ile Ala Asn Asp Arg Tyr Gly Arg Lys Asn Ser Leu Leu Val Leu Ser
                85                  90                  95

Val Ile Phe Met Ile Gly Ala Ala Val Gln Thr Gly Gly Arg Gly Thr
            100                 105                 110

Ile Ala Tyr Ile Tyr Gly Gly Arg Val Ile Ala Gly Phe Gly Ile Gly
        115                 120                 125

Gly Met Ser Ala Ile Thr Pro Ile Tyr Val Ser Glu Asn Cys Pro Pro
    130                 135                 140

Asn Val Arg Gly Arg Ile Ala Gly Leu Phe Gln Glu Phe Leu Val Ile
145                 150                 155                 160

Gly Val Thr Val Ser Tyr Trp Leu Cys Tyr Gly Val Glu Lys Asn Ile
                165                 170                 175

Ala Pro Ser Thr Lys Gln Trp Arg Ile Pro Ile Gly Phe Gln Leu Val
            180                 185                 190

Pro Ser Gly Leu Met Phe Ile Gly Leu Trp Phe Leu Lys Glu Ser Pro
        195                 200                 205

Arg Trp Leu Met Lys Gln Gly Arg Arg Glu Glu Ala Thr Ala Ser Leu
```

```
            210                 215                 220
Ala Phe Thr Arg Arg Ala Asp Pro Asn Ser Asp Glu Val Gln Gln Glu
225                 230                 235                 240

Leu Ala Glu Ile Arg Ala Ser Ile Glu Glu Leu Arg Ser Thr Glu
                245                 250                 255

Gly Val Thr Trp Arg Glu Val Leu Leu Pro Gly Asn Arg Leu Arg Phe
                260                 265                 270

Leu Asn Ala Phe Leu Ile Met Phe Trp Gln Gln Phe Ser Gly Thr Asn
                275                 280                 285

Ser Ile Gly Tyr Tyr Ala Pro Gln Leu Phe Gln Thr Ile Gly Val Ala
                290                 295                 300

Ser Thr Asp Thr Ser Leu Phe Thr Thr Gly Ile Tyr Gly Val Val Lys
305                 310                 315                 320

Val Val Ser Thr Gly Leu Phe Leu Leu Ile Gly Ile Asp Arg Phe Gly
                325                 330                 335

Arg Lys Trp Ser Leu Val Gly Gly Trp Ala Met Ala Val Phe Met
                340                 345                 350

Phe Ile Leu Gly Ala Val Leu Val Ser Tyr Pro Pro Val Asn Thr Asp
                355                 360                 365

Thr Ile Ser Asn Ala Ser Ile Ala Met Ile Val Met Ile Tyr Leu Tyr
                370                 375                 380

Val Ile Ser Tyr Ser Ala Ser Trp Gly Pro Ile Pro Trp Val Tyr Ile
385                 390                 395                 400

Ser Glu Ile Phe Pro Thr Arg Leu Arg Ala Tyr Gly Val Gly Met Gly
                405                 410                 415

Ser Ala Thr Gln Trp Leu Phe Asn Phe Val Val Thr Lys Phe Thr Pro
                420                 425                 430

Ser Ala Ile Ser Asn Ile Gly Trp Arg Thr Phe Ile Met Phe Gly Val
                435                 440                 445

Phe Cys Phe Ala Met Gly Leu Trp Val Cys Ile Phe Ile Lys Glu Thr
                450                 455                 460

Lys Gly Lys Arg Leu Glu Asp Met Asp Asp Ile Phe Gly Gly Lys Thr
465                 470                 475                 480

Val Glu Gln Met Gln Lys Asp Ile Glu Gln Ala Asp Val Glu Glu Gln
                485                 490                 495

Thr Glu Val Glu Lys Thr Gln Thr Arg His Glu Glu Gln Val Val Arg
                500                 505                 510

<210> SEQ ID NO 2
<211> LENGTH: 518
<212> TYPE: PRT
<213> ORGANISM: Aspergillus niger

<400> SEQUENCE: 2

Met Ser Leu Leu Lys Asn Tyr Arg Val Tyr Leu Leu Thr Ala Val Ala
1               5                   10                  15

Tyr Ser Gly Ser Leu Leu Phe Gly Tyr Asp Thr Gly Val Met Gly Ser
                20                  25                  30

Val Leu Ser Leu Thr Ser Phe Lys Glu Asp Phe Gly Ile Pro Thr Gly
                35                  40                  45

Ser Ser Gly Phe Ala Ser Ser Lys Ser Ser Glu Ile Ser Ser Asn Val
                50                  55                  60

Val Ser Leu Leu Thr Ala Gly Cys Phe Phe Gly Ala Ile Phe Ala Ala
65                  70                  75                  80
```

```
Pro Leu Asn Glu Arg Ile Gly Arg Arg Tyr Ala Leu Met Ile Phe Thr
            85                  90                  95
Val Ile Phe Leu Ile Gly Ala Ala Val Gln Val Ala Ser Lys His His
        100                 105                 110
Ile Gly Gln Ile Tyr Gly Gly Arg Val Ile Ala Gly Leu Gly Ile Gly
        115                 120                 125
Gly Met Ser Ser Ile Thr Pro Val Phe Val Ser Glu Asn Cys Pro Pro
130                 135                 140
Ser Ile Arg Gly Arg Val Ala Gly Met Phe Gln Glu Phe Leu Val Ile
145                 150                 155                 160
Gly Ser Thr Phe Ala Tyr Trp Leu Asp Tyr Gly Val Ser Leu His Ile
                165                 170                 175
Pro Ser Ser Thr Lys Gln Trp Arg Val Pro Val Ala Val Gln Leu Ile
            180                 185                 190
Pro Gly Gly Leu Met Leu Leu Gly Leu Phe Phe Leu Lys Glu Ser Pro
        195                 200                 205
Arg Trp Leu Ala Gly Lys Gly Arg His Glu Glu Ala Leu Gln Ser Leu
    210                 215                 220
Ala Tyr Ile Arg Asn Glu Ser Pro Asp Ser Glu Glu Ile Gln Lys Glu
225                 230                 235                 240
Phe Ala Glu Ile Arg Ala Ala Ile Asp Glu Glu Val Ala Ala Thr Glu
                245                 250                 255
Gly Leu Thr Tyr Lys Glu Phe Ile Gln Pro Ser Asn Leu Lys Arg Phe
            260                 265                 270
Gly Phe Ala Phe Thr Leu Met Leu Ser Gln Gln Phe Thr Gly Thr Asn
        275                 280                 285
Ser Ile Gly Tyr Tyr Ala Pro Glu Ile Phe Gln Thr Ile Gly Leu Ser
290                 295                 300
Ala Thr Asn Ser Ser Leu Phe Ala Thr Gly Val Tyr Gly Thr Val Lys
305                 310                 315                 320
Val Val Ala Thr Ala Ile Phe Leu Phe Val Gly Ile Asp Arg Trp Gly
                325                 330                 335
Arg Lys Leu Ser Leu Val Gly Gly Ser Ile Trp Met Ala Ser Met Met
            340                 345                 350
Phe Ile Ile Gly Ala Val Leu Ala Thr His Pro Pro Asp Thr Ser Ala
        355                 360                 365
Ser Gly Val Ser Gln Ala Ser Ile Ala Met Val Val Met Ile Tyr Leu
    370                 375                 380
Tyr Val Ile Gly Tyr Ser Ala Ser Trp Gly Pro Thr Pro Trp Val Tyr
385                 390                 395                 400
Val Ser Glu Ile Phe Pro Thr Arg Leu Arg Ser Tyr Gly Val Gly Leu
                405                 410                 415
Ala Ala Thr Ser Gln Trp Leu Trp Ser Phe Val Val Thr Glu Ile Thr
            420                 425                 430
Pro Lys Ala Val His Asn Ile Gly Trp Arg Thr Phe Leu Met Phe Gly
        435                 440                 445
Ile Phe Cys Val Ala Met Cys Val Phe Val Ile Val Phe Ala Lys Glu
    450                 455                 460
Thr Lys Gly Arg Ser Leu Glu Asp Met Asp Ile Leu Phe Gly Ala Val
465                 470                 475                 480
Asn Glu Ala Asp Arg Arg Ala Ala Val Glu His Thr Met His Lys Arg
                485                 490                 495
Gly Ser Ser His Ile Glu Asp Val Asp Glu Glu Thr Glu Arg Val Arg
```

```
                  500                 505                 510
His Glu Gln Asp Lys Val
            515

<210> SEQ ID NO 3
<211> LENGTH: 537
<212> TYPE: PRT
<213> ORGANISM: Neurospora crassa

<400> SEQUENCE: 3

Met Gly Leu Ser Ile Gly Asn Arg Ile Leu Arg Lys Ile Val Lys Asn
1               5                   10                  15

Glu Ala Met Ala Glu Asp Pro Pro Glu Ile Tyr Gly Trp Arg Val Tyr
            20                  25                  30

Leu Leu Ala Cys Ser Ala Cys Phe Gly Ala Met Ser Phe Gly Trp Asp
        35                  40                  45

Ser Ser Val Ile Gly Gly Val Ile Glu Leu Glu Pro Phe Lys His Asp
    50                  55                  60

Phe Gly Phe Ile Gly Asn Asp Lys Ala Lys Ala Asn Leu Gly Ala Asn
65                  70                  75                  80

Ile Val Ser Thr Leu Gln Ala Gly Cys Phe Leu Gly Ala Leu Ile Ala
                85                  90                  95

Ser Pro Ile Thr Asp Arg Phe Gly Arg Lys Trp Cys Leu Ile Ala Val
            100                 105                 110

Ser Leu Val Val Ile Ile Gly Ile Ile Met Gln Ala Ala Ser Gly
        115                 120                 125

Asn Leu Ala Pro Met Tyr Ile Gly Arg Phe Val Ala Gly Val Gly Val
    130                 135                 140

Gly Ala Ala Ser Cys Ile Asn Pro Val Phe Val Ser Glu Asn Ala Pro
145                 150                 155                 160

Arg Ser Ile Arg Gly Leu Leu Thr Gly Leu Tyr Gln Leu Phe Ile Val
                165                 170                 175

Thr Gly Gly Met Ile Ala Phe Trp Ile Asn Tyr Ser Val Ser Leu His
            180                 185                 190

Phe Lys Gly Lys Ser Met Tyr Ile Phe Pro Leu Ala Ile Gln Gly Leu
        195                 200                 205

Pro Ala Gly Leu Leu Cys Val Cys Met Leu Leu Cys His Glu Ser Pro
    210                 215                 220

Arg Trp Leu Ala Arg Arg Asp Arg Trp Glu Glu Cys Lys Ser Val Leu
225                 230                 235                 240

Ala Arg Ile Arg Asn Leu Pro Pro Asp His Pro Tyr Ile Val Asp Glu
                245                 250                 255

Phe Arg Glu Ile Gln Asp Gln Leu Glu Gln Glu Arg Arg Leu Gln Gly
            260                 265                 270

Asp Ala Thr Tyr Trp Asp Leu Thr Arg Asp Met Trp Thr Val Ala Gly
        275                 280                 285

Asn Arg Lys Arg Ala Leu Ile Ser Ile Phe Leu Met Ile Cys Gln Gln
    290                 295                 300

Met Thr Gly Thr Asn Ala Ile Asn Thr Tyr Ala Pro Thr Ile Phe Lys
305                 310                 315                 320

Asn Leu Gly Ile Thr Gly Thr Ser Thr Ser Leu Phe Ser Thr Gly Ile
                325                 330                 335

Tyr Gly Ile Val Lys Val Val Ser Cys Val Ile Phe Leu Leu Phe Leu
            340                 345                 350
```

```
Ala Asp Ser Leu Gly Arg Arg Arg Ser Leu Leu Trp Thr Ser Ile Ala
        355                 360                 365

Gln Gly Leu Ala Met Phe Tyr Ile Gly Leu Tyr Val Arg Ile Ser Pro
    370                 375                 380

Pro Ile Asp Gly Gln Pro Val Pro Pro Ala Gly Tyr Val Ala Leu Val
385                 390                 395                 400

Cys Ile Phe Leu Phe Ala Ala Phe Phe Gln Phe Gly Trp Gly Pro Ala
                405                 410                 415

Cys Trp Ile Tyr Ala Ser Glu Ile Pro Ala Ala Arg Leu Arg Ser Leu
                420                 425                 430

Asn Val Ser Tyr Ala Ala Ala Thr Gln Trp Leu Phe Asn Phe Val Val
            435                 440                 445

Ala Arg Ala Val Pro Thr Met Leu Val Thr Val Gly Pro His Gly Tyr
    450                 455                 460

Gly Thr Tyr Leu Ile Phe Gly Ser Phe Cys Leu Ser Met Phe Val Phe
465                 470                 475                 480

Val Trp Phe Phe Val Pro Glu Thr Lys Gly Ile Ser Leu Glu His Met
                485                 490                 495

Asp Glu Leu Phe Gly Val Thr Asp Gly Pro Ala Ala Glu Lys Ser Ser
                500                 505                 510

Val His Gly Gly Asp Asp Val Gly Ser Glu Met Gly Lys Gly Asp Gln
            515                 520                 525

Lys Ser Lys His Val Glu Val Tyr Val
        530                 535

<210> SEQ ID NO 4
<211> LENGTH: 531
<212> TYPE: PRT
<213> ORGANISM: Trichoderma reesei

<400> SEQUENCE: 4

Met Gly Val Thr Ser Lys Phe Leu Arg Ala Ile Val Arg Asn Glu Ala
1               5                   10                  15

Met Arg Thr Asp Pro Asp Glu Ile Tyr Gly Trp Arg Val Phe Thr Leu
            20                  25                  30

Val Phe Ser Ala Cys Phe Gly Met Leu Phe Gly Trp Asp Thr Gly
        35                  40                  45

Ser Ile Gly Gly Ile Leu Thr Met Pro Ala Phe Gln Glu Lys Phe His
    50                  55                  60

Tyr Ala His Ser Ser Pro Lys Ala Lys Ser Asn Met Asn Gln Asn Ile
65                  70                  75                  80

Val Ser Thr Leu Gln Ala Gly Cys Phe Ala Ala Cys Phe Phe Thr Ser
                85                  90                  95

Trp Val Thr Asp Arg Tyr Gly Arg Arg Phe Ala Leu Ile Ala Ala Gly
            100                 105                 110

Leu Leu Thr Ile Val Gly Ile Ile Phe Gln Ala Ala Ser Ala Ala Asp
        115                 120                 125

Gly Thr Leu Ala Val Met Tyr Val Gly Arg Phe Ile Ala Gly Leu Gly
    130                 135                 140

Ile Gly Ala Ala Ser Ala Leu Thr Pro Leu Tyr Val Ser Glu Cys Ala
145                 150                 155                 160

Pro Arg Ala Ile Arg Gly Gly Leu Thr Ala Phe Tyr Gln Leu Phe Asn
                165                 170                 175

Val Phe Gly Ile Met Leu Ala Phe Trp Val Asn Tyr Gly Cys Leu Leu
            180                 185                 190
```

His Val Ser Ala Pro Ala Ile Tyr Ile Ile Pro Leu Thr Leu Gln Ala
            195                 200                 205

Leu Pro Ala Val Phe Leu Met Val Gly Met Phe Ile Ser Pro Glu Ser
        210                 215                 220

Pro Arg Trp Cys Ala Arg Arg Asp Asp Trp Asp Arg Ala Thr Lys Val
225                 230                 235                 240

Leu Val Lys Leu Arg Gly Leu Pro Ala Asp Ser Glu Tyr Val Gln Asn
            245                 250                 255

Glu Ile Gln Glu Met Ala Asp Gln Leu Glu His Glu Arg Arg Leu Thr
        260                 265                 270

Gly Asp Ala Thr Phe Lys Thr Leu Leu Arg Glu Met Trp Thr Ile Pro
            275                 280                 285

Gly Asn Arg Asn Arg Ala Val Ile Ser Ile Leu Leu Met Ile Phe Gln
        290                 295                 300

Gln Met Thr Gly Val Asn Ala Ile Asn Tyr Tyr Ala Pro Gln Ile Phe
305                 310                 315                 320

Thr Asn Leu Gly Met Thr Gly Asn Asp Ser Ser Leu Phe Ala Thr Gly
            325                 330                 335

Val Tyr Gly Val Val Lys Thr Ala Ala Cys Ala Val Phe Leu Val Phe
        340                 345                 350

Val Ala Asp Ser Leu Gly Arg Arg Trp Ser Leu Leu Trp Thr Ala Ala
            355                 360                 365

Ala Gln Gly Ile Phe Leu Tyr Ile Val Gly Ile Tyr Gly Arg Val Gln
        370                 375                 380

Pro Pro Ile Ala Gly Gln Pro Val Thr Ala Phe Gly Tyr Val Ala Ile
385                 390                 395                 400

Thr Cys Ile Tyr Leu Trp Ala Ala Ser Phe Gln Phe Gly Trp Gly Pro
            405                 410                 415

Val Cys Trp Ile Leu Val Ser Glu Ile Pro Thr Ala Arg Leu Arg Ala
        420                 425                 430

Met Asn Val Ala Ile Gly Ala Ala Thr Gln Trp Leu Phe Asn Phe Val
            435                 440                 445

Cys Ala Arg Ser Val Leu Thr Met Gln Thr Thr Met Gly Lys Ala Gly
        450                 455                 460

Tyr Gly Met Phe Phe Met Phe Gly Thr Phe Cys Phe Ile Met Gly Ile
465                 470                 475                 480

Phe Val Trp Phe Phe Val Pro Glu Thr Lys Gly Leu Ser Leu Glu His
            485                 490                 495

Met Asp Asp Leu Phe Gly Val Thr Glu Leu Val Lys Lys Val Glu Ala
        500                 505                 510

Glu Pro Glu Leu Gly His Pro Asp Ser Ile Arg Glu Glu Arg Ala Asp
            515                 520                 525

Ile Lys Ser
        530

<210> SEQ ID NO 5
<211> LENGTH: 309
<212> TYPE: PRT
<213> ORGANISM: Trichoderma reesei

<400> SEQUENCE: 5

Met Val Ala Thr Ser Phe Lys Leu Asn Asn Gly Leu Glu Ile Pro Ala
1               5                   10                  15

Val Gly Leu Gly Thr Trp Gln Ser Lys Ala Gly Glu Val Lys Ala Ala

```
                 20                  25                  30
Val Ser Tyr Ala Leu Gln Ile Gly Tyr Lys Leu Ile Asp Gly Ala Tyr
             35                  40                  45
Cys Tyr Gly Asn Glu Asp Glu Val Gly Glu Gly Leu Lys Glu Ala Phe
         50                  55                  60
Ala Ala Gly Val Lys Arg Glu Asp Ile Phe Val Thr Lys Ile Trp
 65                  70                  75                  80
Ala Thr Tyr Asn Thr Arg Val Val Leu Gly Leu Asp Lys Ser Leu Arg
                 85                  90                  95
Ser Leu Gly Leu Asp Tyr Val Asp Leu Leu Val His Trp Pro Val
             100                 105                 110
Leu Leu Asn Pro Glu Gly Asn His Asp Lys Phe Pro Thr Leu Pro Asp
             115                 120                 125
Gly Lys Arg Asp Val Ile Trp Asp Tyr Asn His Val Asp Gly Trp Lys
             130                 135                 140
Gln Met Glu Ala Val Leu Ala Thr Gly Lys Thr Lys Ser Ile Gly Val
145                 150                 155                 160
Ser Asn Tyr Ser Lys Lys Tyr Leu Glu Gln Leu Leu Pro His Ala Thr
                 165                 170                 175
Val Ile Pro Ala Val Asn Gln Ile Glu Asn His Pro Ser Leu Pro Gln
             180                 185                 190
Gln Glu Ile Val Asp Phe Cys Lys Glu Lys Gly Ile His Ile Met Ala
             195                 200                 205
Tyr Ser Pro Leu Gly Ser Thr Gly Ser Pro Leu Met Ser Ala Asp Pro
     210                 215                 220
Val Val Lys Ile Ala Glu Lys Lys Gly Ile Ser Pro Thr Thr Val Leu
225                 230                 235                 240
Leu Ser Tyr His Val Asn Arg Gly Ser Thr Val Leu Ala Lys Ser Val
                 245                 250                 255
Thr Pro Ala Arg Ile Lys Ala Asn Leu Glu Ile Val Asp Leu Asp Asp
             260                 265                 270
Glu Asp Met Lys Leu Leu Asn Asp Tyr Ser Asn Asp Leu Ala Ser Lys
             275                 280                 285
Gly Glu Leu Lys Arg Tyr Val Tyr Pro Pro Phe Gly Ile Asp Phe Gly
             290                 295                 300
Phe Pro Asp Lys Ser
305

<210> SEQ ID NO 6
<211> LENGTH: 412
<212> TYPE: PRT
<213> ORGANISM: Aspergillus niger

<400> SEQUENCE: 6

Met Ala Pro Pro Ala Val Leu Met Val Gly Thr Gly Glu Tyr Thr Thr
 1               5                  10                  15
Gly Tyr Val Gly Gly Thr Ala Ser Thr Ser Asp Lys Lys Val Gly Val
             20                  25                  30
Val Gly Leu Thr Leu Phe Asp Leu Arg Arg Arg Gly Lys Val Gly Asp
             35                  40                  45
Leu Ser Met Val Gly Val Ser Gly Ser Lys Phe Pro Gly Ile Arg Ala
         50                  55                  60
His Leu Gln Lys Asn Ile Ser Glu Val Tyr Asn Gly Leu Asp Val Ser
 65                  70                  75                  80
```

-continued

Phe Thr Ser Phe Pro Ala Asp Asn Thr Ser Asp Pro Glu Ala Tyr Lys
                85                  90                  95

Ala Ala Ile Asp Ala Leu Pro Ala Gly Ser Ala Ile Thr Ile Phe Thr
            100                 105                 110

Pro Asp Pro Thr His Tyr Pro Ile Ala Leu Tyr Ala Ile Gln Arg Lys
        115                 120                 125

Ile His Val Leu Ile Thr Lys Pro Ala Thr Lys Leu Leu Ser Asp His
    130                 135                 140

Leu Asp Leu Leu Ala Glu Ser Arg Lys His Asn Val Val Tyr Ile
145                 150                 155                 160

Glu His His Lys Arg Phe Asp Pro Ala Tyr Ser Asp Ala Arg Ala Lys
                165                 170                 175

Ala Ala Lys Leu Gly Asp Phe Asn Tyr Phe Ser Tyr Met Ser Gln
            180                 185                 190

Pro Lys Ser Gln Leu Glu Thr Phe Lys Ala Trp Ala Gly Lys Asp Ser
        195                 200                 205

Asp Ile Ser Tyr Tyr Leu Asn Ser His His Val Asp Val Asn Glu Ser
    210                 215                 220

Met Val Pro Asp Tyr Val Pro Val Lys Val Thr Ala Ser Ala Ala Thr
225                 230                 235                 240

Gly Thr Ala Val Glu Leu Gly Cys Ala His Glu Thr Glu Asp Thr Ile
                245                 250                 255

Thr Leu Leu Val Glu Trp Lys Lys Lys Asp Gly Ser Arg Met Ala Thr
            260                 265                 270

Gly Val Tyr Thr Ser Ser Trp Thr Ala Pro Gln Arg Ala Gly Val His
        275                 280                 285

Ser Asn Gln Tyr Phe His Tyr Met Gly Ser Lys Gly Glu Ile Arg Val
    290                 295                 300

Asn Gln Ala Lys Arg Gly Tyr Asp Val Ala Glu Asp Glu Ala Gly Leu
305                 310                 315                 320

Ser Trp Ile Asn Pro Phe Tyr Met Lys Tyr Ala Pro Asp Glu Glu Gly
                325                 330                 335

Asn Phe Gly Gly Gln Thr Gly Tyr Gly Tyr Ile Ser Phe Glu Lys Phe
            340                 345                 350

Ile Asp Ala Val Thr Ala Val Asn Glu Gly Arg Leu Thr Leu Asp Gln
        355                 360                 365

Leu Asp Ala Arg Pro Ile Pro Thr Leu Lys Asn Thr Ile Ala Thr Thr
    370                 375                 380

Ala Ile Leu His Ala Gly Arg Ile Ser Leu Asp Glu Lys Arg Ser Val
385                 390                 395                 400

Glu Ile Val Thr Glu Asp Gly Lys Trp Glu Leu Lys
                405                 410

<210> SEQ ID NO 7
<211> LENGTH: 328
<212> TYPE: PRT
<213> ORGANISM: Rhodosporidium toruloides

<400> SEQUENCE: 7

Met Ser Ser Lys Ser Val Pro Thr Val Gln Leu His Asn Gly Lys Ser
1               5                   10                  15

Phe Pro Leu Ile Gly Phe Gly Thr Trp Gln Ser Ala Pro Gly Glu Val
            20                  25                  30

Gly Asn Ala Val Ser Val Ala Leu Lys Ala Gly Tyr Arg His Leu Asp
        35                  40                  45

```
Leu Ala Lys Val Tyr Gln Asn Gln Lys Glu Ile Ala Pro Ala Ile Ala
        50                  55                  60

Asn Ser Gly Val Pro Arg Glu Glu Met Phe Ile Thr Ser Lys Leu Trp
 65                  70                  75                  80

Asn Ser Gln His Arg Pro Asp Leu Val Glu Pro Ala Leu Asp Asp Thr
                    85                  90                  95

Leu Lys Glu Leu Gly Leu Ser Tyr Leu Asp Leu Tyr Leu Ile His Trp
                100                 105                 110

Pro Val Ala Phe Pro Ala Glu Gly Asp Pro His Gln Asn Leu Phe Pro
                115                 120                 125

Lys Ala Asn Asp Asn Glu Val Lys Ile Asp Asp Ser Val Ser Leu Val
            130                 135                 140

Asp Thr Trp Lys Ala Met Ile Lys Leu Leu Asp Thr Gly Lys Val Lys
145                 150                 155                 160

Ser Ile Gly Val Ser Asn Phe Ser Pro Glu Met Val Asp Ala Ile Thr
                    165                 170                 175

Glu Ala Thr Gly Val Lys Pro Val Val Asn Gln Ile Glu Arg His Pro
                180                 185                 190

His Leu Leu Gln Arg Glu Leu Ile Glu His His Lys Lys Ala Asn Ile
            195                 200                 205

Val Ile Thr Ala Tyr Ser Gly Phe Gly Asn Asn Ser Glu Gly Val Pro
210                 215                 220

Leu Leu Val Gln His Pro Ile Val Lys Lys Ile Ala Glu Lys His Gly
225                 230                 235                 240

Ala Asp Gly Gly Gln Val Leu Ile Ala Trp Gly Met His Gly His His
                    245                 250                 255

Ala Ile Ile Pro Lys Ser Val Thr Asp Ser Arg Ile Gln Ser Asn Phe
                260                 265                 270

Lys Ile Ile Gln Ile Ser Asp Glu Asp Val Lys Glu Ile Asp Ser Ile
            275                 280                 285

Gly Glu Lys Glu Pro Arg Arg Phe Asn Thr Pro Ile Arg Tyr Thr Pro
290                 295                 300

Leu Trp Pro Val Asn Cys Phe Asn Glu Glu Ser Glu Arg Ser Ala Lys
305                 310                 315                 320

Tyr Gln Val Lys Ile Lys Gly Ser
                325

<210> SEQ ID NO 8
<211> LENGTH: 691
<212> TYPE: PRT
<213> ORGANISM: Trichoderma reesei

<400> SEQUENCE: 8

Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Leu Ile Cys
            35                  40                  45

Thr Thr Gly Lys Leu Pro Val Pro Trp Pro Thr Leu Val Thr Thr Leu
        50                  55                  60

Gly Tyr Gly Leu Gln Cys Phe Ala Arg Tyr Pro Asp His Met Lys Gln
 65                  70                  75                  80

His Asp Phe Phe Lys Ser Ala Met Pro Glu Gly Tyr Val Gln Glu Arg
```

```
                        85                  90                  95
Thr Ile Phe Phe Lys Asp Asp Gly Asn Tyr Lys Thr Arg Ala Glu Val
                100                 105                 110
Lys Phe Glu Gly Asp Thr Leu Val Asn Arg Ile Glu Leu Lys Gly Ile
                115                 120                 125
Asp Phe Lys Glu Gly Gly Asn Ile Leu Gly His Lys Leu Glu Tyr Asn
            130                 135                 140
Tyr Asn Ser His Asn Val Tyr Ile Thr Ala Asp Lys Gln Lys Asn Gly
145                 150                 155                 160
Ile Lys Ala Asn Phe Lys Ile Arg His Asn Ile Glu Asp Gly Gly Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Tyr Gln Ser Ala Leu Ser
                195                 200                 205
Lys Asp Pro Asn Glu Lys Arg Asp His Met Val Leu Leu Glu Phe Val
            210                 215                 220
Thr Ala Ala Gly Ile Thr His Gly Met Asp Glu Leu Tyr Lys Gly Ser
225                 230                 235                 240
Ser Glu Val Thr Ile Thr Gly Phe Arg Ser Arg Asp Val Arg Phe Pro
                245                 250                 255
Thr Ser Leu Asp Lys Thr Gly Ser Asp Ala Met Asn Ala Ala Gly Asp
            260                 265                 270
Tyr Ser Ala Ala Tyr Cys Ile Leu Glu Thr Asp Ser Ala His Ser Gly
            275                 280                 285
His Gly Met Thr Phe Thr Ile Gly Arg Gly Asn Asp Ile Val Cys Ala
            290                 295                 300
Ala Ile Asn His Val Ala Asp Arg Leu Lys Gly Lys Lys Leu Ser Ser
305                 310                 315                 320
Leu Val Ala Asp Trp Gly Lys Thr Trp Arg Tyr Leu Val Asn Asp Ser
                325                 330                 335
Gln Leu Arg Trp Ile Gly Pro Glu Lys Gly Val Ile His Leu Ala Leu
            340                 345                 350
Gly Ala Val Val Asn Ala Val Trp Asp Leu Trp Ala Lys Thr Leu Asn
            355                 360                 365
Lys Pro Val Trp Arg Ile Val Ala Asp Met Thr Pro Glu Glu Tyr Val
            370                 375                 380
Arg Cys Ile Asp Phe Arg Tyr Ile Thr Asp Ala Ile Thr Pro Glu Glu
385                 390                 395                 400
Ala Val Ala Met Leu Arg Glu Gln Glu Ala Gly Lys Ala Lys Arg Ile
                405                 410                 415
Glu Glu Ala Leu Gln Asn Arg Ala Val Pro Ala Tyr Thr Thr Ser Ala
            420                 425                 430
Gly Trp Leu Gly Tyr Gly Glu Asp Lys Met Lys Gln Leu Leu Arg Glu
            435                 440                 445
Thr Leu Ala Ala Gly Tyr Arg His Phe Lys Val Lys Val Gly Gly Ser
            450                 455                 460
Val Glu Glu Asp Arg Arg Arg Leu Gly Ile Ala Arg Glu Ile Leu Gly
465                 470                 475                 480
Phe Asp Lys Gly Asn Val Leu Met Val Asp Ala Asn Gln Val Trp Ser
                485                 490                 495
Val Pro Glu Ala Ile Asp Tyr Met Lys Gln Leu Ser Glu Tyr Lys Pro
            500                 505                 510
```

```
Trp Phe Ile Glu Glu Pro Thr Ser Pro Asp Ile Met Gly His Lys
            515                 520                 525
Ala Ile Arg Asp Ala Leu Lys Pro Tyr Gly Ile Gly Val Ala Thr Gly
        530                 535                 540
Glu Met Cys Gln Asn Arg Val Met Phe Lys Gln Leu Ile Met Thr Gly
545                 550                 555                 560
Ala Ile Asp Ile Cys Gln Ile Asp Ala Cys Arg Leu Gly Gly Val Asn
            565                 570                 575
Glu Val Leu Ala Val Leu Leu Met Ala Lys Lys Tyr Gly Val Pro Ile
        580                 585                 590
Val Pro His Ser Gly Gly Val Gly Leu Pro Glu Tyr Thr Gln His Leu
        595                 600                 605
Ser Thr Ile Asp Tyr Val Val Ser Gly Lys Leu Ser Val Leu Glu
        610                 615                 620
Phe Val Asp His Leu His Glu His Phe Leu His Pro Ser Val Ile Lys
625                 630                 635                 640
Asp Gly Tyr Tyr Gln Thr Pro Thr Glu Ala Gly Tyr Ser Val Glu Met
            645                 650                 655
Lys Pro Glu Ser Met Asp Lys Tyr Glu Tyr Pro Gly Lys Lys Gly Val
        660                 665                 670
Ser Trp Trp Thr Thr Asp Glu Ala Leu Pro Ile Leu Asn Gly Glu Lys
        675                 680                 685
Ile Gly Ser
        690

<210> SEQ ID NO 9
<211> LENGTH: 383
<212> TYPE: PRT
<213> ORGANISM: Aspergillus niger

<400> SEQUENCE: 9

Met Ala Pro Ile Lys Ser Ile Glu Tyr Phe Arg Val Lys Pro Arg Trp
1               5                   10                  15
Leu Phe Val Lys Val Thr Asp Ser Glu Asp Lys Phe Gly Trp Gly Glu
            20                  25                  30
Ala Thr Leu Glu Gly His Thr Gln Ala Val Glu Gly Ala Leu Asp Glu
        35                  40                  45
Ile Ile Gly Arg Ile Val Gly Tyr Glu Ala Asp Ile Glu His Val
    50                  55                  60
Trp Gln Thr Ile Trp Arg Leu Gly Phe Tyr Arg Gly Gly Pro Val Phe
65                  70                  75                  80
Met Ser Ala Leu Ser Gly Ile Asp Ile Ala Leu Trp Asp Leu Lys Gly
                85                  90                  95
Arg Arg Leu Asn Val Pro Val Tyr Gln Leu Leu Gly Gly Lys Val Arg
            100                 105                 110
Asn Lys Val Gln Val Tyr Ala Trp Ile Gly Gly Asp Arg Pro Ser Asp
        115                 120                 125
Val Glu Val Ala Ala Lys Ala Arg Ile Ala Gln Gly Leu Lys Cys Val
    130                 135                 140
Lys Met Asn Ala Thr Glu Asp Met Asn Trp Leu Asp Ser Pro Ser Val
145                 150                 155                 160
Leu Asp Ser Cys Ile Glu Arg Ile Lys Gln Val Lys Ala Leu Gly Leu
                165                 170                 175
Asp Ala Gly Leu Asp Phe His Gly Arg Leu His Arg Pro Met Ala Lys
```

```
                180                 185                 190
Gln Leu Ala Lys Ala Leu Glu Pro Tyr Arg Pro Leu Phe Ile Glu Glu
            195                 200                 205
Pro Leu Leu Val Glu His Pro Glu Ala Ile Lys Gln Leu Ser Gln His
        210                 215                 220
Thr Thr Ile Pro Ile Ala Phe Gly Glu Arg Leu Tyr Thr Arg Trp Asp
225                 230                 235                 240
Val Lys Arg Phe Leu Glu Asp Ala Ser Val Asp Val Leu Gln Pro Asp
                245                 250                 255
Ile Ala His Ala Gly Gly Ile Ser Glu Thr Lys Arg Ile Ala Thr Met
            260                 265                 270
Ala Glu Thr Tyr Asp Val Ala Ile Ala Pro His Cys Pro Leu Gly Pro
        275                 280                 285
Ile Ala Leu Ala Ala Ser Met Gln Val Ala Leu Ser Thr Pro Asn Phe
        290                 295                 300
Val Ile Gln Glu Met Ser Leu Gly Met His Tyr Asn Val Glu Ala Gly
305                 310                 315                 320
Asp Ile Asp Leu Thr Ser Tyr Leu Thr Asn Pro Thr Val Phe Asn Ile
                325                 330                 335
Glu Glu Gly Tyr Val Pro Ala Pro Thr Gly Ala Gly Leu Gly Val Glu
            340                 345                 350
Ile Asp Glu Glu Leu Val Arg Arg Ile Ser Arg Glu Thr Glu Pro Trp
        355                 360                 365
Leu Pro Lys Glu Phe Tyr Gly Val Asp Gly Gly Ile Arg Glu Trp
        370                 375                 380
```

<210> SEQ ID NO 10
<211> LENGTH: 450
<212> TYPE: PRT
<213> ORGANISM: Trichoderma reesei

<400> SEQUENCE: 10

```
Met Ser Glu Val Thr Ile Thr Gly Phe Arg Ser Arg Asp Val Arg Phe
1               5                   10                  15
Pro Thr Ser Leu Asp Lys Thr Gly Ser Asp Ala Met Asn Ala Ala Gly
            20                  25                  30
Asp Tyr Ser Ala Ala Tyr Cys Ile Leu Glu Thr Asp Ser Ala His Ser
        35                  40                  45
Gly His Gly Met Thr Phe Thr Ile Gly Arg Gly Asn Asp Ile Val Cys
    50                  55                  60
Ala Ala Ile Asn His Val Ala Asp Arg Leu Lys Gly Lys Lys Leu Ser
65                  70                  75                  80
Ser Leu Val Ala Asp Trp Gly Lys Thr Trp Arg Tyr Leu Val Asn Asp
                85                  90                  95
Ser Gln Leu Arg Trp Ile Gly Pro Glu Lys Gly Val Ile His Leu Ala
            100                 105                 110
Leu Gly Ala Val Val Asn Ala Val Trp Asp Leu Trp Ala Lys Thr Leu
        115                 120                 125
Asn Lys Pro Val Trp Arg Ile Val Ala Asp Met Thr Pro Glu Glu Tyr
    130                 135                 140
Val Arg Cys Ile Asp Phe Arg Tyr Ile Thr Asp Ala Ile Thr Pro Glu
145                 150                 155                 160
Glu Ala Val Ala Met Leu Arg Glu Gln Glu Ala Gly Lys Ala Lys Arg
                165                 170                 175
```

```
Ile Glu Glu Ala Leu Gln Asn Arg Ala Val Pro Ala Tyr Thr Thr Ser
            180                 185                 190

Ala Gly Trp Leu Gly Tyr Gly Asp Lys Met Lys Gln Leu Leu Arg
        195                 200                 205

Glu Thr Leu Ala Ala Gly Tyr Arg His Phe Lys Val Lys Val Gly Gly
210                 215                 220

Ser Val Glu Glu Asp Arg Arg Arg Leu Gly Ile Ala Arg Glu Ile Leu
225                 230                 235                 240

Gly Phe Asp Lys Gly Asn Val Leu Met Val Asp Ala Asn Gln Val Trp
                245                 250                 255

Ser Val Pro Glu Ala Ile Asp Tyr Met Lys Gln Leu Ser Glu Tyr Lys
            260                 265                 270

Pro Trp Phe Ile Glu Glu Pro Thr Ser Pro Asp Asp Ile Met Gly His
        275                 280                 285

Lys Ala Ile Arg Asp Ala Leu Lys Pro Tyr Gly Ile Gly Val Ala Thr
290                 295                 300

Gly Glu Met Cys Gln Asn Arg Val Met Phe Lys Gln Leu Ile Met Thr
305                 310                 315                 320

Gly Ala Ile Asp Ile Cys Gln Ile Asp Ala Cys Arg Leu Gly Gly Val
                325                 330                 335

Asn Glu Val Leu Ala Val Leu Leu Met Ala Lys Lys Tyr Gly Val Pro
            340                 345                 350

Ile Val Pro His Ser Gly Gly Val Gly Leu Pro Glu Tyr Thr Gln His
        355                 360                 365

Leu Ser Thr Ile Asp Tyr Val Val Val Ser Gly Lys Leu Ser Val Leu
370                 375                 380

Glu Phe Val Asp His Leu His Glu His Phe Leu His Pro Ser Val Ile
385                 390                 395                 400

Lys Asp Gly Tyr Tyr Gln Thr Pro Thr Glu Ala Gly Tyr Ser Val Glu
                405                 410                 415

Met Lys Pro Glu Ser Met Asp Lys Tyr Glu Tyr Pro Gly Lys Lys Gly
            420                 425                 430

Val Ser Trp Trp Thr Thr Asp Glu Ala Leu Pro Ile Leu Asn Gly Glu
        435                 440                 445

Lys Ile
    450

<210> SEQ ID NO 11
<211> LENGTH: 482
<212> TYPE: PRT
<213> ORGANISM: Rhodosporidium toruloides

<400> SEQUENCE: 11

Met Thr Gln Asp Ser Phe Ile Ala Ser Phe Thr Val Glu Asp Leu Arg
1               5                   10                  15

Phe Pro Thr Ser Leu Thr Gly Asp Gly Thr Asp Ala Asn Asn Arg Glu
            20                  25                  30

Cys Asp Tyr Ser Ala Ala Tyr Cys Thr Leu Arg Thr Asn Leu Gly Glu
        35                  40                  45

Val Gly Tyr Gly Leu Thr Phe Thr Ile Gly Arg Gly Asn Asp Ile Val
    50                  55                  60

Cys Ala Ala Val Glu Gln Val Ala Gly Lys Leu Met Asn Met Lys Thr
65                  70                  75                  80

Ala Glu Leu Phe Ser Ala Pro Gly Leu Gly Arg Met Trp Asn Tyr Leu
                85                  90                  95
```

Leu Ser Asp Pro Gln Leu Arg Trp Ile Gly Pro Glu Lys Gly Val Ile
            100                 105                 110

His Ile Ala Thr Ala Ala Val Val Asn Ala Val Trp Asp Met Tyr Ala
            115                 120                 125

Arg His Leu Lys Lys Pro Leu Trp Gln Val Val Ala Glu Phe Thr Pro
            130                 135                 140

Glu Glu Phe Val Ala Ala Thr Thr Phe Arg Tyr Ile Thr Asp Met Ile
145                 150                 155                 160

Thr Pro Glu Glu Ala Leu Ala Leu Leu Lys Glu Lys Glu Ala Gly Lys
                    165                 170                 175

Ala Glu Arg Leu Ala Lys Leu Lys Ala Glu Gly Tyr Pro Ala Tyr Thr
            180                 185                 190

Thr Ser Val Gly Trp Phe Gly Tyr Pro Asp Glu Lys Val Ala Arg Leu
            195                 200                 205

Thr Arg Glu Ala Ile Ala Gln Gly Phe Asn His Phe Lys Met Lys Val
            210                 215                 220

Gly Ala Asp Val Ala Met Asp Gln Arg Arg Leu Ala Leu Ile Arg Ser
225                 230                 235                 240

Ile Ile Asp Asp Pro Lys Glu Cys Glu Gly Arg Pro Val Pro Ser Ala
                    245                 250                 255

Glu Ser Leu Val Gly Lys Asn Ala Gly Pro Thr Gly Ser Val Leu Met
            260                 265                 270

Ile Asp Ser Asn Gln Val Trp Asp Val Arg Glu Ala Ile Asp Tyr Val
            275                 280                 285

Lys Ala Leu Lys Asp Ala Asn Pro Trp Phe Ile Glu Glu Pro Thr Ala
            290                 295                 300

Pro Asp Asp Ile Leu Gly His Ala Glu Ile Arg Lys Gln Leu Lys Pro
305                 310                 315                 320

Tyr Lys Ile Gly Val Ala Thr Gly Glu His Ala His Asn Arg Met Val
                    325                 330                 335

Phe Lys Gln Leu Leu Ala Ala Glu Ala Ile Asp Val Cys Gln Ile Asp
            340                 345                 350

Ser Cys Arg Leu Ala Gly Val Asn Glu Ile Leu Gly Val Leu Leu Met
            355                 360                 365

Ala Ala Lys Lys Gly Val Pro Val Cys Pro His Ala Gly Gly Val Gly
370                 375                 380

Leu Thr Asn Tyr Val Val His Leu Ser Ile Ile Asp Tyr Leu Cys Val
385                 390                 395                 400

Ser Gly Thr Lys Glu Arg Asn Val Leu Glu Tyr Val Asp His Leu His
                    405                 410                 415

Glu His Phe Thr Asn Pro Pro Thr Ile Asn Ser His Gly Tyr Tyr Asn
            420                 425                 430

Ile Pro Ser Asp Pro Thr Glu Gly Tyr Ser Ile Gly Met His Glu Ala
            435                 440                 445

Ser Lys Ala Ala Tyr Val Tyr Pro Asn Gly Ser Tyr Trp Thr Asn Asp
            450                 455                 460

His Ala Ala Ala Arg Leu Val Ala Ile Lys Asn Gly Tyr Ile Lys Ala
465                 470                 475                 480

Gly Ser

<210> SEQ ID NO 12
<211> LENGTH: 335
<212> TYPE: PRT

<213> ORGANISM: Aspergillus niger

<400> SEQUENCE: 12

Met Pro Phe Thr Pro Leu Arg Pro Gly Val Tyr Ala Pro Thr Met Thr
1               5                   10                  15

Phe Phe Asp Pro Ser Thr Glu Asp Leu Asp Val Pro Thr Ile Arg Lys
            20                  25                  30

His Ala Val Arg Leu Ala Lys Ala Gly Leu Val Gly Leu Val Cys Met
        35                  40                  45

Gly Ser Asn Gly Glu Ala Val His Leu Thr Arg Ala Glu Arg Lys Thr
50                  55                  60

Val Ile Asn Glu Thr Arg Ser Ala Leu Val Glu Ala Gly Phe Ser Asn
65                  70                  75                  80

Val Pro Val Ile Ala Gly Ala Ser Glu Gln Ser Ile Arg Gly Thr Ile
                85                  90                  95

Glu Leu Cys Lys Glu Ser Tyr Glu Ala Gly Ala Glu Tyr Ala Leu Ile
            100                 105                 110

Val Pro Pro Ser Tyr Tyr Arg Tyr Ala Thr Gly Asn Asp Gln Thr Leu
        115                 120                 125

Tyr Glu Phe Phe Thr Ser Val Ala Asp Gly Ser Pro Ile Pro Leu Ile
130                 135                 140

Leu Tyr Asn Tyr Pro Gly Ala Val Ala Gly Ile Asp Met Asp Ser Asp
145                 150                 155                 160

Leu Ile Ile Arg Ile Ser Gln His Pro Asn Ile Val Gly Thr Lys Phe
                165                 170                 175

Thr Cys Ala Asn Thr Gly Lys Leu Thr Arg Val Ala Ser Ala Leu His
            180                 185                 190

Ala Ile Thr Pro Pro Ser Pro Leu Ala Pro Ala Gln Arg Lys Phe Pro
        195                 200                 205

Ser Thr Lys Thr Glu Ala Asn His Pro Tyr Val Ala Phe Gly Gly Ile
210                 215                 220

Ala Asp Phe Ser Leu Gln Thr Leu Ala Ser Gly Gly Ser Ala Ile Leu
225                 230                 235                 240

Ala Gly Gly Ala Asn Val Ile Pro Lys Leu Cys Val Gln Ile Phe Asn
                245                 250                 255

Leu Trp Ser Ala Gly Arg Phe Thr Glu Ala Met Glu Ala Gln Glu Leu
            260                 265                 270

Leu Ser Arg Ala Asp Trp Val Leu Thr Lys Ala Ala Ile Pro Gly Thr
        275                 280                 285

Lys Ser Ala Ile Gln Ser Tyr Tyr Gly Tyr Gly Gly Phe Pro Arg Arg
290                 295                 300

Pro Leu Ala Arg Leu Ser Ala Glu Gln Ala Glu Ala Val Ala Glu Lys
305                 310                 315                 320

Ile Lys Asp Ala Met Glu Val Glu Lys Ser Leu Pro Asp Ile Ala
                325                 330                 335

<210> SEQ ID NO 13
<211> LENGTH: 315
<212> TYPE: PRT
<213> ORGANISM: Trichoderma reesei

<400> SEQUENCE: 13

Met Ala Pro Pro Ser Leu Pro Cys Gly Ile Tyr Ala Pro Thr Met Thr
1               5                   10                  15

Phe Phe His Pro Glu Ser Glu Asp Ile Asp Ile Pro Thr Ile Lys His

```
                 20                  25                  30
    His Ala Gln Arg Leu Ala Lys Ala Gly Leu Ala Gly Leu Val Val Met
                 35                  40                  45
    Gly Ser Asn Gly Glu Ala Val His Cys Thr Arg Asp Glu Lys Ile Ala
     50                  55                  60
    Val Leu Ser Ala Thr Arg Glu Ala Leu Asp Ala Ala Gly Phe Gln Ser
     65                  70                  75                  80
    Val Pro Val Leu Phe Gly Ala Thr Glu Gly Ser Val Arg Gly Thr Ile
                     85                  90                  95
    Glu Leu Cys Lys Leu Ala Ala Ala Gly Ala Ala Ala Leu Val
                    100                 105                 110
    Leu Pro Pro Ser Tyr Tyr Arg Ala Gln Thr Asp Glu Ala Ser Ile Glu
                    115                 120                 125
    Ala Tyr Phe Val Ala Val Ala Asp Ala Ser Pro Ile Pro Leu Val Leu
                    130                 135                 140
    Tyr Asn Tyr Pro Gly Ala Val Ser Gly Ile Asp Met Asp Ser Asp Leu
    145                 150                 155                 160
    Leu Ile Arg Leu Ala Gln His Lys Asn Ile Val Gly Thr Lys Phe Thr
                    165                 170                 175
    Cys Gly Asn Thr Gly Lys Leu Thr Arg Val Ala Leu Ala Thr Asp Ala
                    180                 185                 190
    Lys Thr Pro Phe Arg Asp Gly Ser Gly Tyr Met Ala Phe Gly Gly Met
                    195                 200                 205
    Cys Asp Phe Thr Leu Gln Thr Leu Val Ser Gly Gly Ser Gly Ile Ile
                    210                 215                 220
    Ala Gly Gly Ala Asn Val Met Pro Lys Leu Cys Val Lys Val Trp Asp
    225                 230                 235                 240
    Ser Tyr Ser Gln Gly Asn Arg Asp Glu Ala Glu Lys Leu Gln Lys Val
                    245                 250                 255
    Leu Ser Arg Gly Asp Trp Pro Leu Thr Lys Ala Ala Ile Ala Gly Thr
                    260                 265                 270
    Lys Ser Ala Ile Gln Thr Tyr Tyr Gly Tyr Gly Gly Tyr Pro Arg Arg
                    275                 280                 285
    Pro Leu Lys Arg Leu Glu Gln Ala Arg Val Ser Ala Ile Glu Glu Gly
                    290                 295                 300
    Ile Arg Glu Ala Met Glu Ile Glu Lys Thr Leu
    305                 310                 315

<210> SEQ ID NO 14
<211> LENGTH: 320
<212> TYPE: PRT
<213> ORGANISM: Rhodosporidium toruloides

<400> SEQUENCE: 14

Met Pro Ser Thr Lys Phe Gly Lys Asn Leu Pro His Gly Val Tyr Ala
 1                   5                  10                  15
Pro Val Leu Thr Phe Tyr Lys Gly Asn Asp Glu Glu Leu Asp Leu Glu
                    20                  25                  30
Thr Tyr Lys Lys His Val Gln Phe Val Ala Arg Gly Gly Val Asn Ile
                    35                  40                  45
Val Ala Leu Gly Ser Met Gly Glu Ser Val Gln Leu Thr His Gln Glu
                    50                  55                  60
Arg Asn Gln Val Val Lys Ala Ala Arg Ser Ala Leu Asp Ala Asp Ser
 65                  70                  75                  80
```

```
Ser Leu Ser Gln Val Pro Leu Ile Ala Gly Thr Gly Ala Ser Ser Thr
            85                  90                  95

Lys Glu Thr Ile Glu Leu Thr Lys Glu Ala Ala Glu Ala Gly Ala Asp
        100                 105                 110

Phe Ala Met Val Ile Ser Pro Gly Tyr Phe Ala Gly Ala Met Ser Arg
        115                 120                 125

Lys Ala Ile Lys Gln Phe Phe Val Asp Val Ala Glu Ala Ser Pro Ile
130                 135                 140

Pro Val Leu Val Tyr Asn Tyr Pro Gly Ala Ser Ala Gly Ile Asp Ile
145                 150                 155                 160

Asp Ser Asp Leu Met Ala Glu Ile Ala Ala Ala Pro Asn Ile Val
                165                 170                 175

Gly Cys Lys Leu Thr Cys Gly Ser Val Gly Lys Leu Thr Arg Leu Thr
                180                 185                 190

Thr Leu Arg Asp Asp Phe Ala Val Leu Gly Gly Phe Ile Asp Phe Leu
        195                 200                 205

Gly Pro Ser Leu Leu Ala Lys Ala Ala Gly Gly Ile Thr Gly Val Gly
        210                 215                 220

Asn Val Ala Pro Lys Thr Cys Ala Lys Leu Tyr Lys Asp Thr Leu Ala
225                 230                 235                 240

Ala Leu Ser Gly Gln Ala Ser Val Ser Ser Ala Gln Asp Leu Gln Phe
                245                 250                 255

Ile Val Ser Arg Ala Asp Trp Ala Leu Ala Lys Thr Gly Ile Ala Gly
                260                 265                 270

Ala Lys Trp Val Leu Asp Gln Leu Glu Gly Tyr Gly Lys Pro Arg
        275                 280                 285

Arg Pro Leu Leu Pro Phe Asp Glu Ser Asp Gly Lys Gly Lys Gln Leu
        290                 295                 300

Leu Asp Asp Leu Lys Glu Ile Leu Glu Val Glu Lys Ser Leu Gly Ser
305                 310                 315                 320

<210> SEQ ID NO 15
<211> LENGTH: 383
<212> TYPE: PRT
<213> ORGANISM: Aspergillus niger

<400> SEQUENCE: 15

Met Ser Leu Gly Lys Lys Val Thr Leu Asn Ser Gly Ala Gln Ile Pro
1               5                   10                  15

Gln Leu Gly Phe Gly Thr Trp Gln Ser Ala Pro Gly Gln Val Gly Asp
            20                  25                  30

Ala Val Tyr Glu Ala Leu Lys Ala Gly Tyr Arg His Leu Asp Leu Ala
        35                  40                  45

Thr Ile Tyr Gln Asn Gln Arg Glu Val Ala Glu Gly Ile Lys Arg Ala
    50                  55                  60

Tyr Lys Asp Val Pro Gly Leu Lys Arg Glu Asp Ile Phe Ile Thr Ser
65                  70                  75                  80

Lys Leu Trp Asn Ser Gln His Asp Pro Ala Val Val Glu Lys Ala Leu
                85                  90                  95

Asp Glu Cys Leu Ala Glu Leu Glu Leu Asp Tyr Leu Asp Leu Tyr Leu
            100                 105                 110

Val His Trp Pro Val Ser Phe Thr Thr Gly Ser Glu Leu Phe Pro Leu
        115                 120                 125

Val Lys Asp Ser Ser Val Glu Gly Gly Asp Val Val Ile Asn Asp Asp
    130                 135                 140
```

Ile Ser Ile Val Asp Thr Trp Lys Ala Met Thr Gln Leu Pro Lys Ser
145                 150                 155                 160

Lys Ala Arg Thr Val Gly Val Ser Asn His Met Ile Pro His Leu Glu
                165                 170                 175

Ala Ile Ile Asn Ala Thr Gly Val Val Pro Ala Val Asn Gln Ile Glu
            180                 185                 190

Arg His Pro Val Leu Gln Ser Asn Glu Leu Ile Glu Tyr Cys Gln Lys
        195                 200                 205

Lys Gly Ile His Val Thr Ala Tyr Ser Ala Phe Gly Asn Asn Gly Phe
    210                 215                 220

Gly Val Pro Leu Leu Val Thr Arg Pro Glu Val Lys Glu Val Ala Glu
225                 230                 235                 240

Ser Ala Ser Lys Arg Leu Gly Thr Thr Val Thr Pro Ala Gln Val Ile
                245                 250                 255

Leu Ala Trp Ser Gln Val Gly Gly His Ser Val Ile Pro Lys Ser Val
            260                 265                 270

Thr Pro Ser Arg Ile His Glu Asn Phe Lys Glu Val Glu Leu Thr Pro
        275                 280                 285

Glu Glu Ile Ala Lys Val Ser Glu Leu Gly Lys Asp Arg Arg Arg Tyr
    290                 295                 300

Asn Thr Pro Tyr Val Ala Asn Thr Pro Arg Trp Asp Ile Asp Ile Phe
305                 310                 315                 320

Gly Glu Glu Glu Glu Lys Pro Ala Gly His Lys Ile Trp Ser Pro Val
                325                 330                 335

Leu Phe Ala Ala Gly Tyr Ser Ser Ala Trp Val Gly Arg Gly Lys
            340                 345                 350

Val Ser Trp Asp Thr Val His Leu Val Gly Asn His Thr Pro Leu Leu
        355                 360                 365

Arg Gln Gln Thr Thr Pro Arg Phe Ala Arg Leu Ser Phe Gly Ser
    370                 375                 380

<210> SEQ ID NO 16
<211> LENGTH: 314
<212> TYPE: PRT
<213> ORGANISM: Trichoderma reesei

<400> SEQUENCE: 16

Met Pro Ala Thr Leu His Asp Ser Thr Lys Ile Leu Ser Leu Asn Thr
1               5                   10                  15

Gly Ala Gln Ile Pro Gln Ile Gly Leu Gly Thr Trp Gln Ser Lys Glu
                20                  25                  30

Asn Asp Ala Tyr Lys Ala Val Leu Thr Ala Leu Lys Asp Gly Tyr Arg
            35                  40                  45

His Ile Asp Thr Ala Ala Ile Tyr Arg Asn Glu Asp Gln Val Gly Gln
        50                  55                  60

Ala Ile Lys Asp Ser Gly Val Pro Arg Glu Glu Ile Phe Val Thr Thr
65                  70                  75                  80

Lys Leu Trp Cys Thr Gln His His Glu Pro Glu Val Ala Leu Asp Gln
                85                  90                  95

Ser Leu Lys Arg Leu Gly Leu Asp Tyr Val Asp Leu Tyr Leu Met His
            100                 105                 110

Trp Pro Ala Arg Leu Asp Pro Ala Tyr Ile Lys Asn Glu Asp Ile Leu
        115                 120                 125

Ser Val Pro Thr Lys Lys Asp Gly Ser Arg Ala Val Asp Ile Thr Asn

Trp Asn Phe Ile Lys Thr Trp Glu Leu Met Gln Glu Leu Pro Lys Thr
145                 150                 155                 160

Gly Lys Thr Lys Ala Val Gly Val Ser Asn Phe Ser Ile Asn Asn Leu
                165                 170                 175

Lys Asp Leu Leu Ala Ser Gln Gly Asn Lys Leu Thr Pro Ala Ala Asn
            180                 185                 190

Gln Val Glu Ile His Pro Leu Leu Pro Gln Asp Glu Leu Ile Asn Phe
        195                 200                 205

Cys Lys Ser Lys Gly Ile Val Val Glu Ala Tyr Ser Pro Leu Gly Ser
    210                 215                 220

Thr Asp Ala Pro Leu Leu Lys Glu Pro Val Ile Leu Glu Ile Ala Lys
225                 230                 235                 240

Lys Asn Asn Val Gln Pro Gly His Val Val Ile Ser Trp His Val Gln
                245                 250                 255

Arg Gly Tyr Val Val Leu Pro Lys Ser Val Asn Pro Asp Arg Ile Lys
                260                 265                 270

Thr Asn Arg Lys Ile Phe Thr Leu Ser Thr Glu Asp Phe Glu Ala Ile
            275                 280                 285

Asn Asn Ile Ser Lys Glu Lys Gly Glu Lys Arg Val Val His Pro Asn
        290                 295                 300

Trp Ser Pro Phe Glu Val Phe Lys Gly Ser
305                 310

<210> SEQ ID NO 17
<211> LENGTH: 307
<212> TYPE: PRT
<213> ORGANISM: Rhodosporidium toruloides

<400> SEQUENCE: 17

Met Pro Ser Tyr Ile Asp Val Pro Ser Phe Pro Leu Ser His Gly Gly
1               5                   10                  15

Lys Ala Ile Pro Ala Val Gly Leu Gly Thr Trp Gln Ser Asn Pro Gly
                20                  25                  30

Glu Val Ser Asn Ala Val Lys Ile Ala Leu Gln Asn Gly Tyr Arg His
            35                  40                  45

Ile Asp Gly Ala Trp Ile Tyr Gly Asn Glu Lys Glu Val Gly Glu Gly
50                  55                  60

Ile Lys Ala Ser Gly Val Pro Arg Glu Glu Ile Phe Val Thr Ser Lys
65                  70                  75                  80

Leu Trp Cys Thr Lys His Arg Asn Val Glu Ala Ala Val Lys Glu Ser
                85                  90                  95

Leu Glu Leu Leu Gly Leu Asp Tyr Leu Asp Leu Tyr Leu Ile His Trp
            100                 105                 110

Pro Val Pro Leu Asn Gly Gln Gly Asn Asp Pro Lys Phe Pro Lys Leu
        115                 120                 125

Pro Asp Gly Ser Arg Asp Arg Asp Thr Glu Trp Ser Ile Asn Gln Thr
    130                 135                 140

Trp Glu Gln Met Glu Ala Ile Leu Glu Lys Gly Leu Val Lys Ala Ile
145                 150                 155                 160

Gly Val Ser Asn Phe Ser Glu Ala Tyr Leu Asp Gln Leu Leu Thr Thr
                165                 170                 175

Ala Lys Val Val Pro Ala Val Asn Gln Ile Glu Leu His Pro Tyr Leu
            180                 185                 190

```
Pro Gln His Glu Leu Leu Gln Tyr Leu Ala Lys Lys Asn Ile Leu Ala
        195                 200                 205

Glu Ala Tyr Ser Pro Leu Gly Ser Thr Asp Ser Pro Leu Leu Lys Asp
210                 215                 220

Glu Val Ile Lys Lys Ile Ala Asp Lys His Gly Val Ser Val Gly Thr
225                 230                 235                 240

Val Leu Ile Ser Tyr Gln Val Asn Arg Asn Val Val Leu Pro Lys
                245                 250                 255

Ser Val Thr Glu Lys Arg Ile Ile Asp Asn Tyr Lys Ile Val Lys Leu
            260                 265                 270

Asp Glu Glu Asp Met Arg Thr Leu Asn Glu Leu Tyr Lys Thr Lys Gly
        275                 280                 285

Lys Arg Phe Ile Lys Pro Asp Trp Gly Val Asp Leu Lys Phe Ser His
    290                 295                 300

Trp Gly Ser
305

<210> SEQ ID NO 18
<211> LENGTH: 277
<212> TYPE: PRT
<213> ORGANISM: Pseudomonas syringae

<400> SEQUENCE: 18

Met Ala Ser Ala His Thr Thr Gln Thr Pro Phe Asn Arg Leu Leu Leu
1               5                   10                  15

Thr Gly Ala Ala Gly Gly Leu Gly Lys Val Leu Arg Glu Thr Leu Arg
            20                  25                  30

Pro Tyr Ser His Ile Leu Arg Leu Ser Asp Ile Ala Glu Met Ala Pro
        35                  40                  45

Ala Val Gly Asp His Glu Glu Val Gln Val Cys Asp Leu Ala Asp Lys
    50                  55                  60

Asp Ala Val His Arg Leu Val Glu Gly Val Asp Ala Ile Leu His Phe
65                  70                  75                  80

Gly Gly Val Ser Val Glu Arg Pro Phe Glu Glu Ile Leu Gly Ala Asn
                85                  90                  95

Ile Cys Gly Val Phe His Ile Tyr Glu Ala Ala Arg Arg His Gly Val
            100                 105                 110

Lys Arg Val Ile Phe Ala Ser Ser Asn His Val Ile Gly Phe Tyr Lys
        115                 120                 125

Gln Asn Glu Thr Ile Asp Ala His Ser Pro Arg Arg Pro Asp Ser Tyr
    130                 135                 140

Tyr Gly Leu Ser Lys Ser Tyr Gly Glu Asp Met Ala Ser Phe Tyr Phe
145                 150                 155                 160

Asp Arg Tyr Gly Ile Glu Thr Val Ser Ile Arg Ile Gly Ser Ser Phe
                165                 170                 175

Pro Glu Pro Gln Asn Arg Arg Met Met Ser Thr Trp Leu Ser Phe Asp
            180                 185                 190

Asp Leu Thr Arg Leu Leu Glu Arg Ala Leu Tyr Thr Pro Asp Val Gly
        195                 200                 205

His Thr Val Val Tyr Gly Val Ser Asp Asn Lys Thr Val Trp Trp Asp
    210                 215                 220

Asn Arg Phe Ala Ser Lys Leu Asp Tyr Ala Pro Lys Asp Ser Ser Glu
225                 230                 235                 240

Val Phe Arg Ala Lys Val Asp Ala Gln Pro Met Pro Ala Asp Asp Asp
                245                 250                 255
```

```
Pro Ala Met Val Tyr Gln Gly Gly Ala Phe Val Ala Ser Gly Pro Phe
            260                 265                 270

Gly Asp Lys Gly Ser
        275

<210> SEQ ID NO 19
<211> LENGTH: 279
<212> TYPE: PRT
<213> ORGANISM: Limnohabitans sp. Rim47

<400> SEQUENCE: 19

Met Pro Asn Thr Ser Thr Pro Thr Ser Asn Ser Gly Ile Arg Phe Pro
1               5                   10                  15

Arg Leu Leu Leu Thr Gly Ala Gly Asn Leu Gly Gln Glu Leu Arg
            20                  25                  30

Pro Arg Leu Lys Ala Tyr Cys Asp Val Leu Arg Val Ser His Arg Arg
            35                  40                  45

Asp Leu Gly Pro Ala Ala Ala Gly Glu Glu Val Gln Thr Ala Ser Leu
50                  55                  60

Glu Asp Ala Glu His Met Leu Ser Leu Leu Asp Gly Val Ser Ala Val
65                  70                  75                  80

Val His Met Gly Gly Val Ser Thr Glu Gln Pro Trp Ala Pro Ile Leu
                85                  90                  95

Ala Gly Asn Ile Val Gly Met Val Asn Leu Tyr Glu Ala Ala Arg Leu
            100                 105                 110

Lys Gly Val Lys Arg Ile Val Phe Ala Ser Ser Asn His Val Thr Gly
            115                 120                 125

Phe Tyr Arg Gln Asp Glu Val Val Asn Thr Arg Met Pro Pro Lys Pro
130                 135                 140

Asp Gly Phe Tyr Gly Leu Ser Lys Ala Phe Gly Glu Asp Leu Ala Gln
145                 150                 155                 160

Leu Tyr Trp Asp Arg Trp Gly Val Glu Thr Val Ser Ile Arg Ile Gly
                165                 170                 175

Ser Ser Phe Thr Glu Pro Arg Asp Arg Arg Met Leu Ala Thr Tyr Leu
            180                 185                 190

Ser Tyr Asp Asp Leu Glu Arg Leu Val Val Ala Ala Leu Thr Ala Pro
            195                 200                 205

Ile Val Gly His Ser Ile Ile Tyr Gly Met Ser Asp Asn Gln Thr Thr
            210                 215                 220

Trp Trp Asp Asn Thr His Ala Lys His Ile Gly Tyr Arg Pro Gln Asp
225                 230                 235                 240

Ser Ser Asp Val Phe Arg His Ala Val Glu Ala Arg Gln Gln Thr Ile
                245                 250                 255

Asp Lys Gln Asp Pro Ala Ala Ile Tyr Gln Gly Gly Ala Phe Val Lys
            260                 265                 270

Ala Thr Pro His Gly Gly Ser
            275

<210> SEQ ID NO 20
<211> LENGTH: 277
<212> TYPE: PRT
<213> ORGANISM: Artificial Sequence
<220> FEATURE:
<223> OTHER INFORMATION: Synthetic polypeptide
<220> FEATURE:
<221> NAME/KEY: Misc_feature
<222> LOCATION: (43)..(43)
```

<223> OTHER INFORMATION: Xaa is any amino acid other than isoleucine

<400> SEQUENCE: 20

```
Met Ala Ser Ala His Thr Thr Gln Thr Pro Phe Asn Arg Leu Leu Leu
1               5                   10                  15

Thr Gly Ala Ala Gly Gly Leu Gly Lys Val Leu Arg Glu Thr Leu Arg
            20                  25                  30

Pro Tyr Ser His Ile Leu Arg Leu Ser Asp Xaa Ala Glu Met Ala Pro
        35                  40                  45

Ala Val Gly Asp His Glu Glu Val Gln Val Cys Asp Leu Ala Asp Lys
50                  55                  60

Asp Ala Val His Arg Leu Val Glu Gly Val Asp Ala Ile Leu His Phe
65                  70                  75                  80

Gly Gly Val Ser Val Glu Arg Pro Phe Glu Glu Ile Leu Gly Ala Asn
                85                  90                  95

Ile Cys Gly Val Phe His Ile Tyr Glu Ala Ala Arg Arg His Gly Val
            100                 105                 110

Lys Arg Val Ile Phe Ala Ser Ser Asn His Val Ile Gly Phe Tyr Lys
        115                 120                 125

Gln Asn Glu Thr Ile Asp Ala His Ser Pro Arg Arg Pro Asp Ser Tyr
    130                 135                 140

Tyr Gly Leu Ser Lys Ser Tyr Gly Glu Asp Met Ala Ser Phe Tyr Phe
145                 150                 155                 160

Asp Arg Tyr Gly Ile Glu Thr Val Ser Ile Arg Ile Gly Ser Ser Phe
                165                 170                 175

Pro Glu Pro Gln Asn Arg Arg Met Met Ser Thr Trp Leu Ser Phe Asp
            180                 185                 190

Asp Leu Thr Arg Leu Leu Glu Arg Ala Leu Tyr Thr Pro Asp Val Gly
        195                 200                 205

His Thr Val Val Tyr Gly Val Ser Asp Asn Lys Thr Val Trp Trp Asp
    210                 215                 220

Asn Arg Phe Ala Ser Lys Leu Asp Tyr Ala Pro Lys Asp Ser Ser Glu
225                 230                 235                 240

Val Phe Arg Ala Lys Val Asp Ala Gln Pro Met Pro Ala Asp Asp
                245                 250                 255

Pro Ala Met Val Tyr Gln Gly Gly Ala Phe Val Ala Ser Gly Pro Phe
            260                 265                 270

Gly Asp Lys Gly Ser
        275
```

<210> SEQ ID NO 21
<211> LENGTH: 285
<212> TYPE: PRT
<213> ORGANISM: Mus musculus

<400> SEQUENCE: 21

```
Met Lys Val Asp Val Gly Pro Asp Pro Ser Leu Val Tyr Arg Pro Asp
1               5                   10                  15

Val Asp Pro Glu Met Ala Lys Ser Lys Asp Ser Phe Arg Asn Tyr Thr
            20                  25                  30

Ser Gly Pro Leu Leu Asp Arg Val Phe Thr Thr Tyr Lys Leu Met His
        35                  40                  45

Thr His Gln Thr Val Asp Phe Val Ser Arg Lys Arg Ile Gln Tyr Gly
    50                  55                  60

Gly Phe Ser Tyr Lys Lys Met Thr Ile Met Glu Ala Val Gly Met Leu
```

```
                65                  70                  75                  80
Asp Asp Leu Val Asp Glu Ser Asp Pro Asp Val Asp Phe Pro Asn Ser
                    85                  90                  95

Phe His Ala Phe Gln Thr Ala Glu Gly Ile Arg Lys Ala His Pro Asp
                100                 105                 110

Lys Asp Trp Phe His Leu Val Gly Leu Leu His Asp Leu Gly Lys Ile
            115                 120                 125

Met Ala Leu Trp Gly Glu Pro Gln Trp Ala Val Val Gly Asp Thr Phe
130                 135                 140

Pro Val Gly Cys Arg Pro Gln Ala Ser Val Val Phe Cys Asp Ser Thr
145                 150                 155                 160

Phe Gln Asp Asn Pro Asp Leu Gln Asp Pro Arg Tyr Ser Thr Glu Leu
                165                 170                 175

Gly Met Tyr Gln Pro His Cys Gly Leu Glu Asn Val Leu Met Ser Trp
                180                 185                 190

Gly His Asp Glu Tyr Leu Tyr Gln Met Met Lys Phe Asn Lys Phe Ser
            195                 200                 205

Leu Pro Ser Glu Ala Phe Tyr Met Ile Arg Phe His Ser Phe Tyr Pro
210                 215                 220

Trp His Thr Gly Gly Asp Tyr Arg Gln Leu Cys Ser Gln Gln Asp Leu
225                 230                 235                 240

Asp Met Leu Pro Trp Val Gln Glu Phe Asn Lys Phe Asp Leu Tyr Thr
                245                 250                 255

Lys Cys Pro Asp Leu Pro Asp Val Glu Ser Leu Arg Pro Tyr Tyr Gln
                260                 265                 270

Gly Leu Ile Asp Lys Tyr Cys Pro Gly Thr Leu Ser Trp
            275                 280                 285

<210> SEQ ID NO 22
<211> LENGTH: 533
<212> TYPE: PRT
<213> ORGANISM: Saccharomyces cerevisiae
<220> FEATURE:
<221> NAME/KEY: Misc_feature
<222> LOCATION: (69)..(69)
<223> OTHER INFORMATION: Xaa is any amino acid
<220> FEATURE:
<221> NAME/KEY: Misc_feature
<222> LOCATION: (109)..(109)
<223> OTHER INFORMATION: Xaa is any amino acid
<220> FEATURE:
<221> NAME/KEY: Misc_feature
<222> LOCATION: (136)..(136)
<223> OTHER INFORMATION: Xaa is any amino acid
<220> FEATURE:
<221> NAME/KEY: Misc_feature
<222> LOCATION: (158)..(158)
<223> OTHER INFORMATION: Xaa is any amino acid
<220> FEATURE:
<221> NAME/KEY: Misc_feature
<222> LOCATION: (176)..(176)
<223> OTHER INFORMATION: Xaa is any amino acid
<220> FEATURE:
<221> NAME/KEY: Misc_feature
<222> LOCATION: (261)..(261)
<223> OTHER INFORMATION: Xaa is any amino acid
<220> FEATURE:
<221> NAME/KEY: Misc_feature
<222> LOCATION: (405)..(405)
<223> OTHER INFORMATION: Xaa is any amino acid
<220> FEATURE:
<221> NAME/KEY: Misc_feature
<222> LOCATION: (415)..(415)
<223> OTHER INFORMATION: Xaa is any amino acid
<220> FEATURE:
```

-continued

```
<221> NAME/KEY: Misc_feature
<222> LOCATION: (423)..(423)
<223> OTHER INFORMATION: Xaa is any amino acid
<220> FEATURE:
<221> NAME/KEY: Misc_feature
<222> LOCATION: (452)..(452)
<223> OTHER INFORMATION: Xaa is any amino acid

<400> SEQUENCE: 22

Met Thr Glu Asp Asn Ile Ala Pro Ile Thr Ser Val Lys Val Val Thr
1               5                   10                  15

Asp Lys Cys Thr Tyr Lys Asp Asn Glu Leu Leu Thr Lys Tyr Ser Tyr
            20                  25                  30

Glu Asn Ala Val Val Thr Lys Thr Ala Ser Gly Arg Phe Asp Val Thr
        35                  40                  45

Pro Thr Val Gln Asp Tyr Val Phe Lys Leu Asp Leu Lys Lys Pro Glu
    50                  55                  60

Lys Leu Gly Ile Xaa Leu Ile Gly Leu Gly Gly Asn Asn Gly Ser Thr
65                  70                  75                  80

Leu Val Ala Ser Val Leu Ala Asn Lys His Asn Val Glu Phe Gln Thr
                85                  90                  95

Lys Glu Gly Val Lys Gln Pro Asn Tyr Phe Gly Ser Xaa Thr Gln Cys
            100                 105                 110

Ser Thr Leu Lys Leu Gly Ile Asp Ala Glu Gly Asn Asp Val Tyr Ala
        115                 120                 125

Pro Phe Asn Ser Leu Leu Pro Xaa Val Ser Pro Asn Asp Phe Val Val
    130                 135                 140

Ser Gly Trp Asp Ile Asn Ala Asp Leu Tyr Glu Ala Xaa Gln Arg
145                 150                 155                 160

Ser Gln Val Leu Glu Tyr Asp Leu Gln Gln Arg Leu Lys Ala Lys Xaa
            165                 170                 175

Ser Leu Val Lys Pro Leu Pro Ser Ile Tyr Tyr Pro Asp Phe Ile Ala
        180                 185                 190

Ala Asn Gln Asp Glu Arg Ala Asn Asn Cys Ile Asn Leu Asp Glu Lys
    195                 200                 205

Gly Asn Val Thr Thr Arg Gly Lys Trp Thr His Leu Gln Arg Ile Arg
210                 215                 220

Arg Asp Ile Gln Asn Phe Lys Glu Glu Asn Ala Leu Asp Lys Val Ile
225                 230                 235                 240

Val Leu Trp Thr Ala Asn Thr Glu Arg Tyr Val Glu Val Ser Pro Gly
            245                 250                 255

Val Asn Asp Thr Xaa Glu Asn Leu Leu Gln Ser Ile Lys Asn Asp His
        260                 265                 270

Glu Glu Ile Ala Pro Ser Thr Ile Phe Ala Ala Ala Ser Ile Leu Glu
    275                 280                 285

Gly Val Pro Tyr Ile Asn Gly Ser Pro Gln Asn Thr Phe Val Pro Gly
290                 295                 300

Leu Val Gln Leu Ala Glu His Glu Gly Thr Phe Ile Ala Gly Asp Asp
305                 310                 315                 320

Leu Lys Ser Gly Gln Thr Lys Leu Lys Ser Val Leu Ala Gln Phe Leu
            325                 330                 335

Val Asp Ala Gly Ile Lys Pro Val Ser Ile Ala Ser Tyr Asn His Leu
        340                 345                 350

Gly Asn Asn Asp Gly Tyr Asn Leu Ser Ala Pro Lys Gln Phe Arg Ser
    355                 360                 365
```

-continued

```
Lys Glu Ile Ser Lys Ser Ser Val Ile Asp Asp Ile Ile Ala Ser Asn
        370                 375                 380

Asp Ile Leu Tyr Asn Asp Lys Leu Gly Lys Lys Val Asp His Cys Ile
385                 390                 395                 400

Val Ile Lys Tyr Xaa Lys Pro Val Gly Asp Ser Lys Val Ala Xaa Asp
                405                 410                 415

Glu Tyr Tyr Ser Glu Leu Xaa Leu Gly Gly His Asn Arg Ile Ser Ile
            420                 425                 430

His Asn Val Cys Glu Asp Ser Leu Leu Ala Thr Pro Leu Ile Ile Asp
        435                 440                 445

Leu Leu Val Xaa Thr Glu Phe Cys Thr Arg Val Ser Tyr Lys Lys Val
450                 455                 460

Asp Pro Val Lys Glu Asp Ala Gly Lys Phe Glu Asn Phe Tyr Pro Val
465                 470                 475                 480

Leu Thr Phe Leu Ser Tyr Trp Leu Lys Ala Pro Leu Thr Arg Pro Gly
                485                 490                 495

Phe His Pro Val Asn Gly Leu Asn Lys Gln Arg Thr Ala Leu Glu Asn
            500                 505                 510

Phe Leu Arg Leu Leu Ile Gly Leu Pro Ser Gln Asn Glu Leu Arg Phe
        515                 520                 525

Glu Glu Arg Leu Leu
        530
```

<210> SEQ ID NO 23
<211> LENGTH: 387
<212> TYPE: PRT
<213> ORGANISM: Klebsiella pneumoniae

<400> SEQUENCE: 23

```
Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Gln Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Lys Thr Leu His Tyr Leu Arg Glu Ala Gly Ile
    50                  55                  60

Glu Val Ala Ile Phe Asp Gly Val Glu Pro Asn Pro Lys Asp Thr Asn
65                  70                  75                  80

Val Arg Asp Gly Leu Ala Val Phe Arg Arg Glu Gln Cys Asp Ile Ile
                85                  90                  95

Val Thr Val Gly Gly Gly Ser Pro His Asp Cys Gly Lys Gly Ile Gly
            100                 105                 110

Ile Ala Ala Thr His Glu Gly Asp Leu Tyr Gln Tyr Ala Gly Ile Glu
        115                 120                 125

Thr Leu Thr Asn Pro Leu Pro Pro Ile Val Ala Val Asn Thr Thr Ala
    130                 135                 140

Gly Thr Ala Ser Glu Val Thr Arg His Cys Val Leu Thr Asn Thr Glu
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Gly Lys Pro Ala Ala Leu Thr
            180                 185                 190

Ala Ala Thr Gly Met Asp Ala Leu Thr His Ala Val Glu Ala Tyr Ile
        195                 200                 205
```

-continued

```
Ser Lys Asp Ala Asn Pro Val Thr Asp Ala Ala Met Gln Ala Ile
    210                 215                 220

Arg Leu Ile Ala Arg Asn Leu Arg Gln Ala Val Ala Leu Gly Ser Asn
225                 230                 235                 240

Leu Gln Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Pro His Gly Val Ala Asn Ala Val Leu
        275                 280                 285

Leu Pro His Val Ala Arg Tyr Asn Leu Ile Ala Asn Pro Glu Lys Phe
    290                 295                 300

Ala Asp Ile Ala Glu Leu Met Gly Glu Asn Ile Thr Gly Leu Ser Thr
305                 310                 315                 320

Leu Asp Ala Ala Glu Lys Ala Ile Ala Ala Ile Thr Arg Leu Ser Met
                325                 330                 335

Asp Ile Gly Ile Pro Gln His Leu Arg Asp Leu Gly Val Lys Glu Ala
            340                 345                 350

Asp Phe Pro Tyr Met Ala Glu Met Ala Leu Lys Asp Gly Asn Ala Phe
        355                 360                 365

Ser Asn Pro Arg Lys Gly Asn Glu Gln Glu Ile Ala Ala Ile Phe Arg
    370                 375                 380

Gln Ala Phe
385

<210> SEQ ID NO 24
<211> LENGTH: 387
<212> TYPE: PRT
<213> ORGANISM: Escherichia coli

<400> SEQUENCE: 24

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
```

```
                180               185                190
Val Asp Ala Phe Val His Thr Val Glu Gln Tyr Val Thr Lys Pro Val
                195               200                205
Asp Ala Lys Ile Gln Asp Arg Phe Ala Glu Gly Ile Leu Leu Thr Leu
            210               215                220
Ile Glu Asp Gly Pro Lys Ala Leu Lys Glu Pro Glu Asn Tyr Asp Val
225               230                235                240
Arg Ala Asn Val Met Trp Ala Thr Gln Ala Leu Asn Gly Leu Ile
                245                250               255
Gly Ala Gly Val Pro Gln Asp Trp Ala Thr His Met Leu Gly His Glu
            260               265                270
Leu Thr Ala Met His Gly Leu Asp His Ala Gln Thr Leu Ala Ile Val
        275               280                285
Leu Pro Ala Leu Trp Asn Glu Lys Arg Asp Thr Lys Arg Ala Lys Leu
        290               295                300
Leu Gln Tyr Ala Glu Arg Val Trp Asn Ile Thr Glu Gly Ser Asp Asp
305               310                315                320
Glu Arg Ile Asp Ala Ala Ile Ala Ala Thr Arg Asn Phe Phe Glu Gln
                325                330                335
Leu Gly Val Pro Thr His Leu Ser Asp Tyr Gly Leu Asp Gly Ser Ser
                340                345                350
Ile Pro Ala Leu Leu Lys Lys Leu Glu Glu His Gly Met Thr Gln Leu
            355                360                365
Gly Glu Asn His Asp Ile Thr Leu Asp Val Ser Arg Arg Ile Tyr Glu
        370                375                380
Ala Ala Arg
385

<210> SEQ ID NO 25
<211> LENGTH: 269
<212> TYPE: PRT
<213> ORGANISM: Streptomyces venezuelae

<400> SEQUENCE: 25

Met Ser Pro Pro Arg Thr Val Leu Leu Thr Gly Ala Ala Gly Gly Val
1               5                   10                  15
Gly Thr Leu Met Arg Glu Leu Leu Pro Pro Tyr Gly Tyr Glu Leu Arg
                20                  25                  30
Leu Leu Asp Val Ala Pro Val Pro Gly Ala Pro Asp Ala Ile Val Ala
            35                  40                  45
Asp Leu Ala Asp Arg Ala Ala Leu Arg Glu Ala Val Arg Gly Val Asp
        50                  55                  60
Ala Ile Val His Leu Ala Gly Ile Ser Leu Glu Ser Thr Phe Asp Lys
65                  70                  75                  80
Ile Met Ala Ala Asn Ile Ala Gly Thr Tyr Asn Leu Tyr Glu Ala Ala
                85                  90                  95
Arg Glu Glu Gly Val Arg Val Val Phe Ala Ser Ser Asn His Ala
                100                 105                 110
Val Gly Phe Ile Arg Gln Pro Arg Pro Gly Asp Pro Leu Val Pro Val
            115                 120                 125
Asp Thr Pro His Arg Pro Asp Thr Phe Tyr Gly Leu Ser Lys Cys Phe
        130                 135                 140
Gly Glu Asp Leu Ala Gln Leu Tyr Trp Asp Leu His Gly Ile Glu Thr
145                 150                 155                 160
```

```
Val Ser Val Arg Ile Gly Ser Cys Phe Pro Glu Pro Thr Ser Val Arg
            165                 170                 175

Met Leu Ser Met Trp Leu Ser Pro Ala Asp Cys Ala Arg Leu Leu His
            180                 185                 190

Ala Thr Leu Thr Ala Glu Asp Val Ala His Thr Val Val Tyr Gly Ser
            195                 200                 205

Ser Ala Asn Thr Arg Ala Trp Trp Asp Leu Ser Thr Ala Arg Ala Leu
            210                 215                 220

Gly Phe Glu Pro Val Asp Ser Glu Val His Ala Glu Lys Leu Ile
225                 230                 235                 240

Ala Glu Lys Gly Leu Pro Pro Glu Asp Ser Ala Asp Ala Arg Tyr Leu
            245                 250                 255

Gly Gly His Phe Cys Val Asp Pro Pro Arg Trp Pro His
            260                 265

<210> SEQ ID NO 26
<211> LENGTH: 265
<212> TYPE: PRT
<213> ORGANISM: Agrobacterium fabrum

<400> SEQUENCE: 26

Met Lys Arg Leu Leu Val Thr Gly Ala Ala Gly Gln Leu Gly Arg Val
1               5                   10                  15

Met Arg Glu Arg Leu Ala Pro Met Ala Glu Ile Leu Arg Leu Ala Asp
            20                  25                  30

Leu Ser Pro Leu Asp Pro Ala Gly Pro Asn Glu Glu Cys Val Gln Cys
            35                  40                  45

Asp Leu Ala Asp Ala Asn Ala Val Asn Ala Met Val Ala Gly Cys Asp
        50                  55                  60

Gly Ile Val His Leu Gly Gly Ile Ser Val Glu Lys Pro Phe Glu Gln
65                  70                  75                  80

Ile Leu Gln Gly Asn Ile Ile Gly Leu Tyr Asn Leu Tyr Glu Ala Ala
                85                  90                  95

Arg Ala His Gly Gln Pro Arg Ile Val Phe Ala Ser Ser Asn His Thr
            100                 105                 110

Ile Gly Tyr Tyr Pro Gln Thr Glu Arg Leu Gly Pro Asp Val Pro Ala
        115                 120                 125

Arg Pro Asp Gly Leu Tyr Gly Val Ser Lys Cys Phe Gly Glu Asn Leu
130                 135                 140

Ala Arg Met Tyr Phe Asp Lys Phe Gly Gln Glu Thr Ala Leu Val Arg
145                 150                 155                 160

Ile Gly Ser Cys Thr Pro Glu Pro Asn Asn Tyr Arg Met Leu Ser Thr
                165                 170                 175

Trp Phe Ser His Asp Asp Phe Val Ser Leu Ile Glu Ala Val Phe Arg
            180                 185                 190

Ala Pro Val Leu Gly Cys Pro Val Val Trp Gly Ala Ser Ala Asn Asp
        195                 200                 205

Ala Gly Trp Trp Asp Asn Ser His Leu Gly Phe Leu Gly Trp Lys Pro
210                 215                 220

Lys Asp Asn Ala Glu Ala Phe Arg Arg His Ile Thr Glu Thr Thr Pro
225                 230                 235                 240

Pro Pro Asp Pro Asn Asp Ala Leu Val Arg Phe Gln Gly Gly Thr Phe
                245                 250                 255

Val Asp Asn Pro Ile Phe Lys Gln Ser
            260                 265
```

<210> SEQ ID NO 27
<211> LENGTH: 268
<212> TYPE: PRT
<213> ORGANISM: Pseudomonas putida

<400> SEQUENCE: 27

Met Thr Thr Thr Pro Phe Asn Arg Leu Leu Leu Thr Gly Ala Ala Gly
1 5 10 15

Gly Leu Gly Lys Val Leu Arg Glu Arg Leu Lys Gly Tyr Ala Glu Val
20 25 30

Leu Arg Leu Ser Asp Ile Ser Pro Met Ala Pro Ala Ala Gly Pro His
35 40 45

Glu Glu Val Ile Thr Cys Asp Leu Ala Asp Lys Ala Ala Val His Thr
50 55 60

Leu Val Glu Gly Val Asp Ala Ile Ile His Phe Gly Gly Val Ser Thr
65 70 75 80

Glu His Ala Phe Glu Glu Ile Leu Gly Pro Asn Ile Cys Gly Val Phe
85 90 95

His Val Tyr Glu Ala Ala Arg Lys His Gly Val Lys Arg Ile Ile Phe
100 105 110

Ala Ser Ser Asn His Thr Ile Gly Phe Tyr Arg Gln Asp Glu Arg Ile
115 120 125

Asp Ala His Ala Pro Arg Arg Pro Asp Ser Tyr Tyr Gly Leu Ser Lys
130 135 140

Cys Tyr Gly Glu Asp Val Ala Ser Phe Tyr Phe Asp Arg Tyr Gly Ile
145 150 155 160

Glu Thr Val Ser Ile Arg Ile Gly Ser Ser Phe Pro Gln Pro Gln Asn
165 170 175

Leu Arg Met Leu Cys Thr Trp Leu Ser Tyr Asp Asp Leu Val Gln Leu
180 185 190

Ile Glu Arg Gly Leu Phe Thr Pro Gly Val Gly His Thr Ile Val Tyr
195 200 205

Gly Ala Ser Asp Asn Arg Thr Val Trp Trp Asp Asn Arg His Ala Ala
210 215 220

His Leu Gly Tyr Val Pro Lys Asp Ser Ser Glu Thr Phe Arg Ala Ala
225 230 235 240

Val Glu Ala Gln Pro Ala Pro Ala Ala Asp Asp Pro Ser Met Val Tyr
245 250 255

Gln Gly Gly Ala Phe Ala Val Ala Gly Pro Phe Asn
260 265

<210> SEQ ID NO 28
<211> LENGTH: 282
<212> TYPE: PRT
<213> ORGANISM: Ralstonia solanacearum

<400> SEQUENCE: 28

Met Thr Thr Ile His Thr Gln Ala Leu Ala Asp Pro Leu Ala Gly Ile
1 5 10 15

Ala Thr Arg Cys His Arg Leu Leu Leu Thr Gly Ala Gly Gly Asn Leu
20 25 30

Gly Lys Val Leu Arg Glu Arg Leu Thr Arg Tyr Ala Glu Val Leu Arg
35 40 45

Val Ser Asp Ile Thr Asp Leu Gly Ala Ala Arg Ala Gly Glu Glu Val
50 55 60

```
Val Pro Cys Asp Leu Ala Asp Ala Gln Ala Val Asp Ala Leu Val Lys
 65                  70                  75                  80

Gly Val Asp Ala Ile Val His Leu Gly Gly Ile Ser Val Glu Arg Pro
                 85                  90                  95

Phe Asp Glu Ile Leu Pro Ala Asn Ile Gln Gly Thr Tyr His Leu Tyr
            100                 105                 110

Glu Ala Ala Arg Arg His Gly Val Lys Arg Ile Ala Phe Ala Ser Ser
        115                 120                 125

Asn His Ala Ile Gly Phe Tyr Arg Gln Gly Glu Val Ile Asp Ala Arg
    130                 135                 140

Val Pro Thr Arg Pro Asp Gly Tyr Tyr Gly Leu Ser Lys Val Phe Gly
145                 150                 155                 160

Glu Gln Leu Gly Ser Phe Tyr Phe Asp Arg Tyr Gly Ile Glu Thr Val
                165                 170                 175

Ala Ile Arg Ile Gly Ser Ser Phe Pro Glu Ala Lys Asp Arg Arg Met
            180                 185                 190

Leu Val Thr Trp Leu Gly Tyr Asp Asp Leu Glu Gln Leu Ile Arg Arg
        195                 200                 205

Ala Leu Phe Val Pro Asn Val Gly Phe Thr Ile Val Tyr Gly Met Ser
    210                 215                 220

Gly Asn Arg Glu Ala Trp Trp Asn Asn Arg His Ala Ala His Leu Gly
225                 230                 235                 240

Tyr Val Pro Ala Gln Ser Ser Glu Ala Phe Arg Ala Gln Val Glu Ala
                245                 250                 255

Gln Pro Pro Leu Ala Ala Asp Pro Ala Ala Arg Phe Gln Gly Gly
            260                 265                 270

Ala Phe Val Lys Ala Gly Pro Phe Gly Asp
        275                 280

<210> SEQ ID NO 29
<211> LENGTH: 268
<212> TYPE: PRT
<213> ORGANISM: Burkholderia

<400> SEQUENCE: 29

Met Lys Arg Val Leu Ile Thr Gly Ala Ala Gly Val Ile Gly Arg Val
1               5                   10                  15

Leu Arg Ala Gly Phe Ala Gly Gln Tyr Ala Leu Arg Leu Ala Asp Ile
             20                  25                  30

Ala Pro Gln Ala Pro Ala Gly Glu His Glu Glu Ile Val Thr Ala Asp
         35                  40                  45

Ile Thr Arg Pro Glu Arg Leu Arg Glu Ile Met Glu Gly Val Asp Thr
     50                  55                  60

Val Val His Leu Ala Gly Ile Pro Asp Glu Asp Thr Trp Gln Lys Ile
 65                  70                  75                  80

Arg Asp Met Asn Ile Asp Gly Cys Tyr Asn Val Phe Glu Ala Ala Arg
                 85                  90                  95

Gln Ala Gly Val Lys Arg Met Val Phe Ala Ser Ser Asn His Ala Val
            100                 105                 110

Gly Phe His Arg Arg Asp Arg Met Ile Asp Asp Thr Val Met Val Arg
        115                 120                 125

Pro Asp Ser Arg Tyr Gly Val Ser Lys Ala Phe Gly Glu Ala Leu Gly
    130                 135                 140

Arg Leu Tyr Ala Asp Lys Tyr Gly Met Ser Val Ala Cys Leu Arg Ile
```

```
145                 150                 155                 160

Gly Ser Phe Arg Ala Asp Asp Gln Pro Thr Ala Pro Arg His Leu Tyr
                165                 170                 175

Ser Trp Ile Ser His Arg Asp Met Val Gln Leu Thr Arg Arg Cys Ile
                180                 185                 190

Asp Ala Pro Asp Tyr His Phe Val Ile Val Tyr Gly Val Ser Asp Asn
                195                 200                 205

Ala Arg Asn Arg Trp Ser Asn Ala Asn Ala Arg Ala Leu Gly Tyr Arg
                210                 215                 220

Pro Glu Asp Asp Ala Gln Thr His Ala Pro Glu Ile Leu Ala Ser Ala
225                 230                 235                 240

Glu Ala Glu Asp Ala Thr Glu Ala Leu Phe His Gly Phe Gly Cys
                245                 250                 255

Leu Arg Glu Phe Asp Gly Asp Pro His Arg Ile Asp
                260                 265
```

<210> SEQ ID NO 30
<211> LENGTH: 274
<212> TYPE: PRT
<213> ORGANISM: Bradyrhizobium sp. WSM471

<400> SEQUENCE: 30

```
Met Pro Arg Ile Leu Met Thr Gly Ala Ser Gly Gly Ile Gly Thr Arg
1               5                   10                  15

Leu Arg Lys Leu Leu Pro Pro Ile Tyr Pro Asp Leu Leu Ser Asp
                20                  25                  30

Ile Arg Pro Pro Ala Asp Leu Gly Ala Asn Glu Gln Phe Lys Ala Ala
                35                  40                  45

Asp Leu Ser Asp Leu Ala Gln Cys Glu Ala Ile Cys Glu Gly Val Asp
50                  55                  60

Gly Ile Ile His Phe Gly Gly Tyr Ser Val Glu Gly Pro Trp Asn Asp
65                  70                  75                  80

Ile Leu Gln Ala Asn Ile Ile Gly Gly Tyr Asn Leu Phe Glu Ala Ala
                85                  90                  95

Tyr Arg Lys Gly Val Lys Arg Val Val Phe Ala Ser Ser Asn His Ala
                100                 105                 110

Val Gly Phe Tyr Pro Arg His His Lys Ile Gly Thr Asp Val Thr Pro
                115                 120                 125

Arg Pro Asp Gly Arg Tyr Gly Val Ser Lys Val Phe Gly Glu Ala Val
130                 135                 140

Gly Ala Leu Tyr Ala Asp Lys His Gly Leu Lys Val Thr Cys Leu Arg
145                 150                 155                 160

Ile Gly Asn Phe Gly Asp Val Pro Leu Asp His Arg Arg Ile Ser Ile
                165                 170                 175

Trp Leu Lys Pro Glu Asp Leu Val Gln Leu Cys Gln Ile Gly Leu Glu
                180                 185                 190

His Pro Asp Ile His Phe Glu Ile Phe Tyr Gly Val Ser Leu Asn Glu
                195                 200                 205

Arg Ala Trp Trp Asp Asn His Arg Ala Tyr Glu Phe Gly Tyr Arg Pro
                210                 215                 220

Thr Gly Arg Ser Glu Asp His Val Ala His Ala Met Ala Glu Gln Ala
225                 230                 235                 240

Lys Leu Lys Pro Asp Pro Ile Gly Asp His Tyr Gln Gly Gly Ala Phe
                245                 250                 255
```

Cys Ser Asn Glu Phe Asp Gly Asp Thr Ser Arg Ile Ile Asp Trp Asn
            260                 265                 270

Lys Arg

<210> SEQ ID NO 31
<211> LENGTH: 398
<212> TYPE: PRT
<213> ORGANISM: Saccharomyces cerevisiae

<400> SEQUENCE: 31

Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
            20                  25                  30

Val Ala Leu Lys Gly Ala Leu Ala Lys Val Pro Glu Leu Asp Ala Ser
        35                  40                  45

Lys Asp Phe Asp Glu Ile Ile Phe Gly Asn Val Leu Ser Ala Asn Leu
    50                  55                  60

Gly Gln Ala Pro Ala Arg Gln Val Ala Leu Ala Ala Gly Leu Ser Asn
65                  70                  75                  80

His Ile Val Ala Ser Thr Val Asn Lys Val Cys Ala Ser Ala Met Lys
                85                  90                  95

Ala Ile Ile Leu Gly Ala Gln Ser Ile Lys Cys Gly Asn Ala Asp Val
            100                 105                 110

Val Val Ala Gly Gly Cys Glu Ser Met Thr Asn Ala Pro Tyr Tyr Met
        115                 120                 125

Pro Ala Ala Arg Ala Gly Ala Lys Phe Gly Gln Thr Val Leu Val Asp
    130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Glu
                165                 170                 175

Gln Gln Asp Asn Phe Ala Ile Glu Ser Tyr Gln Lys Ser Gln Lys Ser
            180                 185                 190

Gln Lys Glu Gly Lys Phe Asp Asn Glu Ile Val Pro Val Thr Ile Lys
        195                 200                 205

Gly Phe Arg Gly Lys Pro Asp Thr Gln Val Thr Lys Asp Glu Glu Pro
    210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Ala Val Ile Leu Val Ser Glu Lys Val Leu Lys Glu Lys
            260                 265                 270

Asn Leu Lys Pro Leu Ala Ile Ile Lys Gly Trp Gly Glu Ala Ala His
        275                 280                 285

Gln Pro Ala Asp Phe Thr Trp Ala Pro Ser Leu Ala Val Pro Lys Ala
    290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
            340                 345                 350

```
Gly His Pro Leu Gly Cys Ser Gly Ala Arg Val Val Thr Leu Leu
            355                 360                 365

Ser Ile Leu Gln Gln Glu Gly Gly Lys Ile Gly Val Ala Ala Ile Cys
370                 375                 380

Asn Gly Gly Gly Ala Ser Ser Ile Val Ile Glu Lys Ile
385                 390                 395

<210> SEQ ID NO 32
<211> LENGTH: 491
<212> TYPE: PRT
<213> ORGANISM: Saccharomyces cerevisiae

<400> SEQUENCE: 32

Met Lys Leu Ser Thr Lys Leu Cys Trp Cys Gly Ile Lys Gly Arg Leu
1               5                   10                  15

Arg Pro Gln Lys Gln Gln Leu His Asn Thr Asn Leu Gln Met Thr
            20                  25                  30

Glu Leu Lys Lys Gln Lys Thr Ala Glu Gln Lys Thr Arg Pro Gln Asn
            35                  40                  45

Val Gly Ile Lys Gly Ile Gln Ile Tyr Ile Pro Thr Gln Cys Val Asn
50                  55                  60

Gln Ser Glu Leu Glu Lys Phe Asp Gly Val Ser Gln Gly Lys Tyr Thr
65                  70                  75                  80

Ile Gly Leu Gly Gln Thr Asn Met Ser Phe Val Asn Asp Arg Glu Asp
                85                  90                  95

Ile Tyr Ser Met Ser Leu Thr Val Leu Ser Lys Leu Ile Lys Ser Tyr
            100                 105                 110

Asn Ile Asp Thr Asn Lys Ile Gly Arg Leu Glu Val Gly Thr Glu Thr
        115                 120                 125

Leu Ile Asp Lys Ser Lys Ser Val Lys Ser Val Leu Met Gln Leu Phe
130                 135                 140

Gly Glu Asn Thr Asp Val Glu Gly Ile Asp Thr Leu Asn Ala Cys Tyr
145                 150                 155                 160

Gly Gly Thr Asn Ala Leu Phe Asn Ser Leu Asn Trp Ile Glu Ser Asn
                165                 170                 175

Ala Trp Asp Gly Arg Asp Ala Ile Val Val Cys Gly Asp Ile Ala Ile
            180                 185                 190

Tyr Asp Lys Gly Ala Ala Arg Pro Thr Gly Gly Ala Gly Thr Val Ala
        195                 200                 205

Met Trp Ile Gly Pro Asp Ala Pro Ile Val Phe Asp Ser Val Arg Ala
210                 215                 220

Ser Tyr Met Glu His Ala Tyr Asp Phe Tyr Lys Pro Asp Phe Thr Ser
225                 230                 235                 240

Glu Tyr Pro Tyr Val Asp Gly His Phe Ser Leu Thr Cys Tyr Val Lys
                245                 250                 255

Ala Leu Asp Gln Val Tyr Lys Ser Tyr Ser Lys Lys Ala Ile Ser Lys
            260                 265                 270

Gly Leu Val Ser Asp Pro Ala Gly Ser Asp Ala Leu Asn Val Leu Lys
        275                 280                 285

Tyr Phe Asp Tyr Asn Val Phe His Val Pro Thr Cys Lys Leu Val Thr
290                 295                 300

Lys Ser Tyr Gly Arg Leu Leu Tyr Asn Asp Phe Arg Ala Asn Pro Gln
305                 310                 315                 320

Leu Phe Pro Glu Val Asp Ala Glu Leu Ala Thr Arg Asp Tyr Asp Glu
                325                 330                 335
```

-continued

```
Ser Leu Thr Asp Lys Asn Ile Glu Lys Thr Phe Val Asn Val Ala Lys
                340                 345                 350

Pro Phe His Lys Glu Arg Val Ala Gln Ser Leu Ile Val Pro Thr Asn
            355                 360                 365

Thr Gly Asn Met Tyr Thr Ala Ser Val Tyr Ala Ala Phe Ala Ser Leu
        370                 375                 380

Leu Asn Tyr Val Gly Ser Asp Leu Gln Gly Lys Arg Val Gly Leu
385                 390                 395                 400

Phe Ser Tyr Gly Ser Gly Leu Ala Ala Ser Leu Tyr Ser Cys Lys Ile
                405                 410                 415

Val Gly Asp Val Gln His Ile Ile Lys Glu Leu Asp Ile Thr Asn Lys
            420                 425                 430

Leu Ala Lys Arg Ile Thr Glu Thr Pro Lys Asp Tyr Glu Ala Ala Ile
        435                 440                 445

Glu Leu Arg Glu Asn Ala His Leu Lys Lys Asn Phe Lys Pro Gln Gly
    450                 455                 460

Ser Ile Glu His Leu Gln Ser Gly Val Tyr Tyr Leu Thr Asn Ile Asp
465                 470                 475                 480

Asp Lys Phe Arg Arg Ser Tyr Asp Val Lys Lys
                485                 490

<210> SEQ ID NO 33
<211> LENGTH: 160
<212> TYPE: PRT
<213> ORGANISM: Taxus wallichiana var. chinensis

<400> SEQUENCE: 33

Gln Ile Pro Val Gly Val Ala Gly Pro Leu Leu Leu Asn Gly Phe Glu
1               5                   10                  15

Tyr Met Val Pro Met Ala Thr Thr Glu Gly Cys Leu Val Ala Ser Thr
            20                  25                  30

Asn Arg Gly Cys Lys Ala Ile His Met Cys Gly Gly Ala Thr Ser Ile
        35                  40                  45

Leu Leu Arg Asp Gly Met Thr Arg Ala Pro Val Val Arg Phe Gln Ser
    50                  55                  60

Ala Lys Arg Ala Ala Asp Leu Lys Tyr Tyr Ile Glu Asp Pro Thr Asn
65                  70                  75                  80

Ala Glu Asn Leu Ser His Ile Phe Asn Arg Thr Thr Arg Phe Gly Arg
                85                  90                  95

Leu Gln Gly Ile Gln Cys Ala Ile Ala Gly Lys Asn Leu Tyr Met Arg
            100                 105                 110

Phe Cys Cys Phe Thr Gly Asp Ala Met Gly Met Asn Met Val Ser Lys
        115                 120                 125

Gly Val Gln Asn Val Leu Asp Tyr Leu Gln Thr Val Phe Pro Asp Met
    130                 135                 140

Asp Val Ile Ser Val Ser Gly Asn Tyr Cys Ala Asp Lys Lys Pro Ala
145                 150                 155                 160

<210> SEQ ID NO 34
<211> LENGTH: 443
<212> TYPE: PRT
<213> ORGANISM: Saccharomyces cerevisiae

<400> SEQUENCE: 34

Met Ser Leu Pro Phe Leu Thr Ser Ala Pro Gly Lys Val Ile Ile Phe
1               5                   10                  15
```

```
Gly Glu His Ser Ala Val Tyr Asn Lys Pro Ala Val Ala Ala Ser Val
            20                  25                  30

Ser Ala Leu Arg Thr Tyr Leu Leu Ile Ser Glu Ser Ser Ala Pro Asp
            35                  40                  45

Thr Ile Glu Leu Asp Phe Pro Asp Ile Ser Phe Asn His Lys Trp Ser
 50                  55                  60

Ile Asn Asp Phe Asn Ala Ile Thr Glu Asp Gln Val Asn Ser Gln Lys
 65                  70                  75                  80

Leu Ala Lys Ala Gln Gln Ala Thr Asp Gly Leu Ser Gln Glu Leu Val
                85                  90                  95

Ser Leu Leu Asp Pro Leu Leu Ala Gln Leu Ser Glu Ser Phe His Tyr
            100                 105                 110

His Ala Ala Phe Cys Phe Leu Tyr Met Phe Val Cys Leu Cys Pro His
            115                 120                 125

Ala Lys Asn Ile Lys Phe Ser Leu Lys Ser Thr Leu Pro Ile Gly Ala
130                 135                 140

Gly Leu Gly Ser Ser Ala Ser Ile Ser Val Ser Leu Ala Leu Ala Met
145                 150                 155                 160

Ala Tyr Leu Gly Gly Leu Ile Gly Ser Asn Asp Leu Glu Lys Leu Ser
                165                 170                 175

Glu Asn Asp Lys His Ile Val Asn Gln Trp Ala Phe Ile Gly Glu Lys
            180                 185                 190

Cys Ile His Gly Thr Pro Ser Gly Ile Asp Asn Ala Val Ala Thr Tyr
            195                 200                 205

Gly Asn Ala Leu Leu Phe Glu Lys Asp Ser His Asn Gly Thr Ile Asn
            210                 215                 220

Thr Asn Asn Phe Lys Phe Leu Asp Asp Phe Pro Ala Ile Pro Met Ile
225                 230                 235                 240

Leu Thr Tyr Thr Arg Ile Pro Arg Ser Thr Lys Asp Leu Val Ala Arg
                245                 250                 255

Val Arg Val Leu Val Thr Glu Lys Phe Pro Glu Val Met Lys Pro Ile
            260                 265                 270

Leu Asp Ala Met Gly Glu Cys Ala Leu Gln Gly Leu Glu Ile Met Thr
            275                 280                 285

Lys Leu Ser Lys Cys Lys Gly Thr Asp Asp Glu Ala Val Glu Thr Asn
290                 295                 300

Asn Glu Leu Tyr Glu Gln Leu Leu Glu Leu Ile Arg Ile Asn His Gly
305                 310                 315                 320

Leu Leu Val Ser Ile Gly Val Ser His Pro Gly Leu Glu Leu Ile Lys
                325                 330                 335

Asn Leu Ser Asp Asp Leu Arg Ile Gly Ser Thr Lys Leu Thr Gly Ala
            340                 345                 350

Gly Gly Gly Gly Cys Ser Leu Thr Leu Leu Arg Arg Asp Ile Thr Gln
            355                 360                 365

Glu Gln Ile Asp Ser Phe Lys Lys Leu Gln Asp Asp Phe Ser Tyr
            370                 375                 380

Glu Thr Phe Glu Thr Asp Leu Gly Gly Thr Gly Cys Cys Leu Leu Ser
385                 390                 395                 400

Ala Lys Asn Leu Asn Lys Asp Leu Lys Ile Lys Ser Leu Val Phe Gln
                405                 410                 415

Leu Phe Glu Asn Lys Thr Thr Thr Lys Gln Gln Ile Asp Asp Leu Leu
            420                 425                 430
```

```
Leu Pro Gly Asn Thr Asn Leu Pro Trp Thr Ser
        435                 440
```

<210> SEQ ID NO 35
<211> LENGTH: 192
<212> TYPE: PRT
<213> ORGANISM: Homo sapiens

<400> SEQUENCE: 35

```
Met Ala Pro Leu Gly Gly Ala Pro Arg Leu Val Leu Leu Phe Ser Gly
1               5                   10                  15

Lys Arg Lys Ser Gly Lys Asp Phe Val Thr Glu Ala Leu Gln Ser Arg
            20                  25                  30

Leu Gly Ala Asp Val Cys Ala Val Leu Arg Leu Ser Gly Pro Leu Lys
        35                  40                  45

Glu Gln Tyr Ala Gln Glu His Gly Leu Asn Phe Gln Arg Leu Leu Asp
    50                  55                  60

Thr Ser Thr Tyr Lys Glu Ala Phe Arg Lys Asp Met Ile Arg Trp Gly
65                  70                  75                  80

Glu Glu Lys Arg Gln Ala Asp Pro Gly Phe Phe Cys Arg Lys Ile Val
                85                  90                  95

Glu Gly Ile Ser Gln Pro Ile Trp Leu Val Ser Asp Thr Arg Arg Val
            100                 105                 110

Ser Asp Ile Gln Trp Phe Arg Glu Ala Tyr Gly Ala Val Thr Gln Thr
        115                 120                 125

Val Arg Val Val Ala Leu Glu Gln Ser Arg Gln Gln Arg Gly Trp Val
    130                 135                 140

Phe Thr Pro Gly Val Asp Asp Ala Glu Ser Glu Cys Gly Leu Asp Asn
145                 150                 155                 160

Phe Gly Asp Phe Asp Trp Val Ile Glu Asn His Gly Val Glu Gln Arg
                165                 170                 175

Leu Glu Glu Gln Leu Glu Asn Leu Ile Glu Phe Ile Arg Ser Arg Leu
            180                 185                 190
```

<210> SEQ ID NO 36
<211> LENGTH: 396
<212> TYPE: PRT
<213> ORGANISM: Saccharomyces cerevisiae

<400> SEQUENCE: 36

```
Met Thr Val Tyr Thr Ala Ser Val Thr Ala Pro Val Asn Ile Ala Thr
1               5                   10                  15

Leu Lys Tyr Trp Gly Lys Arg Asp Thr Lys Leu Asn Leu Pro Thr Asn
            20                  25                  30

Ser Ser Ile Ser Val Thr Leu Ser Gln Asp Asp Leu Arg Thr Leu Thr
        35                  40                  45

Ser Ala Ala Thr Ala Pro Glu Phe Glu Arg Asp Thr Leu Trp Leu Asn
    50                  55                  60

Gly Glu Pro His Ser Ile Asp Asn Glu Arg Thr Gln Asn Cys Leu Arg
65                  70                  75                  80

Asp Leu Arg Gln Leu Arg Lys Glu Met Glu Ser Lys Asp Ala Ser Leu
                85                  90                  95

Pro Thr Leu Ser Gln Trp Lys Leu His Ile Val Ser Glu Asn Asn Phe
            100                 105                 110

Pro Thr Ala Ala Gly Leu Ala Ser Ser Ala Ala Gly Phe Ala Ala Leu
        115                 120                 125
```

Val Ser Ala Ile Ala Lys Leu Tyr Gln Leu Pro Gln Ser Thr Ser Glu
130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175

Asp Ser Met Ala Val Gln Ile Ala Asp Ser Ser Asp Trp Pro Gln Met
            180                 185                 190

Lys Ala Cys Val Leu Val Ser Asp Ile Lys Lys Asp Val Ser Ser
        195                 200                 205

Thr Gln Gly Met Gln Leu Thr Val Ala Thr Ser Glu Leu Phe Lys Glu
210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
            260                 265                 270

Tyr Met Asn Asp Thr Ser Lys Arg Ile Ile Ser Trp Cys His Thr Ile
        275                 280                 285

Asn Gln Phe Tyr Gly Glu Thr Ile Val Ala Tyr Thr Phe Asp Ala Gly
290                 295                 300

Pro Asn Ala Val Leu Tyr Tyr Leu Ala Glu Asn Glu Ser Lys Leu Phe
305                 310                 315                 320

Ala Phe Ile Tyr Lys Leu Phe Gly Ser Val Pro Gly Trp Asp Lys Lys
                325                 330                 335

Phe Thr Thr Glu Gln Leu Glu Ala Phe Asn His Gln Phe Glu Ser Ser
            340                 345                 350

Asn Phe Thr Ala Arg Glu Leu Asp Leu Glu Leu Gln Lys Asp Val Ala
        355                 360                 365

Arg Val Ile Leu Thr Gln Val Gly Ser Gly Pro Gln Glu Thr Asn Glu
370                 375                 380

Ser Leu Ile Asp Ala Lys Thr Gly Leu Pro Lys Glu
385                 390                 395

<210> SEQ ID NO 37
<211> LENGTH: 368
<212> TYPE: PRT
<213> ORGANISM: Sulfolobus shibatae

<400> SEQUENCE: 37

Met Pro Asp Ile Val Asn Arg Lys Val Glu His Val Glu Ile Ala Ala
1               5                   10                  15

Phe Glu Asn Val Asp Gly Leu Ser Ser Ser Thr Phe Leu Asn Asp Val
                20                  25                  30

Ile Leu Val His Gln Gly Phe Pro Gly Ile Ser Phe Ser Glu Ile Asn
            35                  40                  45

Thr Lys Thr Lys Phe Phe Arg Lys Glu Ile Ser Val Pro Val Met Val
        50                  55                  60

Thr Gly Met Thr Gly Gly Arg Asn Glu Leu Gly Arg Ile Asn Lys Ile
65                  70                  75                  80

Ile Ala Glu Val Ala Glu Lys Phe Gly Ile Pro Met Gly Val Gly Ser
                85                  90                  95

Gln Arg Val Ala Ile Glu Lys Ala Glu Ala Arg Glu Ser Phe Ala Ile
            100                 105                 110

```
Val Arg Lys Val Ala Pro Thr Ile Pro Ile Ile Ala Asn Leu Gly Met
            115                 120                 125

Pro Gln Leu Val Lys Gly Tyr Gly Leu Lys Glu Phe Gln Asp Ala Ile
130                 135                 140

Gln Met Ile Glu Ala Asp Ala Ile Ala Val His Leu Asn Pro Ala Gln
145                 150                 155                 160

Glu Val Phe Gln Pro Glu Gly Glu Pro Glu Tyr Gln Ile Tyr Ala Leu
                165                 170                 175

Glu Lys Leu Arg Asp Ile Ser Lys Glu Leu Ser Val Pro Ile Ile Val
            180                 185                 190

Lys Glu Ser Gly Asn Gly Ile Ser Met Glu Thr Ala Lys Leu Leu Tyr
            195                 200                 205

Ser Tyr Gly Ile Lys Asn Phe Asp Thr Ser Gly Gln Gly Gly Thr Asn
            210                 215                 220

Trp Ile Ala Ile Glu Met Ile Arg Asp Ile Arg Arg Gly Asn Trp Lys
225                 230                 235                 240

Ala Glu Ser Ala Lys Asn Phe Leu Asp Trp Gly Val Pro Thr Ala Ala
                245                 250                 255

Ser Ile Met Glu Val Arg Tyr Ser Val Pro Asp Ser Phe Leu Val Gly
            260                 265                 270

Ser Gly Gly Ile Arg Ser Gly Leu Asp Ala Ala Lys Ala Ile Ala Leu
            275                 280                 285

Gly Ala Asp Ile Ala Gly Met Ala Leu Pro Val Leu Lys Ser Ala Ile
            290                 295                 300

Glu Gly Lys Glu Ser Leu Glu Gln Phe Phe Arg Lys Ile Ile Phe Glu
305                 310                 315                 320

Leu Lys Ala Ala Met Met Leu Thr Gly Ser Lys Asp Val Asp Ala Leu
                325                 330                 335

Lys Lys Thr Ser Ile Val Ile Leu Gly Lys Leu Lys Glu Trp Ala Glu
            340                 345                 350

Tyr Arg Gly Ile Asn Leu Ser Ile Tyr Glu Lys Val Arg Lys Arg Glu
            355                 360                 365

<210> SEQ ID NO 38
<211> LENGTH: 751
<212> TYPE: PRT
<213> ORGANISM: Aspergillus niger

<400> SEQUENCE: 38

Met Tyr Arg Ile Ser Asn Ile Tyr Val Leu Ala Gly Phe Gly Thr Ile
1               5                   10                  15

Gly Gly Ala Leu Phe Gly Phe Asp Val Ser Ser Met Ser Ala Trp Ile
            20                  25                  30

Gly Thr Asp Gln Tyr Leu Glu Tyr Phe Asn His Pro Asp Ser Asp Leu
        35                  40                  45

Gln Gly Gly Ile Thr Ala Ser Met Ser Ala Gly Ser Phe Ala Gly Ala
    50                  55                  60

Leu Ala Ala Gly Phe Ile Ser Asp Arg Ile Gly Arg Arg Tyr Ser Leu
65                  70                  75                  80

Met Leu Ala Cys Cys Ile Trp Val Ile Gly Ala Ala Ile Gln Cys Ser
                85                  90                  95

Ala Gln Asn Val Ala His Leu Val Ala Gly Arg Val Ile Ser Gly Leu
            100                 105                 110

Ser Val Gly Ile Thr Ser Ser Gln Val Cys Val Tyr Leu Ala Glu Leu
```

```
              115                 120                 125
Ala Pro Ala Arg Ile Arg Gly Arg Ile Val Gly Ile Gln Gln Trp Ala
            130                 135                 140
Ile Glu Trp Gly Met Leu Ile Met Tyr Leu Ile Ser Tyr Gly Cys Gly
145                 150                 155                 160
Gln Gly Leu Ala Gly Ala Ala Ser Phe Arg Val Ser Trp Gly Val Gln
                165                 170                 175
Gly Ile Pro Ala Leu Ile Leu Leu Ala Ala Leu Pro Phe Phe Pro Glu
            180                 185                 190
Ser Pro Arg Trp Leu Ala Ser Lys Glu Arg Trp Glu Glu Ala Leu Asp
                195                 200                 205
Thr Leu Ala Leu Leu His Ala Lys Gly Asp Arg Asn Asp Pro Val Val
            210                 215                 220
Gln Val Glu Tyr Glu Val Gln Glu Ala Ala Arg Ile Ala Gln Glu
225                 230                 235                 240
Ala Lys Asp Ile Ser Phe Phe Ser Leu Phe Gly Pro Lys Ile Trp Lys
                245                 250                 255
Arg Thr Leu Cys Gly Val Ser Ala Gln Val Trp Gln Gln Leu Leu Gly
            260                 265                 270
Gly Asn Val Ala Met Tyr Tyr Val Val Tyr Ile Phe Asn Met Ala Gly
            275                 280                 285
Met Ser Gly Asn Thr Thr Leu Tyr Ser Ser Ala Ile Gln Tyr Val Ile
290                 295                 300
Phe Leu Val Thr Thr Gly Thr Ile Leu Pro Phe Val Asp Arg Ile Gly
305                 310                 315                 320
Arg Arg Leu Leu Leu Leu Thr Gly Ser Val Leu Cys Met Ala Cys His
                325                 330                 335
Phe Ala Ile Ala Gly Leu Met Ala Ser Arg Gly His His Val Asp Ser
            340                 345                 350
Val Asp Gly Asn Ala Asn Leu Lys Trp Ser Ile Thr Gly Pro Pro Gly
            355                 360                 365
Lys Gly Val Ile Ala Cys Ser Tyr Ile Phe Val Ala Val Tyr Gly Phe
            370                 375                 380
Thr Trp Ala Pro Val Ala Trp Ile Tyr Ala Ser Glu Val Phe Pro Leu
385                 390                 395                 400
Lys Tyr Arg Ala Lys Gly Val Gly Leu Ser Ala Ala Gly Asn Trp Ile
                405                 410                 415
Phe Asn Phe Ala Leu Ala Tyr Phe Val Ala Pro Ala Phe Thr Asn Ile
            420                 425                 430
Gln Trp Lys Thr Tyr Ile Ile Phe Gly Val Phe Cys Thr Val Met Thr
            435                 440                 445
Phe His Val Phe Phe Phe Tyr Pro Glu Thr Ala Arg Arg Ser Leu Glu
            450                 455                 460
Asp Ile Asp Leu Met Phe Glu Thr Asp Met Lys Pro Trp Lys Thr His
465                 470                 475                 480
Gln Ile His Asp Arg Phe Gly Glu Glu Val Glu Arg His Lys His Lys
                485                 490                 495
Asp Met Ala Asp Gln Glu Lys Gly Val Val Ser Thr His Asp Glu Met
            500                 505                 510
Ala Gly Ser Val Ser Lys Gly Glu Glu Leu Ile Lys Glu Asn Met Arg
            515                 520                 525
Met Lys Val Val Met Glu Gly Ser Val Asn Gly His Gln Phe Lys Cys
            530                 535                 540
```

```
Thr Gly Glu Gly Glu Gly Asn Pro Tyr Met Gly Thr Gln Thr Met Arg
545                 550                 555                 560

Ile Lys Val Ile Glu Gly Pro Leu Pro Phe Ala Phe Asp Ile Leu
            565                 570                 575

Ala Thr Ser Phe Met Tyr Gly Ser Arg Thr Phe Ile Lys Tyr Pro Lys
            580                 585                 590

Gly Ile Pro Asp Phe Phe Lys Gln Ser Phe Pro Glu Gly Phe Thr Trp
            595                 600                 605

Glu Arg Val Thr Arg Tyr Glu Asp Gly Val Val Thr Val Met Gln
610                 615                 620

Asp Thr Ser Leu Glu Asp Gly Cys Leu Val Tyr His Val Gln Val Arg
625                 630                 635                 640

Gly Val Asn Phe Pro Ser Asn Gly Pro Val Met Gln Lys Lys Thr Lys
            645                 650                 655

Gly Trp Glu Pro Asn Thr Glu Met Met Tyr Pro Ala Asp Gly Gly Leu
            660                 665                 670

Arg Gly Tyr Thr His Met Ala Leu Lys Val Asp Gly Gly His Leu
            675                 680                 685

Ser Cys Ser Phe Val Thr Thr Tyr Arg Ser Lys Lys Thr Val Gly Asn
            690                 695                 700

Ile Lys Met Pro Gly Ile His Ala Val Asp His Arg Leu Glu Arg Leu
705                 710                 715                 720

Glu Glu Ser Asp Asn Glu Met Phe Val Gln Arg Glu His Ala Val
                725                 730                 735

Ala Lys Phe Ala Gly Leu Gly Gly Met Asp Glu Leu Tyr Lys
            740                 745                 750

<210> SEQ ID NO 39
<211> LENGTH: 540
<212> TYPE: PRT
<213> ORGANISM: Rhodotorula toruloides NP11

<400> SEQUENCE: 39

Met Ala Pro Pro Lys Arg Ser Leu Val Thr Arg Phe Thr Thr Asn
1               5                   10                  15

Asn Tyr Val Ala Gly Met Leu Pro Thr Leu Ala Gly Phe Met Phe Gly
            20                  25                  30

Cys Asp Leu Ile Ser Met Ser Gly Gln Val Ser Asn Pro Ala Tyr Leu
            35                  40                  45

Glu Gln Phe Asn His Pro Asn Ser Asn Leu Gln Gly Ala Ile Thr Ala
            50                  55                  60

Ala Met Pro Ala Gly Ser Phe Gly Gly Ala Leu Ile Asn Ser Tyr Leu
65              70                  75                  80

Ser Asp Lys Ile Gly Arg Lys Trp Cys Ile Ile Ser Gly Trp Val
            85                  90                  95

Trp Val Leu Gly Cys Ile Ile Gln Ala Ala Ser Phe Asn Val Arg Thr
            100                 105                 110

Leu Val Ala Gly Arg Val Val Ala Gly Leu Ala Val Gly Leu Gly Ser
            115                 120                 125

Ala Ile Val Thr Ile Tyr Gln Ala Glu Ile Thr Arg Pro Ala Ile Arg
            130                 135                 140

Gly Arg Ile Val Ala Thr Gln Gln Leu Ala Ile Thr Phe Ser Glu Leu
145                 150                 155                 160

Leu Gln Tyr Phe Val Ser Phe Gly Cys Ser Tyr Ile Ala Asn Asp Ala
```

```
                165                 170                 175
Ser Phe Arg Met Pro Trp Ala Leu Gln Ala Ile Pro Gly Leu Ile Leu
                180                 185                 190

Gly Ile Leu Met Phe Ala Phe Pro Glu Ser Pro Arg Trp Leu Met Asp
            195                 200                 205

His Gly Arg Glu Glu Gln Ala Leu Gln Ile Leu Ala Asp Val His Ala
        210                 215                 220

Glu Gly Glu Thr Glu Asn Glu Leu Val Gln Leu Glu Tyr Leu Glu Ile
225                 230                 235                 240

Lys Arg Gln Val Glu Phe Asp Arg Thr Leu Ala Ala Arg Ser Tyr Leu
                245                 250                 255

Asp Leu Leu Lys Pro Glu Tyr Phe Arg Arg Thr Phe Leu Ala Cys Ile
            260                 265                 270

Thr Gln Met Trp Ser Gln Leu Ser Gly Asn Asn Val Met Met Tyr Tyr
        275                 280                 285

Val Val Tyr Val Phe Gln Ser Ala Gly Ile Val Gly Arg Arg Gly Gly
290                 295                 300

Leu Ile Ala Ser Gly Val Gln Tyr Ala Leu His Phe Val Ala Thr Ile
305                 310                 315                 320

Pro Ala Val Ile Trp Val Asp Lys Trp Gly Arg Arg Pro Thr Met Met
                325                 330                 335

Ile Gly Met Phe Ala Met Gly Cys Cys Leu Phe Ala Val Gly Ala Ile
            340                 345                 350

Gln Ala Thr Leu Gly Gln Pro Leu His Ser Gly Ser Ser Ala Thr Thr
        355                 360                 365

Thr Trp Thr Ile Val Gly His Thr Ser Ala Arg Asn Ala Val Ile Val
370                 375                 380

Leu Ser Tyr Ile Phe Val Met Leu Phe Ser Met Thr Tyr Gly Pro Cys
385                 390                 395                 400

Ser Trp Ile Phe Pro Ser Glu Ile His His Met Arg Val Arg Gly Lys
                405                 410                 415

Ala Val Ser Ala Ala Thr Ala Thr Asn Trp Met Phe Asn Phe Ala Leu
            420                 425                 430

Ala Trp Ser Thr Pro Pro Ala Phe Arg Asn Ile Gln Tyr Lys Thr Tyr
        435                 440                 445

Phe Val Tyr Gly Thr Phe Cys Ile Cys Ala Ala Ile Asn Val Phe Phe
450                 455                 460

Met Phe Pro Glu Thr Lys Gly Arg Thr Leu Glu Glu Met Asp Asp Leu
465                 470                 475                 480

Phe Ala Ala Gly His Ala Phe Ser Ala Trp Arg Leu Ser Ser Val Pro
                485                 490                 495

Lys Lys Thr Leu Ala Glu Val Glu Ala Glu Val Ala Asp Ser Asp Met
            500                 505                 510

Arg Ser Glu Gly Asp Asn Lys His Thr Met Asn His Ile Glu Lys Ser
        515                 520                 525

Ser Ser Asp His Leu Glu Gln Ala Gly Arg His Val
530                 535                 540
```

ENGINEERED MICROORGANISMS FOR PRODUCTION OF COMMODITY CHEMICALS AND CELLULAR BIOMASS

CROSS-REFERENCE

This application is a national stage filing under 35 U.S.C. § 371 of PCT/US2017/054759, filed Oct. 2, 2017, which claims the benefit of U.S. Provisional Patent Application No. 62/403,523, filed Oct. 3, 2016, which applications are incorporated herein by reference in their entirety.

INTRODUCTION

Citrus pulp and sugar beet pulp are pectin-rich agricultural wastes that are globally produced in significant amounts and have the potential to contribute towards the greater bioeconomy as a source of raw, inexpensive carbohydrate biomass. In the 2014/2015 orange harvest, Brazil and the USA generated 1.4 million tons of orange juice concentrate (65° Brix), corresponding to about 1.9 million metric tons of citrus pulp (dry matter). Likewise, the 2013 worldwide sugar beet pulp harvest generated 246 million metric tons of sugar beet, resulting in 12.3 million metric tons of beet pulp (dry matter). There is currently limited use for these waste streams. In some cases, pulps are dried, pelleted, and repurposed as an inexpensive livestock feed, however this application is barely profitable due to high production costs. There is a need in the art for technologies that can cost-effectively transform pectin-rich waste streams into value-added products of commercial interest.

SUMMARY

The present disclosure provides methods producing various commodity products, the methods involving culturing a host cell that is genetically modified to produce a uronate dehydrogenase (UDH) that converts a sugar acid (e.g., an aldaric acid, a uronic acid) to its corresponding 1,5-aldonolactone, that uses $NADP^+$ or $NAD^+$ as a cofactor, and that produces NADPH or NADH, respectively, where the host cell coexpresses an endogenous or a heterologous reductase that utilizes the produced NADPH or NADH to generate the commodity product or a precursor thereof. The present disclosure provides genetically modified microbial host cells that are genetically modified to convert D-galacturonic acid to glycerol. The present disclosure provides a method of producing downstream products of glycerol and pyruvate in a genetically modified microbial host cell, the method involving culturing a genetically modified microbial host cell of the present disclosure in a culture medium comprising D-galacturonic acid. The present disclosure provides a host cell genetically modified to produce a modified uronate dehydrogenase that produces NADPH. The present disclosure provides variant UDH polypeptides that utilize $NADP^+$, nucleic acids and recombinant expression vectors encoding the variant UDH polypeptides; and host cells genetically modified with the nucleic acids or recombinant expression vectors.

Pectin-rich agricultural waste streams are composed of several classes of polysaccharides that can be cheaply and efficiently depolymerized into their component monosaccharides via enzymatic, chemical and/or thermal treatment prior to fermentation and bioconversion to chemical bioproducts. Pectin is the major polysaccharide found in the soft tissues of plants, such as the rinds of citrus fruit and pulp of sugar beets. The backbone of a plant pectin is a linear chain of α-(1-4)-linked D-galacturonic acid units. Pectin-rich waste streams often contain the polysaccharides cellulose and hemicellulose, whose backbone sugars are largely composed of D-glucose (also known as dextrose) and xylose, respectively. For example, the depolymerization of the component pectin and cellulose in orange pulp waste via enzymatic and steam treatment results in a heterogeneous mixture of D-galacturonic acid, D-glucose, D-fructose, and other minor monosaccharide fractions.

Many naturally-occurring microorganisms have been characterized for their ability to utilize D-galacturonic acid; however, these organisms do not generate useful metabolic products in appreciable amounts and/or are physiologically stressed in pectin hydrolysate conditions. For example, *Escherichia coli* uses the bacterial isomerase pathway for D-galacturonic acid catabolism and accumulates mixed acid fermentation byproducts, such as ethanol, lactate, succinate, acetate and formate. However, due to low inhibitor tolerance and pH sensitivity, *E. coli* fermentations must be buffered to a neutral pH. The resulting bioprocesses are susceptible to contaminating microbes and have high operating costs compared to unbuffered, anaerobic processes.

Engineered *E. coli* and filamentous fungi with heterologously expressed enzymes or modified metabolisms have been characterized for their ability to bioconvert D-galacturonic acid to useful bioproducts, such as meso-galactaric (mucic) acid, L-galactonate, and L-ascorbic acid. These strain technologies have not reached their full commercial potential likely due to flux/redox imbalances and an inability to perform economically favorable anaerobic fermentations. Additionally, filamentous fungi can require long growth phases, slowing the productivity of bioprocesses.

Yeasts, such as *Saccharomyces cerevisiae*, are a preferred microorganism for commercial scale fermentation processes for several reasons, including resistance to contaminants, bacteriophages, chemicals acting as growth inhibitors, and low pH. It also tolerates high osmotic pressures, enabling the use of a concentrated culture medium, and dense concentrations of bioconversion products. Additionally, yeasts can accumulate biomass quickly and in an anaerobic fermentation. Consequently, the expression of heterologous enzymes for bioconversion of D-galacturonic acid to useful bioproducts in yeast is the preferred path for industrial pectin waste hydrolysate utilization. Unfortunately, wild-type *Saccharomyces cerevisiae* is unable to utilize D-galacturonic acid as a carbon source. In pectin-fed yeast fermentations, D-galacturonic acid collects in high amounts in the fermentation broths and is not converted to downstream products.

The present disclosure provides efficient microbial strain technologies and metabolic fermentation, for the bioconversion of pectin-rich waste streams to useful bio-based commodity chemicals and biofuels. The present disclosure provides microbial host cells that are genetically modified to convert D-galacturonic acid to useful metabolic products, such as meso-galactaric acid (aka mucic acid), L-galactonate, 2-keto-3-deoxy-1-galactonate, pyruvate, and glycerol. Methods are described for producing meso-galactaric acid in a metabolically redox-balanced and highly productive manner that allows for anaerobic fermentation. In some cases, e.g., where the microbial host is a yeast, such as *S. cerevisiae*, heterologous expression of a D-galacturonic acid transporter is described; this heterologous D-galacturonic acid transporter provides for co-utilization of D-galacturonic acid and D-glucose, the major monosaccharides found in pectin waste hydrolysate. Additionally, in cases where the microbial host is a yeast, such as *S. cerevisiae*, the heterologous expression of catabolic enzymes provides for growth of the yeast strain on D-galacturonic acid.

In addition to the beneficial environmental impact of utilizing a waste-stream, the fermentation technologies described herein achieve three design goals set to optimize the productivity of bioconversions and economic viability. First, the technology allows for anaerobic fermentation, eliminating the need for culture oxygenation. This lowers operating costs by simplifying the metabolic requirements of high-density fermentation cultures. Second, co-utilization of the major component monosaccharides in the hydrolysate broth (for example, D-galacturonic acid and D-glucose; or D-galacturonic acid and D-fructose) allows for productive conversion of the predominant, energy-rich biomass sugars. Third, fermentations can be conducted at low pH, discouraging contaminant growth and eliminating the need to buffer the hydrolysate mixture, which will likely equilibrate at pH of 3.5 (the pKa of D-galacturonic acid).

BRIEF DESCRIPTION OF THE DRAWINGS

FIG. 2-FIG. 5 provide amino acid sequences of D-galacturonic acid transporters (SEQ ID NOs:1-4).

FIG. 6-FIG. 8 provide amino acid sequences of D-galacturonic acid reductases (SEQ ID NOs: 5-7).

FIG. 9-FIG. 12 provide amino acid sequences of L-galactonate dehydratase (SEQ ID NOs: 8-11).

FIG. 13-FIG. 15 provide amino acid sequences of 2-keto-3-deoxy-1-galactonate aldolases (SEQ ID NOs: 12-14).

FIG. 16-FIG. 18 provide amino acid sequences of L-glyceraldehyde reductases (SEQ ID NOs: 15-17).

FIG. 19 provides an amino acid sequence of *Pseudomonas syringae* uronate dehydrogenase (UDH) (SEQ ID NO: 18).

FIG. 20 provides an amino acid sequence of *Limnohabitans* sp. Rim47 UDH (SEQ ID NO: 19).

FIG. 21 provides an amino acid sequence of a variant UDH that utilizes NADP$^+$ (SEQ ID NO: 20).

FIG. 22 provides an amino acid sequence of a MIOX polypeptide (SEQ ID NO: 21).

FIG. 23 provides an amino acid sequence of a MIPS polypeptide (SEQ ID NO: 22).

FIGS. 24A and 24B provide amino acid sequences of 1,3-propanediol oxidoreductases. FIG. 24A: SEQ ID NO: 23; FIG. 24B: SEQ ID NO: 24

FIG. 28 is a schematic depiction of use of UDH as a redox tool to redirect reducing equivalents.

FIG. 39 depicts *E. coli* production of L-galactonate by expression on *A. niger* D-galacturonic acid reductase (GAAA).

FIG. 42 depicts expression of *A. niger* An14g04280 transporter (amino acid sequence depicted in FIG. 3) in *S. cerevisiae* expressing D-galUA consumption pathway allows for import of D-galacturonate while co-consuming glucose.

FIG. 47-52 provide amino acid sequences of UDH polypeptides (SEQ ID NOs: 25-30).

FIG. 53 provides results from end-point anaerobic yeast fermentation.

FIG. 55 provides an amino acid sequence of a D-galacturonic acid transporter.

FIG. 57 provides an amino acid sequence of a D-galacturonic acid transporter.

DEFINITIONS

Figure 1:
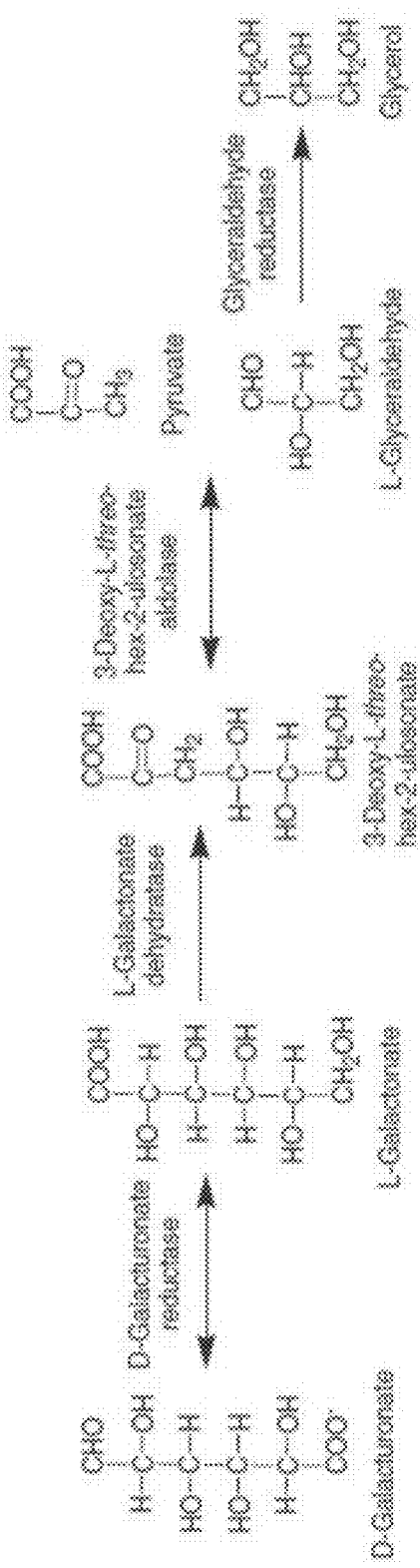
FIG. 1 is a schematic depiction of conversion of D-galacturonic acid to glycerol.

The terms "nucleic acid," used herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus. The term "heterologous enzyme" refers to an enzyme that is not normally found in a given cell in nature. The term encompasses an enzyme that is: (a) exogenous to a given cell (i.e., encoded by a nucleotide sequence that is not naturally present in the host cell or not naturally present in a given context in the host cell); and (b) naturally found in the host cell (e.g., the enzyme is encoded by a nucleotide sequence that is endogenous to the cell) but that is produced in an unnatural amount (e.g., greater or lesser than that naturally found) in the host cell.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more metabolic pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation.

A "genetically modified host cell" (also referred to as a "recombinant host cell") is a host cell into which has been introduced a heterologous nucleic acid, e.g., a heterologous recombinant expression vector. For example, a eukaryotic host cell is a genetically modified eukaryotic host cell (e.g., a genetically modified yeast cell; a genetically modified fungal cell), by virtue of introduction into a suitable eukaryotic host cell (e.g., a yeast cell) of a heterologous nucleic acid, e.g., an exogenous nucleic acid that is foreign to (not normally found in nature in) the eukaryotic host cell, or a recombinant nucleic acid that is not normally found in the eukaryotic host cell.

The term "in vitro", as used herein in connection with a host cell (e.g., a genetically modified host cell of the present disclosure), refers to a living cell that is not within a multicellular organism, and that can carry out a process (e.g., an anabolic or catabolic process) as described herein. An "in vitro" host cell can be present in a container (e.g., a test tube (e.g., an Eppendorf tube), a fermentation flask, a fermentation vat, etc. The term "in vitro", as used herein in connection with a host cell that is genetically modified to carry a process (e.g., an anabolic or catabolic process) as described herein, is in contrast to a cell-free process that is carried out not within a cell, but in the absence of a cell. An "in vitro" host cell (e.g., a genetically modified host cell of the present disclosure) is generally speaking a unicellular organism (e.g., a bacterium, a yeast, a fungus), e.g., a cell that can grow in suspension as a unicellular entity.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bio. 215:403-10.

The terms "carbonaceous material" or "biomass" as used herein includes a biological materials that can be converted into a biofuel, chemical or other end product. One exemplary source of carbonaceous material is an agricultural product. One exemplary source of carbonaceous material is plant matter. Plant matter can be, for example, woody plant matter, non-woody plant matter, cellulosic material, lignocellulosic material, hemicellulosic material, carbohydrates, pectin, starch, inulin, fructans, glucans, corn, sugar cane, grasses, switchgrass, bamboo, and material derived from these. Plant matter can also be residual spent solids from alcoholic fermentation from materials such as corn and which contain lignin, starch, cellulose, hemicellulose, and proteins. Plant matter can be further described by reference to the chemical species present, such as proteins, polysaccharides (such as chitin) and oils. Polysaccharides include polymers of various monosaccharides and derivatives of monosaccharides including glucose, fructose, lactose, galacturonic acid, rhamnose, etc. Plant matter also includes agricultural waste byproducts or side streams such as pomace, corn steep liquor, corn steep solids, corn stover, corn stillage, corn cobs, corn grain, bagasse, soy stems, soy leaves, soy pods, soy molasses, soy flakes, pennycress seeds or seed cake, distillers grains, peels, pits, fermentation waste, wood chips, saw dust, wood flour, wood pulp, paper pulp, paper pulp waste steams straw, lumber, sewage, seed cake, husks, rice hulls, leaves, grass clippings, food waste restaurant waste, or cooking oil. These materials can come from farms, forestry, industrial sources, households, etc. Plant matter also includes maltose, corn syrup, Distillers Dried Solubles (DDS), Distillers Dried Grains (DDG), Condensed Distillers Solubles (CDS), Distillers Wet Grains (DWG), or Distillers Dried Grains with Solubles (DDGS).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a genetically modified host cell" includes a plurality of such cells and reference to "the D-galacturonic acid reductase" includes reference to one or more D-galacturonic acid reductases and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods producing various commodity products, the methods involving culturing a host cell that is genetically modified to produce a uronate dehydrogenase (UDH) that converts a sugar acid (e.g., an aldaric acid, a uronic acid) to its corresponding 1,5-aldonolactone, that uses $NADP^+$ or $NAD^+$ as a cofactor, and that produces NADPH or NADH, respectively, where the host cell coexpresses an endogenous or a heterologous reductase that utilizes the produced NADPH or NADH to generate the commodity product or a precursor thereof. The present disclosure provides genetically modified microbial host cells that are genetically modified to convert D-galacturonic acid to glycerol. The present disclosure provides a method of producing downstream products of glycerol and pyruvate in a genetically modified microbial host cell, the method involving culturing a genetically modified microbial host cell of the present disclosure in a culture medium comprising D-galacturonic acid. The present disclosure provides host cell genetically modified to produce a modified uronate dehydrogenase that produces NADPH. The present disclosure provides variant UDH polypeptides that utilize $NADP^+$, nucleic acids and recombinant expression vectors encoding the variant UDH polypeptides; and host cells genetically modified with the nucleic acids or recombinant expression vectors.

Genetically Modified Host Cells for Cofactor Balancing in Production of Commodity Products or Precursors Thereof The present disclosure provides a genetically modified host cell (e.g., an in vitro microbial host cell) that is genetically modified with a uronate dehydrogenase (UDH) that utilizes $NADP^+$ or $NAD^+$ as a co-factor. The UDH is a heterologous UDH, which may be a variant UDH. In some cases, the UDH is a variant (or "modified") UDH. In some cases, the UDH utilizes both $NADP^+$ and $NAD^+$. In some cases, the UDH utilizes $NADP^+$ preferentially over $NAD^+$. The UDH can function as a redox engineering tool for co-production of mucic acid and reduced metabolites from pectin biomass. Thus, the genetically modified host cell can produce a variety of anabolic pathway products that are produced by anabolic pathways that require a reductase enzyme, and a cofactor such as NADPH or NADH, for production of the anabolic pathway product. The genetically modified host cells can produce a variety of products anaerobically. For example, a genetically modified host cell of the present disclosure (where the genetically modified host cell is genetically modified to produced a heterologous UDH that utilizes $NADP^+$ or $NAD^+$ as a co-factor) provides for redirection of reducing equivalents via UDH activity in anaerobic glycerol to 1,3-propanediol fermentations. The UDH can function as a redox-coupling tool by $NADP^+$ utilization. The heterologous UDH can convert D-glucuronic acid to D-glucaro-1,5-lactone.

The present disclosure provides a genetically modified host cell (e.g., an in vitro microbial host cell) that converts D-galacturonic acid to mucic acid. The genetically modified host cell is capable of producing mucic acid anaerobically. The genetically modified host cell is genetically modified with a heterologous uronate dehydrogenase (UDH) that utilizes $NADP^+$ or $NAD^+$ as a co-factor instead of NADPH or NADH. Thus, the genetically modified host cell can produce mucic acid anaerobically. The mucic acid so produced can be further converted to adipic acid through the oxorhenium-complex-catalyzed deoxydehydration (DODH) reaction and subsequent Pt/C-catalyzed transfer hydrogenation. Li et al. (2014) *Angew. Chemie Int'l Edition* 53:4200; and WO 2015/084265. Adipic acid can be made into nylon (e.g., nylon-6,6 polyamide).

The present disclosure provides a genetically modified host cell (e.g., an in vitro microbial host cell) genetically modified with: a) a heterologous nucleic acid comprising a nucleotide sequence encoding a heterologous modified UDH, where the heterologous modified UDH uses NADP$^+$ or NAD$^+$ as a cofactor, and produces NADPH or NADH, respectively, and wherein the heterologous modified UDH converts a sugar acid (e.g., an aldaric acid, a uronic acid) to its corresponding 1,5-aldonolactone, wherein the host cell coexpresses an endogenous or a heterologous reductase that utilizes the produced NADPH or NADH; and b) one or more heterologous nucleic acids comprising heterologous nucleotide sequences encoding one or more enzymes of an anabolic pathway, wherein the anabolic pathway requires the reductase that utilizes the produced NADPH or NADH. As noted above, the heterologous modified UDH converts a sugar acid (e.g., an aldaric acid, a uronic acid) to its corresponding 1,5-aldonolactone. In some cases, the sugar acid is D-galacturonic acid, and the 1,-5-aldonolactone is D-galactaro-1,5-lactone. Thus, e.g., in some cases, the heterologous modified UDH converts D-galacturonate to D-galactaro-1,5-lactone. In some cases, the sugar acid is D-glucuronic acid, and the 1,5-aldonolactone is D-glucaro-1,5-lactone. Thus, in some cases, the heterologous modified UDH converts D-glucuronic acid to D-glucaro-1,5-lactone. In some cases, the sugar acid is D-guluronic acid, and the 1,5-aldonolactone is D-gularo-1,5-lactone.

The present disclosure provides a genetically modified host cell (e.g., an in vitro microbial host cell) genetically modified with: a) a heterologous nucleic acid comprising a nucleotide sequence encoding a heterologous modified UDH, where the heterologous modified UDH uses NADP$^+$ or NAD$^+$ as a cofactor, and produces NADPH or NADH, respectively, and wherein the heterologous modified UDH converts a sugar acid (e.g., an aldaric acid, a uronic acid) to its corresponding 1,5-aldonolactone, wherein the host cell coexpresses an endogenous or a heterologous reductase that utilizes the produced NADPH or NADH; and b) one or more heterologous nucleic acids comprising heterologous nucleotide sequences encoding one or more enzymes of an anabolic pathway, wherein the anabolic pathway requires the reductase that utilizes the produced NADPH or NADH. As noted above, the heterologous modified UDH converts an aldaric acid to its corresponding 1,5-aldonolactone. In some cases, the aldaric acid is D-galacturonic acid, and the 1,-5-aldonolactone is D-galactaro-1,5-lactone. Thus, e.g., in some cases, the heterologous modified UDH converts D-galacturonate to D-galactaro-1,5-lactone. In some cases, the aldaric acid is D-glucuronic acid, and the 1,5-aldonolactone is D-glucaro-1,5-lactone. Thus, in some cases, the heterologous modified UDH converts D-glucuronic acid to D-glucaro-1,5-lactone. In some cases, the sugar acid is D-guluronic acid, and the 1,5-aldonolactone is D-gularo-1,5-lactone.

In some cases, a genetically modified host cell of the present disclosure is a prokaryotic host cell that comprises a genetic modification in an endogenous uxaC gene, such that the genetically modified prokaryotic host cell does not produce functional uxaC.

As noted above, a genetically modified host cell of the present disclosure is genetically modified with one or more heterologous nucleic acids comprising heterologous nucleotide sequences encoding one or more enzymes of an anabolic pathway, where the anabolic pathway requires the reductase that utilizes the produced NADPH or NADH. In some cases, the one or more anabolic pathway enzymes comprises a glycerol dehydratase and the reductase is a 1,3-propanediol oxidoreductase. In some cases, the 1,3-propanediol oxidoreductase comprises an amino acid sequence having at least 40% amino acid sequence identity to the 1,3-propanediol oxidoreductase amino acid sequence depicted in FIG. 24A (SEQ ID NO:23) or the alcohol dehydrogenase amino acid sequence depicted in FIG. 24B (SEQ ID NO:24). In some cases, the genetically modified host cell, when cultured in a culture medium comprising dextrose and galacturonic acid, produces mucic acid and 1,3-propanediol. In some cases, the genetically modified host cell, when cultured in a culture medium comprising glycerol and galacturonic acid, produces mucic acid and 1,3-propanediol. In some cases, the one or more anabolic pathway enzymes comprise CoA-dependent succinate semialdehyde dehydrogenase, 4-hydroxybutyrate dehydrogenase, 4-hydroxybutyryl-CoA reductase, and alcohol dehydrogenase, wherein the reductase is 4-hydroxybutyryl-CoA reductase. In some cases, the genetically modified host cell, when cultured in a culture medium comprising dextrose and galacturonic acid, produces mucic acid and 1,4-butanediol. In some cases, the one or more anabolic pathway enzymes comprises methylglyoxyl reductase (mgsA in *E. coli*), glycerol dehydrogenase, (gldA, *E. coli*; dhaD in *Klebsiella*), and aldo-keto reductase or 1,2-propanediol oxidoreductase (fucO).

In some cases, the one or more anabolic pathway enzymes comprises a glycerol dehydratase and wherein the reductase is a 1,3-propanediol oxidoreductase. In some cases, the 1,3-propanediol oxidoreductase comprises an amino acid sequence having at least 40%, at least 50%, at least 60%, at least 70%, at least 80%, at least 85%, at least 90%, at least 95%, at least 98%, at least 99%, or 100%, amino acid sequence identity to the 1,3-propanediol oxidoreductase amino acid sequence depicted in FIG. 24A. In some cases, the genetically modified host cell, when cultured in a culture medium comprising dextrose and galacturonic acid, produces mucic acid and 1,3-propanediol. In some cases, the one or more anabolic pathway enzymes comprise a 4-hydroxybutyrate dehydrogenase and wherein the reductase is an aldehyde/alcohol dehydrogenase. In some cases, the genetically modified host cell, when cultured in a culture medium comprising dextrose and galacturonic acid, produces mucic acid and 1,4-butanediol. In some cases, the one or more anabolic pathway enzymes comprises an aldo-keo reductase or a glycerol dehydrogenase and wherein the reductase is an aldo-keo reductase or a glycerol dehydrogenase. In some cases, the genetically modified host cell, when cultured in a culture medium comprising dextrose and galacturonic acid, produces mucic acid and 1,2-propanediol. In some cases, the one or more anabolic pathway enzymes comprise myo-inositol-1-phosphate synthase (MIPS) and myo-inositol oxygenase (MIOX). In some cases, the one or more anabolic pathway enzymes comprise one or more heterologous mevalonate pathway enzymes. In some cases, the one or more anabolic pathway enzymes comprise one or more heterologous benzylisoquinoline alkaloid pathway enzymes. In some cases, the one or more anabolic pathway enzymes comprise one or more heterologous polyketide pathway enzymes.

Transporter

In some cases, a genetically modified host cell of the present disclosure is a yeast cell, and the yeast cell is genetically modified, as described above, and is also genetically modified with a heterologous nucleic acid comprising a nucleotide sequence encoding a heterologous D-galacturonic acid transporter. In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in one of FIG. 2-5 (SEQ ID NOs.: 1-4). In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in FIG. 2 (SEQ ID NO:1). In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in FIG. 3 (SEQ ID NO:2). In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in FIG. 4 (SEQ ID NO:3). In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in FIG. 5 (SEQ ID NO:4). In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in FIG. 55 (SEQ ID NO:38). In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in FIG. 57 (SEQ ID NO:39).

Modified UDH

In some cases, a genetically modified host cell of the present disclosure is genetically modified with a heterologous nucleic acid comprising a nucleotide sequence encoding a heterologous UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 20 (SEQ ID NO:19).

In some cases, the heterologous modified UDH comprises one or more amino acid substitutions in the NAD$^+$ binding motif such that the variant UDH binds NADP$^+$. In some cases, the heterologous modified UDH comprises an amino acid sequence having at least 40% amino acid sequence identity to the amino acid sequence depicted in FIG. 19 (SEQ ID NO:18), wherein one, two, or three of amino acids D42, I43, and A44 are substituted. In some cases, the heterologous modified UDH comprises an amino acid sequence having at least 80% amino acid sequence identity to the amino acid sequence depicted in FIG. 19 (SEQ ID NO:18), wherein one, two, or three of amino acids D42, I43, and A44 are substituted. In some cases, the heterologous modified UDH comprises wherein amino acid I43 is substituted with a positively charged amino acid. In some cases, the heterologous modified UDH comprises an I43R substitution. In some cases, the heterologous modified UDH comprises an amino acid sequence having at least 40% amino acid sequence identity to the amino acid sequence depicted in FIG. 21 (SEQ ID NO:20), wherein X is arginine, histidine, or lysine.

In some cases, a genetically modified host cell of the present disclosure is genetically modified with a heterologous nucleic acid comprising a nucleotide sequence encoding a variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18), where one, two, or three of amino acids D42, I43, and A44 are substituted. In some cases, the variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18); and comprises an amino acid substitution at D42, i.e., where amino acid 42 is other than aspartic acid (e.g., where amino acid 42 is Gly, Ala, Val, Leu, Ile, Pro, Phe, Tyr, Trp, Ser, Thr, Cys, Met, Asn, Gln, Lys, Arg, His, or Glu). In some cases, the variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18); and comprises an amino acid substitution at I43, i.e., where amino acid 43 is other than isoleucine (e.g., where amino acid 43 is Gly, Ala, Val, Leu, Pro, Phe, Tyr, Trp, Ser, Thr, Cys, Met, Asn, Gln, Lys, Arg, His, Asp, or Glu). In some cases, the variant UDH comprises an I43R substitution. In some cases, the variant UDH comprises an I43H substitution. In some cases, the variant UDH comprises an I43K substitution. In some cases, the variant UDH comprises an I43A substitution. In some cases, the variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18); and comprises an amino acid substitution at A44, i.e., where amino acid 44 is other than alanine (e.g., where amino acid 44 is Gly, Val, Leu, Ile, Pro, Phe, Tyr, Trp, Ser, Thr, Cys, Met, Asn, Gln, Lys, Arg, His, Asp, or Glu).

In some cases, a genetically modified host cell of the present disclosure is genetically modified with a heterologous nucleic acid comprising a nucleotide sequence encoding a variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 21 (SEQ ID NO:20), where X is an amino acid other than isoleucine; e.g., where X is a charged amino acid. In some cases, X is arginine. In some cases, X is histidine. In some cases, X is lysine.

In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO: 25), wherein one, two, or three of amino acids D35, V36, and A37 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 35 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 35 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 35 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47(SEQ ID NO:25), wherein amino acid 36 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 36 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 36 is Lys.

In some cases, a variant UDH polypeptide of the present disclosure comprises an amino acid sequence having at least 50%, at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein one, two, or three of amino acids D33, L34, and S35 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 33 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 33 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 33 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 34 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 34 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 34 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 35 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 35 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 35 is Lys.

In some cases, a variant UDH polypeptide of the present disclosure comprises an amino acid sequence having at least 50%, at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), wherein one, two, or three of amino acids D37, 138, and S39 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 37 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 37 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 37 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 38 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 38 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 38 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 39 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 39 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 39 is Lys.

In some cases, a variant UDH polypeptide of the present disclosure comprises an amino acid sequence having at least 50%, at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), wherein one, two, or three of amino acids D51, I52, and T53 is substituted with arginine, histidine, or lysine. In some cases, a variant UDH polypeptide of the present disclosure comprises an amino acid sequence having at least 50% amino acid sequence identity to the amino acid sequence depicted in FIG. 50 (SEQ ID NO:28), where amino acid 51 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 51 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 51 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 52 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 52 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 52 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 53 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 53 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 53 is Lys.

In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), wherein one, two, or three of amino acids D31, I32, and A33 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 31 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 31 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 31 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 32 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 32 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 32 is Lys.

In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), wherein one, two, or three of amino acids D32, I33, and R34 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 32 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 32 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 32 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 33 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 33 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 33 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 34 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 34 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 34 is Lys.

In some cases, the nucleotide sequence encoding a heterologous UDH polypeptide is operably linked to a transcriptional control element (e.g., a promoter) that is active in the host cell. In some cases, the promoter is a constitutive promoter. In some cases, the promoter is a regulatable promoter. In some cases, the promoter is an inducible promoter. Suitable promoters are known in the art. A number of suitable promoters are described below.

UDH

In some cases, a suitable heterologous UDH utilizes $NADP^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 20 (SEQ ID NO:19).

In some cases, a suitable heterologous UDH utilizes $NAD^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 19 (SEQ ID NO:18).

In some cases, a suitable heterologous UDH utilizes $NAD^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 47 (SEQ ID NO:25).

In some cases, a suitable heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 48 (SEQ ID NO:26).

In some cases, a suitable heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 49 (SEQ ID NO:27).

In some cases, a suitable heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 50 (SEQ ID NO:28).

In some cases, a suitable heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 51 (SEQ ID NO:29).

In some cases, a suitable heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 52 (SEQ ID NO:30).

Production of Mucic Acid

The present disclosure provides a genetically modified host cell (e.g., an in vitro host cell) that converts D-galacturonic acid to mucic acid. Mucic acid is also known as galactaric or meso-galactaric acid. The genetically modified host cell is capable of producing mucic acid anaerobically. The genetically modified host cell is genetically modified with a heterologous nucleic acid comprising a nucleotide sequence encoding a uronate dehydrogenase (UDH) that utilizes NADP$^+$ or NAD$^+$ as a co-factor instead of NADPH or NADH. Thus, the genetically modified host cell can produce mucic acid anaerobically.

In some cases, a genetically modified host cell of the present disclosure is genetically modified with a heterologous nucleic acid comprising a nucleotide sequence encoding a heterologous UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 20 (SEQ ID NO:19).

In some cases, a genetically modified host cell of the present disclosure is genetically modified with a heterologous nucleic acid comprising a nucleotide sequence encoding a variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18), where one, two, or three of amino acids D42, I43, and A44 are substituted. In some cases, the variant UDH comprises an I43R substitution. In some cases, the variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18); and comprises an amino acid substitution at D42, i.e., where amino acid 42 is other than aspartic acid (e.g., where amino acid 42 is Gly, Ala, Val, Leu, Ile, Pro, Phe, Tyr, Trp, Ser, Thr, Cys, Met, Asn, Gln, Lys, Arg, His, or Glu). In some cases, the variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18); and comprises an amino acid substitution at I43, i.e., where amino acid 43 is other than isoleucine (e.g., where amino acid 43 is Gly, Ala, Val, Leu, Pro, Phe, Tyr, Trp, Ser, Thr, Cys, Met, Asn, Gln, Lys, Arg, His, Asp, or Glu). In some cases, the variant UDH comprises an I43R substitution. In some cases, the variant UDH comprises an I43H substitution. In some cases, the variant UDH comprises an I43K substitution. In some cases, the variant UDH comprises an I43A substitution. In some cases, the variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18); and comprises an amino acid substitution at A44, i.e., where amino acid 44 is other than alanine (e.g., where amino acid 44 is Gly, Val, Leu, Ile, Pro, Phe, Tyr, Trp, Ser, Thr, Cys, Met, Asn, Gln, Lys, Arg, His, Asp, or Glu).

In some cases, a genetically modified host cell of the present disclosure is genetically modified with a heterologous nucleic acid comprising a nucleotide sequence encoding a variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 21 (SEQ ID NO:20), where X is an amino acid other than isoleucine; e.g., where X is a charged amino acid. In some cases, X is arginine. In some cases, X is histidine. In some cases, X is lysine.

In some cases, a genetically modified host cell of the present disclosure is genetically modified with a heterologous nucleic acid comprising a nucleotide sequence encoding a heterologous UDH, where the heterologous UDH utilizes NADP$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 20 (SEQ ID NO:19).

In some cases, a genetically modified host cell of the present disclosure is genetically modified with a heterologous nucleic acid comprising a nucleotide sequence encoding a heterologous UDH, where the heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 19 (SEQ ID NO:18).

In some cases, a genetically modified host cell of the present disclosure is genetically modified with a heterologous nucleic acid comprising a nucleotide sequence encoding a heterologous UDH, where the heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 47 (SEQ ID NO:25).

In some cases, a genetically modified host cell of the present disclosure is genetically modified with a heterologous nucleic acid comprising a nucleotide sequence encoding a heterologous UDH, where the heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 48 (SEQ ID NO:26).

In some cases, a genetically modified host cell of the present disclosure is genetically modified with a heterologous nucleic acid comprising a nucleotide sequence encoding a heterologous UDH, where the heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 49 (SEQ ID NO:27).

In some cases, a genetically modified host cell of the present disclosure is genetically modified with a heterologous nucleic acid comprising a nucleotide sequence encoding a heterologous UDH, where the heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 50 (SEQ ID NO:28).

In some cases, a genetically modified host cell of the present disclosure is genetically modified with a heterologous nucleic acid comprising a nucleotide sequence encoding a heterologous UDH, where the heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 51 (SEQ ID NO:29).

In some cases, a genetically modified host cell of the present disclosure is genetically modified with a heterologous nucleic acid comprising a nucleotide sequence encoding a heterologous UDH, where the heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 52 (SEQ ID NO:30).

In some cases, the genetically modified host cell is genetically modified such that it does not produce a functional uronate isomerase. For example, in some cases, the genetically modified host cell is genetically modified such that the endogenous uronate isomerase-encoding nucleotide sequence is functionally disabled. For example, in some cases, all or part of a uxaC gene (encoding uronate isomerase) is deleted.

In some cases, the genetically modified host cell is genetically modified such that D-galacturonic acid is not metabolized. For example, in some cases, all or part of a garD gene (encoding galactarate dehydratase) is deleted.

In some cases, a genetically modified host cell of the present disclosure is genetically modified to produce a variant UDH, as described above; and is further genetically modified to produce one or more heterologous enzymes that convert mucic acid to downstream products.

In some cases, the nucleotide sequence encoding a heterologous UDH polypeptide is operably linked to a transcriptional control element (e.g., a promoter) that is active in the host cell. In some cases, the promoter is a constitutive promoter. In some cases, the promoter is a regulatable promoter. In some cases, the promoter is an inducible promoter.

Production of Glucaric Acid

In some cases, a genetically modified host cell of the present disclosure is genetically modified to produce glucaric acid. In some cases, a genetically modified host cell of the present disclosure is genetically modified with one or more heterologous nucleic acids comprising nucleotide sequences encoding: a) a heterologous UDH polypeptide as described above; b) a myo-inositol-1-phosphate synthase (MIPS); and c) a myo-inositol oxygenase (MIOX).

In some cases, the MIPS polypeptide comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the MIPS amino acid sequence depicted in FIG. 23 (SEQ ID NO:22).

In some cases, the MIOX polypeptide comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the MIOX amino acid sequence depicted in FIG. 22 (SEQ ID NO:21).

In some cases, the nucleotide sequence encoding a heterologous UDH polypeptide is operably linked to a transcriptional control element (e.g., a promoter) that is active in the host cell. In some cases, the promoter is a constitutive promoter. In some cases, the promoter is a regulatable promoter. In some cases, the promoter is an inducible promoter.

In some cases, the nucleotide sequence encoding a heterologous MIPS polypeptide is operably linked to a transcriptional control element (e.g., a promoter) that is active in the host cell. In some cases, the promoter is a constitutive promoter. In some cases, the promoter is a regulatable promoter. In some cases, the promoter is an inducible promoter.

In some cases, the nucleotide sequence encoding a heterologous MIOX polypeptide is operably linked to a transcriptional control element (e.g., a promoter) that is active in the host cell. In some cases, the promoter is a constitutive promoter. In some cases, the promoter is a regulatable promoter. In some cases, the promoter is an inducible promoter.

Production of 1,3-Propanediol

In some cases, a genetically modified host cell of the present disclosure is genetically modified to produce 1,3-propanediol. In some cases, a genetically modified host cell of the present disclosure is genetically modified with one or more heterologous nucleic acids comprising nucleotide sequences encoding: a) a heterologous UDH polypeptide as described above; and b) a heterologous 1,3-propanediol oxidoreductase. In some cases, a genetically modified host cell of the present disclosure is genetically modified with one or more heterologous nucleic acids comprising nucleotide sequences encoding: a) a heterologous UDH polypeptide as described above; b) a glycerol dehydratase; and c) 1,3-propanediol oxidoreductase.

The glycerol dehydratase can be an enzyme comprising an alpha, a beta, and a gamma subunit. For example, the alpha subunit of the glycerol dehydratase In some cases, the 1,3-propanediol oxidoreductase polypeptide comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the 1,3-propanediol oxidoreductase amino acid sequence depicted in FIG. 24A (SEQ ID NO:23). See also, Jiang et al. (2016) Biotechnol. Biofuels 9:57.

In some cases, the nucleotide sequence encoding a heterologous UDH polypeptide is operably linked to a transcriptional control element (e.g., a promoter) that is active in the host cell. In some cases, the promoter is a constitutive promoter. In some cases, the promoter is a regulatable promoter. In some cases, the promoter is an inducible promoter.

In some cases, the nucleotide sequence encoding a heterologous 1,3-propanediol oxidoreductase polypeptide is operably linked to a transcriptional control element (e.g., a promoter) that is active in the host cell. In some cases, the promoter is a constitutive promoter. In some cases, the promoter is a regulatable promoter. In some cases, the promoter is an inducible promoter.

Production of an Anabolic Pathway Product

In some cases, a genetically modified host cell of the present disclosure is genetically modified to produce an anabolic pathway product, where the anabolic pathway requires NADH or NADPH.

In some cases, the anabolic pathway is a mevalonate pathway. Mevalonate pathway enzymes are described above. Thus, in some cases, a genetically modified host cell of the present disclosure is genetically modified with one or more heterologous nucleic acids comprising nucleotide sequences encoding: a) a heterologous UDH polypeptide as described above; and b) one or more mevalonate pathway enzymes, as described above. In some cases, the nucleotide sequence encoding a heterologous UDH polypeptide is operably linked to a transcriptional control element (e.g., a promoter) that is active in the host cell. In some cases, the promoter is a constitutive promoter. In some cases, the promoter is a regulatable promoter. In some cases, the promoter is an inducible promoter. In some cases, the nucleotide sequence encoding a heterologous mevalonate pathway enzyme is operably linked to a transcriptional control element (e.g., a promoter) that is active in the host cell. In some cases, the promoter is a constitutive promoter. In some cases, the promoter is a regulatable promoter. In some cases, the promoter is an inducible promoter.

In some cases, the anabolic pathway is an alkaloid biosynthetic pathway. Alkaloid biosynthetic enzymes are described above. Thus, in some cases, a genetically modified host cell of the present disclosure is genetically modified with one or more heterologous nucleic acids comprising nucleotide sequences encoding: a) a heterologous UDH polypeptide as described above; and b) one or more alkaloid biosynthetic enzymes, as described above.

In some cases, the anabolic pathway is a polyketide biosynthetic pathway. Polyketide biosynthetic enzymes are described above. Thus, in some cases, a genetically modified host cell of the present disclosure is genetically modified with one or more heterologous nucleic acids comprising nucleotide sequences encoding: a) a heterologous UDH polypeptide as described above; and b) one or more polyketide biosynthetic enzymes, as described above.

Production of 1,2-propanediol and 1,3-propanediol

Figure 25:
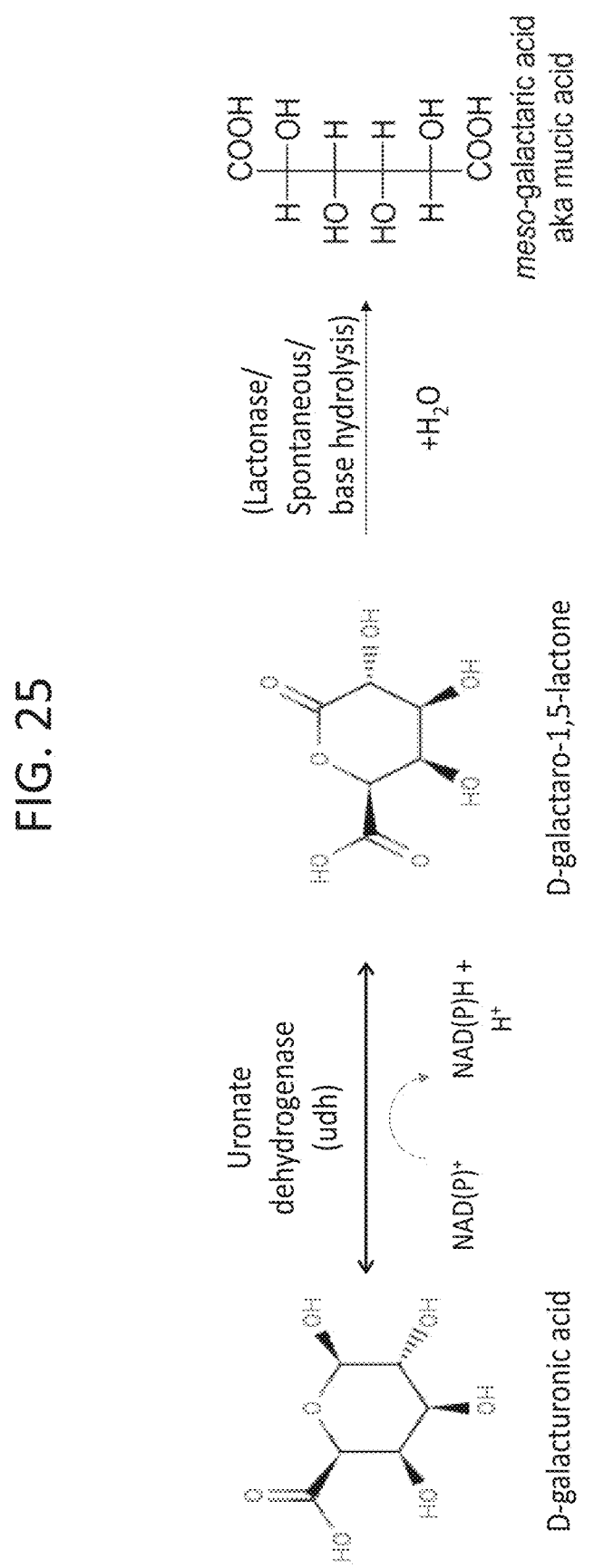
FIG. 25 is a schematic depiction of mucic acid production from D-galacturonate.
Figure 45:
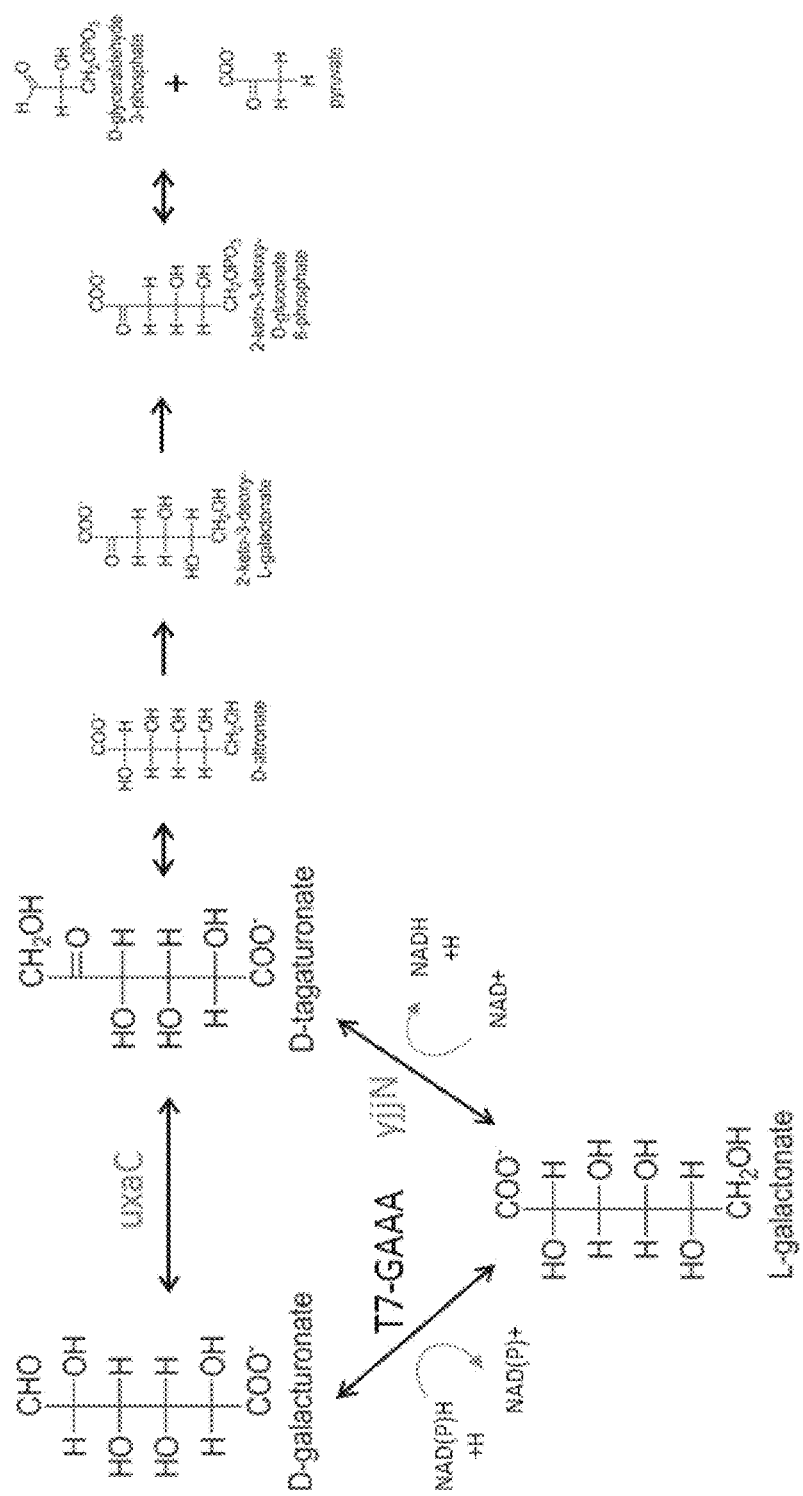
FIG. 45 and FIG. 46 depict bioconversion of D-galacturonate to L-galactonate.

In some cases, production of NAD(P)H is coupled to production of PDO, e.g., 1-2-PDO. For example, conversion of D-galacturonic acid to D-galataro-1,5-lactone (as shown in FIG. 25) is coupled to reduction of intermediates methylglyoxal and lactaldehyde or acetol to produce 1,2-propanediol, as shown in FIG. 45. As shown in FIG. 45, dihydroxyacetone phosphate is converted to methylglyoxal by the action of methylglyoxal synthase. Methylglyoxal is converted to lactaldehyde by the action of glycerol dehydrogenase, which conversion uses NADH as reducing agent; lactaldehyde is then converted to 1,2-propanediol by the action of aldo-ketoreductase, using NADH or NADPH as the reducing agent. Methylglyoxal can also be converted to acetol by the action of aldo-ketoreductase, using NADH or NADPH as the reducing agent; the acetol is then converted to 1,2-propanediol by the action of glycerol dehydrogenase, which conversion uses NADH as reducing agent. Production of 1,2-propanediol (1,2-PDO) is depicted schematically in FIG. 54. In some cases, enzymes used in the production of 1,2-PDO are methylglyoxyl reductase (mgsA in *E. coli*); glycerol dehydrogenase, (gldA, *E. coli*, dhaD in *Klebsiella*); and either aldo-keto reductase or 1,2-propanediol oxidoreductase (fucO).

Figure 29:
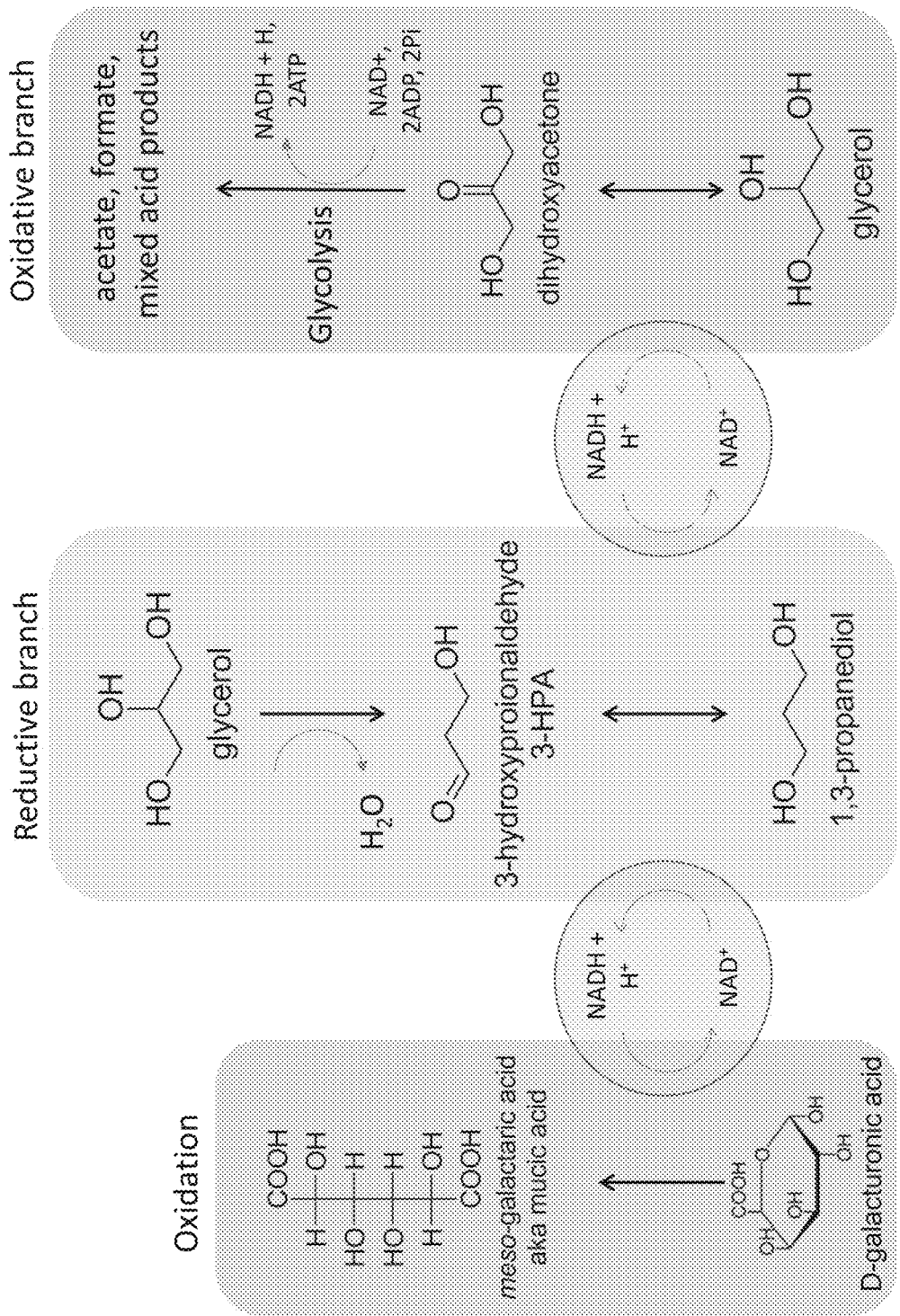
FIG. 29 depicts redirection of reducing equivalents via UDH activity in glycerol to 1,3-propanediol fermentations.

Production of 1,3-PDO can be carried out as depicted schematically in FIG. 29, where conversion of D-galacturonic acid to D-galataro-1,5-lactone (as shown in FIG. 25) is coupled to reduction of 3-hydroxypropionaldehyde, to generate 1,3-PDO.

Production of 1,4-Butanediol

Figure 44:
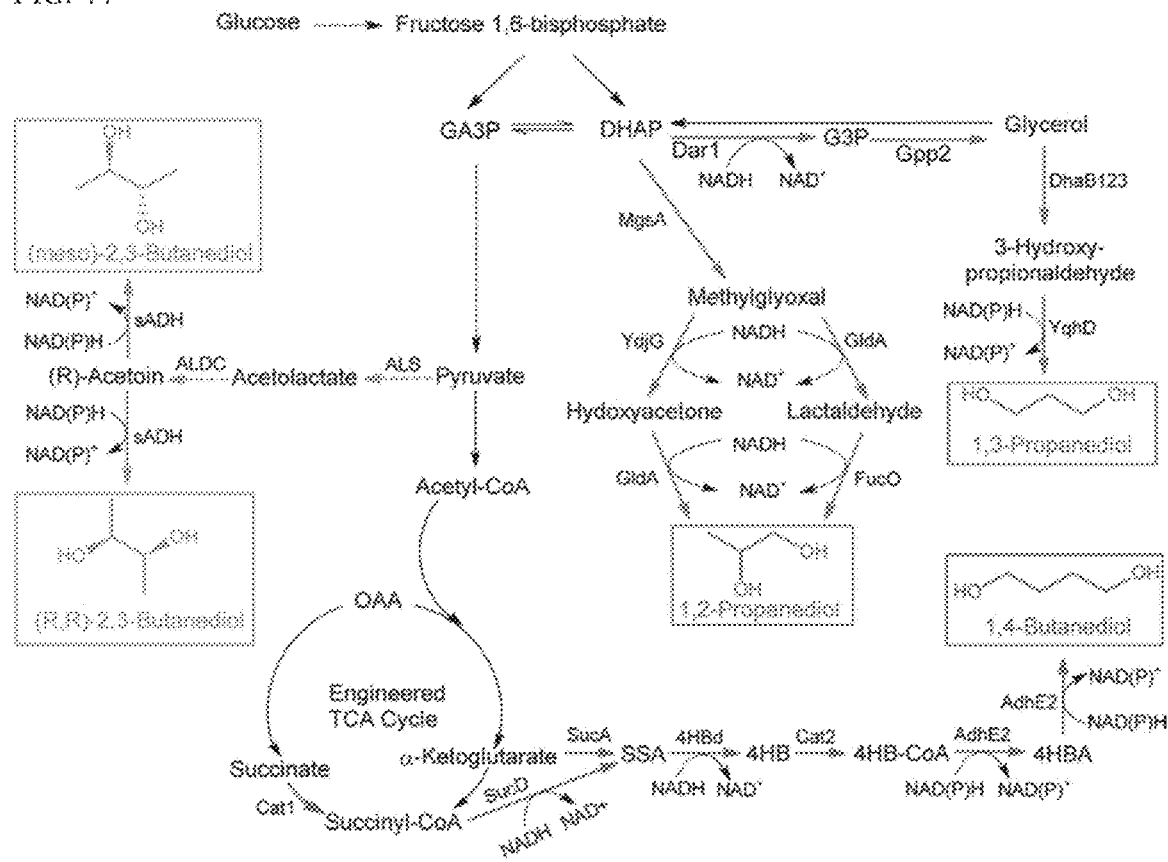
FIG. 44 depicts production of butanediol (BDO) and propanediol (PDO)

In some cases, production of NAD(P)H is coupled to production of BDO, e.g., 1,4-BDO. For example, conversion of D-galacturonic acid to D-galataro-1,5-lactone (as shown in FIG. 25) is coupled to reduction of intermediates succinyl-CoA, succinic semialdehyde (SSA), and 4-HB-CoA, and 4-hydroxybutyraldehyde (4HBA), as depicted in FIG. 44.

In some cases, enzymes catalyzing the biosynthetic reactions to generate 1,4-BDO include one or more of: (1) succinyl-CoA synthetase; (2) CoA-independent succinic semialdehyde dehydrogenase; (3) α-ketoglutarate dehydrogenase; (4) glutamate: succinate semialdehyde transaminase; (5) glutamate decarboxylase; (6) CoA-dependent succinic semialdehyde dehydrogenase; (7) 4-hydroxybutanoate dehydrogenase; (8) α-ketoglutarate decarboxylase; (9) 4-hydroxybutyryl CoA:acetyl-CoA transferase; (10) butyrate kinase; (11) phosphotransbutyrylase; (12) aldehyde dehydrogenase; (13) alcohol dehydrogenase. See, e.g., U.S. Patent Publication No. 2016/0053287.

In some cases, production of NAD(P)H is coupled to production of BDO, e.g., 1,3-BDO. The 1,3-BDO pathway includes an enzyme selected from the group consisting of a 2-amino-4-ketopentanoate (AKP) thiolase, an AKP dehydrogenase, a 2-amino-4-hydroxypentanoate aminotransferase, a 2-amino-4-hydroxypentanoate oxidoreductase (deaminating), a 2-oxo-4-hydroxypentanoate decarboxylase, a 3-hydroxybutyraldehyde reductase, an AKP aminotransferase, an AKP oxidoreductase (deaminating), a 2,4-dioxopentanoate decarboxylase, a 3-oxobutyraldehyde reductase (ketone reducing), a 3-oxobutyraldehyde reductase (aldehyde reducing), a 4-hydroxy-2-butanone reductase, an AKP decarboxylase, a 4-aminobutan-2-one aminotransferase, a 4-aminobutan-2-one oxidoreductase (deaminating), a 4-aminobutan-2-one ammonia-lyase, a butenone hydratase, an AKP ammonia-lyase, an acetylacrylate decarboxylase, an acetoacetyl-CoA reductase (CoA-dependent, aldehyde forming), an acetoacetyl-CoA reductase (CoA-dependent, alcohol forming), an acetoacetyl-CoA reductase (ketone reducing), a 3-hydroxybutyryl-CoA reductase (aldehyde forming), a 3-hydroxybutyryl-CoA reductase (alcohol forming), a 4-hydroxybutyryl-CoA dehydratase, and a crotonase. See, e.g., U.S. Patent Publication No. 2016/0076060.

Production of Xylitol

In some cases, production of NAD(P)H is coupled to production of xylitol, e.g., via xylitol reductase.

Host Cells

Suitable host cells include cells that can be cultured in vitro, e.g., as unicellular organisms. Suitable host cells include yeast cells, fungal cells, insect cells, mammalian cells, algal cells, and bacterial cells. Suitable host cells include filamentous fungal cells; suitable filamentous fungal cells include, e.g., *Aspergillus, Neurospora*, and the like. A suitable host cell includes a microbial host cell (e.g., a bacterium, a yeast cell, a fungal cell) that can be cultured (e.g., culture in vitro) in a container, e.g., a test tube, an Eppendorf tube, a fermentation flask, a fermentation bottle, a fermentation vat, etc. Thus, for example, a suitable host cell is a fermentable cell.

In some cases, the host cell is a eukaryotic cell. In some cases, the eukaryotic host cell is a yeast cell, an algal cell, or a fungal cell. In some cases, the host cell is a prokaryotic cell. In some cases, the host cell is a bacterial cell.

The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Phanerochaete, Pleurotus, Schizophyllum, Talaromyces, Thermoascus, Thielavia, Tolypocladium*, and *Trichoderma*. Examples of suitable filamentous fungal cells include, e.g., *Aspergillus niger, Aspergillus awamori, Aspergillus foetidus, Aspergillus sojae, Aspergillus fumigatus*, and *Aspergillus oryzae*. Another example of a suitable fungal cell is a *Neurospora crassa* cell.

Examples of suitable yeast host cells are strains selected from a cell of a species of *Candida, Kluyveromyces, Saccharomyces, Schizosaccharomyces, Pichia, Hansenula, Yarrowia, Rhodotorula* and *Rhodosporidium*. In one embodiment, the yeast host cell is selected from a *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Schizosaccharomyces pombe, Saccharomyces uvarum, Pichia kluyveri, Yarrowia lipolytica, Candida utilis, Candida cacaoi*, and *Geotrichum fermentans*. Other useful yeast host cells are *Kluyveromyces lactis, Kluyveromyces fragilis, Hansenula polymorpha, Pichia pastoris, Yarrowia lipolytica, Schizosaccharomyces pombe, Ustilgo maylis, Candida maltose, Pichia guillermondii* and *Pichia methanoliol*.

Suitable yeast host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia ptjperi, Pichia stiptis, Pichia methanolica, Pichia* sp., *Saccharomyces cerevisiae, Saccharomyces* sp., *Hansenula polymorpha*, and the like. In some cases, a yeast host cell is *Saccharomyces cerevisiae*; i.e., a genetically modified cell of the present disclosure is a genetically modified *Saccharomyces cerevisiae* cell.

In various embodiments, the yeast is selected from the non-limiting list of genera; *Candida, Cryptococcus, Hansenula, Issatchenki, Kluyveromyces, Komagataella, Lipomyces, Pichia, Rhodosporidium, Rhodotorula, Saccharomyces* or *Yarrowia* species. In various embodiments, the yeast is of a species selected from the group consisting of *Candida albicans, Candida ethanolica, Candrida krusei, Candida methanosorhosa, Candida sonorensis, Candida tropicalis, Cryptococcus curvatus, Hansenula polymorpha, Issatchenki orientalis, Kluyveromyces lactic, Kluyveromyces marxianus, Kluyveromyces thermotolerans, Komagataella pastoris, Lipomyces starkeyi, Pichia angusta, Pichia deserticola, Pichia galeiformis, Pichia kodamae, Pichia kudriavzevii, Pichia membranaefaciens, Pichia anethanolica, Pichia pastoris, Pichia salictaria, Pichia stipitis, Pichia thermotolerans, Pichia trehalophila, Rhodosporidium toruloides, Rhodotorula glutinis, Rhodotorula graminis, Saccharomyces hayanus, Saccharomyces boulardi, Saccharomyces cerevisiae, Saccharomyces kluyveri*, and *Yarrowia lipolytica, Pichia kudriavzevii*.

Illustrative examples of eukaryotic cells include, but are not limited to: *Aspergillus niger. Aspergillus oryzae, Crypthecodinium cohnii, Cunninghamella japonica, Entomophthora coronata, Mortierella alpina, Mucor circinelloides, Neurospora crassa, Pythium ultimum, Schizochytrium limacinum, Thraustochytrium aureum, Trichoderma reesei* and *Xanthophyllomvces dendrorhous*. In general, if a eukaryotic cell is used, a non-pathogenic strain is employed. Illustrative examples of non-pathogenic strains include, but are not limited to: *Pichia pastoris* and *Saccharomyces cerevisiae*. In addition, certain strains, including *Saccharomyces cerevisiae*, have been designated by the Food and Drug Administration as Generally Regarded as Safe (or GRAS) and so can be conveniently employed in various embodiments of the methods of the present disclosure.

The host cell can be a prokaryotic cell. Suitable prokaryotic cells include, but are not limited to, any of a variety of laboratory strains of *Escherichia coli, Lactobacillus* sp., *Salmonella* sp., *Shigella* sp., *Citrobacter, Enterobacter, Clostridium, Klebsiella*, Aerobacter, and the like. See, e.g., Carrier et al. (1992) J. Immunol. 148:1176-1181; U.S. Pat. No. 6,447,784; and Sizemore et al. (1995) Science 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some cases, the host cell is *Escherichia coli*.

Illustrative examples of suitable prokaryotic host cells include, but are not limited to, *Bacillus subtilis, Brevibacterium ammoniagenes, Clostridium beigerinckii, Enterobacter sakazakii, Lactobacillus acidophilus, Lactococcus lactis, Mesorhizobium loti, Pseudomonas aeruginosa, Pseudomonas putida, Rhodobacter capsulatus, Rhodobacter sphaeroides, Salmnonella enterica, Salmonella typhi, Salmonella typhimurium, Shigella fiexneri, Staphylococcus aureus, Streptomyces ambojaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis*, and *Streptomyces vinaceus*.

Methods of Producing a Commodity Product or a Precursor Thereof Using a UDH that Utilizes NADP+ or NAD+ as Cofactor The present disclosure provides method for producing mucic acid and a product of an anabolic pathway or a catabolic pathway that requires an active reductase that utilizes NADH or NADPH, the method comprising culturing, in a culture medium, a genetically modified in vitro host cell, wherein the genetically modified in vitro host cell is genetically modified with: a) a heterologous nucleic acid comprising a nucleotide sequence encoding a heterologous UDH that converts a sugar acid (e.g., an aldaric acid, a uronic acid) to it corresponding 1,5-aldonolactone and that uses NADP+ or NAD+ as a cofactor, and produces NADPH or NADH, respectively, and, wherein the host cell coexpresses an endogenous or a heterologous reductase that utilizes the produced NADPH or NADH; and b) one or more heterologous nucleic acids comprising heterologous nucleotide sequences encoding one or more enzymes of an anabolic pathway, wherein the anabolic pathway requires the reductase that utilizes the produced NADPH or NADH, where the culture medium comprises D-galacturonate and an oxidized substrate for the reductase, or a precursor for the oxidized substrate for the reductase, and wherein each mole of the NADP+ or NAD+ is converted to NADPH or NADH, respectively. In some cases, genetically modified host cell is cultured under anaerobic conditions. In some cases, the product of an anabolic pathway or a catabolic pathway is selected from glycerol, butanol, isobutanol, 1,2-propanediol, 1,3-propanediol, and 1,4-butanediol. In some cases, the product of an anabolic pathway or a catabolic pathway is selected from glycerol, butanol, isobutanol, 1,2-propanediol, 1,3-propanediol, 1,4-butanediol, 2,3-butanediol, glycerol, butanol, mevalonate and its derivatives, isoprenoids, farnesene, a polyketide, and fatty acids. In some cases, the method comprises recovering the mucic acid. In some cases, the recovered mucic acid is chemically modified in one or more cell-free reactions. In some cases, the method comprises recovering the product of the anabolic pathway or catabolic pathway. In some cases, the culture medium comprises dextrose and D-galacturonic acid. In some cases, the host cell is a eukaryotic cell. In some cases, the eukaryotic host cell is a yeast cell, an algal cell, or a fungal cell. In some cases, the host cell is a prokaryotic cell. In some cases, the host cell is a bacterial cell.

In some cases, the product (i.e., the co-product with mucic acid) is ethanol, where glucose or fructose is the cosubstrate; and alcohol dehydrogenase is the reductase enzyme (e.g., ADH1 from *Saccharomyces*) using NAD(P)H produced by UDH activity. In some cases, the co-product (i.e., the co-product with mucic acid) is ethylene glycol (ethane-1,2-diol), where a pentose (e.g., xylose) is present in the culture medium, and where glycolaldehyde dehydrogenase is the reductase enzyme using NAD(P)H produced by UDH activity. In some cases, the product (i.e., the co-product with mucic acid) is ethanol, where acetate is the cosubstrate; and a bifunctional aldehyde-alcohol dehydrogenase (such as adhE from *E. coli*) uses NAD(P)H produced by UDH activity. In some cases, the product (i.e., the co-product with mucic acid) is furfuryl alcohol, where furfural (2-furaldehyde) is the cosubstrate, and an alcohol dehydrogenase (such as ADH6 or ADH7) is the reductase using NAD(P)H produced by UDH activity. In some cases, the product (i.e., the co-product with mucic acid) is 5-hydroxymethyl furfuryl alcohol, where 5-hydroxymethylfuraldehyde (HMF) is the cosubstrate, and an alcohol dehydrogenase (such as ADH6 or ADH7) is the reductase using NAD(P)H produced by UDH activity. Furfural and 5-hydroxymethylfurfural are toxins found in plant hydrolysates that inhibit microbial growth. One physiological means for detoxifying these chemicals is to reduce them to their alcohol forms with NAD(P)H.

The heterologous UDH converts a sugar acid (e.g., an aldaric acid, a uronic acid) to its corresponding 1,5-aldonolactone. In some cases, the sugar acid is D-galacturonic acid, and the 1,-5-aldonolactone is D-galactaro-1,5-lactone. Thus, e.g., in some cases, the heterologous UDH converts D-galacturonate to D-galactaro-1,5-lactone. In some cases, the sugar acid is D-glucuronic acid, and the 1,5-aldonolactone is D-glucaro-1,5-lactone. Thus, in some cases, the heterologous UDH converts D-glucuronic acid to D-glucaro-1,5-lactone. In some cases, the sugar acid is D-guluronic acid, and the 1,5-aldonolactone is D-gularo-1,5-lactone.

The heterologous UDH converts an aldaric acid to its corresponding 1,5-aldonolactone. In some cases, the aldaric acid is D-galacturonic acid, and the 1,-5-aldonolactone is D-galactaro-1,5-lactone. Thus, e.g., in some cases, the heterologous UDH converts D-galacturonate to D-galactaro-1,5-lactone. In some cases, the aldaric acid is D-glucuronic acid, and the 1,5-aldonolactone is D-glucaro-1,5-lactone. Thus, in some cases, the heterologous UDH converts D-glucuronic acid to D-glucaro-1,5-lactone. In some cases, the sugar acid is D-guluronic acid, and the 1,5-aldonolactone is D-gularo-1,5-lactone.

In some cases, the heterologous UDH is a modified UDH that comprises one or more amino acid substitutions in the NAD+ binding motif such that the modified UDH binds NADP+. In some cases, the heterologous modified UDH comprises an amino acid sequence having at least 40% amino acid sequence identity to the amino acid sequence depicted in FIG. 19 (SEQ ID NO: 18), wherein one, two, or three of amino acids D42, I43, and A44 are substituted. In some cases, the heterologous modified UDH comprises an amino acid sequence having at least 80% amino acid sequence identity to the amino acid sequence depicted in FIG. 19 (SEQ ID NO:18), wherein one, two, or three of amino acids D42, I43, and A44 are substituted. In some cases, amino acid I43 is substituted with a positively charged amino acid. In some cases, the heterologous modified UDH comprises an I43R substitution. In some cases, the heterologous modified UDH comprises an amino acid sequence having at least 40% amino acid sequence identity to the amino acid sequence depicted in FIG. 21 (SEQ ID NO:20), wherein X is arginine, histidine, or lysine.

Modified UDH

In some cases, the heterologous modified UDH comprises one or more amino acid substitutions in the NAD+ binding motif such that the variant UDH binds NADP+. In some cases, the heterologous modified UDH comprises an amino acid sequence having at least 40% amino acid sequence identity to the amino acid sequence depicted in FIG. 19 (SEQ ID NO: 18), wherein one, two, or three of amino acids D42, I43, and A44 are substituted. In some cases, the heterologous modified UDH comprises an amino acid sequence having at least 80% amino acid sequence identity to the amino acid sequence depicted in FIG. 19 (SEQ ID NO:18), wherein one, two, or three of amino acids D42, I43, and A44 are substituted. In some cases, the heterologous modified UDH comprises wherein amino acid I43 is substituted with a positively charged amino acid. In some cases, the heterologous modified UDH comprises an I43R substitution. In some cases, the heterologous modified UDH comprises an amino acid sequence having at least 40% amino acid sequence identity to the amino acid sequence depicted in FIG. 21 (SEQ ID NO:20), wherein X is arginine, histidine, or lysine.

In some cases, a genetically modified host cell of the present disclosure is genetically modified with a heterologous nucleic acid comprising a nucleotide sequence encoding a variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18), where one, two, or three of amino acids D42, 143, and A44 are substituted. In some cases, the variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO: 18); and comprises an amino acid substitution at D42, i.e., where amino acid 42 is other than aspartic acid (e.g., where amino acid 42 is Gly, Ala, Val, Leu, lie, Pro, Phe, Tyr, Trp, Ser, Thr, Cys, Met, Asn, Gin, Lys, Arg, His, or Glu). In some cases, the variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18); and comprises an amino acid substitution at I43, i.e., where amino acid 43 is other than isoleucine (e.g., where amino acid 43 is Gly, Ala, Val, Leu, Pro, Phe, Tyr, Trp, Ser, Thr, Cys, Met, Asn, Gin, Lys, Arg, His, Asp, or Glu). In some cases, the variant UDH comprises an I43R substitution. In some cases, the variant UDH comprises an I43H substitution. In some cases, the variant UDH comprises an I43K substitution. In some cases, the variant UDH comprises an I43A substitution. In some cases, the variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18); and comprises an amino acid substitution at A44, i.e., where amino acid 44 is other than alanine (e.g., where amino acid 44 is Gly, Val, Leu, Ile, Pro, Phe, Tyr, Trp, Ser, Thr, Cys, Met, Asn, Gln, Lys, Arg, His, Asp, or Glu).

In some cases, a genetically modified host cell of the present disclosure is genetically modified with a heterologous nucleic acid comprising a nucleotide sequence encoding a variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 21 (SEQ ID NO:20), where X is an amino acid other than isoleucine; e.g., where X is a charged amino acid. In some cases, X is arginine. In some cases, X is histidine. In some cases, X is lysine.

In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein one, two, or three of amino acids D35, V36, and A37 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 35 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 35 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 35 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 36 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 36 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 36 is Lys.

In some cases, a variant UDH polypeptide of the present disclosure comprises an amino acid sequence having at least 50%, at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein one, two, or three of amino acids D33, L34, and S35 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 33 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 33 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 33 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 34 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 34 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 34 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 35 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 35 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 35 is Lys.

In some cases, a variant UDH polypeptide of the present disclosure comprises an amino acid sequence having at least 50%, at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), wherein one, two, or three of amino acids D37, I38, and S39 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 37 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 37 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 37 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 38 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 38 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 38 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 39 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 39 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 39 is Lys.

In some cases, a variant UDH polypeptide of the present disclosure comprises an amino acid sequence having at least 50%, at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), wherein one, two, or three of amino acids D51, I52, and T53 is substituted with arginine, histidine, or lysine. In some cases, a variant UDH polypeptide of the present disclosure comprises an amino acid sequence having at least 50% amino acid sequence identity to the amino acid sequence depicted in FIG. 50 (SEQ ID NO:28), where amino acid 51 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 51 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 51 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 52 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 52 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 52 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 53 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 53 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 53 is Lys.

In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO: 29), wherein one, two, or three of amino acids D31, I32, and A33 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 31 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 31 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 31 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 32 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 32 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 32 is Lys.

In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), wherein one, two, or three of amino acids D32, I33, and R34 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 32 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 32 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 32 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 33 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 33 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 33 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 34 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 34 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 34 is Lys.

In some cases, the nucleotide sequence encoding a heterologous UDH polypeptide is operably linked to a transcriptional control element (e.g., a promoter) that is active in the host cell. In some cases, the promoter is a constitutive promoter. In some cases, the promoter is a regulatable promoter. In some cases, the promoter is an inducible promoter.

UDH

In some cases, a suitable heterologous UDH utilizes NADP$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 20 (SEQ ID NO: 19).

In some cases, a suitable heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 19 (SEQ ID NO: 18).

In some cases, a suitable heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 47 (SEQ ID NO:25).

In some cases, a suitable heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 48 (SEQ ID NO:26).

In some cases, a suitable heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 49 (SEQ ID NO:27).

In some cases, a suitable heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 50 (SEQ ID NO:28).

In some cases, a suitable heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 51 (SEQ ID NO:29).

In some cases, a suitable heterologous UDH utilizes NAD$^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 52 (SEQ ID NO:30).

Heterologous Transporter

In some cases, the host cell is a yeast cell, and wherein the host cell is genetically modified with a heterologous nucleic acid comprising a nucleotide sequence encoding a heterologous D-galacturonic acid transporter. In some cases, the heterologous D-galacturonic acid transporter comprises an amino acid sequence having at least 50% amino acid sequence identity (at least 50%, at least 60%, at least 70%, at least 80%, at least 90%, at least 95%, at least 98%, at least 99%, or 100%, amino acid sequence identity) to the amino acid sequence depicted in one of FIG. 2-5 (SEQ ID NOs.: 1-4). In some cases, the heterologous D-galacturonic acid transporter comprises an amino acid sequence having at least 50% amino acid sequence identity (at least 50%, at least 60%, at least 70%, at least 80%, at least 90%, at least 95%, at least 98%, at least 99%, or 100%, amino acid sequence identity) to the amino acid sequence depicted in FIG. 55 (SEQ ID NO:38). In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in FIG. 57 (SEQ ID NO:39).

Culture Conditions

The present disclosure provides methods of producing various products ("commodity product"; "bioproducts"; etc.) in a genetically modified host cell. In some cases, the products are produced aerobically. In some cases, the products are produced anaerobically. In some cases, the products are produced by a combination of aerobic production and anaerobic production. The methods comprise culturing a genetically modified host cell of the present disclosure under suitable culture conditions to produce the product (anaerobically; aerobically; or a combination of aerobically and anaerobically), where the genetically modified host cell is genetically modified with a heterologous nucleic acid comprising a nucleotide sequence encoding a heterologous UDH polypeptide as described above, where the heterologous UDH utilizes NADP$^+$ or NAD$^+$, and produces NADPH or NADH, respectively. In some cases, the heterologous UDH polypeptide is a modified UDH polypeptide that utilizes NADP$^+$ or NAD$^+$. In some cases, the heterologous UDH polypeptide is a naturally-occurring UDH polypeptide that utilizes NADP$^+$ or NAD$^+$.

Suitable culture conditions include a culture medium comprising a carbon source, which can include D-galacturonate, glycerol, and the like. In some cases, the carbon source is D-galacturonate. In some cases, the carbon source is glycerol. In some cases, the carbon source is dextrose. In some cases, the carbon source is fructose. The carbon source can be provided in the form of an agricultural waste stream. For example, in some cases, the carbon source is provided in the form of pectin, or a pectin-rich food. For example, in some cases, the carbon source is provided in the form of one or more of: fruit pulp, e.g., citrus fruit pulp or apple pulp; the peel of a fruit, e.g., citrus fruit peel, apple peel, etc.; sugar beet pulp; rag and/or seeds of fruit (e.g., citrus fruits; apples; etc.). As another example, in some cases, the carbon source is provided in the form of pectins present in hemicellulose. For example, in some cases, carbon source is provided in the form of lignocellulosic biomass. A lignocellulosic biomass comprises cellulose, hemicelluloses, and lignin. Lignocellulosic biomass can comprise plant cell wall material.

In some cases, the product is purified, e.g., isolated and purified from the culture medium, from a cell lysate, or both. In some cases, the product is at least or about 25%, 30%, 40%, 50%, 60%, 70%, 75%, 80%, 90%, 95%, or 99%, by weight, pure. Purification can be carried out by any known method or combination of methods, which methods include, e.g., column chromatography, phase separation, gas stripping, membrane enhanced separation, fractionation, adsorption/desorption, pervaporation, thermal or vacuum desorption from a solid phase, extraction of the product that is immobilized or absorbed to a solid phase with a solvent, etc. Purity can be assessed by any appropriate method, e.g., by column chromatography, high performance liquid chromatography (HPLC) analysis, or gas chromatograph-mass spectrometry (GC-MS) analysis.

In some cases, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into the desired product. In some cases, the cells in culture produce at least 2 g/L, at least 3 g/L, at least 4 g/L, at least 5 g/L, at least 7 g/L, at least 10 g/L, or more than 50 g/L liquid culture medium.

Products that can be produced using a method of the present disclosure include, but are not limited to, methane, methanol, ethane, ethene, ethanol, n-propane, 1-propene, 1-propanol, propanal, acetone, propionate, n-butane, 1-butene, 1-butanol, butanal, butanoate, isobutanol, isobutanol, 2-methylbutanal, 2-methylbutanol, 3-methylbutanal, 3-methylbutanol, 2-butene, 2-butanol, 2-butanone, 2,3-butanediol, 3-hydroxy-2-butanone, 2,3-butanedione, ethylbenzene, ethenylbenzene, 2-phenylethanol, phenylacetaldehyde, 1-phenylbutane, 4-phenyl-1-butene, 4-phenyl-2-butene, 1-phenyl-2-butene, 1-phenyl-2-butanol, 4-phenyl-2-butanol, 1-phenyl-2-butanone, 4-phenyl-2-butanone, 1-phenyl-2,3-butandiol, 1-phenyl-3-hydroxy-2-butanone, 4-phenyl-3-hydroxy-2-butanone, 1-phenyl-2,3-butanedione, n-pentane, ethylphenol, ethenylphenol, 2-(4-hydroxyphenyl)ethanol, 4-hydroxyphenylacetaldehyde, 1-(4-hydroxyphenyl)butane, 4-(4-hydroxyphenyl)-1-butene, 4-(4-hydroxyphenyl)-2-butene, 1-(4-hydroxyphenyl)-1-butene, 1-(4-hydroxyphenyl)-2-butanol, 4-(4-hydroxyphenyl)-2-butanol, 1-(4-hydroxyphenyl)-2-butanone, 4-(4-hydroxyphenyl)-2-butanone, 1-(4-hydroxyphenyl)-2,3-butandiol, 1-(4-hydroxyphenyl)-3-hydroxy-2-butanone, 4-(4-hydroxyphenyl)-3-hydroxy-2-butanone, 1-(4-hydroxyphenyl)-2,3-butanonedione, indolylethane, indolylethene, 2-(indole-3-)ethanol, n-pentane, 1-pentene, 1-pentanol, pentanal, pentanoate, 2-pentene, 2-pentanol, 3-pentanol, 2-pentanone, 3-pentanone, 4-methylpentanal, 4-methylpentanol, 2,3-pentanediol, 2-hydroxy-3-pentanone, 3-hydroxy-2-pentanone, 2,3-pentanedione, 2-methylpentane, 4-methyl-1-pentene, 4-methyl-2-pentene, 4-methyl-3-pentene, 4-methyl-2-pentanol, 2-methyl-3-pentanol, 4-methyl-2-pentanone, 2-methyl-3-pentanone, 4-methyl-2,3-pentanediol, 4-methyl-2-hydroxy-3-pentanone, 4-methyl-3-hydroxy-2-pentanone, 4-methyl-2,3-pentanedione, 1-phenylpentane, 1-phenyl-1-pentene, 1-phenyl-2-pentene, 1-phenyl-3-pentene, 1-phenyl-2-pentanol, 1-phenyl-3-pentanol, 1-phenyl-2-pentanone, 1-phenyl-3-pentanone, 1-phenyl-2,3-pentanediol, 1-phenyl-2-hydroxy-3-pentanone, 1-phenyl-3-hydroxy-2-pentanone, 1-phenyl-2,3-pentanedione, 4-methyl-1-phenylpentane, 4-methyl-1-phenyl-1-pentene, 4-methyl-1-phenyl-2-pentene, 4-methyl-1-phenyl-3-pentene, 4-methyl-1-phenyl-3-pentanol, 4-methyl-1-phenyl-2-pentanol, 4-methyl-1-phenyl-3-pentanone, 4-methyl-1-phenyl-2-pentanone, 4-methyl-1-phenyl-2,3-pentanediol, 4-methyl-1-phenyl-2,3-pentanedione, 4-methyl-1-phenyl-3-hydroxy-2-pentanone, 4-methyl-1-phenyl-2-hydroxy-3-pentanone, 1-(4-hydroxyphenyl)pentane, 1-(4-hydroxyphenyl)-1-pentene, 1-(4-hydroxyphenyl)-2-pentene, 1-(4-hydroxyphenyl)-3-pentene, 1-(4-hydroxyphenyl)-2-pentanol, 1-(4-hydroxyphenyl)-3-pentanol, 1-(4-hydroxyphenyl)-2-pentanone, 1-(4-hydroxyphenyl)-3-pentanone, 1-(4-hydroxyphenyl)-2,3-pentanediol, 1-(4-hydroxyphenyl)-2-hydroxy-3-pentanone, 1-(4-hydroxyphenyl)-3-hydroxy-2-pentanone, 1-(4-hydroxyphenyl)-2,3-pentanedione, 4-methyl-1-(4-hydroxyphenyl)pentane, 4-methyl-1-(4-hydroxyphenyl)-2-pentene, 4-methyl-1-(4-hydroxyphenyl)-3-pentene, 4-methyl-1-(4-hydroxyphenyl)-1-pentene, 4-methyl-1-(4-hydroxyphenyl)-3-pentanol, 4-methyl-1-(4-hydroxyphenyl)-2-pentanol, 4-methyl-1-(4-hydroxyphenyl)-3-pentanone, 4-methyl-1-(4-hydroxyphenyl)-2-pentanone, 4-methyl-1-(4-hydroxyphenyl)-2,3-pentanediol, 4-methyl-1-(4-hydroxyphenyl)-2,3-pentanedione, 4-methyl-1-(4-hydroxyphenyl)-3-hydroxy-2-pentanone 4-methyl-1-(4-hydroxyphenyl)-2-hydroxy-3-pentanone, 1-indole-3-pentane, 1-(indole-3)-1-pentene, 1-(indole-3)-2-pentene, 1-(indole-3)-3-pentene, 1-(indole-3)-2-pentanol, 1-(indole-3)-3-pentanol, 1-(indole-3)-2-pentanone, 1-(indole-3)-3-pentanone, 1-(indole-3)-2,3-pentanediol, 1-(indole-3)-2-hydroxy-3-pentanone, 1-(indole-3)-3-hydroxy-2-pentanone, 1-(indole-3)-2,3-pentanedione, 4-methyl-1-(indole-3-)pentane, 4-methyl-1-(indole-3)-2-pentene, 4-methyl-1-(indole-3)-3-pentene, 4-methyl-1-(indole-3)-1-pentene, 4-methyl-2-(indole-3)-3-pentanol, 4-methyl-1-(indole-3)-2-pentanol, 4-methyl-1-(indole-3)-3-pentanone, 4-methyl-1-(indole-3)-2-pentanone, 4-methyl-1-(indole-3)-2,3-pentanediol, 4-methyl-1-(indole-3)-2,3-pentanedione, 4-methyl-1-(indole-3)-3-hydroxy-2-pentanone, 4-methyl-1-(indole-3)-2-hydroxy-3-pentanone, n-hexane, 1-hexene, 1-hexanol, hexanal, hexanoate, 2-hexene, 3-hexene, 2-hexanol, 3-hexanol, 2-hexanone, 3-hexanone, 2,3-hexanediol, 2,3-hexanedione, 3,4-hexanediol, 3,4-hexanedione, 2-hydroxy-3-hexanone, 3-hydroxy-2-hexanone, 3-hydroxy-4-hexanone, 4-hydroxy-3-hexanone, 2-methylhexane, 3-methylhexane, 2-methyl-2-hexene, 2-methyl-3- hexene, 5-methyl-1-hexene, 5-methyl-2-hexene, 4-methyl-1-hexene, 4-methyl-2-hexene, 3-methyl-3-hexene, 3-methyl-2-hexene, 3-methyl-1-hexene, 2-methyl-3-hexanol, 5-methyl-2-hexanol, 5-methyl-3-hexanol, 2-methyl-3-hexanone, 5-methyl-2-hexanone, 5-methyl-3-hexanone, 2-methyl-3,4-hexanediol, 2-methyl-3,4-hexanedione, 5-methyl-2,3-hexanediol, 5-methyl-2,3-hexanedione, 4-methyl-2,3-hexanediol, 4-methyl-2,3-hexanedione, 2-methyl-3-hydroxy-4-hexanone, 2-methyl-4-hydroxy-3-hexanone, 5-methyl-2-hydroxy-3-hexanone, 5-methyl-3-hydroxy-2-hexanone, 4-methyl-2-hydroxy-3-hexanone, 4-methyl-3-hydroxy-2-hexanone, 2,5-dimethylhexane, 2,5-dimethyl-2-hexene, 2,5-dimethyl-3-hexene, 2,5-dimethyl-3-hexanol, 2,5-dimethyl-3-hexanone, 2,5-dimethyl-3,4-hexanediol, 2,5-dimethyl-3,4-hexanedione, 2,5-dimethyl-3-hydroxy-4-hexanone, 5-methyl-1-phenylhexane, 4-methyl-1-phenylhexane, 5-methyl-1-phenyl-1-hexene, 5-methyl-1-phenyl-2-hexene, 5-methyl-1-phenyl-3-hexene, 4-methyl-1-phenyl-1-hexene, 4-methyl-1-phenyl-2-hexene, 4-methyl-1-phenyl-3-hexene, 5-methyl-1-phenyl-2-hexanol, 5-methyl-1-phenyl-3-hexanol, 4-methyl-1-phenyl-2-hexanol, 4-methyl-1-phenyl-3-hexanol, 5-methyl-1-phenyl-2-hexanone, 5-methyl-1-phenyl-3-hexanone, 4-methyl-1-phenyl-2-hexanone, 4-methyl-1-phenyl-3-hexanone, 5-methyl-1-phenyl-2,3-hexanediol, 4-methyl-1-phenyl-2,3-hexanediol, 5-methyl-1-phenyl-3-hydroxy-2-hexanone, 5-methyl-1-phenyl-2-hydroxy-3-hexanone, 4-methyl-1-phenyl-3-hydroxy-2-hexanone, 4-methyl-1-phenyl-2-hydroxy-3-hexanone, 5-methyl-1-phenyl-2,3-hexanedione, 4-methyl-1-phenyl-2,3-hexanedione, 4-methyl-1-(4-hydroxyphenyl)hexane, 5-methyl-1-(4-hydroxyphenyl)-1-hexene, 5-methyl-1-(4-hydroxyphenyl)-2-hexene, 5-methyl-1-(4-hydroxyphenyl)-3-hexene, 4-methyl-1-(4-hydroxyphenyl)-1-hexene, 4-methyl-1-(4-hydroxyphenyl)-2-hexene, 4-methyl-1-(4-hydroxyphenyl)-3-hexene, 5-methyl-1-(4-hydroxyphenyl)-2-hexanol, 5-methyl-1-(4-hydroxyphenyl)-3-hexanol, 4-methyl-1-(4-hydroxyphenyl)-2-hexanol, 4-methyl-1-(4-hydroxyphenyl)-3-hexanol, 5-methyl-1-(4-hydroxyphenyl)-2-hexanone, 5-methyl-1-(4-hydroxyphenyl)-3-hexanone, 4-methyl-1-(4-hydroxyphenyl)-2-hexanone, 4-methyl-1-(4-hydroxyphenyl)-3-hexanone, 5-methyl-1-(4-hydroxyphenyl)-2,3-hexanediol, 4-methyl-1-(4-hydroxyphenyl)-2,3-hexanediol, 5-methyl-1-(4-hydroxyphenyl)-3-hydroxy-2-hexanone, 5-methyl-1-(4-hydroxyphenyl)-2-hydroxy-3-hexanone, 4-methyl-1-(4-hydroxyphenyl)-3-hydroxy-2-hexanone, 4-methyl-1-(4-hydroxyphenyl)-2-hydroxy-3-hexanone, 5-methyl-1-(4-hydroxyphenyl)-2,3-hexanedione, 4-methyl-1-(4-hydroxyphenyl)-2,3-hexanedione, 4-methyl-1-(indole-3-)hexane, 5-methyl-1-(indole-3)-1-hexene, 5-methyl-1-(indole-3)-2-hexene, 5-methyl-1-(indole-3)-3-hexene, 4-methyl-1-(indole-3)-1-hexene, 4-methyl-1-(indole-3)-2-hexene, 4-methyl-1-(indole-3)-3-hexene, 5-methyl-1-(indole-3)-2-hexanol, 5-methyl-1-(indole-3)-3-hexanol, 4-methyl-1-(indole-3)-2-hexanol, 4-methyl-1-(indole-3)-3-hexanol, 5-methyl-1-(indole-3)-2-hexanone, 5-methyl-1-(indole-3)-3-hexanone, 4-methyl-1-(indole-3)-2-hexanone, 4-methyl-1-(indole-3)-3-hexanone, 5-methyl-1-(indole-3)-2,3-hexanediol, 4-methyl-1-(indole-3)-2,3-hexanediol, 5-methyl-1-(indole-3)-3-hydroxy-2-hexanone, 5-methyl-1-(indole-3)-2-hydroxy-3-hexanone, 4-methyl-1-(indole-3)-3-hydroxy-2-hexanone, 4-methyl-1-(indole-3)-2-hydroxy-3-hexanone, 5-methyl-1-(indole-3)-2,3-hexanedione, 4-methyl-1-(indole-3)-2,3-hexanedione, n-heptane, 1-heptene, 1-heptanol, heptanal, heptanoate, 2-heptene, 3-heptene, 2-heptanol, 3-heptanol, 4-heptanol, 2-heptanone, 3-heptanone, 4-heptanone, 2,3-heptanediol, 2,3-heptanedione, 3,4-heptanediol, 3,4-heptanedione, 2-hydroxy-3-heptanone, 3-hydroxy-2-heptanone, 3-hydroxy-4-heptanone, 4-hydroxy-3-heptanone, 2-methylheptane, 3-methylheptane, 6-methyl-2-heptene, 6-methyl-3-heptene, 2-methyl-3-heptene, 2-methyl-2-heptene, 5-methyl-2-heptene, 5-methyl-3-heptene, 3-methyl-3-heptene, 2-methyl-3-heptanol, 2-methyl-4-heptanol, 6-methyl-3-heptanol, 5-methyl-3-heptanol, 3-methyl-4-heptanol, 2-methyl-3-heptanone, 2-methyl-4-heptanone, 6-methyl-3-heptanone, 5-methyl-3-heptanone, 3-methyl-4-heptanone, 2-methyl-3,4-heptanediol, 2-methyl-3,4-heptanedione, 6-methyl-3,4-heptanediol, 6-methyl-3,4-heptanedione, 5-methyl-3,4-heptanediol, 5-methyl-3,4-heptanedione, 2-methyl-3-hydroxy-4-heptanone, 2-methyl-4-hydroxy-3-heptanone, 6-methyl-3-hydroxy-4-heptanone, 6-methyl-4-hydroxy-3-heptanone, 5-methyl-3-hydroxy-4-heptanone, 5-methyl-4-hydroxy-3-heptanone, 2,6-dimethylheptane, 2,5-dimethylheptane, 2,6-dimethyl-2-heptene, 2,6-dimethyl-3-heptene, 2,5-dimethyl-2-heptene, 2,5-dimethyl-3-heptene, 3,6-dimethyl-3-heptene, 2,6-dimethyl-3-heptanol, 2,6-dimethyl-4-heptanol, 2,5-dimethyl-3-heptanol, 2,5-dimethyl-4-heptanol, 2,6-dimethyl-3,4-heptanediol, 2,6-dimethyl-3,4-heptanedione, 2,5-dimethyl-3,4-heptanediol, 2,5-dimethyl-3,4-heptanedione, 2,6-dimethyl-3-hydroxy-4-heptanone, 2,6-dimethyl-4-hydroxy-3-heptanone, 2,5-dimethyl-3-hydroxy-4-heptanone, 2,5-dimethyl-4-hydroxy-3-heptanone, n-octane, 1-octene, 2-octene, 1-octanol, octanal, octanoate, 3-octene, 4-octene, 4-octanol, 4-octanone, 4,5-octanediol, 4,5-octanedione, 4-hydroxy-5-octanone, 2-methyloctane, 2-methyl-3-octene, 2-methyl-4-octene, 7-methyl-3-octene, 3-methyl-3-octene, 3-methyl-4-octene, 6-methyl-3-octene, 2-methyl-4-octanol, 7-methyl-4-octanol, 3-methyl-4-octanol, 6-methyl-4-octanol, 2-methyl-4-octanone, 7-methyl-4-octanone, 3-methyl-4-octanone, 6-methyl-4-octanone, 2-methyl-4,5-octanediol, 2-methyl-4,5-octanedione, 3-methyl-4,5-octanediol, 3-methyl-4,5-octanedione, 2-methyl-4-hydroxy-5-octanone, 2-methyl-5-hydroxy-4-octanone, 3-methyl-4-hydroxy-5-octanone, 3-methyl-5-hydroxy-4-octanone, 2,7-dimethyloctane, 2,7-dimethyl-3-octene, 2,7-dimethyl-4-octene, 2,7-dimethyl-4-octanol, 2,7-dimethyl-4-octanone, 2,7-dimethyl-4,5-octanediol, 2,7-dimethyl-4,5-octanedione, 2,7-dimethyl-4-hydroxy-5-octanone, 2,6-dimethyloctane, 2,6-dimethyl-3-octene, 2,6-dimethyl-4-octene, 3,7-dimethyl-3-octene, 2,6-dimethyl-4-octanol, 3,7-dimethyl-4-octanol, 2,6-dimethyl-4-octanone, 3,7-dimethyl-4-octanone, 2,6-dimethyl-4,5-octanediol, 2,6-dimethyl-4,5-octanedione, 2,6-dimethyl-4-hydroxy-5-octanone, 2,6-dimethyl-5-hydroxy-4-octanone, 3,6-dimethyloctane, 3,6-dimethyl-3-octene, 3,6-dimethyl-4-octene, 3,6-dimethyl-4-octanol, 3,6-dimethyl-4-octanone, 3,6-dimethyl-4,5-octanediol, 3,6-dimethyl-4,5-octanedione, 3,6-dimethyl-4-hydroxy-5-octanone, n-nonane, 1-nonene, 1-nonanol, nonanal, nonanoate, 2-methylnonane, 2-methyl-4-nonene, 2-methyl-5-nonene, 8-methyl-4-nonene, 2-methyl-5-nonanol, 8-methyl-4-nonanol, 2-methyl-5-nonanone, 8-methyl-4-nonanone, 8-methyl-4,5-nonanediol, 8-methyl-4,5-nonanedione, 8-methyl-4-hydroxy-5-nonanone, 8-methyl-5-hydroxy-4-nonanone, 2,8-dimethylnonane, 2,8-dimethyl-3-nonene, 2,8-dimethyl-4-nonene, 2,8-dimethyl-5-nonene, 2,8-dimethyl-4-nonanol, 2,8-dimethyl-5-nonanol, 2,8-dimethyl-4-nonanone, 2,8-dimethyl-5-nonanone, 2,8-dimethyl-4,5-nonanediol, 2,8-dimethyl-4,5-nonanedione, 2,8-dimethyl-4-hydroxy-5-nonanone, 2,8-dimethyl-5-hydroxy-4-nonanone, 2,7-dimethylnonane, 3,8-dimethyl-3-nonene, 3,8-dimethyl-4-nonene, 3,8-dimethyl-5-nonene, 3,8-dimethyl-4-nonanol, 3,8-dimethyl-5-nonanol, 3,8-dimethyl-4-nonanone, 3,8-dimethyl-5-nonanone, 3,8-dimethyl-4,5-nonanediol, 3,8-dimethyl-4,5-nonanedione, 3,8- dimethyl-4-hydroxy-5-nonanone, 3,8-dimethyl-5-hydroxy-4-nonanone, n-decane, 1-decene, 1-decanol, decanoate, 2,9-dimethyldecane, 2,9-dimethyl-3-decene, 2,9-dimethyl-4-decene, 2,9-dimethyl-5-decanol, 2,9-dimethyl-5-decanone, 2,9-dimethyl-5,6-decanediol, 2,9-dimethyl-6-hydroxy-5-decanone, 2,9-dimethyl-5,6-decanedionen-undecane, 1-undecene, 1-undecanol, undecanal, undecanoate, n-dodecane, 1-dodecene, 1-dodecanol, dodecanal, dodecanoate, n-dodecane, 1-decadecene, 1-dodecanol, dodecanal, dodecanoate, n-tridecane, 1-tridecene, 1-tridecanol, tridecanal, tridecanoate, n-tetradecane, 1-tetradecene, 1-tetradecanol, tetradecanal, tetradecanoate, n-pentadecane, 1-pentadecene, 1-pentadecanol, pentadecanal, pentadecanoate, n-hexadecane, 1-hexadecene, 1-hexadecanol, hexadecanal, hexadecanoate, n-heptadecane, 1-heptadecene, 1-heptadecanol, heptadecanal, heptadecanoate, n-octadecane, 1-octadecene, 1-octadecanol, octadecanal, octadecanoate, n-nonadecane, 1-nonadecene, 1-nonadecanol, nonadecanal, nonadecanoate, eicosane, 1-eicosene, 1-eicosanol, eicosanal, eicosanoate, 3-hydroxy propanal, 1,3-propanediol, 4-hydroxybutanal, 1,4-butanediol, 3-hydroxy-2-butanone, 2,3-butandiol, 1,5-pentane diol, homocitrate, homoisocitorate, b-hydroxy adipate, glutarate, glutarsemialdehyde, glutaraldehyde, 2-hydroxy-1-cyclopentanone, 1,2-cyclopentanediol, cyclopentanone, cyclopentanol, (S)-2-acetolactate, (R)-2,3-Dihydroxy-isovalerate, 2-oxoisovalerate, isobutyryl-CoA, isobutyrate, isobutyraldehyde, 5-amino pentaldehyde, 1,10-diaminodecane, 1,10-diamino-5-decene, 1,10-diamino-5-hydroxydecane, 1,10-diamino-5-decanone, 1,10-diamino-5, 6-decanediol, 1,10-diamino-6-hydroxy-5-decanone, phenylacetoaldehyde, 1,4-diphenylbutane, 1,4-diphenyl-1-butene, 1,4-diphenyl-2-butene, 1,4-diphenyl-2-butanol, 1,4-diphenyl-2-butanone, 1,4-diphenyl-2,3-butanediol, 1,4-diphenyl-3-hydroxy-2-butanone, 1-(4-hydeoxyphenyl)-4-phenylbutane, 1-(4-hydeoxyphenyl)-4-phenyl-1-butene, 1-(4-hydeoxyphenyl)-4-phenyl-1-butene, 1-(4-hydeoxyphenyl)-4-phenyl-2-butanol, 1-(4-hydeoxyphenyl)-4-phenyl-2-butanone, 1-(4-hydeoxyphenyl)-4-phenyl-2,3-butanediol, 1-(4-hydeoxyphenyl)-4-phenyl-3-hydroxy-2-butanone, 1-(indole-3)-4-phenylbutane, 1-(indole-3)-4-phenyl-1-butene, 1-(indole-3)-4-phenyl-2-butene, 1-(indole-3)-4-phenyl-2-butanol, 1-(indole-3)-4-phenyl-2-butanone, 1-(indole-3)-4-phenyl-2,3-butanediol, 1-(indole-3)-4-phenyl-3-hydroxy-?-butanone, 4-hydroxyphenylacetoaldehyde, 1,4-di(4-hydroxyphenyl)butane, 1,4-di(4-hydroxyphenyl)-1-butene, 1,4-di(4-hydroxyphenyl)-2-butene, 1,4-di(4-hydroxyphenyl)-2-butanol, 1,4-di(4-hydroxyphenyl)-2-butanone, 1,4-di(4-hydroxyphenyl)-2,3-butanediol, 1,4-di(4-hydroxyphenyl)-3-hydroxy-2-butanone, 1-(4-hydroxyphenyl)-4-(indole-3-)butane, 1-(4-hydroxyphenyl)-4-(indole-3)-1-butene, 1-di(4-hydroxyphenyl)-4-(indole-3)-2-butene, 1-(4-hydroxyphenyl)-4-(indole-3)-2-butanol, 1-(4-hydroxyphenyl)-4-(indole-3)-2-butanone, 1-(4-hydroxyphenyl)-4-(indole-3)-2,3-butanediol, 1-(4-hydroxyphenyl-4-(indole-3)-3-hydroxy-2-butanone, indole-3-acetoaldehyde, 1,4-di(indole-3-)butane, 1,4-di(indole-3)-1-butene, 1,4-di(indole-3)-2-butene, 1,4-di(indole-3)-2-butanol, 1,4-di(indole-3)-2-butanone, 1,4-di(indole-3)-2,3-butanediol, 1,4-di(indole-3)-3-hydroxy-2-butanone, succinate semialdehyde, hexane-1,8-dicarboxylic acid, 3-hexene-1,8-dicarboxylic acid, 3-hydroxy-hexane-1,8-dicarboxylic acid, 3-hexanone-1,8-dicarboxylic acid, 3,4-hexanediol-1,8-dicarboxylic acid, 4-hydroxy-3-hexanone-1,8-dicarboxylic acid, fucoidan, iodine, chlorophyll, carotenoid, calcium, magnesium, iron, sodium, potassium, and phosphate.

In some cases, the product is mucic acid. The mucic acid so produced can be further converted to adipic acid through the oxorhenium-complex-catalyzed deoxydehydration (DODH) reaction and subsequent Pt/C-catalyzed transfer hydrogenation. Li et al. (2014) *Angew. Chemie Int'l Edition* 53:4200; and WO 2015/084265. Adipic acid can be made into nylon (e.g., nylon-6,6 polyamide). In some cases, a method of the present disclosure comprises: a) culturing a genetically modified host cell of the present disclosure (e.g., culturing under anaerobic conditions), where the genetically modified host cell is genetically modified to produce a heterologous UDH that utilizes $NADP^+$ or $NAD^+$ as a co-factor; and b) recovering the mucic acid produced. In some cases, a method of the present disclosure comprises: a) culturing a genetically modified host cell of the present disclosure (e.g., culturing under anaerobic conditions), where the genetically modified host cell is genetically modified with a heterologous nucleic acid comprising a nucleotide sequence encoding a heterologous UDH that utilizes $NADP^+$ or $NAD^+$ as a co-factor; b) recovering the mucic acid produced; and c) converting the mucic acid to adipic acid.

In some cases, the product (e.g., the co-product) is 1,3-propanediol. The 1,3-propanediol so produced can be formulated into a variety of industrial products including composites, adhesives, laminates, coatings, moldings, aliphatic polyesters, and co-polyesters. In some cases, a method of the present disclosure comprises: a) culturing a genetically modified host cell of the present disclosure (e.g., culturing under anaerobic conditions), where the genetically modified host cell is genetically modified with one or more heterologous nucleic acids comprising nucleotide sequences encoding: i) a heterologous UDH that utilizes $NADP^+$ or $NAD^+$ as a co-factor; and ii) a heterologous 1,3-propanediol oxidoreductase; and b) recovering the 1,3-propanediol so produced. In some cases, a method of the present disclosure comprises: a) culturing a genetically modified host cell of the present disclosure (e.g., culturing under anaerobic conditions), where the genetically modified host cell is genetically modified with one or more heterologous nucleic acids comprising nucleotide sequences encoding: i) a heterologous UDH that utilizes $NADP^+$ or $NAD^+$ as a co-factor; and ii) a heterologous 1,3-propanediol oxidoreductase; b) recovering the 1,3-propanediol so produced; and c) polymerizing the 1,3-propanediol to produce a polyester.

In some cases, the product is D-galactaric acid. The D-galactaric acid so produced can be used in biopolymer production, among other uses. In some cases, a method of the present disclosure comprises: a) culturing a genetically modified host cell of the present disclosure (e.g., culturing under anaerobic conditions), where the genetically modified host cell is genetically modified with one or more heterologous nucleic acids comprising nucleotide sequences encoding: i) a heterologous UDH that utilizes $NADP^+$ or $NAD^+$ as a co-factor; ii) a MIPS polypeptide; and iii) a MIOX polypeptide; and b) recovering the D-galactaric acid so produced.

Genetically Modified Host Cell for Production of an Aldaric Acid; and Methods of Producing an Aldaric Acid The present disclosure provides a genetically modified in vitro fermentable host cell genetically modified with a heterologous nucleic acid comprising a nucleotide sequence encoding a heterologous UDH, which may be a heterologous modified (variant) UDH, wherein the heterologous UDH converts a sugar acid (e.g., an aldaric acid, a uronic acid) to its corresponding 1,5-aldonolactone, and wherein heterologous UDH uses NADP$^+$ as a cofactor, and produces NADPH.

The heterologous UDH converts a sugar acid to its corresponding 1,5-aldonolactone. In some cases, the sugar acid is D-galacturonic acid, and the 1,-5-aldonolactone is D-galactaro-1,5-lactone. Thus, e.g., in some cases, the heterologous UDH converts D-galacturonate to D-galactaro-1,5-lactone. In some cases, the sugar acid is D-glucuronic acid, and the 1,5-aldonolactone is D-glucaro-1,5-lactone. Thus, in some cases, the heterologous UDH converts D-glucuronic acid to D-glucaro-1,5-lactone. In some cases, the sugar acid is D-guluronic acid, and the 1,5-aldonolactone is D-gularo-1,5-lactone.

The present disclosure provides a genetically modified in vitro fermentable host cell genetically modified with a heterologous nucleic acid comprising a nucleotide sequence encoding a heterologous UDH, which may be a heterologous modified (variant) UDH, wherein the heterologous UDH converts an aldaric acid to its corresponding 1,5-aldonolactone, and wherein heterologous UDH uses NADP$^+$ as a cofactor, and produces NADPH.

The heterologous UDH converts an aldaric acid to its corresponding 1,5-aldonolactone. In some cases, the aldaric acid is D-galacturonic acid, and the 1,-5-aldonolactone is D-galactaro-1,5-lactone. Thus, e.g., in some cases, the heterologous UDH converts D-galacturonate to D-galactaro-1,5-lactone. In some cases, the aldaric acid is D-glucuronic acid, and the 1,5-aldonolactone is D-glucaro-1,5-lactone. Thus, in some cases, the heterologous UDH converts D-glucuronic acid to D-glucaro-1,5-lactone. In some cases, the sugar acid is D-guluronic acid, and the 1,5-aldonolactone is D-gularo-1,5-lactone.

Host Cells

Suitable host cells include cells that can be cultured in vitro, e.g., as unicellular organisms. Suitable host cells include yeast cells, fungal cells, insect cells, mammalian cells, algal cells, and bacterial cells. Suitable host cells include filamentous fungal cells; suitable filamentous fungal cells include, e.g., *Aspergillus*, *Neurospora*, and the like.

In some cases, the host cell is a eukaryotic cell. In some cases, the eukaryotic host cell is a yeast cell, an algal cell, or a fungal cell. In some cases, the host cell is a prokaryotic cell. In some cases, the host cell is a bacterial cell. A suitable host cell includes a microbial host cell (e.g., a bacterium, a yeast cell, a fungal cell) that can be cultured (e.g., culture in vitro) in a container, e.g., a test tube, an Eppendorf tube, a fermentation flask, a fermentation bottle, a fermentation vat, etc. Thus, for example, a suitable host cell is a fermentable cell.

The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Phanerochaete, Pleurotus, Schizophyllum, Talaromyces, Thermoascus, Thielavia, Tolypocladium,* and *Trichoderma*. Examples of suitable filamentous fungal cells include, e.g., *Aspergillus niger, Aspergillus awamori, Aspergillus foetidus, Aspergillus sojae, Aspergillus fumigatus,* and *Aspergillus oryzae*. Another example of a suitable fungal cell is a *Neurospora crassa* cell.

Examples of suitable yeast host cells are strains selected from a cell of a species of *Candida, Kluyveromyces, Saccharomyces, Schizosaccharomyces, Pichia, Hansenula, Yarrowia, Rhodotorula* and *Rhodosporidium*. In one embodiment, the yeast host cell is selected from a *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Schizosaccharomyces pombe, Saccharomyces uvarum, Pichia kluyveri, Yarrowia lipolytica, Candida utilis, Candida cacaoi,* and *Geotrichum fermentans*. Other useful yeast host cells are *Kluyveromyces lactis, Kluyveromyces fragilis, Hansenula polymorpha, Pichia pastoris, Yarrowia lipolytica, Schizosaccharomyces pombe, Ustilgo maylis, Candida maltose, Pichia* guillermondii and *Pichia* methanoliol.

Suitable yeast host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha,* and the like. In some cases, a yeast host cell is *Saccharomyces cerevisiae*; i.e., a genetically modified cell of the present disclosure is a genetically modified *Saccharomyces cerevisiae* cell.

In various embodiments, the yeast is selected from the non-limiting list of genera; *Candida, Cryptococcus, Hansenula, Issatchenki, Kluyveromyces, Komagataella, Lipomyces, Pichia, Rhodosporidium, Rhodotorula, Saccharomyces* or *Yarrowia* species. In various embodiments, the yeast is of a species selected from the group consisting of *Candida albicans, Candida ethanolica, Candida krusei, Candida methanosorhosa, Candida sonorensis, Candida tropicalis, Cryptococcus curvatus, Hansenula polymorpha, Issatchenki orientalis, Kluyveromyces lactic, Kluyveromyces marxianus, Kluyveromyces thermotolerans, Komagataella pastoris, Lipomyces starkeyi, Pichia angusta, Pichia deserticola, Pichia galeiformis, Pichia kodamae, Pichia kudriavzevii, Pichia membranaefaciens, Pichia anethanolica, Pichia pastoris, Pichia salictaria, Pichia stipitis, Pichia thermotolerans, Pichia trehalophila, Rhodosporidium toruloides, Rhodotorula glutinis, Rhodotorula graminis, Saccharomyces hayanus, Saccharomyces boulardi, Saccharomyces cerevisiae Saccharomyces kluyveri,* and *Yarrowia lipolytica, Pichia kudriavzevii*.

Illustrative examples of eukaryotic cells include, but are not limited to: *Aspergillus niger, Aspergillus oryzae, Crypthecodinium cohnii, Cunninghamella japonica, Entomophthora coronata, Mortierella alpina, Mucor circinelloides, Neurospora crassa, Pythium ultimum, Schizochyvtrium limacinum, Thraustochytrium aureum, Trichoderma reesei* and *Xanthophyllomyces dendrorhous*. In general, if a eukaryotic cell is used, a non-pathogenic strain is employed. Illustrative examples of non-pathogenic strains include, but are not limited to: *Pichia pastoris* and *Saccharomyces cerevisiae*. In addition, certain strains, including *Saccharomyces cerevisiae*, have been designated by the Food and Drug Administration as Generally Regarded as Safe (or GRAS) and so can be conveniently employed in various embodiments of the methods of the present disclosure.

The host cell can be a prokaryotic cell. Suitable prokaryotic cells include, but are not limited to, any of a variety of laboratory strains of *Escherichia coli, Lactobacillus* sp., *Salmonella* sp., *Shigella* sp., *Citrobacter, Enterobacter, Clostridium, Klebsiella,* Aerobacter, and the like. See, e.g., Carrier et al. (1992) J. Immunol. 148:1176-1181; U.S. Pat.

No. 6,447,784; and Sizemore et al. (1995) Science 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri*, *Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some cases, the host cell is *Escherichia coli*.

Illustrative examples of suitable prokaryotic host cells include, but are not limited to, *Bacillus subtilis, Brevihacterium ammoniagenes, Clostridium beigerinckii, Enterobacter sakazakii, Lactobacillus acidophilus, Lactococcus lactis, Mesorhizobium loti, Pseudomonas aeruginosa, Pseudomonas putida, Rhodobacter capsulatus, Rhodobacter sphaeroides, Salmonella enterica, Salmonella typhi, Salmonella typhimurium, Shigella* fiexneri, *Staphylococcus aureus, Streptomyces ambojaciens, Streptomyces aureofaciens, Streptomyces aureus, Streptomyes fungicidic, Streptomyces griseochromogenes, Streptomyces griseus, Streptomyces lividans, Streptomyces olivogriseus, Streptomyces rameus, Streptomyces tanashiensis*, and *Streptomyces vinaceus*.

Modified UDH

In some cases, a genetically modified host cell of the present disclosure is genetically modified with a heterologous nucleic acid comprising a nucleotide sequence encoding a heterologous UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 20 (SEQ ID NO: 19).

In some cases, the heterologous modified UDH comprises one or more amino acid substitutions in the NAD$^+$ binding motif such that the variant UDH binds NADP+. In some cases, the heterologous modified UDH comprises an amino acid sequence having at least 40% amino acid sequence identity to the amino acid sequence depicted in FIG. 19 (SEQ ID NO: 18), wherein one, two, or three of amino acids D42, I43, and A44 are substituted. In some cases, the heterologous modified UDH comprises an amino acid sequence having at least 80% amino acid sequence identity to the amino acid sequence depicted in FIG. 19 (SEQ ID NO:18), wherein one, two, or three of amino acids D42, I43, and A44 are substituted. In some cases, the heterologous modified UDH comprises wherein amino acid I43 is substituted with a positively charged amino acid. In some cases, the heterologous modified UDH comprises an I43R substitution. In some cases, the heterologous modified UDH comprises an amino acid sequence having at least 40% amino acid sequence identity to the amino acid sequence depicted in FIG. 21 (SEQ ID NO:20), wherein X is arginine, histidine, or lysine.

In some cases, a genetically modified host cell of the present disclosure is genetically modified with a heterologous nucleic acid comprising a nucleotide sequence encoding a variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18), where one, two, or three of amino acids D42, I43, and A44 are substituted. In some cases, the variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO: 18); and comprises an amino acid substitution at D42, i.e., where amino acid 42 is other than aspartic acid (e.g., where amino acid 42 is Gly, Ala, Val, Leu, Ile, Pro, Phe, Tyr, Trp, Ser, Thr, Cys, Met, Asn, Gln, Lys, Arg, His, or Glu). In some cases, the variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18); and comprises an amino acid substitution at I43, i.e., where amino acid 43 is other than isoleucine (e.g., where amino acid 43 is Gly, Ala, Val, Leu, Pro, Phe, Tyr, Trp, Ser, Thr, Cys, Met, Asn, Gln, Lys, Arg, His, Asp, or Glu). In some cases, the variant UDH comprises an I43R substitution. In some cases, the variant UDH comprises an I43H substitution. In some cases, the variant UDH comprises an I43K substitution. In some cases, the variant UDH comprises an I43A substitution. In some cases, the variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18); and comprises an amino acid substitution at A44, i.e., where amino acid 44 is other than alanine (e.g., where amino acid 44 is Gly, Val, Leu, Ile, Pro, Phe, Tyr, Trp, Ser, Thr, Cys, Met, Asn, Gln, Lys, Arg, His, Asp, or Glu).

In some cases, a genetically modified host cell of the present disclosure is genetically modified with a heterologous nucleic acid comprising a nucleotide sequence encoding a variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 21 (SEQ ID NO:20), where X is an amino acid other than isoleucine; e.g., where X is a charged amino acid. In some cases, X is arginine. In some cases, X is histidine. In some cases, X is lysine.

In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein one, two, or three of amino acids D35, V36, and A37 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 35 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 35 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 35 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 36 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 36 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 36 is Lys.

In some cases, a variant UDH polypeptide of the present disclosure comprises an amino acid sequence having at least 50%, at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO: 26), wherein one, two, or three of amino acids D33, L34, and S35 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 33 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 33 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 33 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 34 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 34 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 34 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 35 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 35 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 35 is Lys.

In some cases, a variant UDH polypeptide of the present disclosure comprises an amino acid sequence having at least 50%, at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), wherein one, two, or three of amino acids D37, I38, and S39 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 37 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 37 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 37 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 38 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 38 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 38 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 39 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 39 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 39 is Lys.

In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), wherein one, two, or three of amino acids D51, I52, and T53 is substituted with arginine, histidine, or lysine. In some cases, a variant UDH polypeptide of the present disclosure comprises an amino acid sequence having at least 50% amino acid sequence identity to the amino acid sequence depicted in FIG. 50 (SEQ ID NO:28), where amino acid 51 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 51 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 51 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 52 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 52 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 52 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 53 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 53 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 53 is Lys.

In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), wherein one, two, or three of amino acids D31, I32, and A33 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 31 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 31 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 31 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 32 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 32 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 32 is Lys.

In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), wherein one, two, or three of amino acids D32, I33, and R34 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 32 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 32 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 32 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 33 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 33 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 33 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 34 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 34 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 34 is Lys.

UDH

In some cases, a suitable heterologous UDH utilizes $NADP^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 20 (SEQ ID NO: 19).

In some cases, a suitable heterologous UDH utilizes $NAD^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 19 (SEQ ID NO: 18).

In some cases, a suitable heterologous UDH utilizes $NAD^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 47 (SEQ ID NO:25).

In some cases, a suitable heterologous UDH utilizes $NAD^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 48 (SEQ ID NO:26).

In some cases, a suitable heterologous UDH utilizes $NAD^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 49 (SEQ ID NO:27).

In some cases, a suitable heterologous UDH utilizes $NAD^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 50 (SEQ ID NO:28).

In some cases, a suitable heterologous UDH utilizes $NAD^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 51 (SEQ ID NO:29).

In some cases, a suitable heterologous UDH utilizes $NAD^+$, and comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in FIG. 52 (SEQ ID NO:30).

Nucleotide Sequence Encoding Heterologous UDH

In some cases, the nucleotide sequence encoding a heterologous UDH polypeptide is operably linked to a transcriptional control element (e.g., a promoter) that is active in the host cell. In some cases, the promoter is a constitutive promoter. In some cases, the promoter is a regulatable promoter. In some cases, the promoter is an inducible promoter.

Method of Producing an Aldaric Acid

The present disclosure provides a method of producing an aldaric acid in a host cell, the method comprising culturing the genetically modified in vitro cell, as described above (a genetically modified in vitro fermentable host cell genetically modified with a heterologous nucleic acid comprising a nucleotide sequence encoding a heterologous modified UDH, wherein the heterologous modified UDH converts a sugar acid (e.g., a uronic acid, an aldaric acid, etc.) to its corresponding 1,5-aldonolactone, and wherein heterologous modified UDH uses $NADP^+$ as a cofactor, and produces NADPH), in a culture medium comprising a uronic acid.

As noted above, the heterologous modified UDH converts a sugar acid to its corresponding 1,5-aldonolactone. In some cases, the sugar acid is D-galacturonic acid, and the 1,-5-aldonolactone is D-galactaro-1,5-lactone. Thus, e.g., in some cases, the heterologous modified UDH converts D-galacturonate to D-galactaro-1,5-lactone. In some cases, the sugar acid is D-glucuronic acid, and the 1,5-aldonolactone is D-glucaro-1,5-lactone. Thus, in some cases, the heterologous modified UDH converts D-glucuronic acid to D-glucaro-1,5-lactone. In some cases, the sugar acid is D-guluronic acid, and the 1,5-aldonolactone is D-gularo-1,5-lactone.

The present disclosure provides a method of producing an aldaric acid in a host cell, the method comprising culturing the genetically modified in vitro cell, as described above (a genetically modified in vitro fermentable host cell genetically modified with a heterologous nucleic acid comprising a nucleotide sequence encoding a heterologous modified UDH, wherein the heterologous modified UDH converts an aldaric acid to its corresponding 1,5-aldonolactone, and wherein heterologous modified UDH uses $NADP^+$ as a cofactor, and produces NADPH), in a culture medium comprising a uronic acid.

As noted above, the heterologous modified UDH converts an aldaric acid to its corresponding 1,5-aldonolactone. In some cases, the aldaric acid is D-galacturonic acid, and the 1,-5-aldonolactone is D-galactaro-1,5-lactone. Thus, e.g., in some cases, the heterologous modified UDH converts D-galacturonate to D-galactaro-1,5-lactone. In some cases, the aldaric acid is D-glucuronic acid, and the 1,5-aldonolactone is D-glucaro-1,5-lactone. Thus, in some cases, the heterologous modified UDH converts D-glucuronic acid to D-glucaro-1,5-lactone. In some cases, the sugar acid is D-guluronic acid, and the 1,5-aldonolactone is D-gularo-1,5-lactone.

In some cases, the D-galactaro-1,5-lactone is converted to mucic acid by action of lactonase (lactonohydrolase). In some cases, the lactonase (lactonohydrolase) is endogenous to the cell. In some cases, the lactonase (lactonohydrolase) is heterologous to the cell.

In some cases, the uronic acid is D-galacturonate.

In some cases, the aldaric acid that is produced is mucic acid, glucaric acid, or mannaric acid. In some cases, the aldaric acid that is produced is mucic acid. In some cases, the aldaric acid that is produced is glucaric acid. In some cases, the aldaric acid that is produced is mannaric acid.

In some cases, the aldaric acid is mucic acid, and wherein the mucic acid is recovered from the cell, the culture medium, or both the cell and the culture medium. The recovered mucic acid can be further modified, e.g., chemically modified in a cell-free reaction, to produce one or more downstream products.

In some cases, the D-galactaro-1,5-lactone is recovered from the cell, the culture medium, or both the cell and the culture medium. In some cases, the recovered D-galactaro-1,5-lactone is converted to mucic acid by base hydrolysis.

In some cases, the D-galactaro-1,5-lactone or the mucic acid is isolated from other components of the cell culture medium using one or more of extraction, continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, absorption chromatography, flash evaporation, high-performance liquid chromatography, precipitation, and ultrafiltration.

In some cases, the genetically modified host cell is cultured in vitro, where the culturing is carried out substantially anaerobically.

Carbon Source

As noted above, a method of the present disclosure comprises culturing a genetically modified host cell of the present disclosure in a culture medium comprising D-galacturonic acid. In some cases, the D-galacturonate is obtained from an agricultural waste stream. In some cases, the agricultural waste stream comprises one or more of apple peels, apple pulp, citrus peels, citrus pulp, and sugar beet pulp. In some cases, the D-galacturonate is from hydrolyzed pectin.

The D-galacturonic acid can be provided in purified form. The D-galacturonic acid can be provided in the form of an agricultural waste stream. For example, in some cases, the D-galacturonic acid is provided in the form of pectin, or a pectin-rich food. For example, in some cases, the D-galacturonic acid is provided in the form of one or more of: fruit pulp, e.g., citrus fruit pulp or apple pulp; the peel of a fruit, e.g., citrus fruit peel, apple peel, etc.; sugar beet pulp; rag and/or seeds of fruit (e.g., citrus fruits; apples; etc.). As another example, in some cases, the D-galacturonic acid is provided in the form of pectins present in hemicellulose. In some cases, the D-galacturonic acid source comprises pectins, also known as pectin polysaccharides, which are rich in galacturonic acid. In some cases, the D-galacturonic acid source comprises homogalacturonans. Homogalacturonans are linear chains of α-(1-4)-linked D-galacturonic acid. In some cases, the D-galacturonic acid source comprises substituted galacturonans. Substituted galacturonans are characterized by the presence of saccharide appendant residues (such as D-xylose or D-apiose in the respective cases of xylogalacturonan and apiogalacturonan) branching from a backbone of D-galacturonic acid residues. In some cases, the D-galacturonic acid source comprises rhamnogalacturonan I pectins. Rhamnogalacturonan I pectins (RG-I) contain a backbone of the repeating disaccharide: 4)-α-D-galacturonic acid-(1,2)-α-L-rhamnose. From many of the rhamnose residues, side chains of various neutral sugars branch off. The neutral sugars are mainly D-galactose, L-arabinose and D-xylose, with the types and proportions of neutral sugars varying with the origin of pectin. In some cases, the D-galacturonic acid source comprises rhamnogalacturonan II. The rhamnogalacturonan II backbone is made exclusively of D-galacturonic acid units. Also, fermentation of pectin-rich agricultural wastes by wild-type Saccharomyces results in accumulation of D-galacturonic acid in the fermentation broth. This can be isolated and used for bioconversions. In some cases, the D-galacturonic acid source comprises apple, citrus, and sugar beet waste. In some cases, the D-galacturonic acid source comprises apple waste. In some cases, the D-galacturonic acid source comprises citrus waste. In some cases, the D-galacturonic acid source comprises sugar beet waste. In some cases, the apple, citrus, or sugar beet waste is crushed or processed into more homogeneous sizes.

For example, in some cases, a genetically modified host cell of the present disclosure is cultured in a culture medium comprising pectin.

Genetically Modified Host Cells that Convert D-Galacturonic Acid to Glycerol for Production of Commodity Products and/or Increased Biomass The present disclosure provides a genetically modified host cell (e.g., an in vitro cell) that is genetically modified to convert D-galacturonic acid to glycerol. Suitable genetically modified host cells include yeast, bacteria, algae, and fungal cells.

In some cases, a genetically modified host cell of the present disclosure is genetically modified with one or more heterologous nucleic acids comprising nucleotide sequences encoding: a) a heterologous D-galacturonate reductase; b) a heterologous L-galactonate dehydratase; c) a heterologous 3-deoxy-L-threo-hex-2-ulosonate aldolase; and d) a heterologous glyceraldehyde reductase.

In some cases, the heterologous D-galacturonate reductase comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the D-galacturonate reductase amino acid sequence depicted in FIG. 6 (SEQ ID NO:5).

In some cases, the heterologous D-galacturonate reductase comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the D-galacturonate reductase amino acid sequence depicted in FIG. 7 (SEQ ID NO:6).

In some cases, the heterologous D-galacturonate reductase comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the D-galacturonate reductase amino acid sequence depicted in FIG. 8 (SEQ ID NO:7).

In some cases, the heterologous L-galactonate dehydratase comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the L-galactonate dehydratase amino acid sequence depicted in FIG. 9 (SEQ ID NO:8).

In some cases, the heterologous L-galactonate dehydratase comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the L-galactonate dehydratase amino acid sequence depicted in FIG. 10 (SEQ ID NO:9).

In some cases, the heterologous L-galactonate dehydratase comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the L-galactonate dehydratase amino acid sequence depicted in FIG. 11 (SEQ ID NO: 10).

In some cases, the heterologous L-galactonate dehydratase comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the L-galactonate dehydratase amino acid sequence depicted in FIG. 12 (SEQ ID NO:11).

In some cases, the heterologous L-galactonate dehydratase is a fusion protein comprising an N-terminal heterologous polypeptide, where the "heterologous polypeptide" is heterologous to the L-galactonate dehydratase, i.e., the "heterologous polypeptide" is other than L-galactonate dehydratase. For example, the fusion protein comprises, in order from N-terminus to C-terminus: a) a heterologous polypeptide; and b) an L-galactonate dehydratase polypeptide. In some cases, the heterologous polypeptide is a fluorescent polypeptide. Suitable fluorescent polypeptides are known in the art and include, but are not limited to, green fluorescent proteins (GFP, AcGFP, ZsGreen), red-shifted GFP (rs-GFP), red fluorescent proteins (RFP, including DsRed2, HcRed1, dsRed-Express, cherry, tdTomato), yellow fluorescent proteins (YFP, Zsyellow), cyan fluorescent proteins (CFP, AmCyan), a blue fluorescent protein (BFP), ametrine, citrine, cerulean, turquoise, VENUS, teal fluorescent protein (TFP), LOV (light, oxygen or voltage) domains, and the phycobiliproteins, as well as the enhanced versions and mutations of these protein.

In some cases, the heterologous 3-deoxy-L-threo-hex-2-ulosonate aldolase comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the 3-deoxy-L-threo-hex-2-ulosonate aldolase amino acid sequence depicted in FIG. 13 (SEQ ID NO: 12).

In some cases, the heterologous 3-deoxy-L-threo-hex-2-ulosonate aldolase comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the 3-deoxy-L-threo-hex-2-ulosonate aldolase amino acid sequence depicted in FIG. 14 (SEQ ID NO: 13).

In some cases, the heterologous 3-deoxy-L-threo-hex-2-ulosonate aldolase comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the 3-deoxy-L-threo-hex-2-ulosonate aldolase amino acid sequence depicted in FIG. 15 (SEQ ID NO: 14).

In some cases, the heterologous glyceraldehyde reductase comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the glyceraldehyde reductase amino acid sequence depicted in FIG. 16 (SEQ ID NO:15).

In some cases, the heterologous glyceraldehyde reductase comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the glyceraldehyde reductase amino acid sequence depicted in FIG. 17 (SEQ ID NO:16).

In some cases, the heterologous glyceraldehyde reductase comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the glyceraldehyde reductase amino acid sequence depicted in FIG. 18 (SEQ ID NO:17).

In some cases, a genetically modified host cell of the present disclosure is genetically modified with one or more heterologous nucleic acids comprising nucleotide sequences encoding: a) a heterologous D-galacturonate reductase comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the D-galacturonate reductase amino acid sequence depicted in FIG. 6 (SEQ ID NO:5); b) a heterologous L-galactonate dehydratase comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the L-galactonate dehydratase amino acid sequence depicted in FIG. 9 (SEQ ID NO:8); c) a heterologous 3-deoxy-L-threo-hex-2-ulosonate aldolase comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the 3-deoxy-L-threo-hex-2-ulosonate aldolase amino acid sequence depicted in FIG. 13 (SEQ ID NO: 12); and d) a heterologous glyceraldehyde reductase comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the glyceraldehyde reductase amino acid sequence depicted in FIG. 16 (SEQ ID NO: 15).

In some cases, a genetically modified host cell of the present disclosure is genetically modified with one or more heterologous nucleic acids comprising nucleotide sequences encoding: a) a heterologous D-galacturonic acid transporter; b) a heterologous D-galacturonate reductase; c) a heterologous L-galactonate dehydratase; d) a heterologous 3-deoxy-L-threo-hex-2-ulosonate aldolase; and e) a heterologous glyceraldehyde reductase.

In some cases, the heterologous D-galacturonic acid transporter comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the D-galacturonic acid transporter amino acid sequence depicted in FIG. 2 (SEQ ID NO:1).

In some cases, the heterologous D-galacturonic acid transporter comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the D-galacturonic acid transporter amino acid sequence depicted in FIG. 3 (SEQ ID NO:2).

In some cases, the heterologous D-galacturonic acid transporter comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the D-galacturonic acid transporter amino acid sequence depicted in FIG. 4 (SEQ ID NO:3).

In some cases, the heterologous D-galacturonic acid transporter comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the D-galacturonic acid transporter amino acid sequence depicted in FIG. 5 (SEQ ID NO:4).

In some cases, the heterologous D-galacturonic acid transporter comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the D-galacturonic acid transporter amino acid sequence depicted in FIG. 55 (SEQ ID NO:38).

In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in FIG. 57 (SEQ ID NO:39).

In some cases, a genetically modified host cell of the present disclosure is genetically modified with one or more heterologous nucleic acids comprising nucleotide sequences encoding: a) a heterologous D-galacturonic acid transporter comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the D-galacturonic acid transporter amino acid sequence depicted in FIG. 2 (SEQ ID NO:1); b) a heterologous D-galacturonate reductase comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the D-galacturonate reductase amino acid sequence depicted in FIG. 6 (SEQ ID NO:5); c) a heterologous L-galactonate dehydratase comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the L-galactonate dehydratase amino acid sequence depicted in FIG. 9 (SEQ ID NO:8); d) a heterologous 3-deoxy-L-threo-hex-2-ulosonate aldolase comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the 3-deoxy-L-threo-hex-2-ulosonate aldolase amino acid sequence depicted in FIG. 13 (SEQ ID NO: 12); and e) a heterologous glyceraldehyde reductase comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the glyceraldehyde reductase amino acid sequence depicted in FIG. 16 (SEQ ID NO: 15).

Host Cells

Suitable host cells include cells that can be cultured in vitro, e.g., as unicellular organisms. Suitable host cells include yeast cells, fungal cells, insect cells, mammalian cells, algal cells, and bacterial cells. Suitable host cells include filamentous fungal cells; suitable filamentous fungal cells include, e.g., *Aspergillus*, *Neurospora*, and the like.

In some cases, the host cell is a eukaryotic cell. In some cases, the eukaryotic host cell is a yeast cell, an algal cell, or a fungal cell. In some cases, the host cell is a prokaryotic cell. In some cases, the host cell is a bacterial cell. A suitable host cell includes a microbial host cell (e.g., a bacterium, a yeast cell, a fungal cell) that can be cultured (e.g., culture in vitro) in a container, e.g., a test tube, an Eppendorf tube, a fermentation flask, a fermentation bottle, a fermentation vat, etc. Thus, for example, a suitable host cell is a fermentable cell.

The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium*, *Agaricus*, *Aspergillus*, *Aureobasidium*, *Chrysosporium*, *Coprinus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Piromyces*, *Phanerochaete*, *Pleurotus*, *Schizophyllum*, *Talaromyces*, *Thermoascus*, *Thielavia*, *Tolypocladium*, and *Trichoderma*. Examples of suitable filamentous fungal cells include, e.g., *Aspergillus niger*, *Aspergillus awamori*, *Aspergillus foetidus*, *Aspergillus sojae*, *Aspergillus fumigatus*, and *Aspergillus oryzae*. Another example of a suitable fungal cell is a *Neurospora crassa* cell.

Examples of suitable yeast host cells are strains selected from a cell of a species of *Candida*, *Kluyveromyces*, *Saccharomyces*, *Schizosaccharomyces*, *Pichia*, *Hansenula*, *Yarrowia*, *Rhodotorula* and *Rhodosporidium*. In one embodiment, the yeast host cell is selected from a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, *Schizosaccharomyces pombe*, *Saccharomyces uvarum*, *Pichia kluyveri*, *Yarrowia lipolytica*, *Candida utilis*, *Candida cacaoi*, and *Geotrichum fermentans*. Other useful yeast host cells are *Kluyveromyces lactis*, *Kluyveromyces fragilis*, *Hansenula polymorpha*, *Pichia pastoris*, *Yarrowia lipolytica*, *Schizosaccharomyces pombe*, *Ustilgo maylis*, *Candida maltose*, *Pichia* guillermondii and *Pichia methanoliol*.

Suitable yeast host cells include, but are not limited to, *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, and the like. In some cases, a yeast host cell is *Saccharomyces cerevisiae*; i.e., a genetically modified cell of the present disclosure is a genetically modified *Saccharomyces cerevisiae* cell.

In various embodiments, the yeast is selected from the non-limiting list of genera; *Candida*, *Cryptococcus*, *Hansenula*, *Issatchenki*, *Kluyveromyces*, *Komagataella*, *Lipomyces*, *Pichia*, *Rhodosporidium*, *Rhodotorula*, *Saccharomyces* or *Yarrowia* species. In various embodiments, the yeast is of a species selected from the group consisting of *Candida albicans*, *Candida ethanolica*, *Candida krusei*, *Candida methanosorhosa*, *Candida sonorensis*, *Candida tropicalis*, *Cryptococcus curvatus*, *Hansenula polymorpha*, *Issatchenki orientalis*, *Kluyveromyces lactic*, *Kluyveromyces marxianus*, *Kluyveromyces thermotolerans*, *Komagataella pastoris*, *Lipomyces starkeyi*, *Pichia angusta*, *Pichia deserticola*, *Pichia galeiformis*, *Pichia kodamae*, *Pichia kudriavzevii*, *Pichia membranaefaciens*, *Pichia anethanolica*, *Pichia pastoris*, *Pichia salictaria*, *Pichia stipitis*, *Pichia thermotolerans*, *Pichia trehalophila*, *Rhodosporidium toruloides*, *Rhodotorula glutinis*, *Rhodotorula graminis*, *Saccharomyces hayanus*, *Saccharomyces boulardi*, *Saccharomyces cerevisiae*, *Saccharomyces kluyveri*, and *Yarrowia lipolytica*, *Pichia kudriavzevii*.

Illustrative examples of eukaryotic cells include, but are not limited to: *Aspergillus niger*, *Aspergillus oryzae*, *Crypthecodinium cohnii*, *Cunninghamella japonica*, *Entomophthora coronata*, *Mortierella alpina*, *Mucor circinelloides*, *Neurospora crassa*, *Pythium ultimum*, *Schizochytrium limacinum*, *Thraustochytrium aureum*, *Trichoderma reesei* and *Xanthophyllomyces dendrorhous*. In general, if a eukaryotic cell is used, a non-pathogenic strain is employed. Illustrative examples of non-pathogenic strains include, but are not limited to: *Pichia pastoris* and *Saccharomyces cerevisiae*. In addition, certain strains, including *Saccharomyces cerevisiae*, have been designated by the Food and Drug Administration as Generally Regarded as Safe (or GRAS) and so can be conveniently employed in various embodiments of the methods of the present disclosure.

The host cell can be a prokaryotic cell. Suitable prokaryotic cells include, but are not limited to, any of a variety of laboratory strains of *Escherichia coli*, *Lactobacillus* sp., *Salmonella* sp., *Shigella* sp., *Citrobacter*, *Enterobacter*, *Clostridium*, *Klebsiella*, *Aerobacter*, and the like. See, e.g., Carrier et al. (1992) J. Immunol. 148:1176-1181; U.S. Pat. No. 6,447,784; and Sizemore et al. (1995) Science 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri*, *Shigella sonnei*, and *Shigella* disenteriae. Typically, the laboratory strain is one that is non-pathogenic. Non-limiting examples of other suitable bacteria include, but are not limited to, *Bacillus subtilis*, *Pseudomonas pudita*, *Pseudomonas aeruginosa*, *Pseudomonas mevalonii*, *Rhodobacter sphaeroides*, *Rhodobacter capsulatus*, *Rhodospirillum rubrum*, *Rhodococcus* sp., and the like. In some cases, the host cell is *Escherichia coli*.

Illustrative examples of suitable prokaryotic host cells include, but are not limited to, *Bacillus subtilis*, *Brevibacterium ammoniagenes*, *Clostridium beigerinckii*, *Enterobacter sakazakii*, *Lactobacillus acidophilus*, *Lactococcus lactis*, *Mesorhizobium loti*, *Pseudomonas aeruginosa*, *Pseudomonas putida*, *Rhodobacter capsulatus*, *Rhodobacter sphaeroides*, *Salmonella enterica*, *Salmonella typhi*, *Salmonella typhimurium*, *Shigella fiexneri*, *Staphylococcus aureus*, *Streptomyces ambojaciens*, *Streptomyces aureofaciens*, *Streptomyces aureus*, *Streptomyces fungicidicus*, *Streptomyces griseochromogenes*, *Streptomyces griseus*, *Streptomyces lividans* *Streptomyces olivogriseus*, *Streptomyces rameus*, *Streptomyces tanashiensis*, and *Streptomyces vinaceus*.

In some cases, a genetically modified host cell of the present disclosure is genetically modified, as described above, to metabolize D-galacturonic acid to glycerol; and is further genetically modified to express one or more enzymes of a biosynthetic pathway, wherein the biosynthetic pathway is: (i) a secondary metabolite biosynthetic pathway, e.g., wherein the secondary metabolite biosynthetic pathway is an isoprenoid biosynthetic pathway, a polyketide biosynthetic pathway, or an alkaloid biosynthetic pathway; (ii) a pathway for the production of a monoacetylated deoxygenated taxane; (iii) a pathway for the production of ferruginol; (iv) a pathway for the production of nootkatone; (v) a pathway for the production of an aromatic compound or aromatic-derived compound, e.g., where the aromatic compound is 3-aminobenzoate or p-hydroxybenzoate (PHB), or where the aromatic-derived compound is muconic acid, an alkaloid, or a flavonoid; and/or (vi) a pathway for the production of short chain dicarboxylic acids.

In some cases, the pyruvate produced as a downstream product of glycerol produced from galacturonic acid is used in a mevalonate pathway. In other cases, other pathways can be co-expressed to convert the end products of the catabolism pathway (pyruvate and glycerol) or the intermediates (e.g. 1-galactonate, keto sugar, 1-glyceraldehyde) into commodity chemicals. For example, L-galactonate could be converted to a 1,4-lactone form and further converted to 1-ascorbic acid.

Products that can be produced using a method of the present disclosure include, but are not limited to, methane, methanol, ethane, ethene, ethanol, n-propane, 1-propene, 1-propanol, propanal, acetone, propionate, n-butane, 1-butene, 1-butanol, butanal, butanoate, isobutanal, isobutanol, 2-methylbutanal, 2-methylbutanol, 3-methylbutanal, 3-methylbutanol, 2-butene, 2-butanol, 2-butanone, 2,3-butanediol, 3-hydroxy-2-butanone, 2,3-butanedione, ethylbenzene, ethenylbenzene, 2-phenylethanol, phenylacetaldehyde, 1-phenylbutane, 4-phenyl-1-butene, 4-phenyl-2-butene, 1-phenyl-2-butene, 1-phenyl-2-butanol, 4-phenyl-2-butanol, 1-phenyl-2-butanone, 4-phenyl-2-butanone, 1-phenyl-2,3-butandiol, 1-phenyl-3-hydroxy-2-butanone, 4-phenyl-3-hydroxy-2-butanone, 1-phenyl-2,3-butanedione, n-pentane, ethylphenol, ethenylphenol, 2-(4-hydroxyphenyl)ethanol, 4-hydroxyphenylacetaldehyde, 1-(4-hydroxyphenyl)butane, 4-(4-hydroxyphenyl)-1-butene, 4-(4-hydroxyphenyl)-2-butene, 1-(4-hydroxyphenyl)-1-butene, 1-(4-hydroxyphenyl)-2-butanol, 4-(4-hydroxyphenyl)-2-butanol, 1-(4-hydroxyphenyl)-2-butanone, 4-(4-hydroxyphenyl)-2-butanone, 1-(4-hydroxyphenyl)-2,3-butandiol, 1-(4-hydroxyphenyl)-3-hydroxy-2-butanone, 4-(4-hydroxyphenyl)-3-hydroxy-2-butanone, 1-(4-hydroxyphenyl)-2,3-butanonedione, indolylethane, indolylethene, 2-(indole-3-)ethanol, n-pentane, 1-pentene, 1-pentanol, pentanal, pentanoate, 2-pentene, 2-pentanol, 3-pentanol, 2-pentanone, 3-pentanone, 4-methylpentanal, 4-methylpentanol, 2,3-pentanediol, 2-hydroxy-3-pentanone, 3-hydroxy-2-pentanone, 2,3-pentanedione, 2-methylpentane, 4-methyl-1-pentene, 4-methyl-2-pentene, 4-methyl-3-pentene, 4-methyl-2-pentanol, 2-methyl-3-pentanol, 4-methyl-2-pentanone, 2-methyl-3-pentanone, 4-methyl-2,3-pentanediol, 4-methyl-2-hydroxy-3-pentanone, 4-methyl-3-hydroxy-2-pentanone, 4-methyl-2,3-pentanedione, 1-phenylpentane, 1-phenyl-1-pentene, 1-phenyl-2-pentene, 1-phenyl-3-pentene, 1-phenyl-2-pentanol, 1-phenyl-3-pentanol, 1-phenyl-2-pentanone, 1-phenyl-3-pentanone, 1-phenyl-2,3-pentanediol, 1-phenyl-2-hydroxy-3-pentanone, 1-phenyl-3-hydroxy-2-pentanone, 1-phenyl-2,3-pentanedione, 4-methyl-1-phenylpentane, 4-methyl-1-phenyl-1-pentene, 4-methyl-1-phenyl-2-pentene, 4-methyl-1-phenyl-3-pentene, 4-methyl-1-phenyl-3-pentanol, 4-methyl-1-phenyl-2-pentanol, 4-methyl-1-phenyl-3-pentanone, 4-methyl-1-phenyl-2-pentanone, 4-methyl-1-phenyl-2,3-pentanediol, 4-methyl-1-phenyl-2,3-pentanedione, 4-methyl-1-phenyl-3-hydroxy-2-pentanone, 4-methyl-1-phenyl-2-hydroxy-3-pentanone, 1-(4-hydroxyphenyl)pentane, 1-(4-hydroxyphenyl)-1-pentene, 1-(4-hydroxyphenyl)-2-pentene, 1-(4-hydroxyphenyl)-3-pentene, 1-(4-hydroxyphenyl)-2-pentanol, 1-(4-hydroxyphenyl)-3-pentanol, 1-(4-hydroxyphenyl)-2-pentanone, 1-(4-hydroxyphenyl)-3-pentanone, 1-(4-hydroxyphenyl)-2,3-pentanediol, 1-(4-hydroxyphenyl)-2-hydroxy-3-pentanone, 1-(4-hydroxyphenyl)-3-hydroxy-2-pentanone, 1-(4-hydroxyphenyl)-2,3-pentanedione, 4-methyl-1-(4-hydroxyphenyl)pentane, 4-methyl-1-(4-hydroxyphenyl)-2-pentene, 4-methyl-1-(4-hydroxyphenyl)-3-pentene, 4-methyl-1-(4-hydroxyphenyl)-1-pentene, 4-methyl-1-(4-hydroxyphenyl)-3-pentanol, 4-methyl-1-(4-hydroxyphenyl)-2-pentanol, 4-methyl-1-(4-hydroxyphenyl)-3-pentanone, 4-methyl-1-(4-hydroxyphenyl)-2-pentanone, 4-methyl-1-(4-hydroxyphenyl)-2,3-pentanediol, 4-methyl-1-(4-hydroxyphenyl)-2,3-pentanedione, 4-methyl-1-(4-hydroxyphenyl)-3-hydroxy-2-pentanone, 4-methyl-1-(4-hydroxyphenyl)-2-hydroxy-3-pentanone, 1-indole-3-pentane, 1-(indole-3)-1-pentene, 1-(indole-3)-2-pentene, 1-(indole-3)-3-pentene, 1-(indole-3)-2-pentanol, 1-(indole-3)-3-pentanol, 1-(indole-3)-2-pentanone, 1-(indole-3)-3-pentanone, 1-(indole-3)-2,3-pentanediol, 1-(indole-3)-2-hydroxy-3-pentanone, 1-(indole-3)-3-hydroxy-2-pentanone, 1-(indole-3)-2,3-pentanedione, 4-methyl-1-(indole-3-)pentane, 4-methyl-1-(indole-3)-2-pentene, 4-methyl-1-(indole-3)-3-pentene, 4-methyl-1-(indole-3)-1-pentene, 4-methyl-2-(indole-3)-3-pentanol, 4-methyl-1-(indole-3)-2-pentanol, 4-methyl-1-(indole-3)-3-pentanone, 4-methyl-1-(indole-3)-2-pentanone, 4-methyl-1-(indole-3)-2,3-pentanediol, 4-methyl-1-(indole-3)-2,3-pentanedione, 4-methyl-1-(indole-3)-3-hydroxy-2-pentanone, 4-methyl-1-(indole-3)-2-hydroxy-3-pentanone, n-hexane, 1-hexene, 1-hexanol, hexanal, hexanoate, 2-hexene, 3-hexene, 2-hexanol, 3-hexanol, 2-hexanone, 3-hexanone, 2,3-hexanediol, 2,3-hexanedione, 3,4-hexanediol, 3,4-hexanedione, 2-hydroxy-3-hexanone, 3-hydroxy-2-hexanone, 3-hydroxy-4-hexanone, 4-hydroxy-3-hexanone, 2-methylhexane, 3-methylhexane, 2-methyl-2-hexene, 2-methyl-3-hexene, 5-methyl-1-hexene, 5-methyl-2-hexene, 4-methyl-1-hexene, 4-methyl-2-hexene, 3-methyl-3-hexene, 3-methyl-2-hexene, 3-methyl-1-hexene, 2-methyl-3-hexanol, 5-methyl-2-hexanol, 5-methyl-3-hexanol, 2-methyl-3-hexanone, 5-methyl-2-hexanone, 5-methyl-3-hexanone, 2-methyl-3,4-hexanediol, 2-methyl-3,4-hexanedione, 5-methyl-2,3-hexanediol, 5-methyl-2,3-hexanedione, 4-methyl-2,3-hexanediol, 4-methyl-2,3-hexanedione, 2-methyl-3-hydroxy-4-hexanone, 2-methyl-4-hydroxy-3-hexanone, 5-methyl-2-hydroxy-3-hexanone, 5-methyl-3-hydroxy-2-hexanone, 4-methyl-2-hydroxy-3-hexanone, 4-methyl-3-hydroxy-2-hexanone, 2,5-dimethylhexane, 2,5-dimethyl-2-hexene, 2,5-dimethyl-3-hexene, 2,5-dimethyl-3-hexanol, 2,5-dimethyl-3-hexanone, 2,5-dimethyl-3,4-hexanediol, 2,5-dimethyl-3,4-hexanedione, 2,5-dimethyl-3-hydroxy-4-hexanone, 5-methyl-1-phenylhexane, 4-methyl-1-phenylhexane, 5-methyl-1-phenyl-1-hexene, 5-methyl-1-phenyl-2-hexene, 5-methyl-1-phenyl-3-hexene, 4-methyl-1-phenyl-1-hexene, 4-methyl-1-phenyl-2-hexene, 4-methyl-1-phenyl-3-hexene, 5-methyl-1-phenyl-2-hexanol, 5-methyl-1-phenyl-3-hexanol, 4-methyl-1-phenyl-2-hexanol, 4-methyl-1-phenyl-3-hexanol, 5-methyl-1-phenyl-2-hexanone, 5-methyl-1-phenyl-3-hexanone, 4-methyl-1-phenyl-2-hexanone, 4-methyl-1-phenyl-3-hexanone, 5-methyl-1-phenyl-2,3-hexanediol, 4-methyl-1-phenyl-2,3-hexanediol, 5-methyl-1-phenyl-3-hydroxy-2-hexanone, 5-methyl-1-phenyl-2-hydroxy-3-hexanone, 4-methyl-1-phenyl-3-hydroxy-2-hexanone, 4-methyl-1-phenyl-2-hydroxy-3-hexanone, 5-methyl-1-phenyl-2,3-hexanedione, 4-methyl-1-phenyl-2,3-hexanedione, 4-methyl-1-(4-hydroxyphenyl)

hexane, 5-methyl-1-(4-hydroxyphenyl)-1-hexene, 5-methyl-1-(4-hydroxyphenyl)-2-hexene, 5-methyl-1-(4-hydroxyphenyl)-3-hexene, 4-methyl-1-(4-hydroxyphenyl)-1-hexene, 4-methyl-1-(4-hydroxyphenyl)-2-hexene, 4-methyl-1-(4-hydroxyphenyl)-3-hexene, 5-methyl-1-(4-hydroxyphenyl)-2-hexanol, 5-methyl-1-(4-hydroxyphenyl)-3-hexanol, 4-methyl-1-(4-hydroxyphenyl)-2-hexanol, 4-methyl-1-(4-hydroxyphenyl)-3-hexanol, 5-methyl-1-(4-hydroxyphenyl)-2-hexanone, 5-methyl-1-(4-hydroxyphenyl)-3-hexanone, 4-methyl-1-(4-hydroxyphenyl)-2-hexanone, 4-methyl-1-(4-hydroxyphenyl)-3-hexanone, 5-methyl-1-(4-hydroxyphenyl)-2,3-hexanediol, 4-methyl-1-(4-hydroxyphenyl)-2,3-hexanediol, 5-methyl-1-(4-hydroxyphenyl)-3-hydroxy-2-hexanone, 5-methyl-1-(4-hydroxyphenyl)-2-hydroxy-3-hexanone, 4-methyl-1-(4-hydroxyphenyl)-3-hydroxy-2-hexanone, 4-methyl-1-(4-hydroxyphenyl)-2-hydroxy-3-hexanone, 5-methyl-1-(4-hydroxyphenyl)-2,3-hexanedione, 4-methyl-1-(4-hydroxyphenyl)-2,3-hexanedione, 4-methyl-1-(indole-3-)hexane, 5-methyl-1-(indole-3)-1-hexene, 5-methyl-1-(indole-3)-2-hexene, 5-methyl-1-(indole-3)-3-hexene, 4-methyl-1-(indole-3)-1-hexene, 4-methyl-1-(indole-3)-2-hexene, 4-methyl-1-(indole-3)-3-hexene, 5-methyl-1-(indole-3)-2-hexanol, 5-methyl-1-(indole-3)-3-hexanol, 4-methyl-1-(indole-3)-2-hexanol, 4-methyl-1-(indole-3)-3-hexanol, 5-methyl-1-(indole-3)-2-hexanone, 5-methyl-1-(indole-3)-3-hexanone, 4-methyl-1-(indole-3)-2-hexanone, 4-methyl-1-(indole-3)-3-hexanone, 5-methyl-1-(indole-3)-2,3-hexanediol, 4-methyl-1-(indole-3)-2,3-hexanediol, 5-methyl-1-(indole-3)-3-hydroxy-2-hexanone, 5-methyl-1-(indole-3)-2-hydroxy-3-hexanone, 4-methyl-1-(indole-3)-3-hydroxy-2-hexanone, 4-methyl-1-(indole-3)-2-hydroxy-3-hexanone, 5-methyl-1-(indole-3)-2,3-hexanedione, 4-methyl-1-(indole-3)-2,3-hexanedione, n-heptane, 1-heptene, 1-heptanol, heptanal, heptanoate, 2-heptene, 3-heptene, 2-heptanol, 3-heptanol, 4-heptanol, 2-heptanone, 3-heptanone, 4-heptanone, 2,3-heptanediol, 2,3-heptanedione, 3,4-heptanediol, 3,4-heptanedione, 2-hydroxy-3-heptanone, 3-hydroxy-2-heptanone, 3-hydroxy-4-heptanone, 4-hydroxy-3-heptanone, 2-methylheptane, 3-methylheptane, 6-methyl-2-heptene, 6-methyl-3-heptene, 2-methyl-3-heptene, 2-methyl-2-heptene, 5-methyl-2-heptene, 5-methyl-3-heptene, 3-methyl-3-heptene, 2-methyl-3-heptanol, 2-methyl-4-heptanol, 6-methyl-3-heptanol, 5-methyl-3-heptanol, 3-methyl-4-heptanol, 2-methyl-3-heptanone, 2-methyl-4-heptanone, 6-methyl-3-heptanone, 5-methyl-3-heptanone, 3-methyl-4-heptanone, 2-methyl-3,4-heptanediol, 2-methyl-3,4-heptanedione, 6-methyl-3,4-heptanediol, 6-methyl-3,4-heptanedione, 5-methyl-3,4-heptanediol, 5-methyl-3,4-heptanedione, 2-methyl-3-hydroxy-4-heptanone, 2-methyl-4-hydroxy-3-heptanone, 6-methyl-3-hydroxy-4-heptanone, 6-methyl-4-hydroxy-3-heptanone, 5-methyl-3-hydroxy-4-heptanone, 5-methyl-4-hydroxy-3-heptanone, 2,6-dimethylheptane, 2,5-dimethylheptane, 2,6-dimethyl-2-heptene, 2,6-dimethyl-3-heptene, 2,5-dimethyl-2-heptene, 2,5-dimethyl-3-heptene, 3,6-dimethyl-3-heptene, 2,6-dimethyl-3-heptanol, 2,6-dimethyl-4-heptanol, 2,5-dimethyl-3-heptanol, 2,5-dimethyl-4-heptanol, 2,6-dimethyl-3,4-heptanediol, 2,6-dimethyl-3,4-heptanedione, 2,5-dimethyl-3,4-heptanediol, 2,5-dimethyl-3,4-heptanedione, 2,6-dimethyl-3-hydroxy-4-heptanone, 2,6-dimethyl-4-hydroxy-3-heptanone, 2,5-dimethyl-3-hydroxy-4-heptanone, 2,5-dimethyl-4-hydroxy-3-heptanone, n-octane, 1-octene, 2-octene, 1-octanol, octanal, octanoate, 3-octene, 4-octene, 4-octanol, 4-octanone, 4,5-octanediol, 4,5-octanedione, 4-hydroxy-5-octanone, 2-methyloctane, 2-methyl-3-octene, 2-methyl-4-octene, 7-methyl-3-octene, 3-methyl-3-octene, 3-methyl-4-octene, 6-methyl-3-octene, 2-methyl-4-octanol, 7-methyl-4-octanol, 3-methyl-4-octanol, 6-methyl-4-octanol, 2-methyl-4-octanone, 7-methyl-4-octanone, 3-methyl-4-octanone, 6-methyl-4-octanone, 2-methyl-4,5-octanediol, 2-methyl-4,5-octanedione, 3-methyl-4,5-octanediol, 3-methyl-4,5-octanedione, 2-methyl-4-hydroxy-5-octanone, 2-methyl-5-hydroxy-4-octanone, 3-methyl-4-hydroxy-5-octanone, 3-methyl-5-hydroxy-4-octanone, 2,7-dimethyloctane, 2,7-dimethyl-3-octene, 2,7-dimethyl-4-octene, 2,7-dimethyl-4-octanol, 2,7-dimethyl-4-octanone, 2,7-dimethyl-4,5-octanediol, 2,7-dimethyl-4,5-octanedione, 2,7-dimethyl-4-hydroxy-5-octanone, 2,6-dimethyloctane, 2,6-dimethyl-3-octene, 2,6-dimethyl-4-octene, 3,7-dimethyl-3-octene, 2,6-dimethyl-4-octanol, 3,7-dimethyl-4-octanol, 2,6-dimethyl-4-octanone, 3,7-dimethyl-4-octanone, 2,6-dimethyl-4,5-octanediol, 2,6-dimethyl-4,5-octanedione, 2,6-dimethyl-4-hydroxy-5-octanone, 2,6-dimethyl-5-hydroxy-4-octanone, 3,6-dimethyloctane, 3,6-dimethyl-3-octene, 3,6-dimethyl-4-octene, 3,6-dimethyl-4-octanol, 3,6-dimethyl-4-octanone, 3,6-dimethyl-4,5-octanediol, 3,6-dimethyl-4,5-octanedione, 3,6-dimethyl-4-hydroxy-5-octanone n-nonane, 1-nonene, 1-nonanol, nonanal, nonanoate, 2-methylnonane, 2-methyl-4-nonene, 2-methyl-5-nonene, 8-methyl-4-nonene, 2-methyl-5-nonanol, 8-methyl-4-nonanol, 2-methyl-5-nonanone, 8-methyl-4-nonanone, 8-methyl-4,5-nonanediol, 8-methyl-4,5-nonanedione, 8-methyl-4-hydroxy-5-nonanone, 8-methyl-5-hydroxy-4-nonanone, 2,8-dimethylnonane, 2,8-dimethyl-3-nonene, 2,8-dimethyl-4-nonene, 2,8-dimethyl-5-nonene, 2,8-dimethyl-4-nonanol, 2,8-dimethyl-5-nonanol, 2,8-dimethyl-4-nonanone, 2,8-dimethyl-5-nonanone, 2,8-dimethyl-4,5-nonanediol, 2,8-dimethyl-4,5-nonanedione, 2,8-dimethyl-4-hydroxy-5-nonanone, 2,8-dimethyl-5-hydroxy-4-nonanone, 2,7-dimethylnonane, 3,8-dimethyl-3-nonene, 3,8-dimethyl-4-nonene, 3,8-dimethyl-5-nonene, 3,8-dimethyl-4-nonanol, 3,8-dimethyl-5-nonanol, 3,8-dimethyl-4-nonanone, 3,8-dimethyl-5-nonanone, 3,8-dimethyl-4,5-nonanediol, 3,8-dimethyl, 5-nonanedione, 3,8-dimethyl-4-hydroxy-5-nonanone, 3,8-dimethyl-5-hydroxy-4-nonanone, n-decane, 1-decene, 1-decanol, decanoate, 2,9-dimethyldecane, 2,9-dimethyl-3-decene, 2,9-dimethyl-4-decene, 2,9-dimethyl-5-decanol, 2,9-dimethyl-5-decanone, 2,9-dimethyl-5,6-decanediol, 2,9-dimethyl-6-hydroxy-5-decanone, 2,9-dimethyl-5,6-decanedionen-undecane, 1-undecene, 1-undecanol, undecanal, undecanoate, n-dodecane, 1-dodecene, 1-dodecanol, dodecanal, dodecanoate, n-dodecane, 1-decadecene, 1-dodecanol, dodecanal, dodecanoate, n-tridecane, 1-tridecene, 1-tridecanol, tridecanal, tridecanoate, n-tetradecane, 1-tetradecene, 1-tetradecanol, tetradecanal, tetradecanoate, n-pentadecane, 1-pentadecene, 1-pentadecanol, pentadecanal, pentadecanoate, n-hexadecane, 1-hexadecene, 1-hexadecanol, hexadecanal, hexadecanoate, n-heptadecane, 1-heptadecene, 1-heptadecanol, heptadecanal, heptadecanoate, n-octadecane, l-octadecene, l-octadecanol, octadecanal, octadecanoate, n-nonadecane, 1-nonadecene, 1-nonadecanol, nonadecanal, nonadecanoate, eicosane, 1-eicosene, 1-eicosanol, eicosanal, eicosanoate, 3-hydroxy propanal, 1,3-propanediol, 4-hydroxybutanal, 1,4-butanediol, 3-hydroxy-2-butanone, 2,3-butandiol, 1,5-pentane diol, homocitrate, homoisocitorate, b-hydroxy adipate, glutarate, glutarsemialdehyde, glutaraldehyde, 2-hydroxy-1-cyclopentanone, 1,2-cyclopentanediol, cyclopentanone, cyclopentanol, (S)-2-acetolactate. (R)-2,3-Dihydroxy-isovalerate, 2-oxoisovalerate, isobutyryl-CoA, isobutyrate, isobutyraldehyde, 5-amino pentaldehyde, 1,10-diaminodecane, 1,10-diamino-5-decene, 1,10-diamino-5-hydroxydecane, 1,10-diamino-5-decanone, 1,10-diamino-5,6-decanediol, 1,10-diamino-6-hydroxy-5-decanone, phenylacetoaldehyde, 1,4-diphenylbutane, 1,4-diphenyl-1-butene, 1,4-diphenyl-2-butene, 1,4-diphenyl-2-butanol, 1,4-diphenyl-2-butanone, 1,4-diphenyl-2,3-butanediol, 1,4-diphenyl-3-hydroxy-2-butanone, 1-(4-hydeoxyphenyl)-4-phenylbutane, 1-(4-hydeoxyphenyl)-4-phenyl-1-butene, 1-(4-hydeoxyphenyl)-4-phenyl-2-butene, 1-(4-hydeoxyphenyl)-4-phenyl-2-butanol, 1-(4-hydeoxyphenyl)-4-phenyl-2-butanone, 1-(4-hydeoxyphenyl)-4-phenyl-2,3-butanediol, 1-(4-hydeoxyphenyl)-4-phenyl-3-hydroxy-2-butanone, 1-(indole-3)-4-phenylbutane, 1-(indole-3)-4-phenyl-1-butene, 1-(indole-3)-4-phenyl-2-butene, 1-(indole-3)-4-phenyl-2-butanol, 1-(indole-3)-4-phenyl-2-butanone, 1-(indole-3)-4-phenyl-2,3-butanediol, 1-(indole-3)-4-phenyl-3-hydroxy-2-butanone, 4-hydroxyphenylacetoaldehyde, 1,4-di(4-hydroxyphenyl)butane, 1,4-di(4-hydroxyphenyl)-1-butene, 1,4-di(4-hydroxyphenyl)-2-butene, 1,4-di(4-hydroxyphenyl)-2-butanol, 1,4-di(4-hydroxyphenyl)-2-butanone, 1,4-di(4-hydroxyphenyl)-2,3-butanediol, 1,4-di(4-hydroxyphenyl)-3-hydroxy-2-butanone, 1-(4-hydroxyphenyl)-4-(indole-3-)butane, 1-(4-hydroxyphenyl)-4-(indole-3)-1-butene, 1-di(4-hydroxyphenyl)-4-(indole-3)-2-butene, 1-(4-hydroxyphenyl)-4-(indole-3)-2-butanol, 1-(4-hydroxyphenyl)-4-(indole-3)-2-butanone, 1-(4-hydroxyphenyl)-4-(indole-3)-2,3-butanediol, 1-(4-hydroxyphenyl)-4-(indole-3)-3-hydroxy-2-butanone, indole-3-acetoaldehyde, 1,4-di(indole-3-)butane, 1,4-di(indole-3)-1-butene, 1,4-di(indole-3)-2-butene, 1,4-di(indole-3)-2-butanol, 1,4-di(indole-3)-2-butanone, 1,4-di(indole-3)-2,3-butanediol, 1,4-di(indole-3)-3-hydroxy-2-butanone, succinate semialdehyde, hexane-1,8-dicarboxylic acid, 3-hexene-1,8-dicarboxylic acid, 3-hydroxy-hexane-1,8-dicarboxylic acid, 3-hexanone-1,8-dicarboxylic acid, 3,4-hexanediol-1,8-dicarboxylic acid, 4-hydroxy-3-hexanone-1, 8-dicarboxylic acid, fucoidan, iodine, chlorophyll, carotenoid, calcium, magnesium, iron, sodium, potassium, and phosphate.

Biosynthetic pathway products produced by such genetically modified host cells include, but are not limited to, isoprenoid compounds, alkaloid compounds, phenylpropanoid compounds, flavonoid compounds, steroid compounds, polyketide compounds, macrolide compounds, sugar alcohols, phenolic compounds, and the like.

As noted above, a subject method provides for production of a biosynthetic pathway product and/or a precursor of a biosynthetic pathway product in a subject genetically modified host cell. A precursor of a biosynthetic pathway product is also referred to as an "intermediate." Exemplary intermediates include, but are not limited to, isoprenoid precursors; alkaloid precursors; phenylpropanoid precursors; flavonoid precursors; steroid precursors; polyketide precursors; macrolide precursors; sugar alcohol precursors; phenolic compound precursors; and the like. See, e.g., Hwang et al. ((2003) *Appl. Environ. Microbiol.* 69:2699-2706; Facchini et al. ((2004) *TRENDS Plant Sci.* 9:116.

Biosynthetic pathway products of interest include, but are not limited to, isoprenoid compounds, alkaloid compounds, phenylpropanoid compounds, flavonoid compounds, steroid compounds, polyketide compounds, macrolide compounds, sugar alcohols, phenolic compounds, and the like.

Genetic Modification to Produce One or More Mevalonate Pathway Enzymes

A genetically modified host cell of the present disclosure can be further genetically modified such that D-galacturonic acid can be used as the carbon source for producing mevalonate or mevalonate pathway products.

Thus, in some cases, a genetically modified host cell of the present disclosure is genetically modified with one or more heterologous nucleic acids comprising nucleotide sequences encoding: a) a heterologous D-galacturonate reductase; b) a heterologous L-galactonate dehydratase; c) a heterologous 3-deoxy-L-threo-hex-2-ulosonate aldolase; d) a heterologous glyceraldehyde reductase; and e) one or more heterologous mevalonate pathway enzymes.

In some cases, a genetically modified host cell of the present disclosure is genetically modified with one or more heterologous nucleic acids comprising nucleotide sequences encoding: a) a heterologous D-galacturonic acid transporter; b) a heterologous D-galacturonate reductase; c) a heterologous L-galactonate dehydratase; d) a heterologous 3-deoxy-L-threo-hex-2-ulosonate aldolase; e) a heterologous glyceraldehyde reductase; and f) one or more heterologous mevalonate pathway enzymes.

The term "mevalonate pathway" or "MEV pathway" is used herein to refer to the biosynthetic pathway that converts acetyl-CoA to isopentenyl pyrophosphate (IPP). The mevalonate pathway comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The "top half" of the mevalonate pathway refers to the enzymes responsible for the conversion of acetyl-CoA to mevalonate. See, e.g., US 2016/0040190.

As used herein, the term "prenyl transferase" is used interchangeably with the terms "isoprenyl diphosphate synthase" and "polyprenyl synthase" (e.g., "GPP synthase," "FPP synthase," "OPP synthase," etc.) to refer to an enzyme that catalyzes the consecutive 1'-4 condensation of isopentenyl diphosphate with allylic primer substrates, resulting in the formation of prenyl diphosphates of various chain lengths.

In some embodiments, nucleotide sequences encoding two or more enzymes in an isoprenoid biosynthetic pathway comprise nucleotide sequences encoding two, three, four, five, six, seven, eight, or more of: an acetoacetyl-CoA thiolase, a hydroxymethyl glutaryl-CoA synthase (HMGS), a hydroxymethyl glutaryl-CoA reductase (HMGR), a mevalonate kinase (MK), a phosphomevalonate kinase (PMK), and a mevalonate pyrophosphate decarboxylase (MPD), an isopentenyl pyrophosphate (IPP) isomerase, a prenyl transferase, and a terpene synthase. Exemplary amino acid sequences of MEV pathway enzymes are: 1) an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the acetoacetyl-CoA thiolase amino acid sequence set forth in SEQ ID NO:31; 2) an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the HMGS amino acid sequence set forth in SEQ ID NO: 32; 3) an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the HMGR amino acid sequence set forth in SEQ ID NO: 33; 4) an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the MK amino acid sequence set forth in SEQ ID NO: 34; 5) an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the PMK amino acid sequence set forth in SEQ ID NO: 35; 6) an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the MPD amino acid sequence set forth in SEQ ID NO: 36; and 7) an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the IPP isomerase amino acid sequence set forth in SEQ ID NO: 37.

Nucleotide sequences encoding mevalonate (MEV) pathway gene products are known in the art, and any known MEV pathway gene product-encoding nucleotide sequence can used to generate a subject genetically modified host cell. For example, nucleotide sequences encoding acetoacetyl-CoA thiolase, HMGS, HMGR, MK, PMK, MPD, and IDI are known in the art. The following are non-limiting examples of known nucleotide sequences encoding MEV pathway gene products, with GenBank Accession numbers and organism following each MEV pathway enzyme, in parentheses: acetoacetyl-CoA thiolase: (NC_000913 REGION: 2324131 . . . 2325315; *E. coli*), (D49362; *Paracoccus denitrificans*), and (L20428; *Saccharomyces cerevisiae*); HMGS: (NC_001145, complement 19061 . . . 20536; *Saccharomyces cerevisiae*), (X96617; *Saccharomyces cerevisiae*), (X83882; *Arabidopsis thaliana*), (AB037907; *Kitasatospora griseola*), and (BT007302; *Homo sapiens*); HMGR: (NM_206548; *Drosophila melanogaster*), (NM_204485; *Gallus gallus*), (AB015627; *Streptomyces* sp. KO-3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734 . . . 118898; *Saccharomyces cerevisiae*)); MK: (L77688; *Arabidopsis thaliana*), and (X55875; *Saccharomyces cerevisiae*); PMK: (AF429385; *Hevea brasiliensis*), (NM_006556; *Homo sapiens*), (NC_001145, complement 712315 . . . 713670; *Saccharomyces cerevisiae*); MPD: (X97557; *Saccharomyces cerevisiae*), (AF290095; *Enterococcus faecium*), and (U49260; *Homo sapiens*); and IDI: (NC_000913, 3031087 . . . 3031635; *E. coli*), and (AF082326; *Haematococcus pluvialis*).

In some embodiments, the HMGR coding region encodes a truncated form of HMGR ("tHMGR") that lacks the transmembrane domain of wild-type HMGR. The transmembrane domain of HMGR contains the regulatory portions of the enzyme and has no catalytic activity.

In some embodiments, a nucleic acid comprises a nucleotide sequence encoding a MEV pathway enzyme that has at least about 45%, at least about 50%, at least about 55%, at least about 57%, at least about 60%, at least about 65%, at least about 70%, at least about 75%, at least about 80%, at least about 85%, at least about 90%, at least about 95%, at least about 98%, or at least about 99% amino acid sequence identity to a known or naturally-occurring MEV pathway enzyme.

The coding sequence of any known MEV pathway enzyme may be altered in various ways known in the art to generate targeted changes in the amino acid sequence of the encoded enzyme. The amino acid sequence of a variant MEV pathway enzyme will in some embodiments be substantially similar to the amino acid sequence of any known MEV pathway enzyme, i.e. will differ by at least one amino acid, and may differ by at least two, at least 5, at least 10, or at least 20 amino acids, but typically not more than about fifty amino acids. The sequence changes may be substitutions, insertions or deletions. For example, as described below, the nucleotide sequence can be altered for the codon bias of a particular host cell. In addition, one or more nucleotide sequence differences can be introduced that result in conservative amino acid changes in the encoded protein.

Exemplary nucleotide sequences encoding MEV pathway enzymes include: 1) nucleotide sequences encoding acetoacetyl-CoA thiolase, HMGS, HMGR, MK, PMK, and MPD (e.g., SEQ ID NO:7 of U.S. Pat. No. 7,192,751); 2) nucleotide sequences encoding the "bottom half" of a mevalonate pathway (e.g., MK, PMK, and MPD; e.g., SEQ ID NO:9 of U.S. Pat. No. 7,192,751); 3) nucleotide sequences encoding MK, PMK, MPD, and isopentenyl pyrophosphate isomerase (idi) (e.g., SEQ ID NO:12 of U.S. Pat. No. 7,192,751); and 4) nucleotide sequences encoding MK, PMK, MPD, idi, and an FPP synthase (e.g., SEQ ID NO: 13 of U.S. Pat. No. 7,192,751; e.g., SEQ ID NO:4 of U.S. Pat. No. 7,183,089).

Mevalonate pathway products include isoprenoid compounds, where isoprenoid compounds comprise one or more isoprene units. The terms "isoprenoid", "isoprenoid compound", "isoprenoid product", "terpene", "terpene compound", "terpenoid", and "terpenoid compound" are used interchangeably herein. They refer to compounds that are capable of being derived from IPP. Non-limiting examples of isoprenoids include: hemiterpenes (derived from 1 isoprene unit) such as isoprene; monoterpenes (derived from 2 isoprene units) such as myrcene; sesquiterpenes (derived from 3 isoprene units) such as amorpha-4,11-diene; diterpenes (derived from four isoprene units) such as taxadiene; triterpenes (derived from 6 isoprene units) such as squalene; tetraterpenes (derived from 8 isoprenoids) such as β-carotene; and polyterpenes (derived from more than 8 isoprene units) such as polyisoprene.

Genetic Modification with One or More Alkaloid Biosynthetic Pathway Enzymes

In some cases, a genetically modified host cell of the present disclosure is genetically modified with one or more heterologous nucleic acids comprising nucleotide sequences encoding: a) a heterologous D-galacturonic acid transporter; b) a heterologous D-galacturonate reductase; c) a heterologous L-galactonate dehydratase; d) a heterologous 3-deoxy-L-threo-hex-2-ulosonate aldolase; e) a heterologous glyceraldehyde reductase; and f) one or more heterologous alkaloid biosynthetic pathway enzymes.

Alkaloid biosynthetic pathway enzymes are known in the art. See, e.g., ((2004) *TRENDS Plant Sci.* 9:116; Pauli and Kutchan ((1998) *Plant J.* 13:793-801; Collu et al. ((2001) *FEBS Lett.* 508:215-220; Schroder et al. ((1999) *FEBS Lett.* 458:97-102. Phenylpropanoid biosynthetic pathway enzymes are known in the art. See, e.g., Mizutani et al. ((1997) *Plant Physiol.* 113:755-763; and Gang et al. ((2002) *Plant Physiol.* 130:1536-1544.

For example, enzymes suitable for producing benzylisoquinoline alkaloid compounds include: tyrosine hydroxylase; 3,4-dihydroxyphenylalanine (DOPA) decarboxylase; monamine oxidase; norcoclaurine synthase; norcoclaurine 6-O-methyltransferase; coclaurine-N-methyltransferase; CYP80B 1 ((S)—N-methylcoclaurine 3'-hydroxylase); 3'-hydroxy-N-methylcoclaurine-4'-O-methyltransferase; etc. See, e.g., WO 2016/049364; and U.S. 2014/0273109.

Alkaloid compounds are a large, diverse group of natural products found in about 20% of plant species. They are generally defined by the occurrence of a nitrogen atom in an oxidative state within a heterocyclic ring. Alkaloid compounds include benzylisoquinoline alkaloid compounds, indole alkaloid compounds, isoquinoline alkaloid compounds, and the like. Alkaloid compounds include monocyclic alkaloid compounds, dicyclic alkaloid compounds, tricyclic alkaloid compounds, tetracyclic alkaloid compounds, as well as alkaloid compounds with cage structures. Alkaloid compounds include: 1) Pyridine group: piperine, coniine, trigonelline, arecaidine, guvacine, pilocarpine, cytisine, sparteine, pelletierine; 2) Pyrrolidine group: hygrine, nicotine, cuscohygrine; 3) Tropine group: atropine, cocaine, ecgonine, pelletierine, scopolamine; 4) Quinoline group: quinine, dihydroquinine, quinidine, dihydroquinidine, strychnine, brucine, and the veratrum alkaloids (e.g., veratrine, cevadine); 5) Isoquinoline group: morphine, codeine, thebaine, papaverine, narcotine, narceine, hydrastine, and berberine; 6) Phenethylamine group: methamphetamine, mescaline, ephedrine; 7) Indole group: tryptamines (e.g., dimethyltryptamine, psilocybin, serotonin), ergolines (e.g., ergine, ergotamine, lysergic acid, etc.), and beta-carbolines (e.g., harmine, yohimbine, reserpine, emetine); 8) Purine group: xanthines (e.g., caffeine, theobromine, theophylline); 9) Terpenoid group: aconite alkaloids (e.g., aconitine), and steroids (e.g., solanine, samandarin); 10) Betaine group: (quaternary ammonium compounds: e.g., muscarine, choline, neurine); and 11) Pyrazole group: pyrazole, fomepizole. Exemplary alkaloid compounds are morphine, berberine, vinblastine, vincristine, cocaine, scopolamine, caffeine, nicotine, atropine, papaverine, emetine, quinine, reserpine, codeine, serotonin, etc. See, e.g., Facchini et al. ((2004) *Trends Plant Science* 9:116).

Genetic Modification with One or More Polyketide Pathway Enzymes

In some cases, a genetically modified host cell of the present disclosure is genetically modified with one or more heterologous nucleic acids comprising nucleotide sequences encoding: a) a heterologous D-galacturonic acid transporter; b) a heterologous D-galacturonate reductase; c) a heterologous L-galactonate dehydratase; d) a heterologous 3-deoxy-L-threo-hex-2-ulosonate aldolase; e) a heterologous glyceraldehyde reductase; and f) one or more heterologous polyketide biosynthetic pathway enzymes.

Polyketide biosynthetic pathway enzymes are known in the art. See e.g., Ikeda et al. ((1999) *Proc. Natl. Acad. Sci. USA* 96:9509-9514; and Ward et al. ((2004) *Antimicrob. Agents Chemother.* 48:4703-4712.

Methods of Producing Downstream Products of Glycerol and/or for Increasing Biomass The present disclosure provides a method of producing glycerol, or a downstream product, in a genetically modified host cell of the present disclosure, where the genetically modified host cell is genetically modified with one or more heterologous nucleic acids comprising nucleotide sequences encoding heterologous enzymes D-galacturonate reductase, L-galactonate dehydratase, 3-dioxy-L-threo-hex-2-ulosonate aldolase. The method generally involves culturing the genetically modified host cell in a suitable culture medium, for a time and under conditions that provide for production of glycerol, or a downstream product, in the cell.

Carbon Source

As noted above, a method of the present disclosure comprises culturing a genetically modified host cell of the present disclosure in a culture medium comprising D-galacturonic acid.

The D-galacturonic acid can be provided in purified form. The D-galacturonic acid can be provided in the form of an agricultural waste stream. For example, in some cases, the D-galacturonic acid is provided in the form of pectin, or a pectin-rich food. For example, in some cases, the D-galacturonic acid is provided in the form of one or more of: fruit pulp, e.g., citrus fruit pulp or apple pulp; the peel of a fruit, e.g., citrus fruit peel, apple peel, etc.; sugar beet pulp; rag and/or seeds of fruit (e.g., citrus fruits; apples; etc.). As another example, in some cases, the D-galacturonic acid is provided in the form of pectins present in hemicellulose. In some cases, the D-galacturonic acid source comprises pectins, also known as pectin polysaccharides, which are rich in galacturonic acid. In some cases, the D-galacturonic acid source comprises homogalacturonans. Homogalacturonans are linear chains of α-(1-4)-linked D-galacturonic acid. In some cases, the D-galacturonic acid source comprises substituted galacturonans. Substituted galacturonans are characterized by the presence of saccharide appendant residues (such as D-xylose or D-apiose in the respective cases of xylogalacturonan and apiogalacturonan) branching from a backbone of D-galacturonic acid residues. In some cases, the D-galacturonic acid source comprises rhamnogalacturonan I pectins. Rhamnogalacturonan I pectins (RG-I) contain a backbone of the repeating disaccharide: 4)-α-D-galacturonic acid-(1,2)-α-L-rhamnose. From many of the rhamnose residues, side chains of various neutral sugars branch off. The neutral sugars are mainly D-galactose, L-arabinose and D-xylose, with the types and proportions of neutral sugars varying with the origin of pectin. In some cases, the D-galacturonic acid source comprises rhamnogalacturonan II. The rhamnogalacturonan II backbone is made exclusively of D-galacturonic acid units. Also, fermentation of pectin-rich agricultural wastes by wild-type *Saccharomyces* results in accumulation of D-galacturonic acid in the fermentation broth. This can be isolated and used for bioconversions. In some cases, the D-galacturonic acid source comprises apple, citrus, and sugar beet waste. In some cases, the D-galacturonic acid source comprises apple waste. In some cases, the D-galacturonic acid source comprises citrus waste. In some cases, the D-galacturonic acid source comprises sugar beet waste. In some cases, the apple, citrus, or sugar beet waste is crushed or processed into more homogeneous sizes.

For example, in some cases, a genetically modified host cell of the present disclosure is cultured in a culture medium comprising pectin.

Culture Conditions and Product Production

In some cases, the genetically modified host cell is cultured under aerobic conditions. In some cases, the genetically modified host cell is cultured under anaerobic conditions.

In some cases, a downstream product is produced. In some cases, the downstream product is purified, e.g., isolated and purified from the culture medium, from a cell lysate, or both. In some cases, the downstream product is at least or about 25%, 30%, 40%, 50%, 60%, 70%, 75%, 80%, 90%, 95%, or 99%, by weight, pure. Purification can be carried out by any known method or combination of methods, which methods include, e.g., column chromatography, phase separation, gas stripping, membrane enhanced separation, fractionation, adsorption/desorption, pervaporation, thermal or vacuum desorption from a solid phase, extraction of the product that is immobilized or absorbed to a solid phase with a solvent, etc. Purity can be assessed by any appropriate method, e.g., by column chromatography, high performance liquid chromatography (HPLC) analysis, or gas chromatograph-mass spectrometry (GC-MS) analysis.

In some cases, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into the desired product. In some cases, the cells in culture produce at least 2 g/L, at least 3 g/L, at least 4 g/L, at least 5 g/L, at least 7 g/L, at least 10 g/L, or more than 50 g/L liquid culture medium.

Variant UDH

The present disclosure provides a variant UDH polypeptide. The variant UDH polypeptide utilizes NADP$^+$. In some cases, the variant UDH polypeptide utilizes both NADP$^+$ and NAD$^+$. In some cases, the variant UDH utilizes NADP$^+$ preferentially over NAD$^+$. In some cases, a variant UDH of the present disclosure comprises one or more amino acid substitutions in the NAD$^+$ binding motif such that the variant UDH binds NADP$^+$.

In some cases, the NAD$^+$ binding motif of a variant UDH of the present disclosure comprises Asp-Val-Ala; Asp-Leu-Ser; Asp-Ile-Thr; Asp-Ile-Ala; Asp-Ile-Ser; or Asp-Ile-Arg; and the NAD$^+$ binding motif comprises one or more amino acid substitutions with a positively charged amino acid. In some cases, the positively charged amino acid is arginine, histidine, or lysine.

In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO: 18), where one, two, or three of amino acids D42, I43, and A44 are substituted. In some cases, the variant UDH comprises an I43R substitution. In some cases, the variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18); and comprises an amino acid substitution at D42, i.e., where amino acid 42 is other than aspartic acid (e.g., where amino acid 42 is Gly, Ala, Val, Leu, Ile, Pro, Phe, Tyr, Trp, Ser, Thr, Cys, Met, Asn, Gin, Lys, Arg, His, or Glu). In some cases, the variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO: 18); and comprises an amino acid substitution at I43, i.e., where amino acid 43 is other than isoleucine (e.g., where amino acid 43 is Gly, Ala, Val, Leu, Pro, Phe, Tyr, Trp, Ser, Thr, Cys, Met, Asn, Gin, Lys, Arg, His, Asp, or Glu). In some cases, the variant UDH comprises an I43R substitution. In some cases, the variant UDH comprises an I43H substitution. In some cases, the variant UDH comprises an I43K substitution.

In some cases, the variant UDH comprises an I43A substitution. In some cases, the variant UDH polypeptide comprising an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 19 (SEQ ID NO:18); and comprises an amino acid substitution at A44, i.e., where amino acid 44 is other than alanine (e.g., where amino acid 44 is Gly, Val, Leu, Ile, Pro, Phe, Tyr, Trp, Ser, Thr, Cys, Met, Asn, Gln, Lys, Arg, His, Asp, or Glu).

In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the UDH amino acid sequence depicted in FIG. 21 (SEQ ID NO:20), where X is an amino acid other than isoleucine; e.g., where X is a charged amino acid. In some cases, X is arginine. In some cases, X is histidine. In some cases, X is lysine.

In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein one, two, or three of amino acids D35, V36, and A37 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 35 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 35 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 35 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 36 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 36 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 47 (SEQ ID NO:25), wherein amino acid 36 is Lys.

In some cases, a variant UDH polypeptide of the present disclosure comprises an amino acid sequence having at least 50%, at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein one, two, or three of amino acids D33, L34, and S35 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 33 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 33 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 33 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 34 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 34 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 34 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 35 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 35 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 48 (SEQ ID NO:26), wherein amino acid 35 is Lys.

In some cases, a variant UDH polypeptide of the present disclosure comprises an amino acid sequence having at least 50%, at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO: 27), wherein one, two, or three of amino acids D37, I38, and S39 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 37 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 37 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 37 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 38 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 38 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 38 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 39 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 39 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 49 (SEQ ID NO:27), where amino acid 39 is Lys.

In some cases, a variant UDH polypeptide of the present disclosure comprises an amino acid sequence having at least 50%, at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), wherein one, two, or three of amino acids D51, I52, and T53 is substituted with arginine, histidine, or lysine. In some cases, a variant UDH polypeptide of the present disclosure comprises an amino acid sequence having at least 50% amino acid sequence identity to the amino acid sequence depicted in FIG. 50 (SEQ ID NO:28), where amino acid 51 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 51 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 51 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 52 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 52 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 52 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 53 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 53 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 50 (SEQ ID NO:28), where amino acid 53 is Lys.

In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), wherein one, two, or three of amino acids D31, I32, and A33 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 31 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 31 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 31 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 32 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 32 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 51 (SEQ ID NO:29), where amino acid 32 is Lys.

In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), wherein one, two, or three of amino acids D32, I33, and R34 is substituted with arginine, histidine, or lysine. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 32 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 32 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 32 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 33 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 33 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 33 is Lys. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 34 is Arg. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 34 is His. In some cases, a variant UDH polypeptide of the present disclosure comprises an amino acid sequence having at least 50%, at least 55%, at least 60%, at least 65%, at least 70%, at least 75%, at least 80%, at least 85%, at least 90%, at least 95%, at least 98%, or at least 99%, amino acid sequence identity to the amino acid sequence depicted in FIG. 52 (SEQ ID NO:30), amino acid 34 is Lys.

Nucleic Acids

The present disclosure provides a nucleic acid comprising a nucleotide sequence encoding a variant UDH polypeptide of the present disclosure. In some cases, the nucleotide sequence is codon optimized for expression in a eukaryotic cell. In some cases, the nucleotide sequence is codon optimized for expression in a yeast cell. In some cases, the nucleotide sequence is codon optimized for expression in a bacterial cell. In some cases, the nucleotide sequence encoding the variant UDH polypeptide is operably linked to a promoter. Suitable promoters are known in the art; a number of promoters are described below.

The present disclosure provides a recombinant expression vector comprising a nucleic acid of the present disclosure, where the nucleic acid comprises a nucleotide sequence encoding a variant UDH of the present disclosure. In some cases, the nucleotide sequence encoding the variant UDH polypeptide is operably linked to a promoter. In some cases, the promoter is a regulatable promoter, e.g., an inducible promoter. In some cases, the promoter is a constitutive promoter.

The present disclosure provides a nucleic acid comprising a nucleotide sequence encoding a variant UDH polypeptide of the present disclosure. In some cases, the nucleotide sequence is optimized for expression in a yeast cell. In some cases, the nucleotide sequence is optimized for expression in a bacterial cell.

The present disclosure provides a recombinant expression vector comprising a nucleic acid of the present disclosure, which nucleic acid comprises a nucleotide sequence encoding a variant UDH polypeptide of the present disclosure. In some cases, the nucleotide sequence is operably linked to a transcriptional control element (e.g., a promoter) that is active in the host cell. In some cases, the promoter is a constitutive promoter. In some cases, the promoter is a regulatable promoter. In some cases, the promoter is an inducible promoter.

As used herein, a "promoter sequence" is a DNA regulatory region capable of binding RNA polymerase and initiating transcription of a downstream (3' direction) coding or non-coding sequence. For purposes of defining the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various prokaryotic and eukaryotic promoters, including inducible promoters, may be used in the various recombinant expression vectors of the present disclosure. The promoter may be a constitutively active promoter, i.e. a promoter is active in the absence externally applied agents, or it may be an inducible promoter (e.g., T7 RNA polymerase promoter, T3 RNA polymerase promoter, Isopropyl-beta-D-thiogalactopyranoside (IPTG)-regulated promoter, heat shock promoter, Tetracycline-regulated promoter, Steroid-regulated promoter, metal-regulated promoter, methionine-inducible promoter; a galactose-inducible promoter, and the like). As used herein, an inducible promoter is a promoter whose activity is regulated upon the application of an agent to the cell, (e.g. doxycycline) or the induced presence of a particular RNA polymerase (e.g., T7 RNA polymerase).

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367-378); a tet promoter (see, e.g., Hillen, W. and Wissmann, A. (1989) In Saenger, W. and Heinemann, U. (eds), *Topics in Molecular and Structural Biology*, Protein-*Nucleic Acid Interaction*. Macmillan, London, UK, Vol. 10, pp. I43-162); an SP6 promoter (see, e.g., Melton et al. (1984) *Nucl. Acids Res.* 12:7035; and the like.

Non-limiting examples of suitable eukaryotic promoters include CMV immediate early, HSV thymidine kinase, early and late SV40, LTRs from retrovirus, and mouse metallothionein-I. Suitable promoters for expression in yeast include, but are not limited to, CYC1, HIS3, GAL1, GAL10, ADH1, PGK, PHO5, GAPDH, ADC1, TRP1, URA3, LEU2, ENO, and TP1; and, e.g., AOX1 (e.g., for use in *Pichia*). Selection of the appropriate vector and promoter is well within the level of ordinary skill in the art. The expression vector may also contain a ribosome binding site for translation initiation and a transcription terminator. The expression vector may also include appropriate sequences for amplifying expression.

In addition, the expression vectors include one or more selectable marker genes to provide a phenotypic trait for selection of transformed host cells such as dihydrofolate reductase or neomycin resistance for eukaryotic cell culture, or such as tetracycline or ampicillin resistance in prokaryotic host cells such as *E. coli*.

Generally, an expression vectors will include origins of replication and selectable markers permitting transformation of the host cell, e.g., the ampicillin resistance gene of *E. coli*, the *S. cerevisiae* TRP1 gene, etc.; and a promoter derived from a highly-expressed gene to direct transcription of the coding sequence. Such promoters can be derived from operons encoding glycolytic enzymes such as 3-phosphoglycerate kinase (PGK), α-factor, acid phosphatase, or heat shock proteins, among others.

In some embodiments, a nucleotide sequence encoding a variant UDH is operably linked to an inducible promoter. Inducible promoters are well known in the art. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (see, e.g., Guzman et al. (1995) *J. Bacteriol.* 177:4121-4130); a xylose-inducible promoter, e.g., Pxyl (see, e.g., Kim et al. (1996) *Gene* 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., CI857-repressed lambda-based expression vectors; see, e.g., Hoffmann et al. (1999) *FEMS Microbiol Lett.* 177(2):327-34); and the like.

In some embodiments, a nucleotide sequence encoding a variant UDH is operably linked to a constitutive promoter. Suitable constitutive promoters for use in prokaryotic cells are known in the art and include, but are not limited to, a sigma70 promoter, e.g., a consensus sigma70 promoter.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, 1986, IRL Press, Wash., D.C.). Alternatively, vectors may be used which promote integration of foreign DNA sequences into the yeast chromosome.

Genetically Modified Host Cells

The present disclosure provides a host cell genetically modified with a nucleic acid, or a recombinant expression vector, as described above, where the nucleic acid or the expression vector comprises a nucleotide sequence encoding a variant UDH of the present disclosure, as described above. In some cases, the host cell is a eukaryotic cell. In some cases, the eukaryotic host cell is a yeast cell, an algal cell, or a fungal cell. In some cases, the host cell is a prokaryotic cell. In some cases, the host cell is a bacterial cell. In some cases, the host cell is an in vitro host cell. A suitable host cell includes a microbial host cell (e.g., a bacterium, a yeast cell, a fungal cell) that can be cultured (e.g., culture in vitro) in a container, e.g., a test tube, an Eppendorf tube, a fermentation flask, a fermentation bottle, a fermentation vat, etc. Thus, for example, a suitable host cell is a fermentable cell.

Suitable host cells include cells that can be cultured in vitro, e.g., as unicellular organisms. Suitable host cells include yeast cells, fungal cells, insect cells, mammalian cells, algal cells, and bacterial cells. Suitable host cells include filamentous fungal cells; suitable filamentous fungal cells include, e.g., *Aspergillus, Neurospora*, and the like.

In some cases, the host cell is a eukaryotic cell. In some cases, the eukaryotic host cell is a yeast cell, an algal cell, or a fungal cell. In some cases, the host cell is a prokaryotic cell. In some cases, the host cell is a bacterial cell. A suitable host cell includes a microbial host cell (e.g., a bacterium, a yeast cell, a fungal cell) that can be cultured (e.g., culture in vitro) in a container, e.g., a test tube, an Eppendorf tube, a fermentation flask, a fermentation bottle, a fermentation vat, etc. Thus, for example, a suitable host cell is a fermentable cell.

The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Phanerochaete, Pleurotus, Schizophyllum, Talaromyces, Thermoascus, Thielavia, Tolypocladium*, and *Trichoderma*. Examples of suitable filamentous fungal cells include, e.g., *Aspergillus niger, Aspergillus awamori, Aspergillus foetidus, Aspergillus sojae, Aspergillus fumigatus*, and *Aspergillus oryzae*. Another example of a suitable fungal cell is a *Neurospora crassa* cell.

Examples of suitable yeast host cells are strains selected from a cell of a species of *Candida, Kluyveromyces, Saccharomyces, Schizosaccharomyces, Pichia, Hansenula, Yarrowia, Rhodotorula* and *Rhodosporidium*. In one embodiment, the yeast host cell is selected from a *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Schizosaccharomyces pombe, Saccharomyces uvarum, Pichia kluyveri, Yarrowia lipolytica, Candida utilis, Candida cacaoi*, and *Geotrichum fermentans*. Other useful yeast host cells are *Kluyveromyces lactis, Kluyveromyces fragilis, Hansenula polymorpha, Pichia pastoris, Yarrowia lipolytica, Schizosaccharomyces pombe, Ustilgo maylis, Candida maltose, Pichia guillermondii* and *Pichia methanoliol*.

Suitable yeast host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha*, and the like. In some cases, a yeast host cell is *Saccharomyces cerevisiae*; i.e., a genetically modified cell of the present disclosure is a genetically modified *Saccharomyces cerevisiae* cell.

In various embodiments, the yeast is selected from the non-limiting list of genera; *Candida, Cryptococcus, Hansenula, Issatchenki, Kluyveromyces, Komagataella, Lipomyces, Pichia, Rhodosporidium, Rhodotorula, Saccharomyces* or *Yarrowia* species. In various embodiments, the yeast is of a species selected from the group consisting of *Candida albicans, Candida ethanolica, Candida krusei, Candida methanosorhosa, Candida sonorensis, Candida tropicalis, Cryptococcus curvatus, Hansenula polymorpha, Issatchenki orientalis, Kluyveromyces lactic, Kluyveromyces marxianus, Kluyveromyces thermotolerans, Komagataella pastoris, Lipomyces starkeyi, Pichia angusta, Pichia deserticola, Pichia galeiformis, Pichia kodamae, Pichia kudriavzevii, Pichia membranaefaciens, Pichia anethanolica, Pichia pastoris, Pichia salictaria, Pichia stipitis, Pichia thermotolerans, Pichia trehalophila, Rhodosporidium toruloides, Rhodotorula glutinis Rhodotorula graminis, Saccharomyces hayanus, Saccharomyces boulardi, Saccharomyces cerevisiae, Saccharomyces kluyveri*, and *Yarrowia lipolytica, Pichia kudriavzevii*.

Illustrative examples of eukaryotic cells include, but are not limited to: *Aspergillus niger, Aspergillus oryzae, Crypthecodinium cohnii, Cunninghamella japonica, Entomophthora coronata, Mortierella alpina, Mucor circinelloides, Neurospora crassa, Pythium ultimum, Schizochytrium limacinum, Thraustochytrium aureum, Trichoderma reesei* and *Xanthophyllomyces dendrorhous*. In general, if a eukaryotic cell is used, a non-pathogenic strain is employed. Illustrative examples of non-pathogenic strains include, but are not limited to: *Pichia pastoris* and *Saccharomyces cerevisiae*. In addition, certain strains, including *Saccharomyces cerevisiae*, have been designated by the Food and Drug Administration as Generally Regarded as Safe (or GRAS) and so can be conveniently employed in various embodiments of the methods of the present disclosure.

The host cell can be a prokaryotic cell. Suitable prokaryotic cells include, but are not limited to, any of a variety of laboratory strains of *Escherichia coli, Lactobacillus* sp., *Salmonella* sp., *Shigella* sp., *Citrobacter, Enterobacter, Clostridium, Klebsiella,* Aerobacter, and the like. See, e.g., Carrier et al. (1992) J. Immunol. 148:1176-1181; U.S. Pat. No. 6,447,784; and Sizemore et al. (1995) Science 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella* disenteriae. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some cases, the host cell is *Escherichia coli*.

Illustrative examples of suitable prokaryotic host cells include, but are not limited to, *Bacillus subtilis, Brevibacterium ammoniagenes, Clostridium beigerinckii, Enterobacter sakazakii, Lactobacillus acidophilus, Lactococcus lactis, Mesorhizobium loti, Pseudomonas aeruginosa, Pseudomonas putida, Rhodobacter capsulatus, Rhodobacter sphaeroides, Salmonella enterica, Salmonella typhi, Salmonella typhimurium, Shigella fiexneri, Staphylococcus aureus, Streptomyces ambojaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis*, and *Streptomyces vinaceus*.

Host Cell Genetically Modified to Produce Heterologous D-Galacturonic Acid Transporter The present disclosure provides a genetically modified eukaryotic cell, where a eukaryotic host cell is genetically modified to produce a heterologous D-galacturonic acid transporter. Such a genetically modified host cell can use used in, e.g., pectin fermentation. See, e.g., WO 2013/155481. In some cases, the genetically modified host cell is an in vitro cell, e.g., an in vitro yeast cell or an in vitro fungal cell. In some cases, the genetically modified host cell is a yeast cell. In some cases, the genetically modified host cell is a fungal cell. Thus, the present disclosure provides a genetically modified eukaryotic cell, where a eukaryotic host cell is genetically modified with a heterologous nucleic acid comprising a nucleotide sequence encoding a heterologous D-galacturonic acid transporter. In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in one of FIG. 2-5 (SEQ ID NOs: 1-4). In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in FIG. 2 (SEQ ID NO:1). In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in FIG. 3 (SEQ ID NO:2). In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in FIG. 4 (SEQ ID NO:3). In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in FIG. 5 (SEQ ID NO:4). In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in FIG. 55 (SEQ ID NO:38). In some cases, the heterologous D-galacturonic acid transporter comprises an amino acid sequence having at least 50%, at least 60%, at least 70%, at least 80%, at least 85%, at least 90%, at least 95%, at least 98%, at least 99%, or 100%, amino acid sequence identity to the amino acid sequence depicted in FIG. 57 (SEQ ID NO:39).

The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Phanerochaete, Pleurotus, Schizophyllum, Talaromyces, Thermoascus, Thielavia, Tolypocladium,* and *Trichoderma.* Examples of suitable filamentous fungal cells include, e.g., *Aspergillus niger, Aspergillus awamori, Aspergillus foetidus, Aspergillus sojae, Aspergillus fumigatus,* and *Aspergillus oryzae.* Another example of a suitable fungal cell is a *Neurospora crassa* cell.

Examples of suitable yeast host cells are strains selected from a cell of a species of *Candida, Kluyveromyces, Saccharomyces, Schizosaccharomyces, Pichia, Hansenula, Yarrowia, Rhodotorula* and *Rhodosporidium.* In one embodiment, the yeast host cell is selected from a *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Schizosaccharomyces pombe, Saccharomyces uvarum, Pichia kluyveri, Yarrowia lipolytica, Candida utilis, Candida cacaoi,* and *Geotrichum fermentans.* Other useful yeast host cells are *Kluyveromyces lactis, Kluyveromyces fragilis, Hansenula polymorpha, Pichia pastoris, Yarrowia lipolytica, Schizosaccharomyces pombe, Ustilgo maylis, Candida maltose, Pichia guillermondii* and *Pichia methanoliol.*

Suitable yeast host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha,* and the like. In some cases, a yeast host cell is *Saccharomyces cerevisiae*; i.e., a genetically modified cell of the present disclosure is a genetically modified *Saccharomyces cerevisiae* cell.

In various embodiments, the yeast is selected from the non-limiting list of genera; *Candida, Cryptococcus, Hansenula, Issatchenki, Kluyveromyces, Komagataella, Lipomyces, Pichia, Rhodosporidium, Rhodotorula, Saccharomyces* or *Yarrowia* species. In various embodiments, the yeast is of a species selected from the group consisting of *Candida albicans, Candida ethanolica, Candida krusei, Candida methanosorhosa, Candida sonorensis, Candida tropicalis, Cryptococcus curvatus, Hansenula polymorpha, Issatchenki orientalis, Kluyveromyces lactic, Kluyveromyces marxianus, Kluyveromyces thermotolerans, Komagataella pastoris, Lipomyces starkeyi, Pichia angusta, Pichia deserticola, Pichia galeiformis, Pichia kodamae, Pichia kudriavzevii, Pichia membranaefaciens, Pichia anethanolica, Pichia pastoris, Pichia salictaria, Pichia stipitis, Pichia thermotolerans, Pichia trehalophila, Rhodosporidium toruloides, Rhodotorula glutinis, Rhodotorula graminis, Saccharomyces hayanus. Saccharomyces boulardi, Saccharomyces cerevisiae, Saccharomyces kluyveri,* and *Yarrowia lipolytica, Pichia kudriavzevii.*

Illustrative examples of eukaryotic cells include, but are not limited to: *Aspergillus niger, Aspergillus oryzae, Crypthecodinium cohnii, Cunninghamella japonica, Entomophthora coronata, Mortierella alpina, Mucor circinelloides, Neurospora crassa, Pythium ultimum, Schizochytrium limacinum, Thraustochytrium aureum, Trichoderma reesei* and *Xanthophyllomyces dendrorhous.* In general, if a eukaryotic cell is used, a non-pathogenic strain is employed. Illustrative examples of non-pathogenic strains include, but are not limited to: *Pichia pastoris* and *Saccharomyces cerevisiae.* In addition, certain strains, including *Saccharomyces cerevisiae,* have been designated by the Food and Drug Administration as Generally Regarded as Safe (or GRAS) and so can be conveniently employed in various embodiments of the methods of the present disclosure.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-136 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A genetically modified host cell genetically modified with:

a) a heterologous nucleic acid comprising a nucleotide sequence encoding a heterologous uronate dehydrogenase (UDH), wherein the heterologous UDH uses $NADP^+$ or $NAD^+$ as a cofactor, and produces NADPH or NADH, respectively, and wherein the heterologous UDH converts a sugar acid (e.g., an aldaric acid, a uronic acid) to its corresponding 1,5-aldonolactone, wherein the host cell coexpresses an endogenous or a heterologous reductase that utilizes the produced NADPH or NADH; and b) one or more heterologous nucleic acids comprising heterologous nucleotide sequences encoding one or more enzymes of an anabolic pathway, wherein the anabolic pathway requires the reductase that utilizes the produced NADPH or NADH.

Aspect 2. The genetically modified host cell of aspect 1, wherein the sugared acid s D-galacturonic acid, and the 1,-5-aldonolactone is D-galactaro-1,5-lactone.

Aspect 3. The genetically modified host cell of aspect 1, wherein the sugared acid is D-glucuronic acid, and the 1,5-aldonolactone is D-glucaro-1,5-lactone.

Aspect 4. The genetically modified host cell of aspect 1, wherein the genetically modified host cell is a prokaryotic host cell that comprises a genetic modification in an endogenous uxaC gene, such that the genetically modified prokaryotic host cell does not produce functional uxaC.

Aspect 5. The genetically modified host cell of aspect 1, wherein the heterologous UDH is a modified UDH that comprises one or more amino acid substitutions in the NAD$^+$ binding motif such that the variant UDH binds NADP$^+$.

Aspect 6. The genetically modified host cell of aspect 5, wherein the heterologous modified UDH comprises an amino acid sequence having at least 40% amino acid sequence identity to the amino acid sequence depicted in FIG. 19 (SEQ ID NO:18), wherein one, two, or three of amino acids D42, I43, and A44 are substituted.

Aspect 7. The genetically modified host cell of aspect 5, wherein the heterologous modified UDH comprises an amino acid sequence having at least 80% amino acid sequence identity to the amino acid sequence depicted in FIG. 19 (SEQ ID NO:18), wherein one, two, or three of amino acids D42, I43, and A44 are substituted.

Aspect 8. The genetically modified host cell of aspect 6 or aspect 7, wherein the heterologous modified UDH comprises wherein amino acid I43 is substituted with a positively charged amino acid.

Aspect 9. The genetically modified host cell of aspect 8, wherein the heterologous modified UDH comprises an I43R substitution.

Aspect 10. The genetically modified host cell of aspect 6, wherein the heterologous modified UDH comprises an amino acid sequence having at least 40% amino acid sequence identity to the amino acid sequence depicted in FIG. 21 (SEQ ID NO:20), wherein X is arginine, histidine, or lysine.

Aspect 11. The genetically modified host cell of aspect 1, wherein the heterologous UDH utilizes NADP$^+$, and wherein the heterologous UDH comprises an amino acid sequence having at least 40%, at least 50%, at least 60%, at least 70%, at least 80%, at least 90%, at least 95%, at least 98%, or at least 99%, amino acid sequence identity to the amino acid sequence depicted in FIG. 20 (SEQ ID NO: 19).

Aspect 12. The genetically modified host cell of aspect 1, wherein the heterologous UDH utilizes NAD$^+$, and wherein the heterologous UDH comprises an amino acid sequence having at least 40%, at least 50%, at least 60%, at least 70%, at least 80%, at least 90%, at least 95%, at least 98%, or at least 99%, amino acid sequence identity to the amino acid sequence depicted in one of FIGS. 19 (SEQ ID NO: 18) and 47-52 (SEQ ID NOs.:25-30).

Aspect 13. The genetically modified host cell of aspect 1, wherein the host cell is a yeast cell, and wherein the host cell is genetically modified with a heterologous nucleic acid comprising a nucleotide sequence encoding a heterologous D-galacturonic acid transporter.

Aspect 14. The genetically modified host cell of aspect 13, wherein the heterologous D-galacturonic acid transporter comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in one of FIG. 2-5 (SEQ ID NOs.:1-4), or as set forth in SEQ ID NO:38 or SEQ ID NO:39.

Aspect 15. The genetically modified host cell of aspect 1, wherein the one or more anabolic pathway enzymes comprises a glycerol dehydratase and wherein the reductase is a 1,3-propanediol oxidoreductase.

Aspect 16. The genetically modified host cell of aspect 15, wherein the 1,3-propanediol oxidoreductase comprises an amino acid sequence having at least 40%, at least 50%, at least 60%, at least 70%, at least 80%, at least 90%, at least 95%, at least 98%, at least 99%, or 100%, amino acid sequence identity to the 1,3-propanediol oxidoreductase amino acid sequence depicted in FIG. 24A (SEQ ID NO:23) or the alcohol dehydrogenase amino acid sequence depicted in FIG. 24B (SEQ ID NO:24).

Aspect 17. The genetically modified host cell of aspect 16, wherein the genetically modified host cell, when cultured in a culture medium comprising dextrose and galacturonic acid, produces mucic acid and 1,3-propanediol.

Aspect 18. The genetically modified host cell of aspect 16, wherein the genetically modified host cell, when cultured in a culture medium comprising glycerol and galacturonic acid, produces mucic acid and 1,3-propanediol.

Aspect 19. The genetically modified host cell of aspect 1, wherein the one or more anabolic pathway enzymes comprise CoA-dependent succinate semialdehyde dehydrogenase, 4-hydroxybutyrate dehydrogenase, 4-hydroxybutyryl-CoA reductase, and alcohol dehydrogenase, wherein the reductase is 4-hydroxybutyryl-CoA reductase.

Aspect 20. The genetically modified host cell of aspect 19, wherein the genetically modified host cell, when cultured in a culture medium comprising dextrose and galacturonic acid, produces mucic acid and 1,4-butanediol.

Aspect 21. The genetically modified host cell of aspect 1, wherein the one or more anabolic pathway enzymes comprises methylglyoxyl reductase (mgsA in *E. coli*), glycerol dehydrogenase, (gldA, *E. coli*, dhaD in *Klebsiella*), and aldo-keto reductase or 1,2-propanediol oxidoreductase (fucO).

Aspect 22. The genetically modified host cell of aspect 21, wherein the genetically modified host cell, when cultured in a culture medium comprising dextrose and galacturonic acid, produces mucic acid and 1,2-propanediol.

Aspect 23. The genetically modified host cell of aspect 1, wherein the one or more anabolic pathway enzymes comprise myo-inositol-1-phosphate synthase (MIPS) and myo-inositol oxygenase (MIOX).

Aspect 24. The genetically modified host cell of aspect 1, wherein the one or more anabolic pathway enzymes comprise one or more heterologous mevalonate pathway enzymes.

Aspect 25. The genetically modified host cell of aspect 1, wherein the one or more anabolic pathway enzymes comprise one or more heterologous benzylisoquinoline alkaloid pathway enzymes.

Aspect 26. The genetically modified host cell of aspect 1, wherein the one or more anabolic pathway enzymes comprise one or more heterologous polyketide pathway enzymes.

Aspect 27. The genetically modified host cell of any one of aspects 1-3, 5-12, and 15-26, wherein the host cell is a eukaryotic cell.

Aspect 28. The genetically modified host cell of aspect 27, wherein the eukaryotic host cell is a yeast cell, an algal cell, or a fungal cell.

Aspect 29. The genetically modified host cell of any one of aspects 1-3, 5-12, and 15-26, wherein the host cell is a prokaryotic cell.

Aspect 30. The genetically modified host cell of aspect 29, wherein the host cell is a bacterial cell.

Aspect 31. A method for producing mucic acid and a product of an anabolic pathway or a catabolic pathway that requires an active reductase that utilizes NADH or NADPH, the method comprising culturing, in a culture medium, a genetically modified host cell, wherein the genetically modified host cell is genetically modified with:

a) a heterologous nucleic acid comprising a nucleotide sequence encoding a heterologous uronate dehydrogenase (UDH) that converts a sugared acid (e.g., an aldaric acid, a uronic acid) to its corresponding 1,5-aldonolactone and that uses $NADP^+$ or $NAD^+$ as a cofactor, and produces NADPH or NADH, respectively, and, wherein the host cell coexpresses an endogenous or a heterologous reductase that utilizes the produced NADPH or NADH; and b) one or more heterologous nucleic acids comprising heterologous nucleotide sequences encoding one or more enzymes of an anabolic pathway, wherein the anabolic pathway requires the reductase that utilizes the produced NADPH or NADH, wherein the culture medium comprises D-galacturonate and an oxidized substrate for the reductase, or a precursor for the oxidized substrate for the reductase, and wherein each mole of the $NADP^+$ or $NAD^+$ is converted to NADPH or NADH, respectively.

Aspect 32. The method of aspect 31, wherein said culturing comprises culturing under anaerobic conditions.

Aspect 33. The method of aspect 31, wherein the product of an anabolic pathway or a catabolic pathway is selected from 1,2-propanediol, 1,3-propanediol, 1,4-butanediol, 2,3-butanediol, glycerol, butanol, mevalonate, a mevalonate derivative, an isoprenoid, farnesene, a polyketide, and a fatty acid.

Aspect 34. The method of aspect 31, comprising recovering the mucic acid.

Aspect 35. The method of aspect 34, wherein the recovered mucic acid is chemically modified in one or more cell-free reactions.

Aspect 36. The method of aspect 31, comprising recovering the product of the anabolic pathway or catabolic pathway.

Aspect 37. The method of aspect 31, wherein the culture medium comprises dextrose and D-galacturonic acid.

Aspect 38. The method of aspect 31, wherein the culture medium comprises glycerol and D-galacturonic acid.

Aspect 39. The method of any one of aspects 31-38, wherein the host cell is a eukaryotic cell.

Aspect 40. The method of aspect 39, wherein the eukaryotic host cell is a yeast cell, an algal cell, or a fungal cell.

Aspect 41. The method of any one of aspects 31-38, wherein the host cell is a prokaryotic cell.

Aspect 42. The method of aspect 41, wherein the host cell is a bacterial cell.

Aspect 43. The method of aspect 31, wherein the sugar acid is D-galacturonic acid, and the 1,-5-aldonolactone is D-galactaro-1,5-lactone.

Aspect 44. The method of aspect 31, wherein the sugar acid is D-glucuronic acid, and the 1,5-aldonolactone is D-glucaro-1,5-lactone.

Aspect 45. The method of any one of aspects 31-43, wherein the heterologous UDH is a modified UDH that comprises one or more amino acid substitutions in the $NAD^+$ binding motif such that the modified UDH binds $NADP^+$.

Aspect 46. The method of aspect 45, wherein the heterologous modified UDH comprises an amino acid sequence having at least 40%, at least 50%, at least 60%, at least 70%, at least 80%, at least 90%, at least 95%, at least 98%, or at least 99%, amino acid sequence identity to the amino acid sequence depicted in FIG. 19 (SEQ ID NO:18), wherein one, two, or three of amino acids D42, I43, and A44 are substituted.

Aspect 47. The method of aspect 45, wherein the heterologous modified UDH comprises an amino acid sequence having at least 80%, at least 90%, at least 95%, at least 98%, or at least 99%, amino acid sequence identity to the amino acid sequence depicted in FIG. 19 (SEQ ID NO: 18), wherein one, two, or three of amino acids D42, I43, and A44 are substituted.

Aspect 48. The method of aspect 46 or aspect 47, wherein amino acid I43 is substituted with a positively charged amino acid.

Aspect 49. The method of aspect 45, wherein the heterologous modified UDH comprises an I43R substitution.

Aspect 50. The method of aspect 45, wherein the heterologous modified UDH comprises an amino acid sequence having at least 40%, at least 50%, at least 60%, at least 70%, at least 80%, at least 90%, at least 95%, at least 98%, or at least 99%, amino acid sequence identity to the amino acid sequence depicted in FIG. 21 (SEQ ID NO:20), wherein X is arginine, histidine, or lysine.

Aspect 51. The method of aspect 31, wherein the heterologous UDH utilizes $NADP^+$, and wherein the heterologous UDH comprises an amino acid sequence having at least 40%, at least 50%, at least 60%, at least 70%, at least 80%, at least 90%, at least 95%, at least 98%, or at least 99%, amino acid sequence identity to the amino acid sequence depicted in FIG. 20 (SEQ ID NO: 19).

Aspect 52. The method of aspect 31, wherein the heterologous UDH utilizes $NAD^+$ and wherein the heterologous UDH comprises an amino acid sequence having at least 40%, at least 50%, at least 60%, at least 70%, at least 80%, at least 90%, at least 95%, at least 98%, or at least 99%, amino acid sequence identity to the amino acid sequence depicted in one of FIGS. 19 (SEQ ID NO: 18) and 47-52 (SEQ ID NOs:25-30).

Aspect 53. The method of any one of aspects 31-40 and 43-52, wherein the host cell is a yeast cell, and wherein the host cell is genetically modified with a heterologous nucleic acid comprising a nucleotide sequence encoding a heterologous D-galacturonic acid transporter.

Aspect 54. The method of aspect 53, wherein the heterologous D-galacturonic acid transporter comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in one of FIG. 2-5 (SEQ ID NOs.:1-4), or as set forth in SEQ ID NO:38 or SEQ ID NO:39.

Aspect 55. A genetically modified, fermentable host cell genetically modified with a heterologous nucleic acid comprising a nucleotide sequence encoding a heterologous uronate dehydrogenase (UDH), wherein the heterologous UDH converts a sugar acid (e.g., an aldaric acid, a uronic acid) to its corresponding 1,5-aldonolactone, and wherein heterologous UDH uses $NADP^+$ as a cofactor, and produces NADPH.

Aspect 56. The genetically modified host cell of aspect 55, wherein the host cell is a eukaryotic cell.

Aspect 57. The genetically modified host cell of aspect 56, wherein the eukaryotic host cell is a yeast cell, an algal cell, or a fungal cell.

Aspect 58. The genetically modified host cell of aspect 57, wherein the host cell is a prokaryotic cell.

Aspect 59. The genetically modified host cell of aspect 58, wherein the host cell is a bacterial cell.

Aspect 60. The genetically modified host cell of aspect 52, wherein the heterologous UDH is a modified UDH that comprises one or more amino acid substitutions in the $NAD^+$ binding motif such that the variant UDH binds $NADP^+$.

Aspect 61. The genetically modified host cell of aspect 60, wherein the heterologous modified UDH comprises an amino acid sequence having at least 40%, at least 50%, at least 60%, at least 70%, at least 80%, at least 90%, at least 95%, at least 98%, or at least 99%, amino acid sequence identity to the amino acid sequence depicted in FIG. 19 (SEQ ID NO: 18), wherein one, two, or three of amino acids D42, I43, and A44 are substituted.

Aspect 62. The genetically modified host cell of aspect 60, wherein the heterologous modified UDH comprises an amino acid sequence having at least 80%, at least 90%, at least 95%, at least 98%, or at least 99%, amino acid sequence identity to the amino acid sequence depicted in FIG. 19 (SEQ ID NO: 18), wherein one, two, or three of amino acids D42, I43, and A44 are substituted.

Aspect 63. The genetically modified host cell of aspect 61 or aspect 62, wherein the heterologous modified UDH comprises wherein amino acid I43 is substituted with a positively charged amino acid.

Aspect 64. The genetically modified host cell of aspect 63, wherein the heterologous modified UDH comprises an I43R substitution.

Aspect 65. The genetically modified host cell of aspect 60, wherein the heterologous modified UDH comprises an amino acid sequence having at least 40%, at least 50%, at least 60%, at least 70%, at least 80%, at least 90%, at least 95%, at least 98%, or at least 99%, amino acid sequence identity to the amino acid sequence depicted in FIG. 21 (SEQ ID NO:20), wherein X is arginine, histidine, or lysine.

Aspect 66. The genetically modified host cell of aspect 55, wherein the heterologous UDH utilizes $NADP^+$, and wherein the heterologous UDH comprises an amino acid sequence having at least 40%, at least 50%, at least 60%, at least 70%, at least 80%, at least 90%, at least 95%, at least 98%, or at least 99%, amino acid sequence identity to the amino acid sequence depicted in FIG. 20 (SEQ ID NO: 19).

Aspect 67. The genetically modified host cell of aspect 55, wherein the heterologous UDH utilizes $NAD^+$, and wherein the heterologous UDH comprises an amino acid sequence having at least 40%, at least 50%, at least 60%, at least 70%, at least 80%, at least 90%, at least 95%, at least 98%, or at least 99%, amino acid sequence identity to the amino acid sequence depicted in one of FIGS. 19 (SEQ ID NO: 18) and 47-52 (SEQ ID NOs.:25-30).

Aspect 68. The genetically modified host cell of aspect 55, wherein the host cell is a yeast cell, and wherein the host cell is genetically modified with a heterologous nucleic acid comprising a nucleotide sequence encoding a heterologous D-galacturonic acid transporter.

Aspect 69. The genetically modified host cell of aspect 68, wherein the heterologous D-galacturonic acid transporter comprises an amino acid sequence having at least 50% amino acid sequence identity to the amino acid sequence depicted in one of FIG. 2-5 (SEQ ID NOs.: 1-4), or to the amino acid sequence depicted in FIG. 55 (SEQ ID NO:38), or to the amino acid sequence depicted in FIG. 57 (SEQ ID NO:39).

Aspect 70. The genetically modified host cell of aspect 55, wherein the sugar acid is D-galacturonic acid, and the 1,-5-aldonolactone is D-galactaro-1,5-lactone.

Aspect 71. The genetically modified host cell of aspect 55, wherein: a) the sugar acid is D-glucuronic acid, and the 1,5-aldonolactone is D-glucaro-1,5-lactone; or b) the sugar acid is D-guluronic acid, and the 1,5-aldonolactone is D-gularo-1,5-lactone.

Aspect 72. A method of producing an aldaric acid in a host cell, the method comprising culturing the genetically modified cell of any one of aspects 55-71 in a culture medium comprising a uronic acid.

Aspect 73. The method of aspect 72, wherein the cell produces D-galactaro-1,5-lactone and wherein the D-galactaro-1,5-lactone is converted to mucic acid by action of lactonase (lactonohydrolase).

Aspect 74. The method of aspect 73, wherein the lactonase (lactonohydrolase) is endogenous to the cell.

Aspect 75. The method of aspect 73, wherein the lactonase (lactonohydrolase) is heterologous to the cell.

Aspect 76. The method of aspect 72, wherein the uronic acid is D-galacturonate.

Aspect 77. The method of aspect 72, wherein the aldaric acid is mucic acid, glucaric acid, or mannaric acid.

Aspect 78. The method of any one of aspects 72-78, wherein the aldaric acid is mucic acid, and wherein the mucic acid is recovered from the cell, the culture medium, or both the cell and the culture medium.

Aspect 79. The method of aspect 72, wherein the cell produces D-galactaro-1,5-lactone and wherein the D-galactaro-1,5-lactone is recovered from the cell, the culture medium, or both the cell and the culture medium.

Aspect 80. The method of aspect 79, wherein the recovered D-galactaro-1,5-lactone is converted to mucic acid by base hydrolysis.

Aspect 81. The method of any one of aspects 72-80, wherein the D-galactaro-1,5-lactone or the mucic acid is isolated from other components of the cell culture medium using one or more of extraction, continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, absorption chromatography, flash evaporation, high-performance liquid chromatography, precipitation, and ultrafiltration.

Aspect 82. The method of any one of aspects 72-80, wherein said culturing is carried out substantially anaerobically.

Aspect 83. The method of any one of aspects 72-80, comprising obtaining the uronic acid from an agricultural waste stream.

Aspect 84. The method of aspect 83, wherein the agricultural waste stream comprises one or more of apple peels, apple pulp, citrus peels, citrus pulp, and sugar beet pulp.

Aspect 85. A host cell genetically modified to convert D-galacturonic acid to a commodity product or precursor thereof, wherein the host cell is genetically modified with one or more heterologous nucleic acids comprising nucleotide sequences encoding:
  a) a heterologous D-galacturonate reductase;
  b) a heterologous L-galactonate dehydratase;
  c) a heterologous 3-deoxy-L-threo-hex-2-ulosonate aldolase; and
  d) a heterologous glyceraldehyde reductase.

Aspect 86. The genetically modified host cell of aspect 85, wherein the host cell is a yeast cell, an algal cell, a fungal cell, or a bacterial cell.

Aspect 87. The genetically modified host cell of aspect 86, wherein the yeast cell is a *Saccharomyces cerevisiae* cell.

Aspect 88. The genetically modified host cell of aspect 85, wherein the heterologous D-galacturonate reductase comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in one of FIG. 6 (SEQ ID NO:5), FIG. 7 (SEQ ID NO:6), and FIG. 8 (SEQ ID NO:7).

Aspect 89. The genetically modified host cell of aspect 85, wherein the heterologous L-galactonate dehydratase comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in one of FIG. 9-FIG. 12 (SEQ ID NOs.: 9-11).

Aspect 90. The genetically modified host cell of aspect 85 or aspect 89, wherein the heterologous L-galactonate dehydratase is a fusion protein comprising an N-terminal heterologous polypeptide.

Aspect 91. The genetically modified host cell of aspect 90, wherein the N-terminal heterologous polypeptide is a fluorescent polypeptide.

Aspect 92. The genetically modified host cell of aspect 85, wherein the heterologous 3-deoxy-L-threo-hex-2-ulosonate aldolase comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in one of FIG. 13-FIG. 15 (SEQ ID NOs.:12-14).

Aspect 93. The genetically modified host cell of aspect 85, wherein the heterologous glyceraldehyde reductase comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in one of FIG. 16-FIG. 18 (SEQ ID NOs.:15-17).

Aspect 94. The genetically modified host cell of aspect 86 or aspect 87, wherein the yeast cell is genetically modified with a heterologous nucleic acid comprising a nucleotide sequence encoding a heterologous D-galacturonic acid transporter that is not substantially inhibited by dextrose or fructose.

Aspect 95. The genetically modified host cell of aspect 94, wherein the heterologous D-galacturonic acid transporter comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in one of FIG. 2-5 (SEQ ID NOs.:1-4), or as set forth in SEQ ID NO:38 or SEQ ID NO:39.

Aspect 96. The genetically modified host cell of any one of aspects 85-95 wherein the host cell is genetically modified with one or more heterologous nucleic acids comprising nucleotide sequences encoding one or more heterologous enzymes of an anabolic pathway.

Aspect 97. The genetically modified host cell of aspect 96, wherein the host cell is genetically modified with one or more heterologous nucleic acids comprising nucleotide sequences encoding one or more heterologous mevalonate pathway enzymes.

Aspect 98. The genetically modified yeast cell of aspect 96, wherein the host cell is genetically modified with one or more heterologous nucleic acids comprising nucleotide sequences encoding one or more heterologous benzylisoquinoline alkaloid pathway enzymes.

Aspect 99. The genetically modified yeast cell of aspect 96, wherein the host cell is genetically modified with one or more heterologous nucleic acids comprising nucleotide sequences encoding one or more heterologous polyketide pathway enzymes.

Aspect 100. A method of producing glycerol, an intermediate, or a downstream anabolic pathway product, in a host cell, the method comprising culturing the genetically modified host cell of any one of aspects 85-99 in a culture medium comprising D-galacturonic acid, wherein said culturing provides for production of glycerol, an intermediate, or a downstream anabolic pathway product.

Aspect 101. The method of aspect 100, wherein the culture medium comprises agricultural waste products.

Aspect 102. The method of aspect 101, wherein the agricultural waste products comprise fruit pulp, fruit peel, sugar beet pulp, or lignocellulosic biomass.

Aspect 103. The method of aspect 102, wherein the fruit pulp and fruit peel are from citrus fruit and/or apples.

Aspect 104. The method of any one of aspects 100-103, wherein the downstream anabolic pathway product is mevalonate, an isoprenoid compound, mucic acid, an alkaloid, or a polyketide.

Aspect 105. The method of aspect 100, wherein the intermediate is L-galactonate, 2-keto-3-deoxy-L-galactonate, or glyceraldehyde.

Aspect 106. The method of aspect 100, wherein the culture medium comprises dextrose or arabinose.

Aspect 107. The method of aspect 100, wherein the downstream product is a product selected from 1,2-propanediol, 1,3-propanediol, 1,4-butanediol, 2,3-butanediol, glycerol, butanol, mevalonate, a mevalonate derivative, an isoprenoid, farnesene, a polyketide, and a fatty acid.

Aspect 108. The method of any one of aspects 101-107, wherein the agricultural waste product is a pectin hydrolysate.

Aspect 109. The method of any one of aspects 100-108, wherein said culturing generates increased host cell mass.

Aspect 110. A variant uronate dehydrogenase (UDH), the variant UDH comprising one or more amino acid substitutions in the NAD$^+$ binding motif such that the variant UDH binds NADP+.

Aspect 111. The variant UDH of aspect 110, wherein the NAD$^+$ binding motif comprises Asp-Val-Ala, Asp-Leu-Ser, Asp-Ile-Thr, Asp-Ile-Ala, Asp-Ile-Ser, or Asp-Ile-Arg, and wherein the NAD$^+$ binding motif comprises one or more amino acid substitutions with a positively charged amino acid.

Aspect 112. The variant UDH of aspect 111, wherein the positively charged amino acid is arginine, histidine, or lysine.

Aspect 113. The variant UDH of aspect 110, comprising an amino acid sequence having at least 40%, at least 50%, at least 60%, at least 70%, at least 80%, at least 90%, at least 95%, at least 98%, or at least 99%, amino acid sequence identity to the amino acid sequence depicted in FIG. 19 (SEQ ID NO:18), wherein one, two, or three of amino acids D42, I43, and A44 are substituted.

Aspect 114. The variant UDH of aspect 113, wherein amino acid I43 is substituted with a positively charged amino acid.

Aspect 115. The variant UDH of aspect 114, comprising an I43R substitution.

Aspect 116. The variant UDH of aspect 110, comprising an amino acid sequence having at least 40%, at least 50%, at least 60%, at least 70%, at least 80%, at least 90%, at least 95%, at least 98%, or at least 99%, amino acid sequence identity to the amino acid sequence depicted in FIG. 21 (SEQ ID NO:20), wherein X is arginine, histidine, or lysine.

Aspect 117. The variant UDH of aspect 110, comprising an amino acid sequence having at least 40%, at least 50%, at least 60%, at least 70%, at least 80%, at least 90%, at least 95%, at least 98%, or at least 99%, amino acid sequence identity to the amino acid sequence depicted in FIG. 47 (SEQ ID NO:25), wherein one, two, or three of amino acids D35, V36, and A37 is substituted with arginine, histidine, or lysine.

Aspect 118. The variant UDH of aspect 110, comprising an amino acid sequence having at least 40%, at least 50%, at least 60%, at least 70%, at least 80%, at least 90%, at least 95%, at least 98%, or at least 99%, amino acid sequence identity to the amino acid sequence depicted in FIG. 48 (SEQ ID NO:26), wherein one, two, or three of amino acids D33, L34, and S35 is substituted with arginine, histidine, or lysine.

Aspect 119. The variant UDH of aspect 110, comprising an amino acid sequence having at least 40%, at least 50%, at least 60%, at least 70%, at least 80%, at least 90%, at least 95%, at least 98%, or at least 99%, amino acid sequence identity to the amino acid sequence depicted in FIG. 49 (SEQ ID NO:27), wherein one, two, or three of amino acids D37, I38, and S39 is substituted with arginine, histidine, or lysine.

Aspect 120. The variant UDH of aspect 110, comprising an amino acid sequence having at least 40%, at least 50%, at least 60%, at least 70%, at least 80%, at least 90%, at least 95%, at least 98%, or at least 99%, amino acid sequence identity to the amino acid sequence depicted in FIG. 50 (SEQ ID NO:28), wherein one, two, or three of amino acids D51, I52, and T53 is substituted with arginine, histidine, or lysine.

Aspect 121. The variant UDH of aspect 110, comprising an amino acid sequence having at least 40%, at least 50%, at least 60%, at least 70%, at least 80%, at least 90%, at least 95%, at least 98%, or at least 99%, amino acid sequence identity to the amino acid sequence depicted in FIG. 51 (SEQ ID NO:29), wherein one, two, or three of amino acids D31, I32, and A33 is substituted with arginine, histidine, or lysine.

Aspect 122. The variant UDH of aspect 110, comprising an amino acid sequence having at least 40%, at least 50%, at least 60%, at least 70%, at least 80%, at least 90%, at least 95%, at least 98%, or at least 99%, amino acid sequence identity to the amino acid sequence depicted in FIG. 52 (SEQ ID NO:30), wherein one, two, or three of amino acids D32, I33, and R34 is substituted with arginine, histidine, or lysine.

Aspect 123. A nucleic acid comprising a nucleotide sequence encoding the variant UDH of any one of aspects 110-122.

Aspect 124. A recombinant expression vector comprising the nucleic acid of aspect 123.

Aspect 125. The recombinant expression vector of aspect 124, wherein the nucleotide sequence is operably linked to a promoter.

Aspect 126. The recombinant expression vector of aspect 125, wherein the promoter is an inducible promoter.

Aspect 127. A host cell genetically modified with the nucleic acid of aspect 123, or the recombinant expression vector of any one of aspects 124-126.

Aspect 128. The genetically modified host cell of aspect 127, wherein the host cell is a eukaryotic cell.

Aspect 129. The genetically modified host cell of aspect 128, wherein the eukaryotic host cell is a yeast cell, an algal cell, or a fungal cell.

Aspect 130. The genetically modified host cell of aspect 127, wherein the host cell is a prokaryotic cell.

Aspect 131. The genetically modified host cell of aspect 130, wherein the host cell is a bacterial cell.

Aspect 132. The genetically modified host cell of any one of aspects 127-131, wherein the host cell is present in a container.

Aspect 133. A genetically modified eukaryotic host cell, wherein the genetically modified eukaryotic host cell is genetically modified to express a heterologous D-galacturonic acid transporter.

Aspect 134. The genetically modified eukaryotic host cell of aspect 133, wherein the heterologous D-galacturonic acid transporter comprises an amino acid sequence having at least 40%, at least 50%, at least 60%, at least 70%, at least 80%, at least 90%, at least 95%, at least 98%, at least 99%, or 100%, amino acid sequence identity to the amino acid sequence depicted in one of FIG. 2-5 (SEQ ID NOs:1-4), or as set forth in SEQ ID NO:38 or SEQ ID NO:39.

Aspect 135. The genetically modified eukaryotic host cell of aspect 133 or aspect 134, wherein the host cell is a yeast cell.

Aspect 136. The genetically modified eukaryotic host cell of aspect 133 or aspect 134, wherein the host cell is a fungal cell.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Redox Coupling of D-Galacturonate to Mucic Acid and Redox Coupling of Glycerol to 1,3-propanediol Materials and Methods

*E. coli* with the following strain background was used: MG1655 (DE3) ΔuxaC ΔgarD Constructs:
1) BBa100/RBS—*Clostridium butyricum* glycerol dehydratase and 1,3-propanediol oxidoreductase (p15a—SPEC)
2) T7—uronate dehydrogenase (ColE1—AMP)
3) Empty vector controls Culturing After constructs were introduced into the host *E. coli* cells, the cells were grown aerobically to optical density (OD) 3 in Terrific Broth (TB), in 100 mL cultures. Isopropyl β-D-1-thiogalactopyranoside (IPTG) added to 1 mM to induce expression, and cells were cultured overnight (ON) at 18° C. The culture was concentrated to OD 20 in M9 minimal media supplemented with 1% casamino acids (CAA), 1% glycerol, 2% D-galacturonic acid (D-galUA)+ IPTG. The culture medium was sparged with $N_2$ in anaerobic culture flasks. The culture medium was collected for high performance liquid chromatography (HPLC) analysis.

Results

Figure 32:
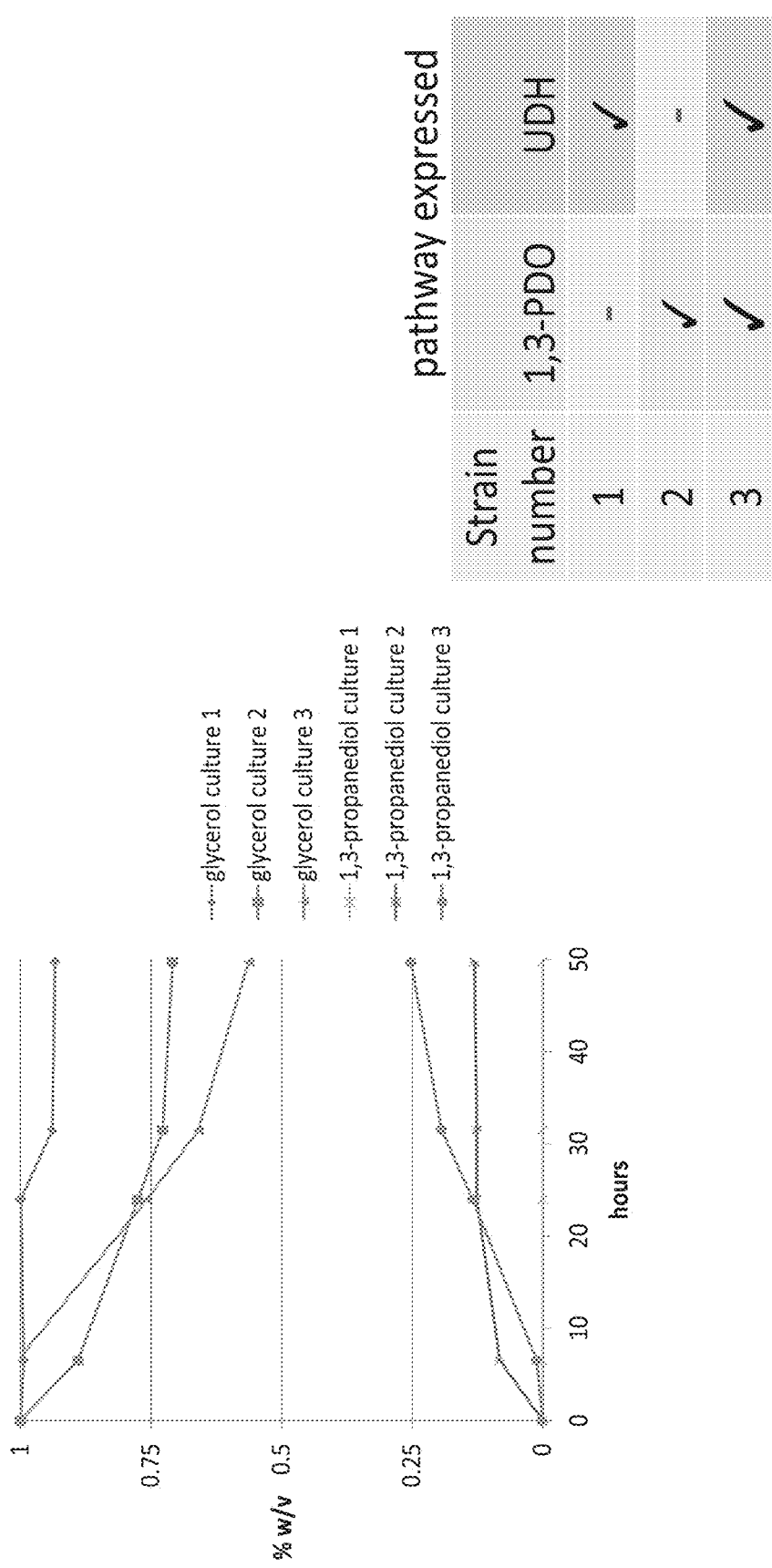
FIG. 32 depicts *E. coli* redox coupling of D-galacturonate to mucic acid and glycerol to 1,3-propanediol.

The data for production of mucic acid are depicted in FIG. 32. As shown in FIG. 32, mucic acid was produced at a rate of 0.320 mg/L/hr/OD.

Figure 33:
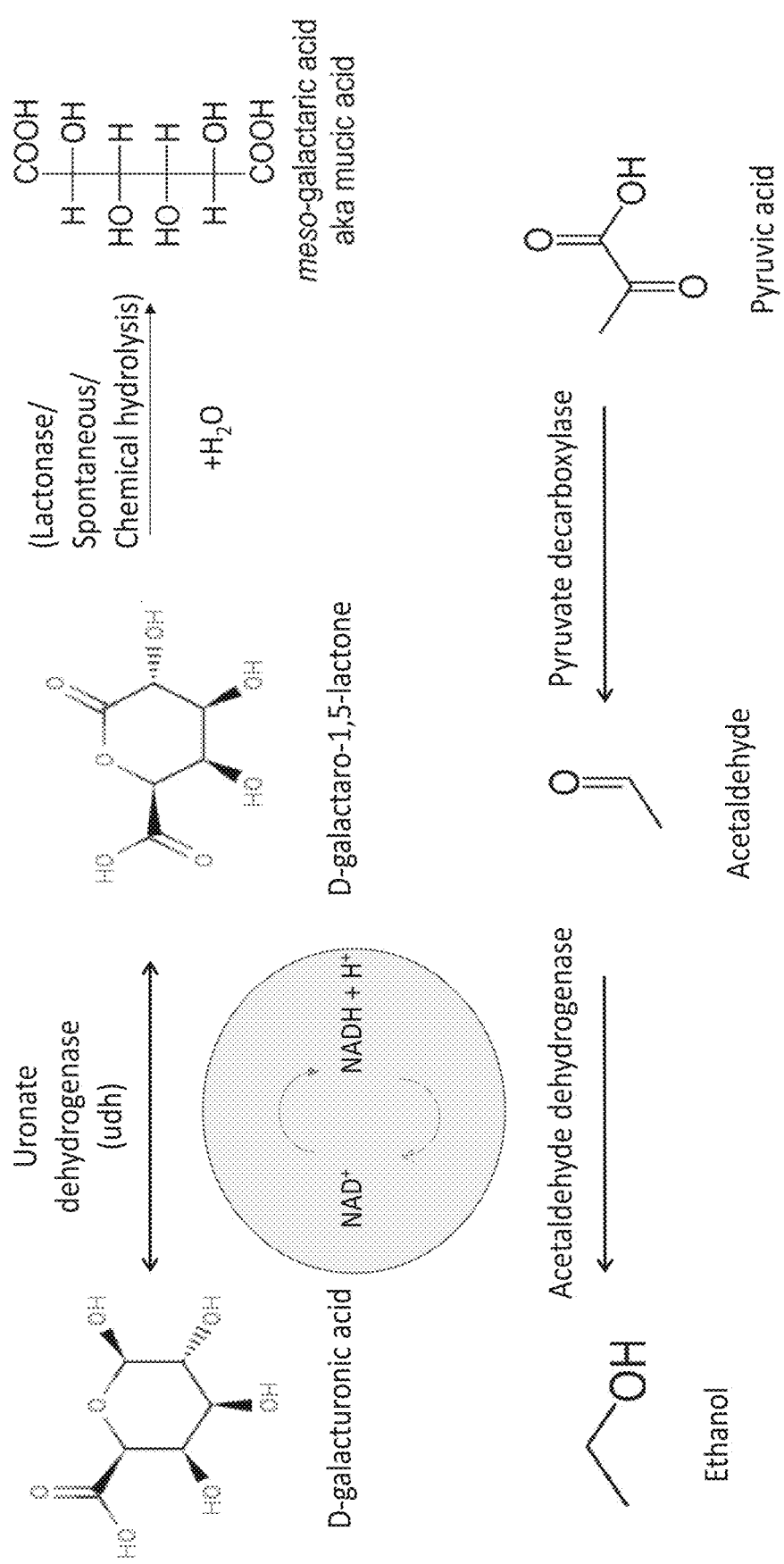
FIG. 33 depicts *Saccharomyces cerevisiae*, expressing uronate dehydrogenase (UDH), producing D-galactaro-1,5-lactone from D-galacturonic acid during reduction of acetaldehyde.

The data for production of 1,3-propanediol are depicted in FIG. 33. As shown in FIG. 33, 1,3-propanediol was produced at a rate of 0.252 mg/L/hr/OD.

Example 2: Identification of Naturally-Occurring NADP$^+$-Utilizing UDH Polypeptides and Engineering NADP$^+$-Utilizing UDH Polypeptides The approach for identifying naturally-occurring NADP$^+$-utilizing UDH polypeptides, and for engineering NADP$^+$-utilizing UDH polypeptides; and the results, are depicted in FIGS. 36-49.

Example 3: End-Point Anaerobic Yeast Fermentation

Results from end-point anaerobic yeast fermentation experiments. All culture media was composed of yeast nitrogen base with the appropriate amino acids added at pH 3.5. The carbohydrates D-galacturonic acid and dextrose were added at 1% and 4%, respectively, in conditions indicated by "+." Strains with and without the D-galacturonic acid transporter (FIG. 3: SEQ ID NO: 2)) and natural NAD+*P. syringae* uronate dehydrogenase (FIG. 19 (SEQ ID NO: 18)) were incubated in media with and without dextrose and galacturonic acid added.

Mucic acid production is dependent on co-expression of the uronate dehydrogenase and the transporter AND co-feeding galacturonic acid and dextrose.

A smaller fraction of the galacturonic acid is converted to mucic acid in the yeast strain expressing only the UDH and not the transporter. This strain is inhibited for D-galacturonic acid import due to the presence of glucose.

The strains expressing uronate dehydrogenase with and without the D-galacturonic acid transporter make similar mucic acid amounts in the absence of dextrose. D-galacturonic acid is imported into the cells, but there is not substrate for an active reductase to use the NADH produced by the UDH activity. Therefore, very little mucic acid is produced.

Figure 35:
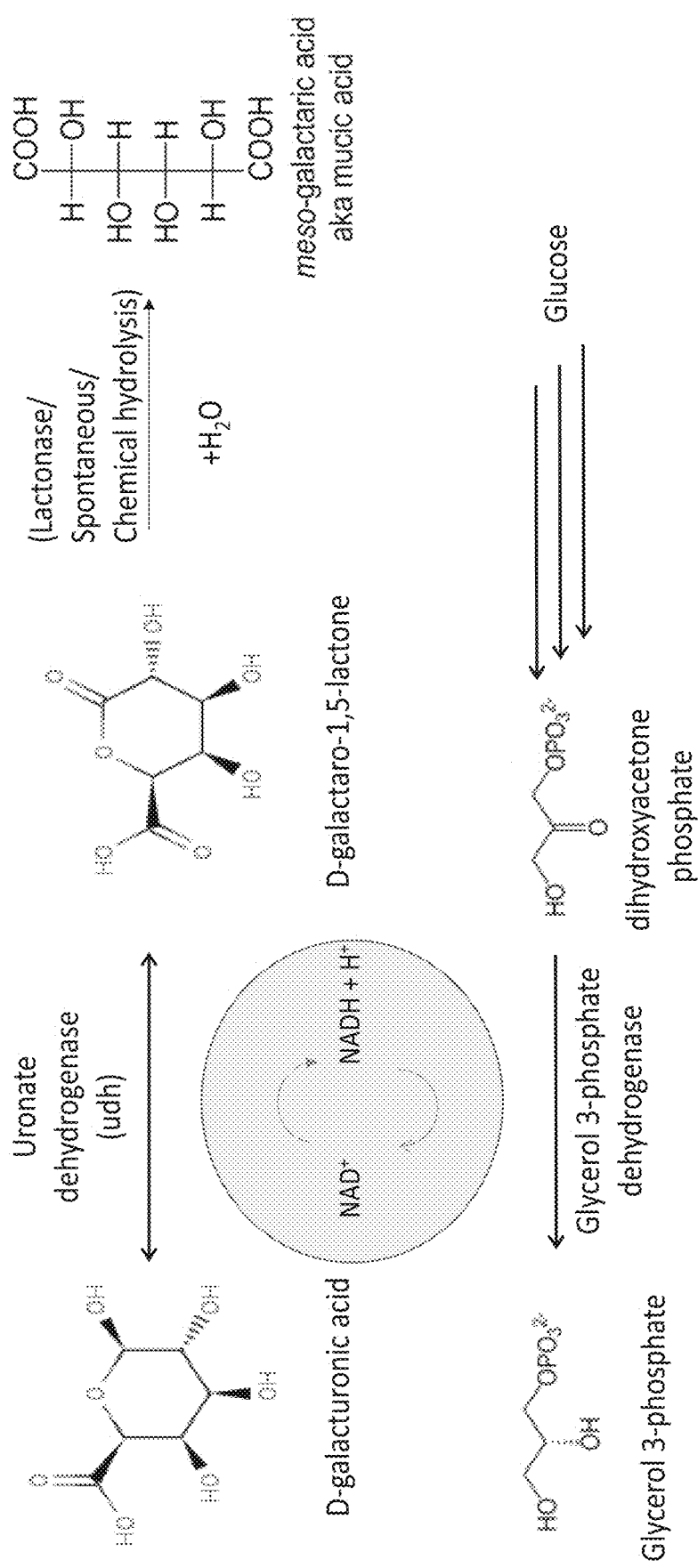
FIG. 35 depicts *S. cerevisiae*, expressing UDH, producing D-galactaro-1,5-lactone from D-galacturonic acid during reduction of dihydroxyacetone phosphate.
Figure 53:
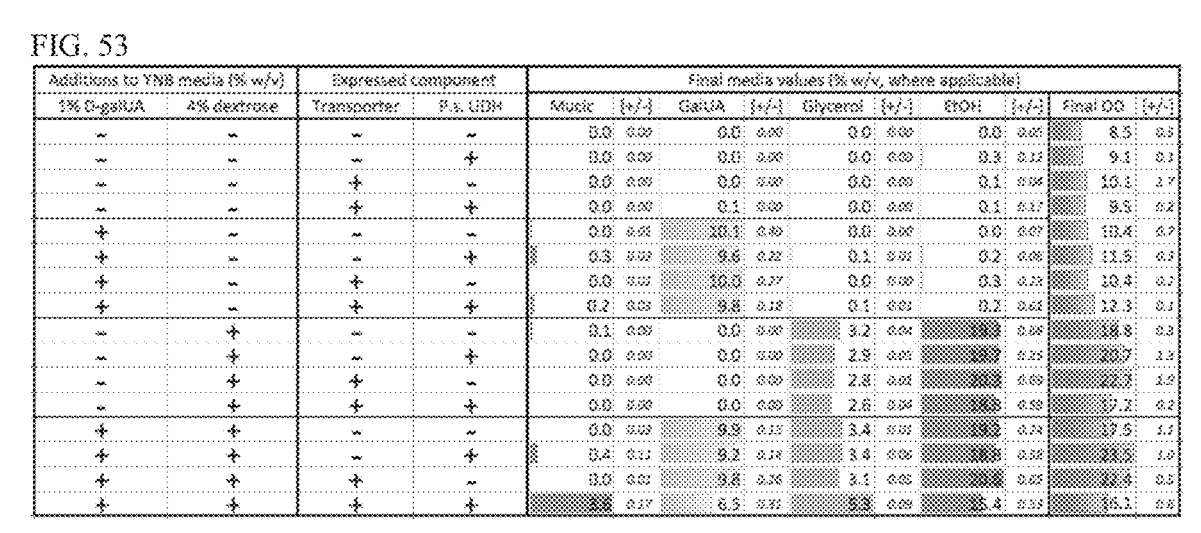

Note that there is more glycerol and less ethanol produced in the mucic acid production strain when fed galacturonic acid and dextrose compared to dextrose alone. This is because the UDH activity increases intracellular NADH levels and the dextrose carbon is shunted to glycerol production by the endogenous glycerol 3-dehydrogenase (NADH+dihydroxyacetone phosphate ↔NAD++glycerol 3-phosphate) and away from ethanol. A schematic of this redox coupling is shown in FIG. 35. FIG. 53 depicts the effects of: 1) expression of a transporter not inhibited by dextrose; and 2) co-feeding with dextrose and D-galacturonic acid.

Figure 26:
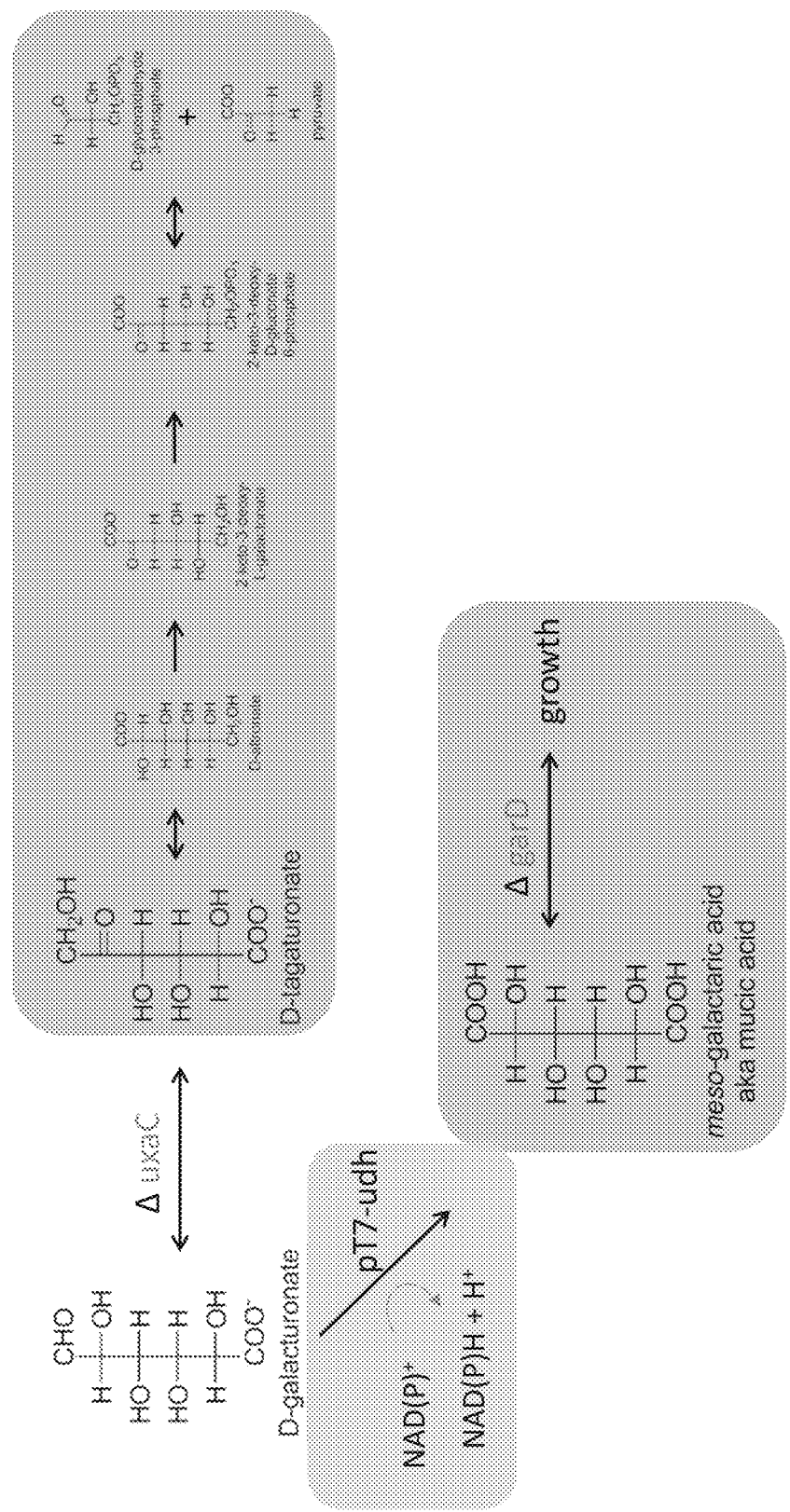
FIG. 26 is a schematic depiction of bioconversion of D-galacturonate to mucic acid.

FIG. 26 is a schematic depiction of bioconversion of D-galacturonate to mucic acid. The *E. coli* strain used was MG1655 (DE3) ΔuxaC, ΔgarD, ΔpT7-udh. Bacterial modification was performed by knocking out D-galacturonic acid and mucic acid catabolism. Direct D-galUA conversion resulted in accumulation of mucic acid.

Figure 27:
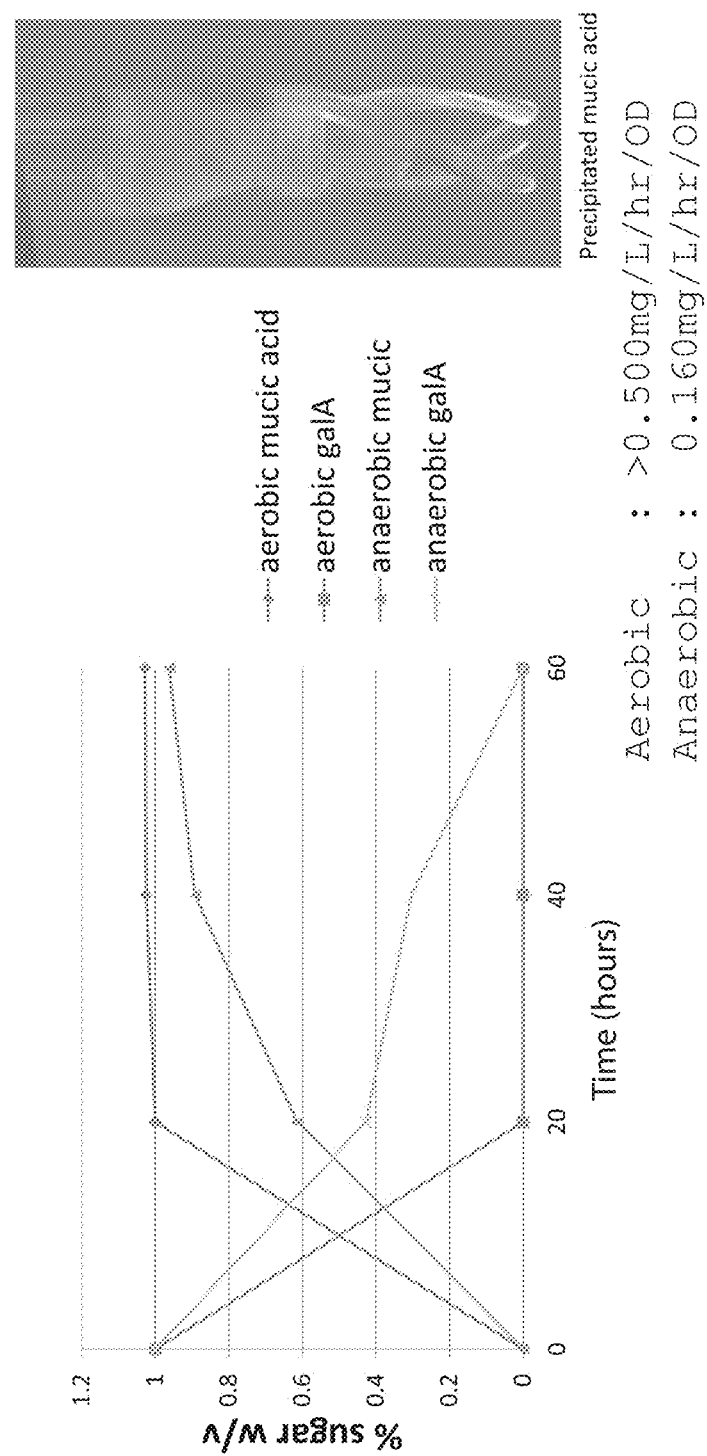
FIG. 27 depicts bioconversion of D-galacturonate to mucic acid.

FIG. 27 depicts bioconversion of D-galacturonate to mucic acid. The *E. coli* strain used was MG1655 (DE3) ΔuxaC, ΔgarD, T7-udh. Results showed fast conversion aerobically; slow conversion anaerobically due to lack of NAD+, where D-galUA consumption or mucic acid production was not observed in the empty vector control.

FIG. 28 shows a schematic depiction of use of UDH as a redox tool to redirect reducing equivalents. The use of UDH as a redox tool to redirect reducing equivalents was applicable to the use of both NADH and NADPH producing urinate dehydrogenases, depending on the corresponding reductase.

Figure 30:
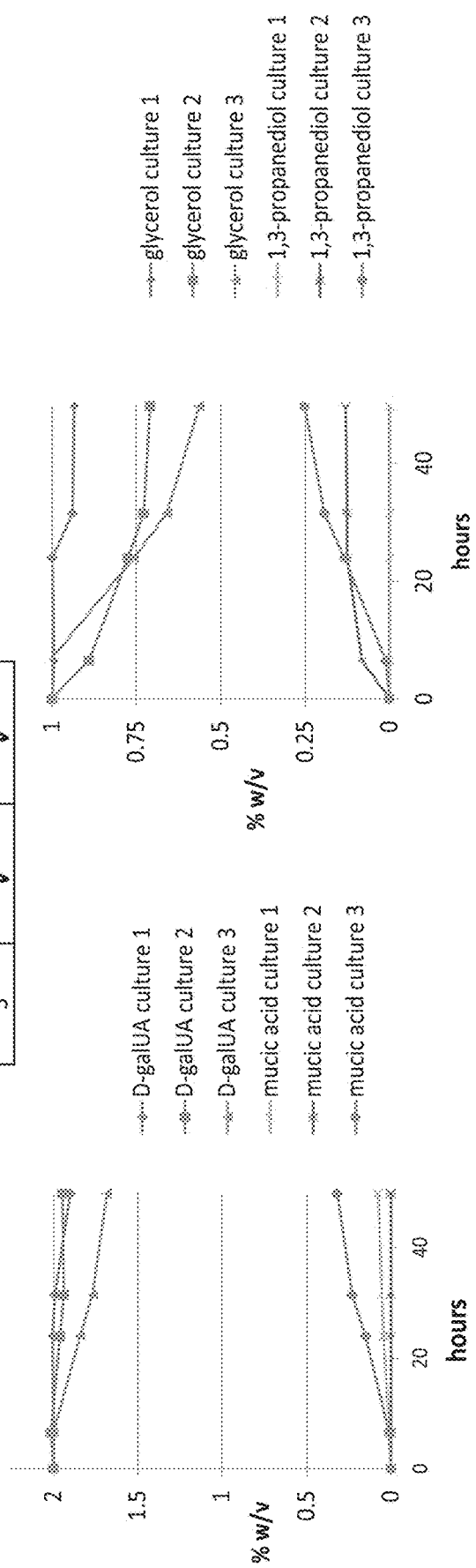
FIG. 30 is a schematic depiction of redox coupling of D-galacturonate to mucic acid and glycerol in *E. coli*.

FIG. 30 is a schematic depiction of redox coupling of D-galacturonate to mucic acid and glycerol to 1,3-propanediol in *E. coli*. FIG. 30 shows a production rate of 0.075 mg/L/hr/OD for Culture 1 of mucic acid (left), 0.320 mg/L/hr/OD for Culture 3 of mucic acid (left). FIG. 30 shows a production rate of 0.130 mg/L/hr/OD for Culture 2 of 1,3-propanediol (right) and 0.252 for Culture 3 of 1,3-propanediol (right).

Figure 31:
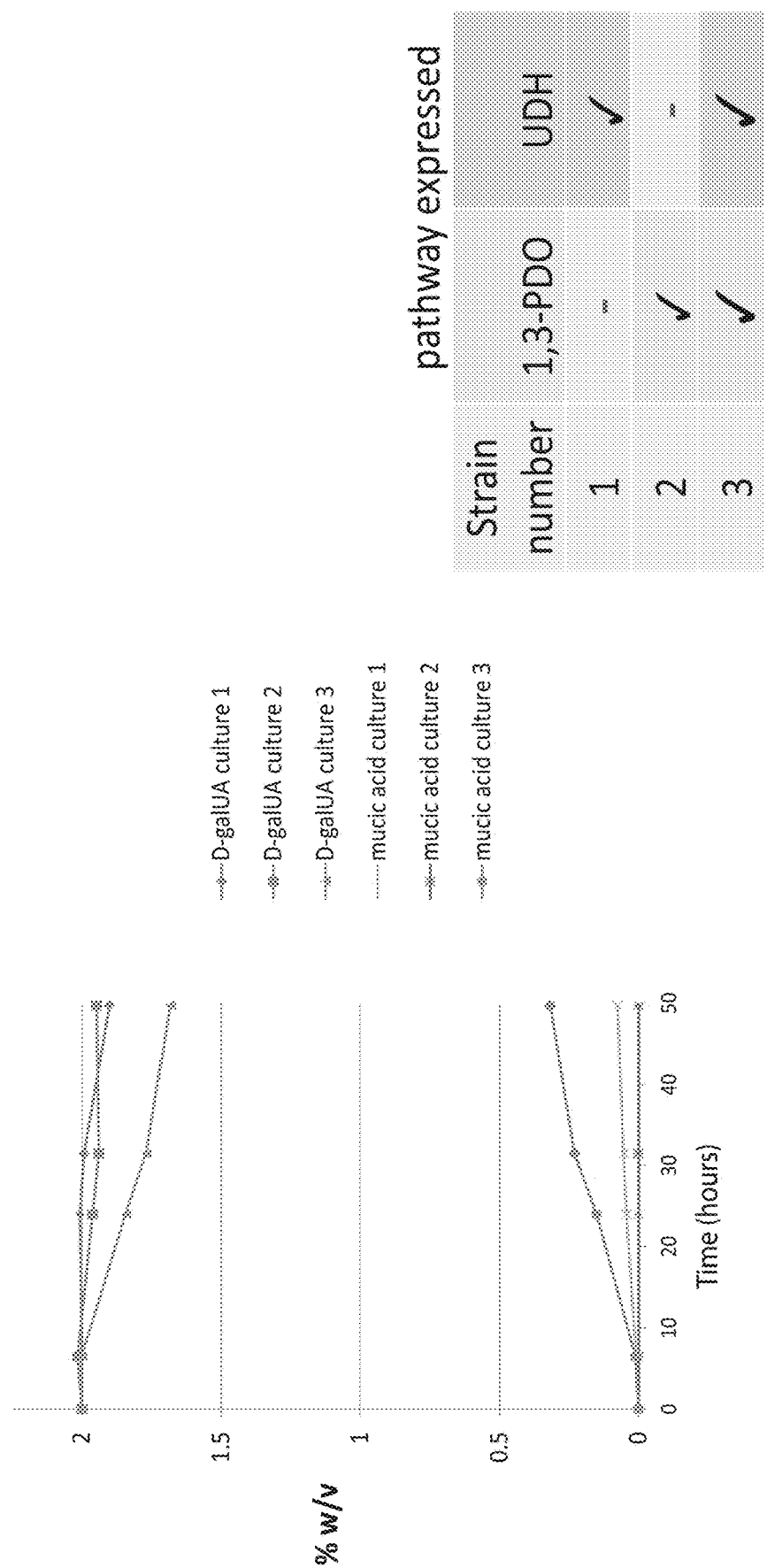
FIG. 31 depicts redox coupling of glycerol D-galacturonate to mucic acid and glycerol to 1,3-propanediol in *E. coli*.

FIG. 31 depicts redox coupling of glycerol D-galacturonate to mucic acid and glycerol to 1,3-propanediol in *E. coli*. FIG. 31 shows a production rate of 0.075 mg/L/hr/OD for Culture 1 of mucic acid (left) and 0.320 mg/L/hr/OD for Culture 3 of mucic acid (left).

Figure 34:
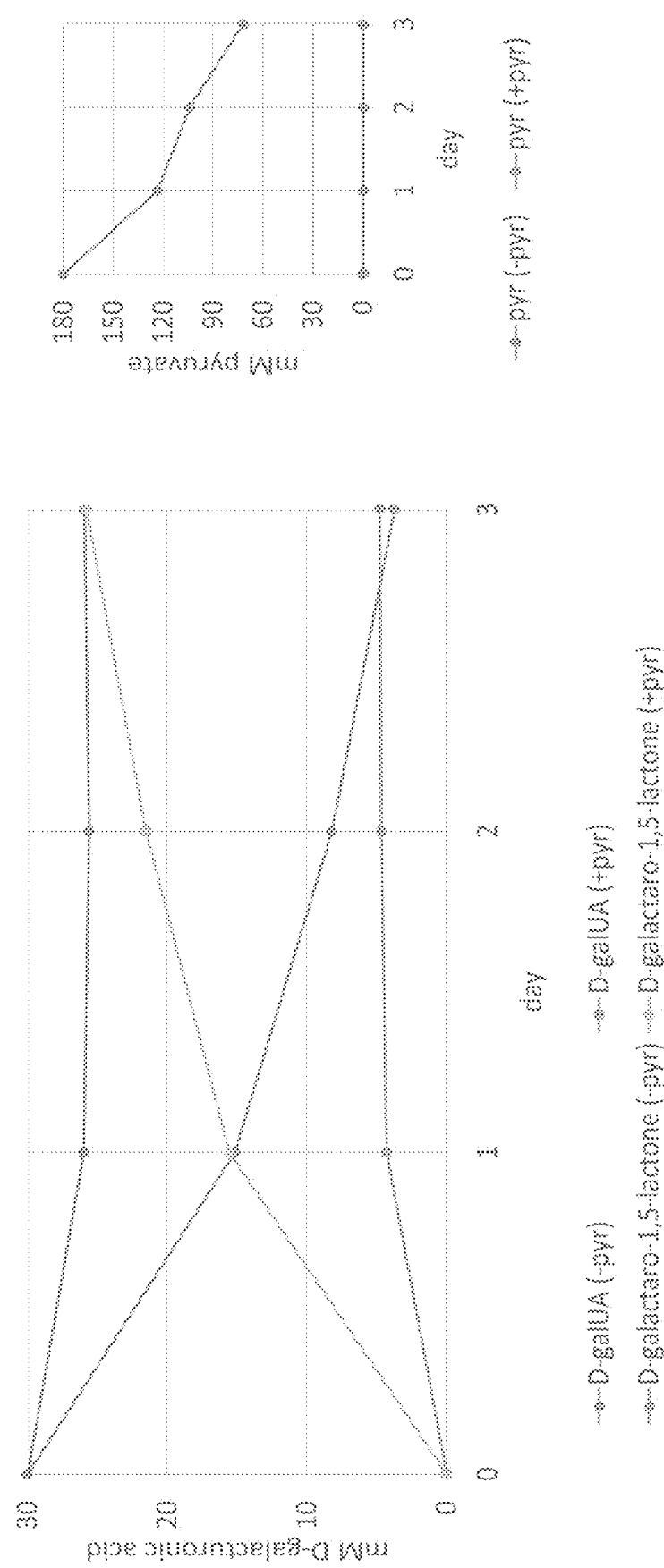
FIG. 34 depicts *S. cerevisiae*, expressing UDH, producing D-galactaro-1,5-lactone from D-galacturonic acid during reduction of acetaldehyde.

FIG. 34 depicts *S. cerevisiae*, expressing UDH, producing D-galactaro-1,5-lactone from D-galacturonic acid during reduction of acetaldehyde. FIG. 34 shows yeast with UDH bioconverting D-galacturonic acid (D-galUA) to D-galactaro-1,5-lactone with and without presence of pyruvate for redox coupling.

Figure 36:
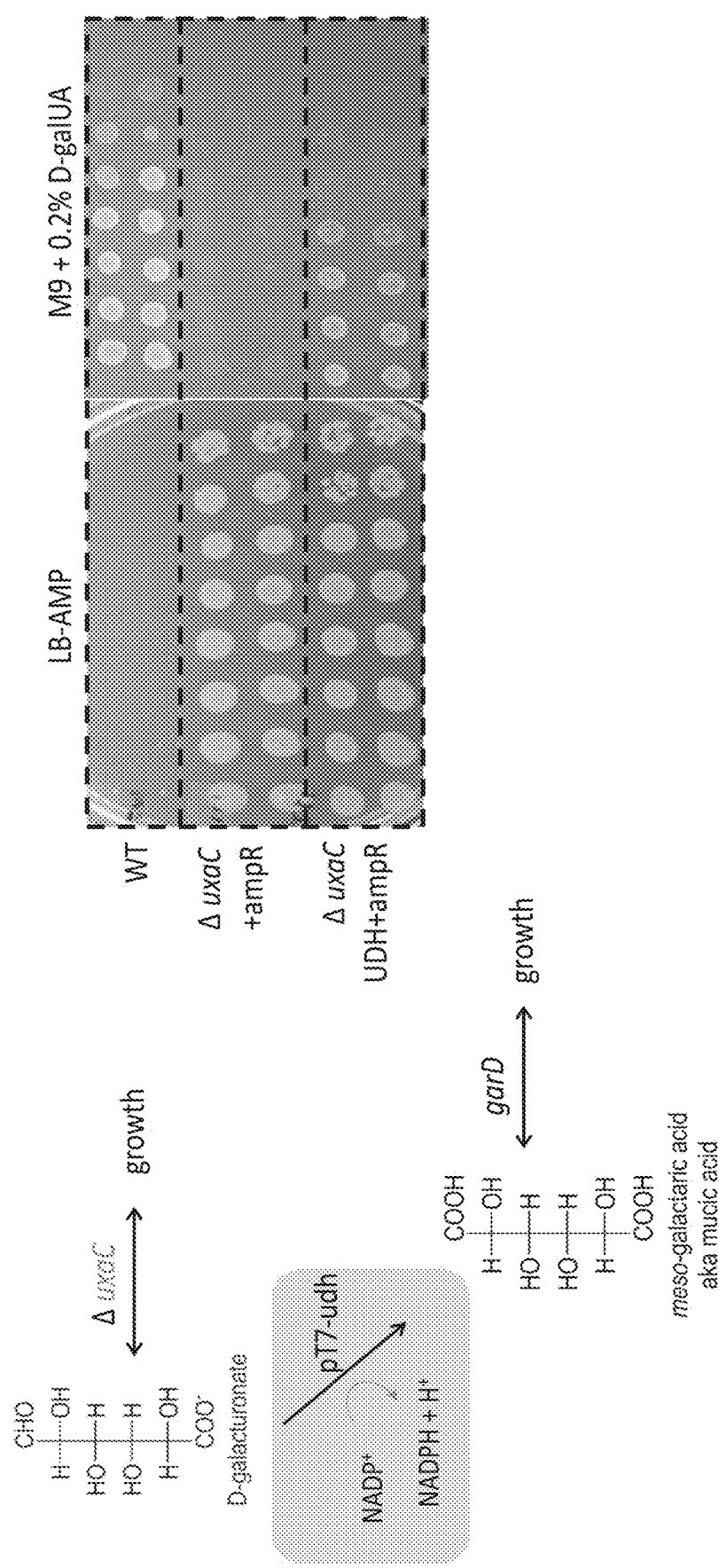
FIG. 36 depicts complementation of D-galacturonic acid growth uxaC knockout uronate dehydrogenase from *Limnohabitans* sp. Rim47.

FIG. 36 depicts complementation of D-galacturonic acid growth uxaC knockout uronate dehydrogenase from *Limnohabitans* sp. Rim47. The strain used was *E. coli* MG1655 (DE3) ΔuxaC, expressing *Limnohabitans* sp. Rim47 dehydrogenase. FIG. 36 shows that UxaC is essential for *E. coli* growth on D-galUA. Expression of the uronate dehydrogenase from *Limnohabitans* sp. Rim47 in the uxaC knockout rescues growth on D-glUA by directing flux to the mucic acid catabolism pathway.

Figure 37:
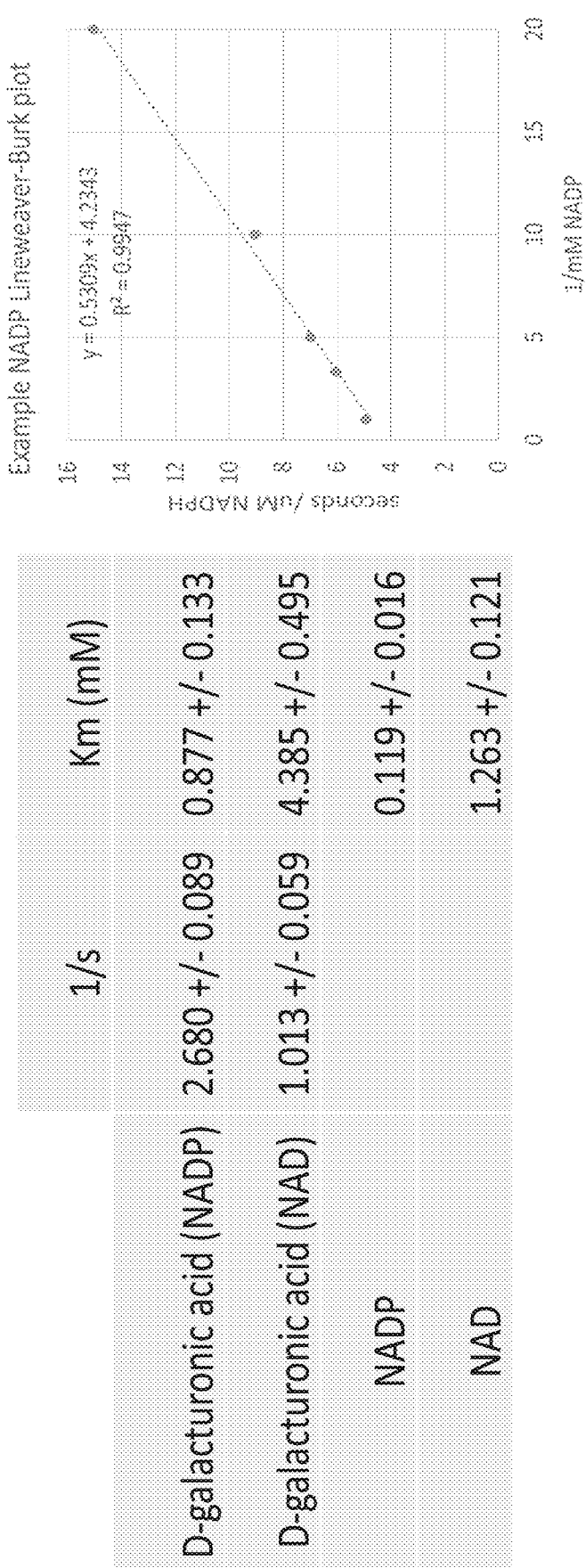
FIG. 37 depicts enzyme kinetics of NADP+ utilizing uronate dehydrogenase from *Limnohabitans* sp. Rim47.

FIG. 37 depicts enzyme kinetics of NADP+ utilizing uronate dehydrogenase from *Limnohabitans* sp. Rim47. Purified hexahistidine tagged enzyme was used in NAD(P)H absorption assay in 1×PBS buffer at 30'C.

Figure 38:
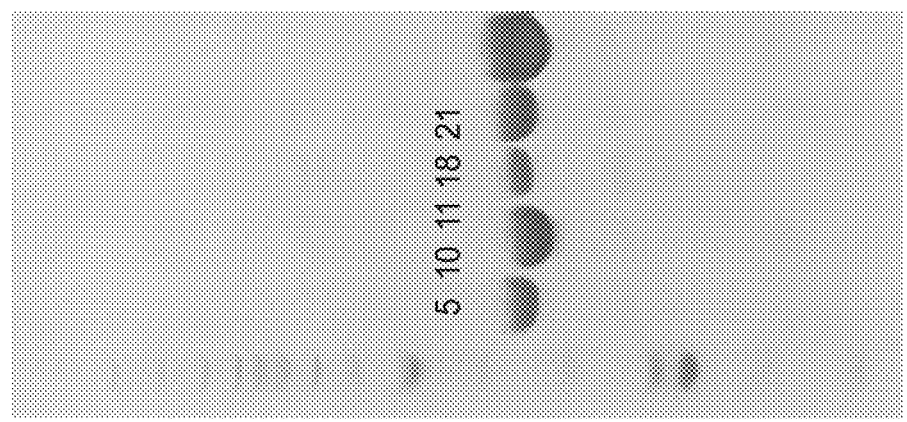
FIG. 38 depicts specific activities of engineered N-terminal hexahistadine tag purified *Pseudomonas syringae* NAD(P)+ utilizing uronate dehydrogenases. (The wild-type (WT) sequence is provided in FIG. 19.)

FIG. 38 depicts specific activities of engineered N-terminal hexahistadine tag purified *Pseudomonas syringae* NAD(P)+ utilizing uronate dehydrogenases. (The wild-type (WT) sequence is provided in FIG. 19.)

FIG. 39 depicts *E. coli* production of L-galactonate by expression on *A. niger* D-galacturonic acid reductase (GAAA). The Example strain used was MG1655(DE3) ΔuxaC ΔyjjN, T7-GAAA. The Example strain shows knock out of D-galacturonic acid and L-galactonate catabolism (uxaC and yjjN, respectively) and expressed *A. niger* D-galacturonic acid reductase (GAAA) to bioconvert D-galacturonic acid to L-galactonate. D-galUA consumption or L-galacturonic acid production was not observed in the empty vector control.

Figure 40:
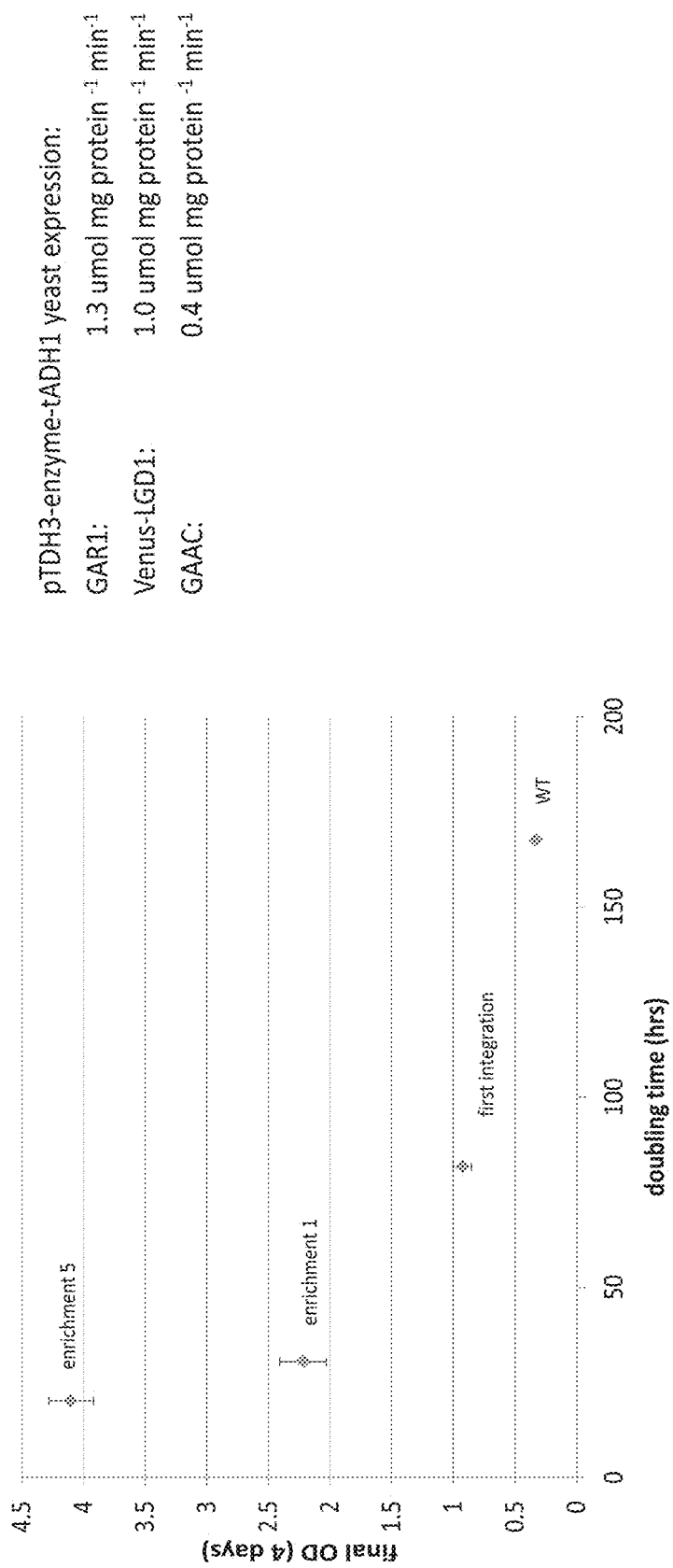
FIG. 40 depicts *S. cerevisiae* growth in D-galacturonic acid media via expression of fungal pathway.
Figure 41:
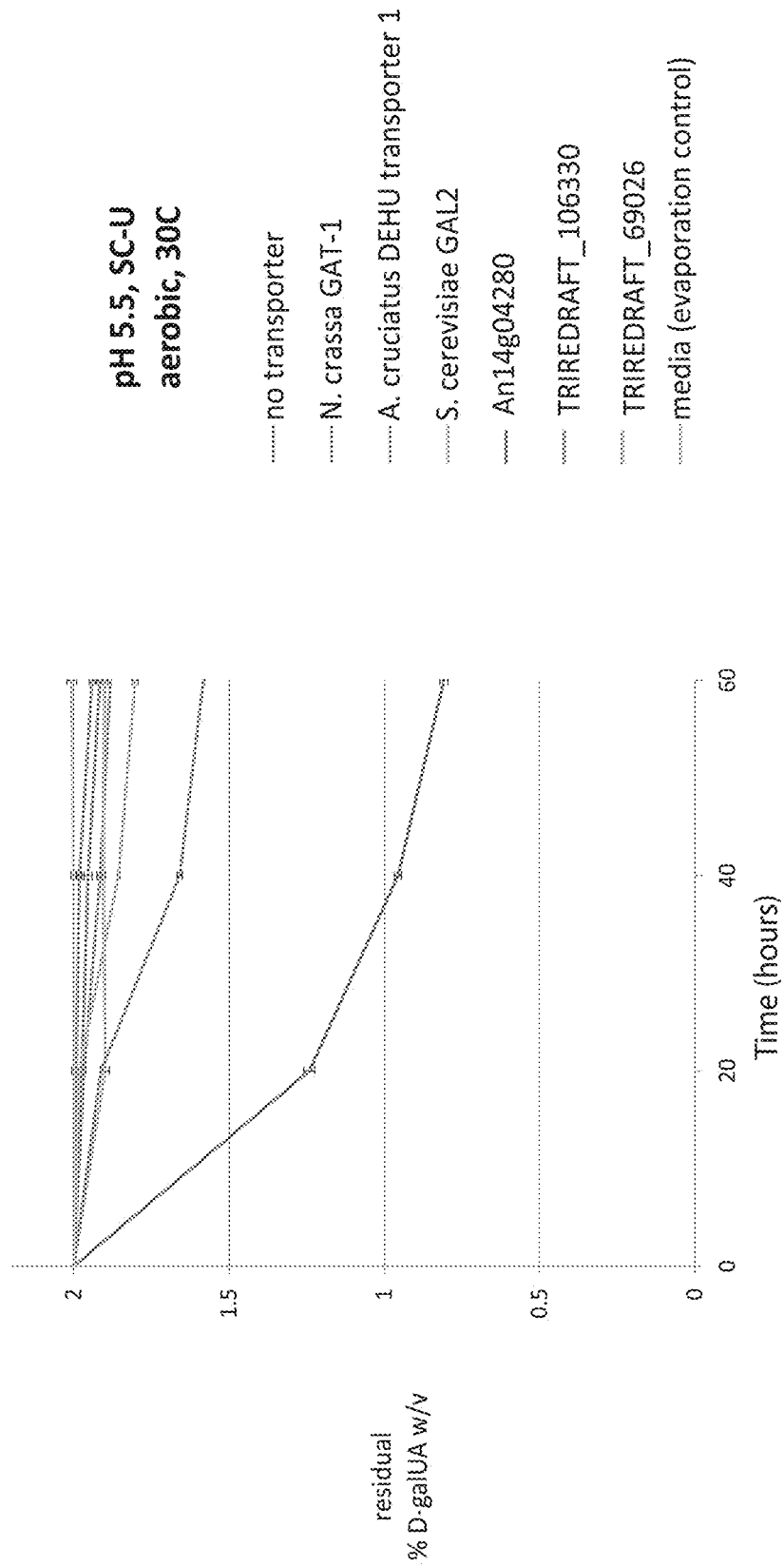
FIG. 41 depicts heterologous expression of fungal D-galacturonic acid transporters in *S. cerevisiae* allows for import of D-galacturonate in high pH media.
Figure 43:
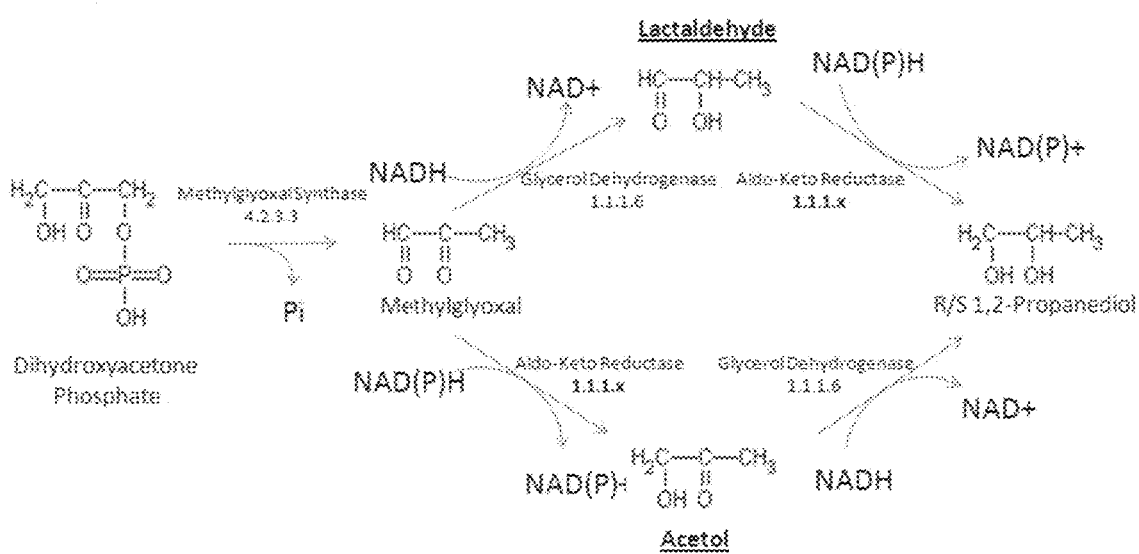
FIG. 43 depicts production of 1,2-propanediol from dihydroxyacetone phosphate.

FIG. 40 depicts *S. cerevisiae* growth in D-galacturonic acid media via expression of fungal pathway. *S. cerevisiae* was grown in SC-2% D-galacturonic acid at 30'C with 50 mL cultures in baffled flasks and had a pH of 3.2.

FIG. 42 depicts expression of *A. niger* An14g04280 transporter in *S. cerevisiae* expressing D-galUA consumption pathway, which allows for import of D-galacturonate while co-consuming glucose. Hydrolysed CPW or SBP biomass had glucose and D-galUA.

Figure 46:
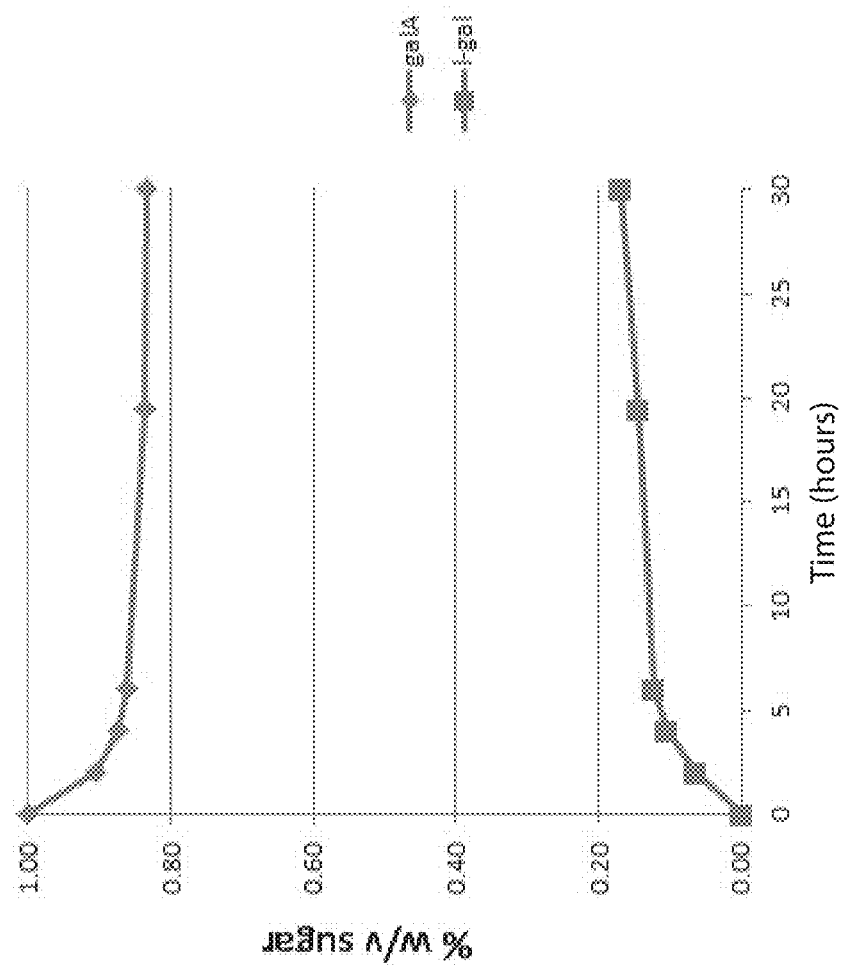

FIG. 45 and FIG. 46 depict bioconversion of D-galacturonate to L-galactonate. The strain used was MG1655 (DE3) ΔuxaC ΔyjjN, T7-GAAA. The strain was grown to OD1 in LB, and IPTG was added to 1 mM ON at 18'C to induce. The strain was concentrated to OD 10 in 1% D-galUA M9+0.2% CAA+IPTG in 50 mL of a baffled flask. D-galUA consumption or L-galUA production was not observed in the empty vector control.

Figure 54:
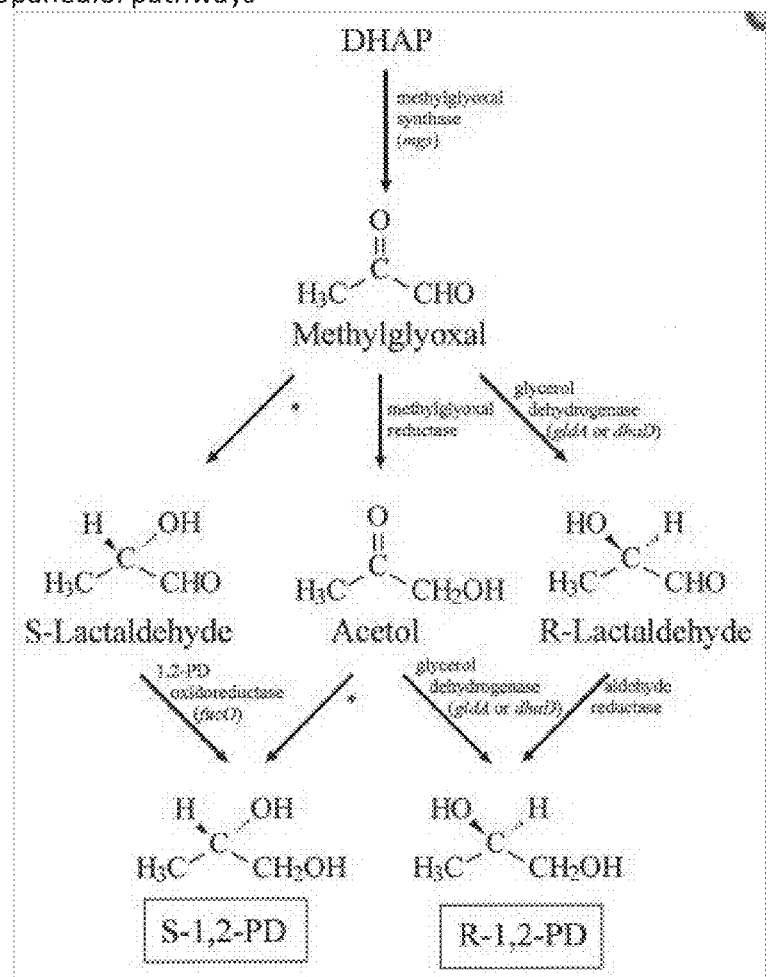
FIG. 54 depicts pathways for production of 1,2-propanediol.

FIG. 54 depicts pathways for production of 1,2-propanediol, which shows methylgyoxyl reductase (mgsA in *E. coli*), glycerol dehydrogenase (gldA, *E. coli*, dhaD in *Klebsiella*), aldo-keto reductase or 1,2-propanediol oxidoreductase (fucO).

Example 4: Production of Mucic Acid

Figure 56:
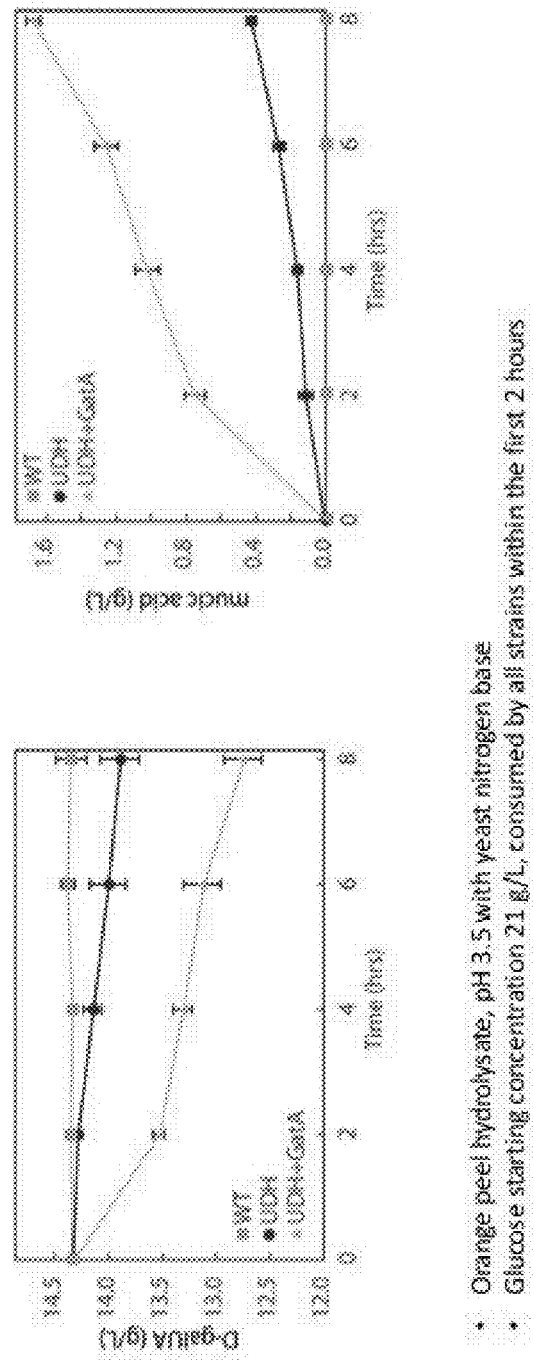
FIG. 56 depicts production of mucic acid by yeast genetically modified such that the yeast cells synthesize both GatA and UDH.

FIG. 56 provides data showing that yeast that are genetically modified, such that they produce a D-galacturonic acid transporter (GatA) and uronate dehydrogenase (UDH), can convert D-galacturonic acid from raw orange peel hydrolysate into mucic acid at levels significantly higher than in control yeast not genetically modified to include GatA. The data show that the D-galacturonic acid transporter allows for uptake of galacturonic acid (GA) and conversion of GA into mucic acid. Mucic acid was produced in the culture medium at concentrations of from 0.8 g/L to 1.6 g/L after culturing for a time period of from 2 hours to 8 hours.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. An in vitro genetically modified host cell genetically modified with:
 a) a heterologous nucleic acid comprising a nucleotide sequence encoding a heterologous uronate dehydrogenase (UDH),
 wherein the heterologous UDH uses NADP⁺ or NAD⁺ as a cofactor, and produces NADPH or NADH, respectively, and wherein the heterologous UDH converts a sugar acid to its corresponding 1,5-aldonolactone, wherein the host cell coexpresses an endogenous or a heterologous reductase that utilizes the produced NADPH or NADH; and wherein:
  i) the heterologous modified UDH comprises an amino acid sequence having at least 95% amino acid sequence identity to the amino acid sequence set forth in SEQ ID NO:18, wherein two or three of amino acids D42, I43, and A44 are substituted; or
  ii) the heterologous modified UDH comprises an amino acid sequence having at least 95% amino acid sequence identity to the amino acid sequence set forth in SEQ ID NO:20, wherein X is arginine, histidine, or lysine; or
  iii) the heterologous UDH utilizes NADP⁺, and wherein the heterologous UDH comprises an amino acid sequence having at least 95% amino acid sequence identity to the amino acid sequence set forth in SEQ ID NO:19;
 and
 b) one or more heterologous nucleic acids comprising heterologous nucleotide sequences encoding one or more enzymes of an anabolic pathway, wherein the anabolic pathway requires the reductase that utilizes the produced NADPH or NADH.

2. The genetically modified host cell of claim 1, wherein:
 a) the sugar acid is D-galacturonic acid, and the 1,-5-aldonolactone is D-galactaro-1,5-lactone; or
 b) the sugar acid is D-glucuronic acid, and the 1,5-aldonolactone is D-glucaro-1,5-lactone.

3. The genetically modified host cell of claim 1, wherein the genetically modified host cell is a prokaryotic host cell that comprises a genetic modification in an endogenous gene encoding uronate isomerase, such that the genetically modified prokaryotic host cell does not produce functional uronate isomerase.

4. The genetically modified host cell of claim 1, wherein the host cell is a yeast cell, and wherein the host cell is genetically modified with a heterologous nucleic acid comprising a nucleotide sequence encoding a heterologous D-galacturonic acid transporter.

5. The genetically modified host cell of claim 1, wherein the one or more anabolic pathway enzymes comprises:
 a) a glycerol dehydratase and wherein the reductase is a 1,3-propanediol oxidoreductase; or
 b) CoA-dependent succinate semialdehyde dehydrogenase, 4-hydroxybutyrate dehydrogenase, 4-hydroxybutyryl-CoA reductase, and alcohol dehydrogenase, wherein the reductase is 4-hydroxybutyryl-CoA reductase; or
 c) methylglyoxyl reductase (mgsA in E. coli), glycerol dehydrogenase, (gldA, E. coli, dhaD in Klebsiella), and aldo-keto reductase or 1,2-propanediol oxidoreductase (fucO); or
 d) myo-inositol-1-phosphate synthase (MIPS) and myo-inositol oxygenase (MIOX); or
 e) one or more heterologous mevalonate pathway enzymes; or
 f) one or more heterologous benzylisoquinoline alkaloid pathway enzymes; or
 g) one or more heterologous polyketide pathway enzymes.

6. The genetically modified host cell of claim 1, wherein the host cell is a eukaryotic cell.

7. The genetically modified host cell of claim 1, wherein the host cell is a prokaryotic cell.

8. The genetically modified host cell of claim 1, wherein the heterologous modified UDH comprises an amino acid sequence having at least 98% amino acid sequence identity to the amino acid sequence set forth in SEQ ID NO:18, wherein two or three of amino acids D42, I43, and A44 are substituted.

9. The genetically modified host cell of claim 1, wherein the heterologous modified UDH comprises an amino acid sequence having at least 98% amino acid sequence identity to the amino acid sequence set forth in SEQ ID NO:20, wherein X is arginine, histidine, or lysine.

10. The genetically modified host cell of claim 1, wherein the heterologous UDH utilizes NADP⁺, and wherein the heterologous UDH comprises an amino acid sequence having at least 98% amino acid sequence identity to the amino acid sequence set forth in SEQ ID NO:19.

11. The genetically modified host cell of claim 1, wherein the one or more anabolic pathway enzymes comprises a glycerol dehydratase and wherein the reductase is a 1,3-propanediol oxidoreductase.

12. An in vitro genetically modified, fermentable host cell genetically modified with a heterologous nucleic acid comprising a nucleotide sequence encoding a heterologous uronate dehydrogenase (UDH), wherein the heterologous UDH converts a sugar acid to its corresponding 1,5-aldonolactone, and wherein:
 a) the heterologous modified UDH comprises an amino acid sequence having at least 95% amino acid sequence identity to the amino acid sequence set forth in SEQ ID NO:18, wherein two or three of amino acids D42, I43, and A44 are substituted; or
 b) the heterologous modified UDH comprises an amino acid sequence having at least 95% amino acid sequence identity to the amino acid sequence set forth in SEQ ID NO:20, wherein X is arginine, histidine, or lysine; or
 c) the heterologous UDH utilizes NADP⁺, and wherein the heterologous UDH comprises an amino acid sequence having at least 95% amino acid sequence identity to the amino acid sequence set forth in SEQ ID NO:19.

13. The genetically modified host cell of claim 12, wherein the host cell is a eukaryotic cell.

14. The genetically modified host cell of claim 12, wherein the host cell is a prokaryotic cell.

15. The genetically modified host cell of claim 12, wherein the host cell is a yeast cell, and wherein the host cell is genetically modified with a heterologous nucleic acid comprising a nucleotide sequence encoding a heterologous D-galacturonic acid transporter.

16. The genetically modified host cell of claim 12, wherein:
 a) the sugar acid is D-galacturonic acid, and the 1,-5-aldonolactone is D-galactaro-1,5-lactone; or
 b) the sugar acid is D-glucuronic acid, and the 1,5-aldonolactone is D-glucaro-1,5-lactone.

17. The genetically modified host cell of claim 12, wherein the heterologous modified UDH comprises an amino acid sequence having at least 98% amino acid sequence identity to the amino acid sequence set forth in SEQ ID NO:18, wherein two or three of amino acids D42, I43, and A44 are substituted.

18. The genetically modified host cell of claim 12, wherein the heterologous modified UDH comprises an amino acid sequence having at least 98% amino acid sequence identity to the amino acid sequence set forth in SEQ ID NO:20, wherein X is arginine, histidine, or lysine.

19. The genetically modified host cell of claim 12, wherein the heterologous UDH utilizes $NADP^+$, and wherein the heterologous UDH comprises an amino acid sequence having at least 98% amino acid sequence identity to the amino acid sequence set forth in SEQ ID NO:19.

\* \* \* \* \*

UNITED STATES PATENT AND TRADEMARK OFFICE
CERTIFICATE OF CORRECTION

PATENT NO. : 11,332,723 B2
APPLICATION NO. : 16/336403
DATED : May 17, 2022
INVENTOR(S) : John E. Dueber et al.

It is certified that error appears in the above-identified patent and that said Letters Patent is hereby corrected as shown below:

In the Specification

In Column 26, Line 2, please replace "Candrida" with --Candida--

In Column 26, Line 23, please replace "Xanthophyllomvces" with --Xanthophyllomyces--

In Column 26, Line 59, please replace "Salmnonella" with --Salmonella--

In Column 29, Line 22, please replace "lie" with --Ile--

In Column 29, Line 23, please replace "Gin" with --Gln--

In Column 29, Line 33, please replace "Gin" with --Gln--

In Column 41, Line 32, please replace "4-diphenyl-1-" with --4-diphenyl-2- --

In Column 41, Line 45, please replace "hydroxy-?-butanone" with --hydroxy-2-butanone--

In Column 44, Line 51, please replace "Schizochyvtrium" with --Schizochytrium--

In Column 45, Line 15, please replace "Brevihacterium" with --Brevibacterium--

In Column 45, Line 23, please replace "Streptomyes fungicidic" with --Streptomyces fungicidicus--

In Column 50, Line 51, please replace "132" with --I32--

In Column 51, Line 34, please replace "133" with --I33--

In Column 64, Line 37, please replace "5-nonanedione" with --4-nonanedione--

Signed and Sealed this
Fifth Day of July, 2022

Katherine Kelly Vidal
*Director of the United States Patent and Trademark Office*